US010744199B2

(12) United States Patent
Kanekiyo et al.

(10) Patent No.: US 10,744,199 B2
(45) Date of Patent: Aug. 18, 2020

(54) EPSTEIN-BARR VIRUS VACCINES

(71) Applicant: The USA, as represented by the Secretary, Department of Health and Human Services, Bethesda, MD (US)

(72) Inventors: Masaru Kanekiyo, Chevy Chase, MD (US); Gary J. Nabel, Chestnut Hill, MA (US); Jeffrey Cohen, Silver Springs, MD (US); Wei Bu, Potomac, MD (US)

(73) Assignee: The USA, as represented by the Secretary, Dept. of Health and Human Services, Bethesda, MD (US)

( * ) Notice: Subject to any disclaimer, the term of this patent is extended or adjusted under 35 U.S.C. 154(b) by 183 days.

(21) Appl. No.: 15/028,655

(22) PCT Filed: Oct. 10, 2014

(86) PCT No.: PCT/US2014/060142

§ 371 (c)(1),
(2) Date: Apr. 11, 2016

(87) PCT Pub. No.: WO2015/054639

PCT Pub. Date: Apr. 16, 2015

(65) Prior Publication Data

US 2016/0303224 A1 Oct. 20, 2016

Related U.S. Application Data

(60) Provisional application No. 61/921,284, filed on Dec. 27, 2013, provisional application No. 61/889,840, filed on Oct. 11, 2013.

(51) Int. Cl.

| | |
|---|---|
| ***A61K 39/245*** | (2006.01) |
| ***A61K 39/12*** | (2006.01) |
| ***C07K 14/00*** | (2006.01) |
| ***C07K 14/005*** | (2006.01) |
| ***C07K 14/195*** | (2006.01) |
| ***C07K 16/08*** | (2006.01) |
| ***C12N 7/00*** | (2006.01) |
| *A61K 39/00* | (2006.01) |

(52) U.S. Cl.

CPC ............ *A61K 39/245* (2013.01); *A61K 39/12* (2013.01); *C07K 14/00* (2013.01); *C07K 14/005* (2013.01); *C07K 14/195* (2013.01); *C07K 16/085* (2013.01); *C12N 7/00* (2013.01); *A61K 2039/55505* (2013.01); *A61K 2039/575* (2013.01); *A61K 2039/64* (2013.01); *C07K 2317/33* (2013.01); *C07K 2317/76* (2013.01); *C07K 2319/00* (2013.01); *C07K 2319/40* (2013.01); *C07K 2319/735* (2013.01); *C12N 2710/16222* (2013.01); *C12N 2710/16234* (2013.01); *C12N 2710/16271* (2013.01)

(58) Field of Classification Search

None

See application file for complete search history.

(56) References Cited

U.S. PATENT DOCUMENTS

| | | | |
|---|---|---|---|
| 7,094,598 | B2 | 8/2006 | Nabel et al. |
| 7,097,841 | B2 | 8/2006 | Carter et al. |
| 7,608,268 | B2 | 10/2009 | Carter et al. |
| 9,441,019 | B2 | 9/2016 | Nabel et al. |
| 2002/0054882 | A1 | 5/2002 | Okuno et al. |
| 2005/0042229 | A1 | 2/2005 | Yang et al. |
| 2005/0108791 | A1 | 5/2005 | Edgerton |
| 2006/0251679 | A1 | 11/2006 | Carter et al. |
| 2007/0082054 | A1 | 4/2007 | Mooter et al. |
| 2007/0224205 | A1 | 9/2007 | Powell et al. |
| 2008/0299151 | A1 | 12/2008 | Fomsgaard |
| 2009/0233377 | A1 | 9/2009 | Iwahori et al. |
| 2010/0137412 | A1 | 6/2010 | Zhou et al. |
| 2010/0285982 | A1 | 11/2010 | Golding et al. |
| 2010/0297174 | A1 | 11/2010 | Garcia-Sastre et al. |
| 2011/0038025 | A1 | 2/2011 | Naitou et al. |
| 2011/0059130 | A1 | 3/2011 | Yusibov |

(Continued)

FOREIGN PATENT DOCUMENTS

| | | | |
|---|---|---|---|
| EP | 1504037 | | 12/2009 |
| WO | WO 03/094849 | A2 | 11/2003 |

(Continued)

OTHER PUBLICATIONS

Ruiss et al. "A Virus-Like Particle-Based Epstein-Barr Virus Vaccine", J. Virol. 2011; 85(24): 13105-13113.*

(Continued)

*Primary Examiner* — Stacy B Chen

(74) *Attorney, Agent, or Firm* — Sheridan Ross P.C.

(57) ABSTRACT

Vaccines are provided that elicit neutralizing antibodies to Epstein-Barr virus (EBV). Some vaccines comprise nanoparticles that display envelope proteins from EBV on their surface. The nanoparticles comprise fusion proteins comprising a monomeric subunit of a self-assembly protein, such as ferritin, joined to at least a portion of an EBV envelope protein. The fusion proteins self-assemble to form the envelope protein-displaying nanoparticles. Such vaccines can be used to vaccinate an individual against infection by different types of Epstein-Barr viruses as well as Epstein-Barr viruses that are antigenically divergent from the virus from which the EBV envelope protein was obtained. Also provided are fusion proteins and nucleic acid molecules encoding such proteins.

9 Claims, 25 Drawing Sheets

Specification includes a Sequence Listing.

(56) References Cited

U.S. PATENT DOCUMENTS

2011/0177122 A1 7/2011 Nabel et al.
2011/0212128 A1 9/2011 Galarza et al.

FOREIGN PATENT DOCUMENTS

WO WO 2009/109428 9/2009
WO WO 2010/036948 4/2010
WO WO 2010/117786 10/2010
WO WO 2011/035422 3/2011
WO WO 2011/044152 4/2011
WO WO 2012/162428 11/2012
WO WO 2013/044203 A2 * 3/2013
WO WO 2015/054639 4/2015
WO WO 2016/021209 2/2016

OTHER PUBLICATIONS

Lee et al. "Viruses and Virus-Like Protein Assemblies—Chemically Programmable Nanoscale Building Blocks", Nano Res. 2009; 2: 349-364.*

Greenstone et al. "Chimeric papillomavirus virus-like particles elicit antitumor immunity against the E7 oncoprotein in an HPV16 tumor model", Proc. Natl. Acad. Sci. USA, 1998; 95: 1800-1805.*

Gowans et al. (US 2003/0211996 A1).*

Bernacchioni et al. "Loop Electrostatics Modulates the Intersubunit Interactions in Ferritin", ACS Chem. Biol. 2014; 9: 2517-2525.*

A3KF33, UniProtKB A3KF33_I57A5, Sep. 21, 2011 [online]. [Retrieved on Feb. 26, 2013]. Retrieved from the internet <URL: http://www.uniprot.org/uniprot/A3KF33.txt?version=36>.

Bachmann, M.F., et al., "Neutralizing antiviral B cell responses," Annu Rev Immunol, 1997, 15:235-270.

Caton, A.J., et al., "The antigenic structure of the influenza virus A/PR/8/34 hemagglutinin (H1 subtype)," Cell, 1982, 31:417-427.

Cohen et al., "Ferritin as an Endogenous MRI Reporter for Non-invasive Imaging Neoplasia of Gene Expression in C6 Glioma Tumors," Neoplasia, Feb. 2005, 7(2):109-117.

C0LT38, UniProtKB C0LT38_9INFB, Sep. 21, 2011 [online]. [Retrieved on Feb. 26, 2013]. Retrieved from the internet <URL: http://www.uniprot.org/uniprot/C0LT38.txt?version=18>.

Corti, D., et al., "Heterosubtypic neutralizing antibodies are produced by individuals immunized with a seasonal influenza vaccine," J Clin Invest, 2010, 120:1663-1673.

Corti, D., et al., "A neutralizing antibody selected from plasma cells that binds to group 1 and group 2 influenza A hemagglutinins," Science, 2011, 333:850-856.

Dintzis, H.M. et al., "Molecular determinants of immunogenicity: the immunon model of immune response," Proc Natl Acad Sci USA, 1976, 73:3671-3675.

Ekiert, D.C., et al., "A highly conserved neutralizing epitope on group 2 influenza A viruses," Science, 2011, 333:843-850.

Ekiert, D.C., et al., "Antibody recognition of a highly conserved influenza virus epitope," Science, 2009, 324:246-251.

Haynes, J.R., "Influenza virus-like particle vaccines," Expert Rev Vaccines, 2009, 8:435-445.

Kang, S.M., et al., "Influenza vaccines based on virus-like particles", Virus Research, Amsterdam, NL, vol. 143, No. 2, Aug. 1, 2009 (Aug. 1, 2009), pp. 140-146.

Kashyap, A.K., et al., "Combinatorial antibody libraries from survivors of the Turkish H5N1 avian influenza outbreak reveal virus neutralization strategies," Proc Natl Acad Sci USA, 2008, 105:5986-5991.

Kong, W.P., et al., "Protective immunity to lethal challenge of the 1918 pandemic influenza virus by vaccination," Proc Natl Acad Sci USA, 2006, 103:15987-15991.

Krause, J.C., et al., "A broadly neutralizing human monoclonal antibody that recognizes a conserved, novel epitope on the globular head of the influenza H1N1 virus hemagglutinin," J Virol, 2011, 85:10905-10908.

Lambert, L.C., et al., "Influenza vaccines for the future," N Engl J Med, 2010, 363, 2036-2044.

Lee, L.A., et al., "Adaptations of nanoscale viruses and other protein cages for medical applications", Nanomedicine: Nanotechnology, Biology and Medicine, Elsevier, NL, vol. 2, No. 3, Sep. 1, 2006 (Sep. 1, 2006), pp. 137-149.

Li, C.Q. et al., "Ferritin nanoparticle technology: A new platform for antigen presentation and vaccine development," Industrial Biotechnol 2, 143-147 (2006).

Meldrum, F.C., et al., "Magnetoferritin: in vitro synthesis of a novel magnetic protein," Science, 1992, 257:522-523.

Nabel, G.J., et al., "Induction of unnatural immunity: prospects for a broadly protective universal influenza vaccine," Nat Med, 2010, 16:1389-1391.

Okuno, Y., et al., "A common neutralizing epitope conserved between the hemagglutinins of influenza A virus H1 and H2 strains," J Virol, 1993, 67:2552-2558.

Roldao, A., et al., "Virus-like particles in vaccine development," Expert Rev Vaccines, 2010, 9:1149-1176.

Sheridan, C., "Flu vaccine makers upgrade technology—and pray for time," Nat Biotechnol, 2009, 27:489-491.

Steel et al. "Influenza Virus Vaccine Based on the Conserved Hemagglutinin Stalk Domain," MBIO, American Society for Microbiology, May 2010, vol. 1, No. 1, pp. e00018-10/1-9.

Sui, J., et al., "Structural and functional bases for broad-spectrum neutralization of avian and human influenza A viruses," Nat Struct Mol Biol, 2009, 16:265-273.

Treanor, J.J., et al., "Safety and immunogenicity of a recombinant hemagglutinin vaccine for H5 influenza in humans," Vaccine, 2001, 19:1732-1737.

Treanor, J.J., "Safety and immunogenicity of a baculovirus-expressed hemagglutinin influenza vaccine: a randomized controlled trial," JAMA,2007, 297:1577-1582.

Wang, T.T., et al., "Broadly protective monoclonal antibodies against H3 influenza viruses following sequential immunization with different hemagglutinins," PLoS Pathog, 2010, vol. 6, Issue 2, e1000796.

Wei, C.J., et al., Cross-neutralization of 1918 and 2009 influenza viruses: role of glycans in viral evolution and vaccine design. Sci Transl Med, 2010, 2, 24ra21.

Wei, C.J., et al., "Induction of broadly neutralizing H1N1 influenza antibodies by vaccination," Science, 2010, 329:1060-1064.

Wei, C.J., et al., "Comparative efficacy of neutralizing antibodies elicited by recombinant hemagglutinin proteins from avian H5N1 influenza virus," J Virol, 2008, 82:6200-6208.

Whittle, J.R., et al., "Broadly neutralizing human antibody that recognizes the receptor-binding pocket of influenza virus hemagglutinin," Proc Natl Acad Sci USA, 2011, 108:14216-14221.

WHO Reference on Animal Influenza Diagnosis and Surveillance, 2002, Department of Communicable Disease Surveillance and Response, World Health Organization).

Wu, C.Y., et al., "Mammalian expression of virus-like particles for advanced mimicry of authentic influenza virus," PLoS One 5, 2010, e9784.

Xiong, A.S., et al., "PCR-based accurate synthesis of long DNA sequences," Nat Protoc, 2006, 1(2):791-797.

Yamashita, I., et al., "Ferritin in the field of nanodevices," Biochim Biophys Acta, 2010, 1800:846-857.

Yang, Z.Y., et al., "Immunization by avian H5 influenza hemagglutinin mutants with altered receptor binding specificity," Sciencel, 2007, 317:825-828).

Yassine et al. "Hemagglutinin-stem nanoparticles generate heterosubypic influenza protection." Nature Medicine, Sep. 2015, vol. 21, No. 9, pp. 1065-1070.

Zhang, Y., et al., "Self-Assembly in the Ferritin Nano-Cage Protein Super Family," Int. J. Mol. Sci., 2011, 12:5406-5421.

Kossovsky N et al: "Nanocrystalline Epstein-Barr virus decoys.", Journal of Applied Biomaterials: An Official Journal of the Society for Biomaterials, vol. 2, No. 4, Jan. 1991 (Jan. 1991), pp. 251-259.

Kanekiyo Masuru et al: "Self-assembling influenza nanoparticle vaccines elicit broadly neutralizing H1N1 antibodies", Nature (London), vol. 499, No. 7456, Jul. 4, 2013 (Jul. 4, 2013).

(56) References Cited

OTHER PUBLICATIONS

H. Vallhov et al: "Exosomes Containing Glycoprotein 350 Released by EBV-Transformed B Cells Selectively Target B Cells through CD21 and Block EBV Infection in Vitro", The Journal of Immunology, vol. 186, No. 1, Jan. 1, 2011, pp. 73-82.
Pulford D et al: "Expression of the Epstein-Barr Virus Envelope Fusion Glycoprotein GP85 Gene by a Recombinant Baculovirus", Journal of General Virology, vol. 75, No. 11, Nov. 1, 1994 (Nov. 1, 1994), pp. 3241-3248.
International Search Report and Written Opinion prepared by the European Patent Office dated Feb. 5, 2015, for International Application No. PCT/US2014/060142.
GenBank Accession No. 3EGM_A submitted Sep. 11, 2008, 2 pages.
GenBank Accession No. AAP34324, submitted May 1, 2003, 2 pages.
Harrison "The Structure and Function of Ferritin," Biochemical Education, 1986, vol. 14, No. 4, pp. 154-162.
He et al. "Presenting native-like trimeric HIV-1 antigens with self-assembling nanoparticles," Nature Communications, Jun. 2016, vol. 7, 12041, 15 pages.
Kanekiyo et al. "Rational Design of an Epstein-Barr Virus Vaccine Targeting the Receptor-Binding Site," Cell, Aug. 2015, vol. 162, No. 5, pp. 1090-1100.
Lopez-Sagaseta et al. "Self-assembling protein nanoparticles in the design of vaccines," Computational and Structural Biotechnology Journal, 2016, vol. 14, pp. 58-68.
Zhang et al. "Universal Influenza Vaccines, a Dream to Be Realized Soon," Viruses, 2014, vol. 6, pp. 1974-1991.
Official Action for European Patent Application No. 14799574.0, dated Nov. 13, 2017 4 pages.
English Translation of Official Action for China Patent Application No. 201480066333.2, dated Sep. 17, 2018 15 pages.
English Translation of Official Action for China Patent Application No. 201480066333.2, dated Mar. 20, 2019 5 pages.
Official Action for European Patent Application No. 14799574.0, dated Nov. 21, 2018 5 pages.

* cited by examiner

- gH-ferritin + gL = gH/gL-nanoparticle
- gH-ferritin + gL + gp42 = gH/gL/gp42-nanoparticle
- gH + gL + encapsulin gp42 = gH/gL/gp42 nanoparticle

SEQUENCE LISTING

```
<160> NUMBER OF SEQ ID NOS: 146

<210> SEQ ID NO 1
<211> LENGTH: 504
<212> TYPE: DNA
<213> ORGANISM: Helicobacter pylori

<400> SEQUENCE: 1

atgttatcaa aagacatcat taagttgcta aacgaacaag tgaataagga aatgaactct      60

tccaacttgt atatgagcat gagttcatgg tgctataccc atagcttaga tggcgcgggg     120

cttttcttgt ttgaccatgc ggctgaagaa tacgagcatg ctaaaaagct tattatcttc     180

ttgaatgaaa acaatgtgcc tgtgcaattg accagcatca gcgcgcctga gcataagttt     240

gaaggtttga ctcaaatttt ccaaaaagcc tatgaacatg agcaacacat cagcgagtct     300

attaacaata tcgtagatca cgccataaaa agcaaagatc atgcgacttt caatttcttg     360

caatggtatg tggctgaaca gcatgaagaa gaagtgcttt tcaaggatat tttggataaa     420

attgagttga ttggtaatga aaaccatggc ttgtatttag ccgatcagta tgtcaaaggg     480

atcgctaaaa gcaggaaatc ttaa                                            504


<210> SEQ ID NO 2
<211> LENGTH: 167
<212> TYPE: PRT
<213> ORGANISM: Helicobacter pylori

<400> SEQUENCE: 2

Met Leu Ser Lys Asp Ile Ile Lys Leu Leu Asn Glu Gln Val Asn Lys
1               5                   10                  15

Glu Met Asn Ser Ser Asn Leu Tyr Met Ser Met Ser Ser Trp Cys Tyr
            20                  25                  30

Thr His Ser Leu Asp Gly Ala Gly Leu Phe Leu Phe Asp His Ala Ala
        35                  40                  45

Glu Glu Tyr Glu His Ala Lys Lys Leu Ile Ile Phe Leu Asn Glu Asn
    50                  55                  60

Asn Val Pro Val Gln Leu Thr Ser Ile Ser Ala Pro Glu His Lys Phe
65                  70                  75                  80

Glu Gly Leu Thr Gln Ile Phe Gln Lys Ala Tyr Glu His Glu Gln His
                85                  90                  95

Ile Ser Glu Ser Ile Asn Asn Ile Val Asp His Ala Ile Lys Ser Lys
            100                 105                 110

Asp His Ala Thr Phe Asn Phe Leu Gln Trp Tyr Val Ala Glu Gln His
        115                 120                 125

Glu Glu Glu Val Leu Phe Lys Asp Ile Leu Asp Lys Val Glu Leu Ile
    130                 135                 140

Gly Asn Glu Asn His Gly Leu Tyr Leu Ala Asp Gln Tyr Val Lys Gly
145                 150                 155                 160
```

Ile Ala Lys Ser Arg Lys Ser
165

<210> SEQ ID NO 3
<211> LENGTH: 504
<212> TYPE: DNA
<213> ORGANISM: Helicobacter pylori

<400> SEQUENCE: 3
ttaagatttc ctgcttttag cgatcccttt gacatactga tcggctaaat acaagccatg 60
gttttcatta ccaatcaact caattttatc caaaatatcc ttgaaaagca cttcttcttc 120
atgctgttca gccacatacc attgcaagaa attgaaagtc gcatgatctt tgctttttat 180
ggcgtgatct acgatattgt taatagactc gctgatgtgt tgctcatgtt cataggcttt 240
ttggaaaatt tgagtcaaac cttcaaactt atgctcaggc gcgctgatgc tggtcaattg 300
cacaggcaca ttgttttcat tcaagaagat aataagcttt ttagcatgct cgtattcttc 360
agccgcatgg tcaaacaaga aaagccccgc gccatctaag ctatgggtat agcaccatga 420
actcatgctc atatacaagt tggaagagtt catttcctta ttcacttgtt cgtttagcaa 480
cttaatgatg tcttttgata acat 504

<210> SEQ ID NO 4

<400> SEQUENCE: 4

000

<210> SEQ ID NO 5
<211> LENGTH: 165
<212> TYPE: PRT
<213> ORGANISM: Escherichia coli

<400> SEQUENCE: 5

Met Leu Lys Pro Glu Met Ile Glu Lys Leu Asn Glu Gln Met Asn Leu
1 5 10 15

Glu Leu Tyr Ser Ser Leu Leu Tyr Gln Gln Met Ser Ala Trp Cys Ser
20 25 30

Tyr His Thr Phe Glu Gly Ala Ala Ala Phe Leu Arg Arg His Ala Gln
35 40 45

Glu Glu Met Thr His Met Gln Arg Leu Phe Asp Tyr Leu Thr Asp Thr
50 55 60

Gly Asn Leu Pro Arg Ile Asn Thr Val Glu Ser Pro Phe Ala Glu Tyr
65 70 75 80

Ser Ser Leu Asp Glu Leu Phe Gln Glu Thr Tyr Lys His Glu Gln Leu
85 90 95

Ile Thr Gln Lys Ile Asn Glu Leu Ala His Ala Ala Met Thr Asn Gln
100 105 110

Asp Tyr Pro Thr Phe Asn Phe Leu Gln Trp Tyr Val Ser Glu Gln His
115 120 125

Glu Glu Glu Lys Leu Phe Lys Ser Ile Ile Asp Lys Leu Ser Leu Ala
130 135 140

Gly Lys Ser Gly Glu Gly Leu Tyr Phe Ile Asp Lys Glu Leu Ser Thr
145 150 155 160

Leu Asp Ala Gln Asn
165

<210> SEQ ID NO 6

<400> SEQUENCE: 6

000

<210> SEQ ID NO 7

<400> SEQUENCE: 7

000

<210> SEQ ID NO 8
<211> LENGTH: 173
<212> TYPE: PRT
<213> ORGANISM: Rana catesbeiana

<400> SEQUENCE: 8

Met Glu Ser Gln Val Arg Gln Asn Phe His Gln Asp Cys Glu Ala Gly
1 5 10 15

Leu Asn Arg Thr Val Asn Leu Lys Phe His Ser Ser Tyr Val Tyr Leu
20 25 30

Ser Met Ala Ser Tyr Phe Asn Arg Asp Asp Val Ala Leu Ser Asn Phe
35 40 45

Ala Lys Phe Phe Arg Glu Arg Ser Glu Glu Glu Lys Glu His Ala Glu
50 55 60

Lys Leu Ile Glu Tyr Gln Asn Gln Arg Gly Gly Arg Val Phe Leu Gln
65 70 75 80

Ser Val Glu Lys Pro Glu Arg Asp Asp Trp Ala Asn Gly Leu Glu Ala
85 90 95

Leu Gln Thr Ala Leu Lys Leu Gln Lys Ser Val Asn Gln Ala Leu Leu
100 105 110

Asp Leu His Ala Val Ala Ala Asp Lys Ser Asp Pro His Met Thr Asp
115 120 125

Phe Leu Glu Ser Pro Tyr Leu Ser Glu Ser Val Glu Thr Ile Lys Lys
130 135 140

Leu Gly Asp His Ile Thr Ser Leu Lys Lys Leu Trp Ser Ser His Pro
145 150 155 160

Gly Met Ala Glu Tyr Leu Phe Asn Lys His Thr Leu Gly
165 170

<210> SEQ ID NO 9

<400> SEQUENCE: 9

000

<210> SEQ ID NO 10
<211> LENGTH: 531
<212> TYPE: DNA
<213> ORGANISM: Artificial Sequence
<220> FEATURE:
<223> OTHER INFORMATION: Synthetic

<400> SEQUENCE: 10
tccggagaga gccaggtgag gcagcagttc agcaaggaca tcgagaagct gctgaacgag 60
caggtgaaca aggagatgca gagcagcaac ctgtacatga gcatgagcag ctggtgctac 120
acccacagcc tggacggcgc cggcctgttc ctgttcgacc acgccgccga ggagtacgag 180
cacgccaaga agctgatcat cttcctgaac gagaacaacg tgcccgtgca gctgaccagc 240
atcagcgccc ccgagcacaa gttcgagggc ctgacccaga tcttccagaa ggcctacgag 300
cacgagcagc acatcagcga gagcatcaac aacatcgtgg accacgccat caagagcaag 360
gaccacgcca ccttcaactt cctgcagtgg tacgtggccg agcagcacga ggaggaggtg 420
ctgttcaagg acatcctgga caagatcgag ctgatcggca acgagaacca cggcctgtac 480
ctggccgacc agtacgtgaa gggcatcgcc aagagcagga agagcggatc c 531

<210> SEQ ID NO 11
<211> LENGTH: 177
<212> TYPE: PRT
<213> ORGANISM: Artificial Sequence
<220> FEATURE:
<223> OTHER INFORMATION: Synthetic

<400> SEQUENCE: 11

Ser Gly Glu Ser Gln Val Arg Gln Gln Phe Ser Lys Asp Ile Glu Lys
1 5 10 15

Leu Leu Asn Glu Gln Val Asn Lys Glu Met Gln Ser Ser Asn Leu Tyr
20 25 30

Met Ser Met Ser Ser Trp Cys Tyr Thr His Ser Leu Asp Gly Ala Gly
35 40 45

Leu Phe Leu Phe Asp His Ala Ala Glu Glu Tyr Glu His Ala Lys Lys
50 55 60

Leu Ile Ile Phe Leu Asn Glu Asn Asn Val Pro Val Gln Leu Thr Ser
65 70 75 80

Ile Ser Ala Pro Glu His Lys Phe Glu Gly Leu Thr Gln Ile Phe Gln
85 90 95

Lys Ala Tyr Glu His Glu Gln His Ile Ser Glu Ser Ile Asn Asn Ile
100 105 110

Val Asp His Ala Ile Lys Ser Lys Asp His Ala Thr Phe Asn Phe Leu
115 120 125

Gln Trp Tyr Val Ala Glu Gln His Glu Glu Glu Val Leu Phe Lys Asp
130 135 140

Ile Leu Asp Lys Ile Glu Leu Ile Gly Asn Glu Asn His Gly Leu Tyr
145 150 155 160

Leu Ala Asp Gln Tyr Val Lys Gly Ile Ala Lys Ser Arg Lys Ser Gly
165 170 175

Ser

<210> SEQ ID NO 12
<211> LENGTH: 531
<212> TYPE: DNA
<213> ORGANISM: Artificial Sequence
<220> FEATURE:
<223> OTHER INFORMATION: Synthetic

<400> SEQUENCE: 12
ggatccgctc ttcctgctct tggcgatgcc cttcacgtac tggtcggcca ggtacaggcc 60
gtggttctcg ttgccgatca gctcgatctt gtccaggatg tccttgaaca gcacctcctc 120
ctcgtgctgc tcggccacgt accactgcag gaagttgaag gtggcgtggt ccttgctctt 180
gatggcgtgg tccacgatgt tgttgatgct ctcgctgatg tgctgctcgt gctcgtaggc 240
cttctggaag atctgggtca ggccctcgaa cttgtgctcg ggggcgctga tgctggtcag 300
ctgcacgggc acgttgttct cgttcaggaa gatgatcagc ttcttggcgt gctcgtactc 360
ctcggcggcg tggtcgaaca ggaacaggcc ggcgccgtcc aggctgtggg tgtagcacca 420
gctgctcatg ctcatgtaca ggttgctgct ctgcatctcc ttgttcacct gctcgttcag 480

```
cagcttctcg atgtccttgc tgaactgctg cctcacctgg ctctctccgg a            531


<210> SEQ ID NO 13
<211> LENGTH: 516
<212> TYPE: DNA
<213> ORGANISM: Artificial Sequence
<220> FEATURE:
<223> OTHER INFORMATION: Synthetic

<400> SEQUENCE: 13

tccggagaga gccaggtgag gcagaacttc aagcccgaga tggaggagaa gctgaacgag     60

cagatgaacc tggagctgta cagcagcctg ctgtaccagc agatgagcgc ctggtgcagc    120

taccacacct tcgagggcgc cgccgccttc ctgaggaggc acgcccagga ggagatgacc    180

cacatgcaga ggctgttcga ctacctgacc gacaccggca acctgcccag gatcaacacc    240

gtggagagcc ccttcgccga gtacagcagc ctggacgagc tgttccagga gacctacaag    300

cacgagcagc tgatcaccca gaagatcaac gagctggccc acgccgccat gaccaaccag    360

gactacccca ccttcaactt cctgcagtgg tacgtgagcg agcagcacga ggaggagaag    420

ctgttcaaga gcatcatcga caagctgagc ctggccggca agagcggcga gggcctgtac    480

ttcatcgaca aggagctgag caccctggac ggatcc                              516


<210> SEQ ID NO 14
<211> LENGTH: 172
<212> TYPE: PRT
<213> ORGANISM: Artificial Sequence
<220> FEATURE:
<223> OTHER INFORMATION: Synthetic

<400> SEQUENCE: 14

Ser Gly Glu Ser Gln Val Arg Gln Asn Phe Lys Pro Glu Met Glu Glu
1               5                   10                  15

Lys Leu Asn Glu Gln Met Asn Leu Glu Leu Tyr Ser Ser Leu Leu Tyr
            20                  25                  30

Gln Gln Met Ser Ala Trp Cys Ser Tyr His Thr Phe Glu Gly Ala Ala
        35                  40                  45

Ala Phe Leu Arg Arg His Ala Gln Glu Glu Met Thr His Met Gln Arg
    50                  55                  60

Leu Phe Asp Tyr Leu Thr Asp Thr Gly Asn Leu Pro Arg Ile Asn Thr
65                  70                  75                  80

Val Glu Ser Pro Phe Ala Glu Tyr Ser Ser Leu Asp Glu Leu Phe Gln
                85                  90                  95

Glu Thr Tyr Lys His Glu Gln Leu Ile Thr Gln Lys Ile Asn Glu Leu
            100                 105                 110

Ala His Ala Ala Met Thr Asn Gln Asp Tyr Pro Thr Phe Asn Phe Leu
        115                 120                 125

Gln Trp Tyr Val Ser Glu Gln His Glu Glu Glu Lys Leu Phe Lys Ser
    130                 135                 140

Ile Ile Asp Lys Leu Ser Leu Ala Gly Lys Ser Gly Glu Gly Leu Tyr
145                 150                 155                 160

Phe Ile Asp Lys Glu Leu Ser Thr Leu Asp Gly Ser
                165                 170


<210> SEQ ID NO 15
<211> LENGTH: 516
<212> TYPE: DNA
<213> ORGANISM: Artificial Sequence
```

<220> FEATURE:
<223> OTHER INFORMATION: Synthetic

<400> SEQUENCE: 15
ggatccgtcc agggtgctca gctccttgtc gatgaagtac aggccctcgc cgctcttgcc 60
ggccaggctc agcttgtcga tgatgctctt gaacagcttc tcctcctcgt gctgctcgct 120
cacgtaccac tgcaggaagt tgaaggtggg gtagtcctgg ttggtcatgg cggcgtgggc 180
cagctcgttg atcttctggg tgatcagctg ctcgtgcttg taggtctcct ggaacagctc 240
gtccaggctg ctgtactcgg cgaaggggct ctccacggtg ttgatcctgg gcaggttgcc 300
ggtgtcggtc aggtagtcga acagcctctg catgtgggtc atctcctcct gggcgtgcct 360
cctcaggaag gcggcggcgc cctcgaaggt gtggtagctg caccaggcgc tcatctgctg 420
gtacagcagg ctgctgtaca gctccaggtt catctgctcg ttcagcttct cctccatctc 480
gggcttgaag ttctgcctca cctggctctc tccgga 516

<210> SEQ ID NO 16
<211> LENGTH: 792
<212> TYPE: DNA
<213> ORGANISM: Thermotoga maritima

<400> SEQUENCE: 16
atggagttcc tgaagaggag cttcgcccct ctgaccgaga agcagtggca ggagatcgac 60
aacagggcca gggagatctt caagacccag ctgtacggca ggaagttcgt ggacgtggag 120
ggcccctacg gctgggagta cgccgcccac cccctgggcg aggtggaggt gctgagcgac 180
gagaacgagg tggtgaagtg gggcctgagg aagagcctgc ccctgatcga gctgagggcc 240
accttcaccc tggacctgtg ggagctggac aacctggaga ggggcaagcc caacgtggac 300
ctgagcagcc tggaggagac cgtgaggaag gtggccgagt tcgaggacga ggtgatcttc 360
aggggctgcg agaagagcgg cgtgaagggc ctgctgagct tcgaggagag gaagatcgag 420
tgcggcagca cccccaagga cctgctggag gccatcgtga gggccctgag catcttcagc 480
aaggacggca tcgagggccc ctacaccctg gtgatcaaca ccgacaggtg gatcaacttc 540
ctgaaggagg aggccggcca ctacccccctg gagaagaggg tggaggagtg cctgaggggc 600
ggcaagatca tcaccacccc caggatcgag gacgccctgg tggtgagcga gaggggcggc 660
gacttcaagc tgatcctggg ccaggacctg agcatcggct acgaggacag ggagaaggac 720
gccgtgaggc tgttcatcac cgagaccttc accttccagg tggtgaaccc cgaggccctg 780
atcctgctga ag 792

<210> SEQ ID NO 17
<211> LENGTH: 264
<212> TYPE: PRT
<213> ORGANISM: Thermotoga maritima

<400> SEQUENCE: 17

Met Glu Phe Leu Lys Arg Ser Phe Ala Pro Leu Thr Glu Lys Gln Trp
1 5 10 15

Gln Glu Ile Asp Asn Arg Ala Arg Glu Ile Phe Lys Thr Gln Leu Tyr
20 25 30

Gly Arg Lys Phe Val Asp Val Glu Gly Pro Tyr Gly Trp Glu Tyr Ala
35 40 45

Ala His Pro Leu Gly Glu Val Glu Val Leu Ser Asp Glu Asn Glu Val
50 55 60

-continued

```
Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
        195                 200                 205

Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys
            260
```

<210> SEQ ID NO 18
<211> LENGTH: 792
<212> TYPE: DNA
<213> ORGANISM: Thermotoga maritima

<400> SEQUENCE: 18

```
cttcagcagg atcagggcct cggggttcac cacctggaag gtgaaggtct cggtgatgaa      60

cagcctcacg gcgtccttct ccctgtcctc gtagccgatg ctcaggtcct ggcccaggat     120

cagcttgaag tcgccgcccc tctcgctcac caccagggcg tcctcgatcc tgggggtggt     180

gatgatcttg ccgcccctca ggcactcctc caccctcttc tccagggggt agtggccggc     240

ctcctccttc aggaagttga tccacctgtc ggtgttgatc accagggtgt aggggccctc     300

gatgccgtcc ttgctgaaga tgctcagggc cctcacgatg gcctccagca ggtccttggg     360

ggtgctgccg cactcgatct tcctctcctc gaagctcagc aggcccttca cgccgctctt     420

ctcgcagccc ctgaagatca cctcgtcctc gaactcggcc accttcctca cggtctcctc     480

caggctgctc aggtccacgt tgggcttgcc cctctccagg ttgtccagct cccacaggtc     540

cagggtgaag gtggccctca gctcgatcag gggcaggctc ttcctcaggc cccacttcac     600

cacctcgttc tcgtcgctca gcacctccac ctcgcccagg gggtgggcgg cgtactccca     660

gccgtagggg ccctccacgt ccacgaactt cctgccgtac agctgggtct tgaagatctc     720

cctggccctg ttgtcgatct cctgccactg cttctcggtc agaggggcga agctcctctt     780

caggaactcc at                                                         792
```

<210> SEQ ID NO 19

<400> SEQUENCE: 19

000

<210> SEQ ID NO 20
<211> LENGTH: 192
<212> TYPE: PRT
<213> ORGANISM: Artificial Sequence
<220> FEATURE:
<223> OTHER INFORMATION: Synthetic

<400> SEQUENCE: 20

```
Met Ser Gln Ala Ile Gly Ile Leu Glu Leu Thr Ser Ile Ala Ala Gly
1               5                   10                  15

Met Glu Leu Gly Asp Ala Met Leu Lys Ser Ala Asn Val Asp Leu Leu
            20                  25                  30

Val Ser Lys Thr Ile Ser Pro Gly Lys Phe Leu Leu Met Leu Gly Gly
        35                  40                  45

Asp Ile Gly Ala Ile Gln Gln Ala Ile Glu Thr Gly Thr Ser Gln Ala
    50                  55                  60

Gly Glu Leu Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Trp Ser Val Ala Ala Cys Ile Ser Ala Ala
            100                 105                 110

Asp Arg Ala Val Lys Gly Ser Asn Val Thr Leu Val Arg Val His Met
        115                 120                 125

Ala Phe Gly Ile Gly Gly Lys Cys Tyr Met Val Val Ala Gly Asp Val
    130                 135                 140

Ser Asp Val Ala Leu Ala Val Thr Val Ala Ser Ser Ser Ala Gly Ala
145                 150                 155                 160

Tyr Gly Leu Leu Val Tyr Ala Ser Leu Ile Pro Arg Pro His Glu Ala
                165                 170                 175

Met Trp Arg Gln Met Val Glu Gly Leu Glu His His His His His His
            180                 185                 190
```

<210> SEQ ID NO 21

<400> SEQUENCE: 21

000

<210> SEQ ID NO 22

<400> SEQUENCE: 22

000

<210> SEQ ID NO 23
<211> LENGTH: 318
<212> TYPE: PRT
<213> ORGANISM: Acidianus ambivalens
<220> FEATURE:
<221> NAME/KEY: misc_feature
<222> LOCATION: (31)..(31)
<223> OTHER INFORMATION: Xaa can be any naturally occurring amino acid

<400> SEQUENCE: 23

```
Met Pro Lys Pro Tyr Val Ala Ile Asn Met Ala Glu Leu Lys Asn Glu
1               5                   10                  15

Pro Lys Thr Phe Glu Met Phe Ala Ser Val Gly Pro Lys Val Xaa Met
```

-continued

```
            20                  25                  30

Val Thr Ala Arg His Pro Gly Phe Val Gly Phe Gln Asn His Ile Gln
        35                  40                  45

Ile Gly Ile Leu Pro Phe Gly Asn Arg Tyr Gly Gly Ala Lys Met Asp
    50                  55                  60

Met Thr Lys Glu Ser Ser Thr Val Arg Val Leu Gln Tyr Thr Phe Trp
65                  70                  75                  80

Lys Asp Trp Lys Asp His Glu Glu Met His Arg Gln Asn Trp Ser Tyr
                85                  90                  95

Leu Phe Arg Leu Cys Tyr Ser Cys Ala Ser Gln Met Ile Trp Gly Pro
            100                 105                 110

Trp Glu Pro Ile Tyr Glu Ile Ile Tyr Ala Asn Met Pro Ile Asn Thr
        115                 120                 125

Glu Met Thr Asp Phe Thr Ala Val Val Gly Lys Lys Phe Ala Glu Gly
    130                 135                 140

Lys Pro Leu Asp Ile Pro Val Ile Ser Gln Pro Tyr Gly Lys Arg Val
145                 150                 155                 160

Val Ala Phe Ala Glu His Ser Val Ile Pro Gly Lys Glu Lys Gln Phe
                165                 170                 175

Glu Asp Ala Ile Val Arg Thr Leu Glu Met Leu Lys Lys Ala Pro Gly
            180                 185                 190

Phe Leu Gly Ala Met Val Leu Lys Glu Ile Gly Val Ser Gly Ile Gly
        195                 200                 205

Ser Met Gln Phe Gly Ala Lys Gly Phe His Gln Val Leu Glu Asn Pro
    210                 215                 220

Gly Ser Leu Glu Pro Asp Pro Asn Asn Val Met Tyr Ser Val Pro Glu
225                 230                 235                 240

Ala Lys Asn Thr Pro Gln Gln Tyr Ile Val His Val Glu Trp Ala Asn
                245                 250                 255

Thr Asp Ala Leu Met Phe Gly Met Gly Arg Val Leu Leu Tyr Pro Glu
            260                 265                 270

Leu Arg Gln Val His Asp Glu Val Leu Asp Thr Leu Val Tyr Gly Pro
        275                 280                 285

Tyr Ile Arg Ile Leu Asn Pro Met Met Glu Gly Thr Phe Trp Arg Glu
    290                 295                 300

Tyr Leu Asn Glu Gln Ala Trp Arg His Pro Gln Phe Gly Gly
305                 310                 315
```

<210> SEQ ID NO 24

<400> SEQUENCE: 24

000

<210> SEQ ID NO 25

<400> SEQUENCE: 25

000

<210> SEQ ID NO 26
<211> LENGTH: 154
<212> TYPE: PRT
<213> ORGANISM: Aquifex pyrophilus

<400> SEQUENCE: 26

```
Met Gln Ile Tyr Glu Gly Lys Leu Thr Ala Glu Gly Leu Arg Phe Gly
```

```
1               5                   10                  15

Ile Val Ala Ser Arg Phe Asn His Ala Leu Val Asp Arg Leu Val Glu
            20                  25                  30

Gly Ala Ile Asp Cys Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asn Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg
145                 150


<210> SEQ ID NO 27

<400> SEQUENCE: 27

000


<210> SEQ ID NO 28

<400> SEQUENCE: 28

000


<210> SEQ ID NO 29
<211> LENGTH: 242
<212> TYPE: PRT
<213> ORGANISM: Bacillus stearothermophilus

<400> SEQUENCE: 29

Ala Ala Ala Lys Pro Ala Thr Thr Glu Gly Glu Phe Pro Glu Thr Arg
1               5                   10                  15

Glu Lys Met Ser Gly Ile Arg Arg Ala Ile Ala Lys Ala Met Val His
            20                  25                  30

Ser Lys His Thr Ala Pro His Val Thr Leu Met Asp Glu Ala Asp Val
        35                  40                  45

Thr Lys Leu Val Ala His Arg Lys Lys Phe Lys Ala Ile Ala Ala Glu
    50                  55                  60

Lys Gly Ile Lys Leu Thr Phe Leu Pro Tyr Val Val Lys Ala Leu Val
65                  70                  75                  80

Ser Ala Leu Arg Glu Tyr Pro Val Leu Asn Thr Ser Ile Asp Asp Glu
                85                  90                  95

Thr Glu Glu Ile Ile Gln Lys His Tyr Tyr Asn Ile Gly Ile Ala Ala
            100                 105                 110

Asp Thr Asp Arg Gly Leu Leu Val Pro Val Ile Lys His Ala Asp Arg
        115                 120                 125

Lys Pro Ile Phe Ala Leu Ala Gln Glu Ile Asn Glu Leu Ala Glu Lys
    130                 135                 140

Ala Arg Asp Gly Lys Leu Thr Pro Gly Glu Met Lys Gly Ala Ser Cys
```

-continued

```
145                 150                 155                 160

Thr Ile Thr Asn Ile Gly Ser Ala Gly Gly Gln Trp Phe Thr Pro Val
                165                 170                 175

Ile Asn His Pro Glu Val Ala Ile Leu Gly Ile Gly Arg Ile Ala Glu
            180                 185                 190

Lys Pro Ile Val Arg Asp Gly Glu Ile Val Ala Ala Pro Met Leu Ala
        195                 200                 205

Leu Ser Leu Ser Phe Asp His Arg Met Ile Asp Gly Ala Thr Ala Gln
    210                 215                 220

Lys Ala Leu Asn His Ile Lys Arg Leu Leu Ser Asp Pro Glu Leu Leu
225                 230                 235                 240

Leu Met


<210> SEQ ID NO 30

<400> SEQUENCE: 30

000


<210> SEQ ID NO 31
<211> LENGTH: 2721
<212> TYPE: DNA
<213> ORGANISM: Epstein Barr Virus

<400> SEQUENCE: 31

atggaagccg ccctgctggt gtgccagtac actattcaga gcctgattca tctgaccggg     60

gaggaccctg gatttttcaa tgtggaaatc cctgagttcc cattttaccc cacctgcaac    120

gtctgtacag ccgacgtgaa cgtcaccatt aatttcgatg tgggcgggaa gaaacaccag    180

ctggacctgg attttggcca gctgacccca catacaaaag ccgtgtatca gcccagaggg    240

gctttcggag gcagcgagaa cgcaacaaat ctgtttctgc tggagctgct gggagcagga    300

gaactggctc tgaccatgag gtccaagaaa ctgcccatca atgtgaccac aggagaggaa    360

cagcaggtca gtctggaatc agtggacgtc tacttccagg atgtgtttgg caccatgtgg    420

tgccaccatg ccgagatgca gaatcctgtg tacctgatcc ccgaaaccgt cccttatatt    480

aagtgggaca actgtaatag cactaacatt accgcagtgg tccgggcaca ggggctggac    540

gtgaccctgc cactgtcact gcccacaagc gcccaggata gcaacttctc cgtgaaaacc    600

gagatgctgg gaaatgagat cgacattgaa tgcatcatgg aggatggaga aattagccag    660

gtgctgcctg gcgataacaa gtttaatatc acctgttccg gctacgaatc tcacgtccca    720

agtgggggaa tcctgacatc tactagtccc gtggccactc caattcccgg aaccggctac    780

gcttatagcc tgagactgac ccctaggcca gtctcacgct tcctgggcaa caatagcatt    840

ctgtacgtgt tttattccgg aaacggacca aaggcttctg gaggggacta ttgcatccag    900

agtaatattg tgttctcaga cgagatccca gccagccagg atatgcccac taacactacc    960

gacattacct acgtgggcga taatgccact tattccgtgc ctatggtcac aagcgaagac   1020

gctaactccc caaatgtgac cgtcacagca ttctgggcct ggcccaacaa tactgagacc   1080

gattttaagt gcaaatggac actgacttca ggcaccccta gcgggtgtga aaacatctct   1140

ggcgccttcg ctagtaatcg aacctttgat attacagtgt ccggcctggg gactgcccca   1200

aaaaccctga tcattacccg gacagctact aacgcaacaa ctaccacaca caaagtgatc   1260

ttcagcaaag ctcccgagtc cactaccaca tctcctaccc tgaacactac cgggtttgcc   1320

gaccccaata caactaccgg actgcctagc tccacccatg tgccaacaaa cctgactgca   1380
```

```
ccagcatcca ccggacctac agtgtctact gccgatgtca ccagtcccac acctgccgga   1440

acaacttctg gcgctagtcc cgtgacccca tcacccagcc cttgggacaa tgggacagag   1500

agtaaggccc ctgatatgac ttctagtacc tcaccagtca ccacaccaac ccccaacgca   1560

acaagcccta ctccagccgt gactaccccc acacctaatg ctaccagccc aacacccgca   1620

gtgacaactc ctaccccaaa cgccacttcc ccaaccctgg ggaagacatc acccactagc   1680

gccgtgacca cacccacccc taatgctacc tctcctacac tgggaaaaac ttccccaacc   1740

tctgcagtga ctaccccaac ccccaacgcc acaagcccca ctctgggcaa gaccagtcct   1800

acatcagctg tcacaactcc taccccaaat gcaactgggc caaccgtggg agagacatcc   1860

ccccaggcta acgcaacaaa tcacactctg ggaggcacca gtcccacacc tgtggtcacc   1920

tcacagccca agaacgccac aagcgctgtg accacaggcc agcataatat cacatcaagc   1980

tccacttcta gtatgagcct gcgcccttca agcaacccag agacactgtc ccatctact    2040

agtgacaatt caaccagcca catgcctctg ctgacatctg cacatccaac tgggggagaa   2100

aacatcactc aggtcacccc cgcctccatt tctacccacc atgtgtccac atcctctcca   2160

gcaccccgac ctggaactac cagccaggca tccggaccag gaaatagttc aaccagcaca   2220

aagcctggcg aggtgaacgt cacaaaaggg actccccctc agaatgctac ctcacctcag   2280

gcaccaagcg gccagaaaac agctgtgcct actgtcacct ccacaggcgg gaaggcaaac   2340

tctacaactg gaggcaaaca caccacaggg catggagctc gcactagcac cgaaccaact   2400

accgactacg gggagattc cacaactcca aggcccagat acaatgccac cacatatctg    2460

ccaccctcta ccagctccaa gctgcgaccc agatggacat tcactagtcc tccagtgact   2520

accgcacagg ctacagtgcc agtcccacct acttctcagc ctagattttc taacctgagt   2580

atgctggtgc tgcagtgggc aagcctggca gtcctgaccc tgctgctgct gctggtcatg   2640

gctgactgtg cattccggag aaacctgtcc acttcacaca cttacaccac ccccccttac   2700

gatgacgcag agacttatgt c                                               2721
```

<210> SEQ ID NO 32
<211> LENGTH: 907
<212> TYPE: PRT
<213> ORGANISM: Epstein Barr Virus

<400> SEQUENCE: 32

```
Met Glu Ala Ala Leu Leu Val Cys Gln Tyr Thr Ile Gln Ser Leu Ile
1               5                   10                  15

His Leu Thr Gly Glu Asp Pro Gly Phe Phe Asn Val Glu Ile Pro Glu
            20                  25                  30

Phe Pro Phe Tyr Pro Thr Cys Asn Val Cys Thr Ala Asp Val Asn Val
        35                  40                  45

Thr Ile Asn Phe Asp Val Gly Gly Lys Lys His Gln Leu Asp Leu Asp
    50                  55                  60

Phe Gly Gln Leu Thr Pro His Thr Lys Ala Val Tyr Gln Pro Arg Gly
65                  70                  75                  80

Ala Phe Gly Gly Ser Glu Asn Ala Thr Asn Leu Phe Leu Leu Glu Leu
                85                  90                  95

Leu Gly Ala Gly Glu Leu Ala Leu Thr Met Arg Ser Lys Lys Leu Pro
            100                 105                 110

Ile Asn Val Thr Thr Gly Glu Glu Gln Gln Val Ser Leu Glu Ser Val
        115                 120                 125
```

-continued

```
Asp Val Tyr Phe Gln Asp Val Phe Gly Thr Met Trp Cys His His Ala
    130                 135                 140

Glu Met Gln Asn Pro Val Tyr Leu Ile Pro Glu Thr Val Pro Tyr Ile
145                 150                 155                 160

Lys Trp Asp Asn Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
        195                 200                 205

Ile Glu Cys Ile Met Glu Asp Gly Glu Ile Ser Gln Val Leu Pro Gly
    210                 215                 220

Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
                245                 250                 255

Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
        275                 280                 285

Gly Pro Lys Ala Ser Gly Gly Asp Tyr Cys Ile Gln Ser Asn Ile Val
    290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
        355                 360                 365

Thr Ser Gly Thr Pro Ser Gly Cys Glu Asn Ile Ser Gly Ala Phe Ala
    370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Glu Ser Thr Thr Thr Ser Pro
            420                 425                 430

Thr Leu Asn Thr Thr Gly Phe Ala Asp Pro Asn Thr Thr Thr Gly Leu
        435                 440                 445

Pro Ser Ser Thr His Val Pro Thr Asn Leu Thr Ala Pro Ala Ser Thr
    450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Trp Asp
                485                 490                 495

Asn Gly Thr Glu Ser Lys Ala Pro Asp Met Thr Ser Ser Thr Ser Pro
            500                 505                 510

Val Thr Thr Pro Thr Pro Asn Ala Thr Ser Pro Thr Pro Ala Val Thr
        515                 520                 525

Thr Pro Thr Pro Asn Ala Thr Ser Pro Thr Pro Ala Val Thr Thr Pro
    530                 535                 540

Thr Pro Asn Ala Thr Ser Pro Thr Leu Gly Lys Thr Ser Pro Thr Ser
```

-continued

```
545                 550                 555                 560

Ala Val Thr Thr Pro Thr Pro Asn Ala Thr Ser Pro Thr Leu Gly Lys
                565                 570                 575

Thr Ser Pro Thr Ser Ala Val Thr Thr Pro Thr Pro Asn Ala Thr Ser
            580                 585                 590

Pro Thr Leu Gly Lys Thr Ser Pro Thr Ser Ala Val Thr Thr Pro Thr
        595                 600                 605

Pro Asn Ala Thr Gly Pro Thr Val Gly Glu Thr Ser Pro Gln Ala Asn
    610                 615                 620

Ala Thr Asn His Thr Leu Gly Gly Thr Ser Pro Thr Pro Val Val Thr
625                 630                 635                 640

Ser Gln Pro Lys Asn Ala Thr Ser Ala Val Thr Thr Gly Gln His Asn
                645                 650                 655

Ile Thr Ser Ser Ser Thr Ser Ser Met Ser Leu Arg Pro Ser Ser Asn
            660                 665                 670

Pro Glu Thr Leu Ser Pro Ser Thr Ser Asp Asn Ser Thr Ser His Met
        675                 680                 685

Pro Leu Leu Thr Ser Ala His Pro Thr Gly Gly Glu Asn Ile Thr Gln
    690                 695                 700

Val Thr Pro Ala Ser Ile Ser Thr His His Val Ser Thr Ser Ser Pro
705                 710                 715                 720

Ala Pro Arg Pro Gly Thr Thr Ser Gln Ala Ser Gly Pro Gly Asn Ser
                725                 730                 735

Ser Thr Ser Thr Lys Pro Gly Glu Val Asn Val Thr Lys Gly Thr Pro
            740                 745                 750

Pro Gln Asn Ala Thr Ser Pro Gln Ala Pro Ser Gly Gln Lys Thr Ala
        755                 760                 765

Val Pro Thr Val Thr Ser Thr Gly Gly Lys Ala Asn Ser Thr Thr Gly
    770                 775                 780

Gly Lys His Thr Thr Gly His Gly Ala Arg Thr Ser Thr Glu Pro Thr
785                 790                 795                 800

Thr Asp Tyr Gly Gly Asp Ser Thr Thr Pro Arg Pro Arg Tyr Asn Ala
                805                 810                 815

Thr Thr Tyr Leu Pro Pro Ser Thr Ser Ser Lys Leu Arg Pro Arg Trp
            820                 825                 830

Thr Phe Thr Ser Pro Pro Val Thr Thr Ala Gln Ala Thr Val Pro Val
        835                 840                 845

Pro Pro Thr Ser Gln Pro Arg Phe Ser Asn Leu Ser Met Leu Val Leu
    850                 855                 860

Gln Trp Ala Ser Leu Ala Val Leu Thr Leu Leu Leu Leu Leu Val Met
865                 870                 875                 880

Ala Asp Cys Ala Phe Arg Arg Asn Leu Ser Thr Ser His Thr Tyr Thr
                885                 890                 895

Thr Pro Pro Tyr Asp Asp Ala Glu Thr Tyr Val
            900                 905
```

<210> SEQ ID NO 33
<211> LENGTH: 2721
<212> TYPE: DNA
<213> ORGANISM: Epstein Barr Virus

<400> SEQUENCE: 33

```
gacataagtc tctgcgtcat cgtaaggggg ggtggtgtaa gtgtgtgaag tggacaggtt      60

tctccggaat gcacagtcag ccatgaccag cagcagcagc agggtcagga ctgccaggct     120
```

-continued

```
tgcccactgc agcaccagca tactcaggtt agaaaatcta ggctgagaag taggtgggac    180
tggcactgta gcctgtgcgg tagtcactgg aggactagtg aatgtccatc tgggtcgcag    240
cttggagctg gtagagggtg gcagatatgt ggtggcattg tatctgggcc ttggagttgt    300
ggaatctccc ccgtagtcgg tagttggttc ggtgctagtg cgagctccat gccctgtggt    360
gtgtttgcct ccagttgtag agtttgcctt cccgcctgtg gaggtgacag taggcacagc    420
tgttttctgg ccgcttggtg cctgaggtga ggtagcattc tgagggggag tcccttttgt    480
gacgttcacc tcgccaggct ttgtgctggt tgaactattt cctggtccgg atgcctggct    540
ggtagttcca ggtcggggtg ctggagagga tgtggacaca tggtgggtag aaatggaggc    600
gggggtgacc tgagtgatgt tttctccccc agttggatgt gcagatgtca gcagaggcat    660
gtggctggtt gaattgtcac tagtagatgg ggacagtgtc tctgggttgc ttgaagggcg    720
caggctcata ctagaagtgg agcttgatgt gatattatgc tggcctgtgg tcacagcgct    780
tgtggcgttc ttgggctgtg aggtgaccac aggtgtggga ctggtgcctc ccagagtgtg    840
atttgttgcg ttagcctggg gggatgtctc tcccacggtt ggcccagttg catttggggt    900
aggagttgtg acagctgatg taggactggt cttgcccaga gtggggcttg tggcgttggg    960
ggttggggta gtcactgcag aggttgggga agtttttccc agtgtaggag aggtagcatt   1020
aggggtgggt gtggtcacgg cgctagtggg tgatgtcttc cccagggttg gggaagtggc   1080
gtttggggta ggagttgtca ctgcgggtgt tgggctggta gcattaggtg tgggggtagt   1140
cacggctgga gtagggcttg ttgcgttggg ggttggtgtg gtgactggtg aggtactaga   1200
agtcatatca ggggccttac tctctgtccc attgtcccaa gggctgggtg atggggtcac   1260
gggactagcg ccagaagttg ttccggcagg tgtgggactg gtgacatcgg cagtagacac   1320
tgtaggtccg gtggatgctg gtgcagtcag gtttgttggc acatgggtgg agctaggcag   1380
tccggtagtt gtattggggt cggcaaaccc ggtagtgttc agggtaggag atgtggtagt   1440
ggactcggga gctttgctga agatcacttt gtgtgtggta gttgttgcgt tagtagctgt   1500
ccgggtaatg atcagggttt ttggggcagt ccccaggccg gacactgtaa tatcaaaggt   1560
tcgattacta gcgaaggcgc cagagatgtt ttcacacccg ctaggggtgc ctgaagtcag   1620
tgtccatttg cacttaaaat cggtctcagt attgttgggc caggcccaga atgctgtgac   1680
ggtcacattt ggggagttag cgtcttcgct tgtgaccata ggcacggaat aagtggcatt   1740
atcgcccacg taggtaatgt cggtagtgtt agtgggcata tcctggctgg ctgggatctc   1800
gtctgagaac acaatattac tctggatgca atagtcccct ccagaagcct ttggtccgtt   1860
tccggaataa aacacgtaca gaatgctatt gttgcccagg aagcgtgaga ctggcctagg   1920
ggtcagtctc aggctataag cgtagccggt tccgggaatt ggagtggcca cgggactagt   1980
agatgtcagg attcccccac ttgggacgtg agattcgtag ccggaacagg tgatattaaa   2040
cttgttatcg ccaggcagca cctggctaat ttctccatcc tccatgatgc attcaatgtc   2100
gatctcattt cccagcatct cggttttcac ggagaagttg ctatcctggg cgcttgtggg   2160
cagtgacagt ggcagggtca cgtccagccc ctgtgcccgg accactgcgg taatgttagt   2220
gctattacag ttgtcccact taatataagg gacggtttcg gggatcaggt acacaggatt   2280
ctgcatctcg gcatggtggc accacatggt gccaaacaca tcctggaagt agacgtccac   2340
tgattccaga ctgacctgct gttcctctcc tgtggtcaca ttgatgggca gtttcttgga   2400
cctcatggtc agagccagtt ctcctgctcc cagcagctcc agcagaaaca gatttgttgc   2460
```

```
gttctcgctg cctccgaaag cccctctggg ctgatacacg gcttttgtat gtggggtcag   2520
ctggccaaaa tccaggtcca gctggtgttt cttcccgccc acatcgaaat taatggtgac   2580
gttcacgtcg gctgtacaga cgttgcaggt ggggtaaaat gggaactcag ggatttccac   2640
attgaaaaat ccagggtcct ccccggtcag atgaatcagg ctctgaatag tgtactggca   2700
caccagcagg gcggcttcca t                                             2721
```

<210> SEQ ID NO 34
<211> LENGTH: 2577
<212> TYPE: DNA
<213> ORGANISM: Epstein Barr Virus

<400> SEQUENCE: 34

```
gaagccgccc tgctggtgtg ccagtacact attcagagcc tgattcatct gaccggggag     60
gaccctggat tttcaatgt ggaaatccct gagttcccat tttaccccac ctgcaacgtc    120
tgtacagccg acgtgaacgt caccattaat ttcgatgtgg gcgggaagaa acaccagctg    180
gacctggatt ttggccagct gaccccacat acaaaagccg tgtatcagcc cagaggggct    240
ttcggaggca gcgagaacgc aacaaatctg tttctgctgg agctgctggg agcaggagaa    300
ctggctctga ccatgaggtc caagaaactg cccatcaatg tgaccacagg agaggaacag    360
caggtcagtc tggaatcagt ggacgtctac ttccaggatg tgtttggcac catgtggtgc    420
caccatgccg agatgcagaa tcctgtgtac ctgatccccg aaaccgtccc ttatattaag    480
tgggacaact gtaatagcac taacattacc gcagtggtcc gggcacaggg gctggacgtg    540
accctgccac tgtcactgcc cacaagcgcc caggatagca acttctccgt gaaaaccgag    600
atgctgggaa atgagatcga cattgaatgc atcatggagg atggagaaat tagccaggtg    660
ctgcctggcg ataacaagtt taatatcacc tgttccggct acgaatctca cgtcccaagt    720
gggggaatcc tgacatctac tagtcccgtg gccactccaa ttcccggaac cggctacgct    780
tatagcctga gactgacccc taggccagtc tcacgcttcc tgggcaacaa tagcattctg    840
tacgtgtttt attccggaaa cggaccaaag gcttctggag ggactattg catccagagt    900
aatattgtgt tctcagacga gatcccagcc agccaggata tgcccactaa cactaccgac    960
attacctacg tgggcgataa tgccacttat tccgtgccta tggtcacaag cgaagacgct   1020
aactccccaa atgtgaccgt cacagcattc tgggcctggc ccaacaatac tgagaccgat   1080
tttaagtgca aatggacact gacttcaggc accccctagcg ggtgtgaaaa catctctggc   1140
gccttcgcta gtaatcgaac ctttgatatt acagtgtccg gcctggggac tgccccaaaa   1200
accctgatca ttacccggac agctactaac gcaacaacta ccacacacaa agtgatcttc   1260
agcaaagctc ccgagtccac taccacatct cctaccctga acactaccgg gtttgccgac   1320
cccaatacaa ctaccggact gcctagctcc acccatgtgc caacaaacct gactgcacca   1380
gcatccaccg gacctacagt gtctactgcc gatgtcacca gtcccacacc tgccggaaca   1440
acttctggcg ctagtcccgt gaccccatca cccagccctt gggacaatgg gacagagagt   1500
aaggcccctg atatgacttc tagtacctca ccagtcacca caccaacccc caacgcaaca   1560
agccctactc cagccgtgac tacccccaca cctaatgcta ccagcccaac acccgcagtg   1620
acaactccta ccccaaacgc cacttcccca accctgggga agacatcacc cactagcgcc   1680
gtgaccacac ccacccctaa tgctacctct cctacactgg gaaaaacttc cccaacctct   1740
gcagtgacta ccccaacccc caacgccaca agccccactc tgggcaagac cagtcctaca   1800
tcagctgtca caactcctac cccaaatgca actgggccaa ccgtgggaga gacatccccc   1860
```

```
caggctaacg caacaaatca cactctggga ggcaccagtc ccacacctgt ggtcacctca   1920

cagcccaaga acgccacaag cgctgtgacc acaggccagc ataatatcac atcaagctcc   1980

acttctagta tgagcctgcg cccttcaagc aacccagaga cactgtcccc atctactagt   2040

gacaattcaa ccagccacat gcctctgctg acatctgcac atccaactgg gggagaaaac   2100

atcactcagg tcaccccccgc ctccatttct acccaccatg tgtccacatc ctctccagca   2160

ccccgacctg gaactaccag ccaggcatcc ggaccaggaa atagttcaac cagcacaaag   2220

cctggcgagg tgaacgtcac aaaagggact ccccctcaga atgctacctc acctcaggca   2280

ccaagcggcc agaaaacagc tgtgcctact gtcacctcca caggcgggaa ggcaaactct   2340

acaactggag gcaaacacac cacagggcat ggagctcgca ctagcaccga accaactacc   2400

gactacgggg gagattccac aactccaagg cccagataca atgccaccac atatctgcca   2460

ccctctacca gctccaagct gcgacccaga tggacattca ctagtcctcc agtgactacc   2520

gcacaggcta cagtgccagt cccacctact tctcagccta gattttctaa cctgagt      2577


<210> SEQ ID NO 35
<211> LENGTH: 859
<212> TYPE: PRT
<213> ORGANISM: Epstein Barr Virus

<400> SEQUENCE: 35

Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
```

```
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr Thr His
                405                 410                 415

Lys Val Ile Phe Ser Lys Ala Pro Glu Ser Thr Thr Thr Ser Pro Thr
            420                 425                 430

Leu Asn Thr Thr Gly Phe Ala Asp Pro Asn Thr Thr Thr Gly Leu Pro
        435                 440                 445

Ser Ser Thr His Val Pro Thr Asn Leu Thr Ala Pro Ala Ser Thr Gly
    450                 455                 460

Pro Thr Val Ser Thr Ala Asp Val Thr Ser Pro Thr Pro Ala Gly Thr
465                 470                 475                 480

Thr Ser Gly Ala Ser Pro Val Thr Pro Ser Pro Ser Pro Trp Asp Asn
                485                 490                 495

Gly Thr Glu Ser Lys Ala Pro Asp Met Thr Ser Ser Thr Ser Pro Val
            500                 505                 510

Thr Thr Pro Thr Pro Asn Ala Thr Ser Pro Thr Pro Ala Val Thr Thr
        515                 520                 525

Pro Thr Pro Asn Ala Thr Ser Pro Thr Pro Ala Val Thr Thr Pro Thr
    530                 535                 540

Pro Asn Ala Thr Ser Pro Thr Leu Gly Lys Thr Ser Pro Thr Ser Ala
545                 550                 555                 560

Val Thr Thr Pro Thr Pro Asn Ala Thr Ser Pro Thr Leu Gly Lys Thr
                565                 570                 575

Ser Pro Thr Ser Ala Val Thr Thr Pro Thr Pro Asn Ala Thr Ser Pro
            580                 585                 590

Thr Leu Gly Lys Thr Ser Pro Thr Ser Ala Val Thr Thr Pro Thr Pro
        595                 600                 605

Asn Ala Thr Gly Pro Thr Val Gly Glu Thr Ser Pro Gln Ala Asn Ala
    610                 615                 620

Thr Asn His Thr Leu Gly Gly Thr Ser Pro Thr Pro Val Val Thr Ser
625                 630                 635                 640

Gln Pro Lys Asn Ala Thr Ser Ala Val Thr Thr Gly Gln His Asn Ile
                645                 650                 655

Thr Ser Ser Ser Thr Ser Ser Met Ser Leu Arg Pro Ser Ser Asn Pro
            660                 665                 670
```

```
Glu Thr Leu Ser Pro Ser Thr Ser Asp Asn Ser Thr Ser His Met Pro
        675                 680                 685

Leu Leu Thr Ser Ala His Pro Thr Gly Gly Glu Asn Ile Thr Gln Val
    690                 695                 700

Thr Pro Ala Ser Ile Ser Thr His His Val Ser Thr Ser Ser Pro Ala
705                 710                 715                 720

Pro Arg Pro Gly Thr Thr Ser Gln Ala Ser Gly Pro Gly Asn Ser Ser
                725                 730                 735

Thr Ser Thr Lys Pro Gly Glu Val Asn Val Thr Lys Gly Thr Pro Pro
            740                 745                 750

Gln Asn Ala Thr Ser Pro Gln Ala Pro Ser Gly Gln Lys Thr Ala Val
        755                 760                 765

Pro Thr Val Thr Ser Thr Gly Gly Lys Ala Asn Ser Thr Thr Gly Gly
    770                 775                 780

Lys His Thr Thr Gly His Gly Ala Arg Thr Ser Thr Glu Pro Thr Thr
785                 790                 795                 800

Asp Tyr Gly Gly Asp Ser Thr Thr Pro Arg Pro Arg Tyr Asn Ala Thr
                805                 810                 815

Thr Tyr Leu Pro Pro Ser Thr Ser Ser Lys Leu Arg Pro Arg Trp Thr
            820                 825                 830

Phe Thr Ser Pro Pro Val Thr Thr Ala Gln Ala Thr Val Pro Val Pro
        835                 840                 845

Pro Thr Ser Gln Pro Arg Phe Ser Asn Leu Ser
    850                 855
```

<210> SEQ ID NO 36
<211> LENGTH: 2577
<212> TYPE: DNA
<213> ORGANISM: Epstein Barr Virus

<400> SEQUENCE: 36

```
actcaggtta gaaaatctag gctgagaagt aggtgggact ggcactgtag cctgtgcggt     60

agtcactgga ggactagtga atgtccatct gggtcgcagc ttggagctgg tagagggtgg    120

cagatatgtg gtggcattgt atctgggcct tggagttgtg gaatctcccc cgtagtcggt    180

agttggttcg gtgctagtgc gagctccatg ccctgtggtg tgtttgcctc cagttgtaga    240

gtttgccttc ccgcctgtgg aggtgacagt aggcacagct gttttctggc cgcttggtgc    300

ctgaggtgag gtagcattct gagggggagt cccttttgtg acgttcacct cgccaggctt    360

tgtgctggtt gaactatttc ctggtccgga tgcctggctg gtagttccag gtcggggtgc    420

tggagaggat gtggacacat ggtgggtaga aatggaggcg ggggtgacct gagtgatgtt    480

ttctccccca gttggatgtg cagatgtcag cagaggcatg tggctggttg aattgtcact    540

agtagatggg gacagtgtct ctgggttgct tgaagggcgc aggctcatac tagaagtgga    600

gcttgatgtg atattatgct ggcctgtggt cacagcgctt gtggcgttct tgggctgtga    660

ggtgaccaca ggtgtgggac tggtgcctcc cagagtgtga tttgttgcgt tagcctgggg    720

ggatgtctct cccacggttg gcccagttgc atttggggta ggagttgtga cagctgatgt    780

aggactggtc ttgcccagag tggggcttgt ggcgttgggg gttggggtag tcactgcaga    840

ggttggggaa gtttttccca gtgtaggaga ggtagcatta ggggtgggtg tggtcacggc    900

gctagtgggt gatgtcttcc ccagggttgg ggaagtggcg tttggggtag gagttgtcac    960

tgcgggtgtt gggctggtag cattaggtgt gggggtagtc acggctggag tagggcttgt   1020
```

-continued

```
tgcgttgggg gttggtgtgg tgactggtga ggtactagaa gtcatatcag gggccttact   1080

ctctgtccca ttgtcccaag ggctgggtga tggggtcacg ggactagcgc cagaagttgt   1140

tccggcaggt gtgggactgg tgacatcggc agtagacact gtaggtccgg tggatgctgg   1200

tgcagtcagg tttgttggca catgggtgga gctaggcagt ccggtagttg tattggggtc   1260

ggcaaacccg gtagtgttca gggtaggaga tgtggtagtg gactcgggag ctttgctgaa   1320

gatcactttg tgtgtggtag ttgttgcgtt agtagctgtc cgggtaatga tcagggtttt   1380

tggggcagtc cccaggccgg acactgtaat atcaaaggtt cgattactag cgaaggcgcc   1440

agagatgttt tcacacccgc taggggtgcc tgaagtcagt gtccatttgc acttaaaatc   1500

ggtctcagta ttgttgggcc aggcccagaa tgctgtgacg gtcacatttg gggagttagc   1560

gtcttcgctt gtgaccatag gcacggaata agtggcatta tcgcccacgt aggtaatgtc   1620

ggtagtgtta gtgggcatat cctggctggc tgggatctcg tctgagaaca caatattact   1680

ctggatgcaa tagtcccctc cagaagcctt tggtccgttt ccggaataaa acacgtacag   1740

aatgctattg ttgcccagga agcgtgagac tggcctaggg gtcagtctca ggctataagc   1800

gtagccggtt ccgggaattg gagtggccac gggactagta gatgtcagga ttcccccact   1860

tgggacgtga gattcgtagc cggaacaggt gatattaaac ttgttatcgc caggcagcac   1920

ctggctaatt tctccatcct ccatgatgca ttcaatgtcg atctcatttc ccagcatctc   1980

ggttttcacg gagaagttgc tatcctgggc gcttgtgggc agtgacagtg gcagggtcac   2040

gtccagcccc tgtgcccgga ccactgcggt aatgttagtg ctattacagt tgtcccactt   2100

aatataaggg acggtttcgg ggatcaggta cacaggattc tgcatctcgg catggtggca   2160

ccacatggtg ccaaacacat cctggaagta gacgtccact gattccagac tgacctgctg   2220

ttcctctcct gtggtcacat tgatgggcag tttcttggac ctcatggtca gagccagttc   2280

tcctgctccc agcagctcca gcagaaacag atttgttgcg ttctcgctgc ctccgaaagc   2340

ccctctgggc tgatacacgg cttttgtatg tggggtcagc tggccaaaat ccaggtccag   2400

ctggtgtttc ttcccgccca catcgaaatt aatggtgacg ttcacgtcgg ctgtacagac   2460

gttgcaggtg gggtaaaatg ggaactcagg gatttccaca ttgaaaaatc cagggtcctc   2520

cccggtcaga tgaatcaggc tctgaatagt gtactggcac accagcaggg cggcttc      2577
```

<210> SEQ ID NO 37
<211> LENGTH: 1407
<212> TYPE: DNA
<213> ORGANISM: Epstein Barr Virus

<400> SEQUENCE: 37

```
gaagccgccc tgctggtgtg ccagtacact attcagagcc tgattcatct gaccggggag     60

gaccctggat tttcaatgt ggaaatccct gagttcccat tttaccccac ctgcaacgtc    120

tgtacagccg acgtgaacgt caccattaat ttcgatgtgg gcgggaagaa acaccagctg    180

gacctggatt ttggccagct gaccccacat acaaaagccg tgtatcagcc cagaggggct    240

ttcggaggca gcgagaacgc aacaaatctg tttctgctgg agctgctggg agcaggagaa    300

ctggctctga ccatgaggtc caagaaactg cccatcaatg tgaccacagg agaggaacag    360

caggtcagtc tggaatcagt ggacgtctac ttccaggatg tgtttggcac catgtggtgc    420

caccatgccg agatgcagaa tcctgtgtac ctgatccccg aaaccgtccc ttatattaag    480

tgggacaact gtaatagcac taacattacc gcagtggtcc gggcacaggg gctggacgtg    540

accctgccac tgtcactgcc cacaagcgcc caggatagca acttctccgt gaaaaccgag    600
```

```
atgctgggaa atgagatcga cattgaatgc atcatggagg atggagaaat tagccaggtg    660

ctgcctggcg ataacaagtt taatatcacc tgttccggct acgaatctca cgtcccaagt    720

gggggaatcc tgacatctac tagtcccgtg gccactccaa ttcccggaac cggctacgct    780

tatagcctga gactgacccc taggccagtc tcacgcttcc tgggcaacaa tagcattctg    840

tacgtgtttt attccggaaa cggaccaaag gcttctggag gggactattg catccagagt    900

aatattgtgt tctcagacga gatcccagcc agccaggata tgcccactaa cactaccgac    960

attacctacg tgggcgataa tgccacttat tccgtgccta tggtcacaag cgaagacgct   1020

aactccccaa atgtgaccgt cacagcattc tgggcctggc ccaacaatac tgagaccgat   1080

tttaagtgca aatggacact gacttcaggc acccctagcg ggtgtgaaaa catctctggc   1140

gccttcgcta gtaatcgaac ctttgatatt acagtgtccg gcctggggac tgccccaaaa   1200

accctgatca ttacccggac agctactaac gcaacaacta ccacacacaa agtgatcttc   1260

agcaaagctc ccgagtccac taccacatct cctaccctga acactaccgg gtttgccgac   1320

cccaatacaa ctaccggact gcctagctcc acccatgtgc caacaaacct gactgcacca   1380

gcatccaccg gacctacagt gtctact                                       1407
```

<210> SEQ ID NO 38
<211> LENGTH: 469
<212> TYPE: PRT
<213> ORGANISM: Epstein Barr Virus

<400> SEQUENCE: 38

```
Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220
```

```
Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr Thr His
                405                 410                 415

Lys Val Ile Phe Ser Lys Ala Pro Glu Ser Thr Thr Thr Ser Pro Thr
            420                 425                 430

Leu Asn Thr Thr Gly Phe Ala Asp Pro Asn Thr Thr Thr Gly Leu Pro
        435                 440                 445

Ser Ser Thr His Val Pro Thr Asn Leu Thr Ala Pro Ala Ser Thr Gly
    450                 455                 460

Pro Thr Val Ser Thr
465
```

<210> SEQ ID NO 39
<211> LENGTH: 1407
<212> TYPE: DNA
<213> ORGANISM: Epstein Barr Virus

<400> SEQUENCE: 39

```
agtagacact gtaggtccgg tggatgctgg tgcagtcagg tttgttggca catgggtgga      60

gctaggcagt ccggtagttg tattggggtc ggcaaacccg gtagtgttca gggtaggaga     120

tgtggtagtg gactcgggag ctttgctgaa gatcactttg tgtgtggtag ttgttgcgtt     180

agtagctgtc cgggtaatga tcagggtttt tggggcagtc cccaggccgg acactgtaat     240

atcaaaggtt cgattactag cgaaggcgcc agagatgttt tcacacccgc taggggtgcc     300

tgaagtcagt gtccatttgc acttaaaatc ggtctcagta ttgttgggcc aggcccagaa     360

tgctgtgacg gtcacatttg gggagttagc gtcttcgctt gtgaccatag gcacggaata     420

agtggcatta tcgcccacgt aggtaatgtc ggtagtgtta gtgggcatat cctggctggc     480

tgggatctcg tctgagaaca caatattact ctggatgcaa tagtcccctc cagaagcctt     540

tggtccgttt ccggaataaa acacgtacag aatgctattg ttgcccagga agcgtgagac     600

tggcctaggg gtcagtctca ggctataagc gtagccggtt ccgggaattg gagtggccac     660

gggactagta gatgtcagga ttccccccact tgggacgtga gattcgtagc cggaacaggt     720
```

-continued gatattaaac ttgttatcgc caggcagcac ctggctaatt tctccatcct ccatgatgca 780
ttcaatgtcg atctcatttc ccagcatctc ggttttcacg gagaagttgc tatcctgggc 840
gcttgtgggc agtgacagtg gcagggtcac gtccagcccc tgtgcccgga ccactgcggt 900
aatgttagtg ctattacagt tgtcccactt aatataaggg acggtttcgg ggatcaggta 960
cacaggattc tgcatctcgg catggtggca ccacatggtg ccaaacacat cctggaagta 1020
gacgtccact gattccagac tgacctgctg ttcctctcct gtggtcacat tgatgggcag 1080
tttcttggac ctcatggtca gagccagttc tcctgctccc agcagctcca gcagaaacag 1140
atttgttgcg ttctcgctgc ctccgaaagc ccctctgggc tgatacacgg cttttgtatg 1200
tggggtcagc tggccaaaat ccaggtccag ctggtgtttc ttcccgccca catcgaaatt 1260
aatggtgacg ttcacgtcgg ctgtacagac gttgcaggtg gggtaaaatg ggaactcagg 1320
gatttccaca ttgaaaaatc cagggtcctc cccggtcaga tgaatcaggc tctgaatagt 1380
gtactggcac accagcaggg cggcttc 1407

<210> SEQ ID NO 40
<211> LENGTH: 450
<212> TYPE: DNA
<213> ORGANISM: Epstein Barr Virus

<400> SEQUENCE: 40
gccctgctgg tgtgccagta cactattcag agcctgattc atctgaccgg ggaggaccct 60
ggatttttca atgtggaaat ccctgagttc ccattttacc ccacctgcaa cgtctgtaca 120
gccgacgtga acgtcaccat taatttcgat gtgggcggga agaaacacca gctggacctg 180
gattttggcc agctgacccc acatacaaaa gccgtgtatc agcccagagg ggctttcgga 240
ggcagcgaga acgcaacaaa tctgtttctg ctggagctgc tgggagcagg agaactggct 300
ctgaccatga ggtccaagaa actgcccatc aatgtgacca caggagagga acagcaggtc 360
agtctggaat cagtggacgt ctacttccag gatgtgtttg gcaccatgtg gtgccaccat 420
gccgagatgc agaatcctgt gtacctgatc 450

<210> SEQ ID NO 41
<211> LENGTH: 150
<212> TYPE: PRT
<213> ORGANISM: Epstein Barr Virus

<400> SEQUENCE: 41

Ala Leu Leu Val Cys Gln Tyr Thr Ile Gln Ser Leu Ile His Leu Thr
1 5 10 15

Gly Glu Asp Pro Gly Phe Phe Asn Val Glu Ile Pro Glu Phe Pro Phe
20 25 30

Tyr Pro Thr Cys Asn Val Cys Thr Ala Asp Val Asn Val Thr Ile Asn
35 40 45

Phe Asp Val Gly Gly Lys Lys His Gln Leu Asp Leu Asp Phe Gly Gln
50 55 60

Leu Thr Pro His Thr Lys Ala Val Tyr Gln Pro Arg Gly Ala Phe Gly
65 70 75 80

Gly Ser Glu Asn Ala Thr Asn Leu Phe Leu Leu Glu Leu Leu Gly Ala
85 90 95

Gly Glu Leu Ala Leu Thr Met Arg Ser Lys Lys Leu Pro Ile Asn Val
100 105 110

Thr Thr Gly Glu Glu Gln Gln Val Ser Leu Glu Ser Val Asp Val Tyr 115 120 125

Phe Gln Asp Val Phe Gly Thr Met Trp Cys His His Ala Glu Met Gln
130 135 140

Asn Pro Val Tyr Leu Ile
145 150

<210> SEQ ID NO 42
<211> LENGTH: 450
<212> TYPE: DNA
<213> ORGANISM: Epstein Barr Virus

<400> SEQUENCE: 42
gatcaggtac acaggattct gcatctcggc atggtggcac cacatggtgc caaacacatc 60
ctggaagtag acgtccactg attccagact gacctgctgt tcctctcctg tggtcacatt 120
gatgggcagt ttcttggacc tcatggtcag agccagttct cctgctccca gcagctccag 180
cagaaacaga tttgttgcgt tctcgctgcc tccgaaagcc cctctgggct gatacacggc 240
ttttgtatgt ggggtcagct ggccaaaatc caggtccagc tggtgtttct tcccgcccac 300
atcgaaatta atggtgacgt tcacgtcggc tgtacagacg ttgcaggtgg ggtaaaatgg 360
gaactcaggg atttccacat tgaaaaatcc agggtcctcc ccggtcagat gaatcaggct 420
ctgaatagtg tactggcaca ccagcagggc 450

<210> SEQ ID NO 43
<211> LENGTH: 423
<212> TYPE: DNA
<213> ORGANISM: Epstein Barr Virus

<400> SEQUENCE: 43
tgtaatagca ctaacattac cgcagtggtc cgggcacagg ggctggacgt gaccctgcca 60
ctgtcactgc ccacaagcgc ccaggatagc aacttctccg tgaaaaccga gatgctggga 120
aatgagatcg acattgaatg catcatggag gatggagaaa ttagccaggt gctgcctggc 180
gataacaagt ttaatatcac ctgttccggc tacgaatctc acgtcccaag tgggggaatc 240
ctgacatcta ctagtcccgt ggccactcca attcccggaa ccggctacgc ttatagcctg 300
agactgaccc ctaggccagt ctcacgcttc ctgggcaaca atagcattct gtacgtgttt 360
tattccggaa acggaccaaa ggcttctgga ggggactatt gcatccagag taatattgtg 420
ttc 423

<210> SEQ ID NO 44
<211> LENGTH: 141
<212> TYPE: PRT
<213> ORGANISM: Epstein Barr Virus

<400> SEQUENCE: 44

Cys Asn Ser Thr Asn Ile Thr Ala Val Val Arg Ala Gln Gly Leu Asp
1 5 10 15

Val Thr Leu Pro Leu Ser Leu Pro Thr Ser Ala Gln Asp Ser Asn Phe
20 25 30

Ser Val Lys Thr Glu Met Leu Gly Asn Glu Ile Asp Ile Glu Cys Ile
35 40 45

Met Glu Asp Gly Glu Ile Ser Gln Val Leu Pro Gly Asp Asn Lys Phe
50 55 60

Asn Ile Thr Cys Ser Gly Tyr Glu Ser His Val Pro Ser Gly Gly Ile
65 70 75 80

-continued

Leu Thr Ser Thr Ser Pro Val Ala Thr Pro Ile Pro Gly Thr Gly Tyr
85 90 95

Ala Tyr Ser Leu Arg Leu Thr Pro Arg Pro Val Ser Arg Phe Leu Gly
100 105 110

Asn Asn Ser Ile Leu Tyr Val Phe Tyr Ser Gly Asn Gly Pro Lys Ala
115 120 125

Ser Gly Gly Asp Tyr Cys Ile Gln Ser Asn Ile Val Phe
130 135 140

<210> SEQ ID NO 45
<211> LENGTH: 423
<212> TYPE: DNA
<213> ORGANISM: Epstein Barr Virus

<400> SEQUENCE: 45
gaacacaata ttactctgga tgcaatagtc ccctccagaa gcctttggtc cgtttccgga 60
ataaaacacg tacagaatgc tattgttgcc caggaagcgt gagactggcc taggggtcag 120
tctcaggcta taagcgtagc cggttccggg aattggagtg gccacgggac tagtagatgt 180
caggattccc ccacttggga cgtgagattc gtagccggaa caggtgatat taaacttgtt 240
atcgccaggc agcacctggc taatttctcc atcctccatg atgcattcaa tgtcgatctc 300
atttcccagc atctcggttt tcacggagaa gttgctatcc tgggcgcttg tgggcagtga 360
cagtggcagg gtcacgtcca gcccctgtgc ccggaccact gcggtaatgt tagtgctatt 420
aca 423

<210> SEQ ID NO 46
<211> LENGTH: 330
<212> TYPE: DNA
<213> ORGANISM: Epstein Barr Virus

<400> SEQUENCE: 46
actaacacta ccgacattac ctacgtgggc gataatgcca cttattccgt gcctatggtc 60
acaagcgaag acgctaactc cccaaatgtg accgtcacag cattctgggc ctggcccaac 120
aatactgaga ccgattttaa gtgcaaatgg acactgactt caggcacccc tagcgggtgt 180
gaaaacatct ctggcgcctt cgctagtaat cgaacctttg atattacagt gtccggcctg 240
gggactgccc caaaaaccct gatcattacc cggacagcta ctaacgcaac aactaccaca 300
cacaaagtga tcttcagcaa agctcccgag 330

<210> SEQ ID NO 47
<211> LENGTH: 110
<212> TYPE: PRT
<213> ORGANISM: Epstein Barr Virus

<400> SEQUENCE: 47

Thr Asn Thr Thr Asp Ile Thr Tyr Val Gly Asp Asn Ala Thr Tyr Ser
1 5 10 15

Val Pro Met Val Thr Ser Glu Asp Ala Asn Ser Pro Asn Val Thr Val
20 25 30

Thr Ala Phe Trp Ala Trp Pro Asn Asn Thr Glu Thr Asp Phe Lys Cys
35 40 45

Lys Trp Thr Leu Thr Ser Gly Thr Pro Ser Gly Cys Glu Asn Ile Ser
50 55 60

Gly Ala Phe Ala Ser Asn Arg Thr Phe Asp Ile Thr Val Ser Gly Leu
65 70 75 80

Gly Thr Ala Pro Lys Thr Leu Ile Ile Thr Arg Thr Ala Thr Asn Ala
85 90 95

Thr Thr Thr Thr His Lys Val Ile Phe Ser Lys Ala Pro Glu
100 105 110

<210> SEQ ID NO 48
<211> LENGTH: 330
<212> TYPE: DNA
<213> ORGANISM: Epstein Barr Virus

<400> SEQUENCE: 48
ctcgggagct ttgctgaaga tcactttgtg tgtggtagtt gttgcgttag tagctgtccg 60
ggtaatgatc agggtttttg gggcagtccc caggccggac actgtaatat caaaggttcg 120
attactagcg aaggcgccag agatgttttc acacccgcta ggggtgcctg aagtcagtgt 180
ccatttgcac ttaaaatcgg tctcagtatt gttgggccag gcccagaatg ctgtgacggt 240
cacatttggg gagttagcgt cttcgcttgt gaccataggc acggaataag tggcattatc 300
gcccacgtag gtaatgtcgg tagtgttagt 330

<210> SEQ ID NO 49
<211> LENGTH: 948
<212> TYPE: DNA
<213> ORGANISM: Epstein Barr Virus

<400> SEQUENCE: 49
gaagccgccc tgctggtgtg ccagtacact attcagagcc tgattcatct gaccggggag 60
gaccctggat tttcaatgt ggaaatccct gagttcccat tttaccccac ctgcaacgtc 120
tgtacagccg acgtgaacgt caccattaat ttcgatgtgg gcgggaagaa acaccagctg 180
gacctggatt ttggccagct gaccccacat acaaaagccg tgtatcagcc cagaggggct 240
ttcggaggca gcgagaacgc aacaaatctg tttctgctgg agctgctggg agcaggagaa 300
ctggctctga ccatgaggtc caagaaactg cccatcaatg tgaccacagg agaggaacag 360
caggtcagtc tggaatcagt ggacgtctac ttccaggatg tgtttggcac catgtggtgc 420
caccatgccg agatgcagaa tcctgtgtac ctgatccccg aaaccgtccc ttatattaag 480
tgggacaact gtaatagcac taacattacc gcagtggtcc gggcacaggg gctggacgtg 540
accctgccac tgtcactgcc cacaagcgcc caggatagca acttctccgt gaaaaccgag 600
atgctgggaa atgagatcga cattgaatgc atcatggagg atggagaaat tagccaggtg 660
ctgcctggcg ataacaagtt taatatcacc tgttccggct acgaatctca cgtcccaagt 720
gggggaatcc tgacatctac tagtcccgtg gccactccaa ttcccggaac cggctacgct 780
tatagcctga gactgacccc taggccagtc tcacgcttcc tgggcaacaa tagcattctg 840
tacgtgtttt attccggaaa cggaccaaag gcttctggag gggactattg catccagagt 900
aatattgtgt tctcagacga gatcccagcc agccaggata tgcccact 948

<210> SEQ ID NO 50
<211> LENGTH: 316
<212> TYPE: PRT
<213> ORGANISM: Epstein Barr Virus

<400> SEQUENCE: 50

Glu Ala Ala Leu Leu Val Cys Gln Tyr Thr Ile Gln Ser Leu Ile His
1 5 10 15

Leu Thr Gly Glu Asp Pro Gly Phe Phe Asn Val Glu Ile Pro Glu Phe
20 25 30

```
Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr
305                 310                 315
```

<210> SEQ ID NO 51
<211> LENGTH: 948
<212> TYPE: DNA
<213> ORGANISM: Epstein Barr Virus

<400> SEQUENCE: 51

```
agtgggcata tcctggctgg ctgggatctc gtctgagaac acaatattac tctggatgca      60

atagtcccct ccagaagcct ttggtccgtt tccggaataa aacacgtaca gaatgctatt     120

gttgcccagg aagcgtgaga ctggcctagg ggtcagtctc aggctataag cgtagccggt     180

tccgggaatt ggagtggcca cgggactagt agatgtcagg attcccccac ttgggacgtg     240

agattcgtag ccggaacagg tgatattaaa cttgttatcg ccaggcagca cctggctaat     300

ttctccatcc tccatgatgc attcaatgtc gatctcattt cccagcatct cggttttcac     360

ggagaagttg ctatcctggg cgcttgtggg cagtgacagt ggcagggtca cgtccagccc     420

ctgtgcccgg accactgcgg taatgttagt gctattacag ttgtcccact taatataagg     480
```

-continued

```
gacggtttcg gggatcaggt acacaggatt ctgcatctcg gcatggtggc accacatggt    540

gccaaacaca tcctggaagt agacgtccac tgattccaga ctgacctgct gttcctctcc    600

tgtggtcaca ttgatgggca gtttcttgga cctcatggtc agagccagtt ctcctgctcc    660

cagcagctcc agcagaaaca gatttgttgc gttctcgctg cctccgaaag cccctctggg    720

ctgatacacg gcttttgtat gtggggtcag ctggccaaaa tccaggtcca gctggtgttt    780

cttcccgccc acatcgaaat taatggtgac gttcacgtcg gctgtacaga cgttgcaggt    840

ggggtaaaat gggaactcag ggatttccac attgaaaaat ccagggtcct ccccggtcag    900

atgaatcagg ctctgaatag tgtactggca caccagcagg gcggcttc                 948
```

<210> SEQ ID NO 52
<211> LENGTH: 1272
<212> TYPE: DNA
<213> ORGANISM: Epstein Barr Virus

<400> SEQUENCE: 52

```
gaagccgccc tgctggtgtg ccagtacact attcagagcc tgattcatct gaccggggag     60

gaccctggat ttttcaatgt ggaaatccct gagttcccat ttaccccac ctgcaacgtc    120

tgtacagccg acgtgaacgt caccattaat ttcgatgtgg gcgggaagaa acaccagctg    180

gacctggatt ttggccagct gaccccacat acaaaagccg tgtatcagcc cagaggggct    240

ttcggaggca gcgagaacgc aacaaatctg tttctgctgg agctgctggg agcaggagaa    300

ctggctctga ccatgaggtc caagaaactg cccatcaatg tgaccacagg agaggaacag    360

caggtcagtc tggaatcagt ggacgtctac ttccaggatg tgtttggcac catgtggtgc    420

caccatgccg agatgcagaa tcctgtgtac ctgatccccg aaaccgtccc ttatattaag    480

tgggacaact gtaatagcac taacattacc gcagtggtcc gggcacaggg gctggacgtg    540

accctgccac tgtcactgcc cacaagcgcc caggatagca acttctccgt gaaaaccgag    600

atgctgggaa atgagatcga cattgaatgc atcatggagg atggagaaat tagccaggtg    660

ctgcctggcg ataacaagtt taatatcacc tgttccggct acgaatctca cgtcccaagt    720

gggggaatcc tgacatctac tagtcccgtg gccactccaa ttcccggaac cggctacgct    780

tatagcctga gactgacccc taggccagtc tcacgcttcc tgggcaacaa tagcattctg    840

tacgtgtttt attccggaaa cggaccaaag gcttctggag ggactattg catccagagt    900

aatattgtgt tctcagacga gatcccagcc agccaggata tgcccactaa cactaccgac    960

attacctacg tgggcgataa tgccacttat tccgtgccta tggtcacaag cgaagacgct   1020

aactccccaa atgtgaccgt cacagcattc tgggcctggc ccaacaatac tgagaccgat   1080

tttaagtgca aatggacact gacttcaggc accccctagcg ggtgtgaaaa catctctggc   1140

gccttcgcta gtaatcgaac ctttgatatt acagtgtccg gcctggggac tgccccaaaa   1200

accctgatca ttacccggac agctactaac gcaacaacta ccacacacaa agtgatcttc   1260

agcaaagctc cc                                                       1272
```

<210> SEQ ID NO 53
<211> LENGTH: 424
<212> TYPE: PRT
<213> ORGANISM: Epstein Barr Virus

<400> SEQUENCE: 53

```
Glu Ala Ala Leu Leu Val Cys Gln Tyr Thr Ile Gln Ser Leu Ile His
1               5                   10                  15
```

-continued

```
Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr Thr His
                405                 410                 415

Lys Val Ile Phe Ser Lys Ala Pro
            420
```

<210> SEQ ID NO 54
<211> LENGTH: 1272
<212> TYPE: DNA
<213> ORGANISM: Epstein Barr Virus

<400> SEQUENCE: 54
gggagctttg ctgaagatca ctttgtgtgt ggtagttgtt gcgttagtag ctgtccgggt 60
aatgatcagg gtttttgggg cagtccccag gccggacact gtaatatcaa aggttcgatt 120
actagcgaag gcgccagaga tgttttcaca cccgctaggg gtgcctgaag tcagtgtcca 180
tttgcactta aaatcggtct cagtattgtt gggccaggcc cagaatgctg tgacggtcac 240
atttggggag ttagcgtctt cgcttgtgac cataggcacg gaataagtgg cattatcgcc 300
cacgtaggta atgtcggtag tgttagtggg catatcctgg ctggctggga tctcgtctga 360
gaacacaata ttactctgga tgcaatagtc ccctccagaa gcctttggtc cgtttccgga 420
ataaaacacg tacagaatgc tattgttgcc caggaagcgt gagactggcc taggggtcag 480
tctcaggcta taagcgtagc cggttccggg aattggagtg gccacgggac tagtagatgt 540
caggattccc ccacttggga cgtgagattc gtagccggaa caggtgatat taaacttgtt 600
atcgccaggc agcacctggc taatttctcc atcctccatg atgcattcaa tgtcgatctc 660
atttcccagc atctcggttt tcacggagaa gttgctatcc tgggcgcttg tgggcagtga 720
cagtggcagg gtcacgtcca gcccctgtgc ccggaccact gcggtaatgt tagtgctatt 780
acagttgtcc cacttaatat aagggacggt ttcggggatc aggtacacag gattctgcat 840
ctcggcatgg tggcaccaca tggtgccaaa cacatcctgg aagtagacgt ccactgattc 900
cagactgacc tgctgttcct ctcctgtggt cacattgatg ggcagtttct tggacctcat 960
ggtcagagcc agttctcctg ctcccagcag ctccagcaga aacagatttg ttgcgttctc 1020
gctgcctccg aaagcccctc tggctgata cacggctttt gtatgtgggg tcagctggcc 1080
aaaatccagg tccagctggt gtttcttccc gcccacatcg aaattaatgg tgacgttcac 1140
gtcggctgta cagacgttgc aggtggggta aaatgggaac tcagggattt ccacattgaa 1200
aaatccaggg tcctccccgg tcagatgaat caggctctga atagtgtact ggcacaccag 1260
cagggcggct tc 1272

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61
<211> LENGTH: 2118
<212> TYPE: DNA
<213> ORGANISM: Epstein Barr Virus

<400> SEQUENCE: 61

```
atgcagctcc tgtgcgtgtt ctgtctggtg ctgctgtggg aagtgggagc cgcttctctg     60
agtgaggtga agctgcacct ggacattgaa ggccacgcct cccattacac tatcccttgg    120
accgagctga tggctaaagt gccaggactg tctcctgagg ctctgtggcg ggaagctaat    180
gtgaccgagg atctggcctc tatgctgaac agatacaagc tgatctataa aaccagtggc    240
acactgggga ttgctctggc tgagccagtg gacatccccg ccgtgtcaga aggaagcatg    300
caggtggatg ctagtaaggt gcatccaggg gtgattagcg gactgaacag cccagcttgc    360
atgctgagcg ctcctctgga gaaacagctc ttctactata tcggcaccat gctgcctaat    420
acacggccac acagctacgt gttttatcag ctcagatgtc atctgtccta cgtggccctg    480
tctattaacg ggacaagtt ccagtataca ggagctatga cttccaaatt tctgatggga    540
acttacaagc gggtgaccga gaaaggcgat gaacacgtgc tgtctctggt gttcgggaag    600
acaaaagacc tgcccgatct gagaggaccc ttttcctacc cttctctgac tagtgcccag    660
tcaggcgact atagcctggt gatcgtgacc acattcgtgc actacgctaa cttccataat    720
tattttgtgc ccaatctgaa ggatatgttt tcccgggccg tgaccatgac agccgcttct    780
tacgctagat atgtgctgca gaagctggtg ctgctggaga tgaaaggcgg gtgccgggag    840
cctgaactgg acactgaaac cctgactacc atgttcgagg tgtccgtggc cttctttaaa    900
gtgggacacg ctgtgggaga gacaggaaac ggatgcgtgg acctgagatg gctggccaag    960
agcttctttg aactgaccgt gctgaaagat atcattggaa tctgttacgg cgccacagtg   1020
aaaggaatgc agagctatgg cctggagagg ctggccgcta tgctgatggc caccgtgaag   1080
atggaggaac tgggccacct gacaactgag aaacaggaat acgctctgag gctggctacc   1140
gtgggatacc caaaggccgg ggtgtattcc ggactgattg gaggcgccac atctgtgctg   1200
ctgagtgctt ataataggca cccactgttc cagcccctgc atacagtgat gcgcgagact   1260
ctgtttatcg ggtctcatgt ggtgctgcgg gaactgagac tgaatgtgac cacacaggga   1320
cccaacctgg ccctgtacca gctcctgagt actgccctgt gctcagctct ggagattgga   1380
gaagtgctga ggggactggc cctggggacc gagtcaggac tgttcagccc ttgttatctg   1440
tcactgaggt ttgacctgac tcgcgataag ctgctgagca tggccccaca ggaagctacc   1500
ctggaccagg ccgctgtgag caatgccgtg gatggattcc tgggcaggct gtccctggag   1560
agggaagacc gcgatgcctg gcacctgcca gcttacaagt gcgtggaccg cctggataaa   1620
gtgctgatga tcattcccct gatcaacgtg accttcatca ttagctccga cagggaagtg   1680
agaggcagcg ctctgtacga agcttccact acctatctgt ctagttcact gtttctgtca   1740
```

```
cctgtgatta tgaataagtg tagccaggga gctgtggctg gagagcccag acagatccca   1800

aagattcaga acttcacacg cactcagaaa agttgcatct tctgtggctt tgccctgctg   1860

tcatacgatg agaaagaagg gctggagaca actacctata ttacatctca ggaagtgcag   1920

aacagtatcc tgagctccaa ttacttcgac tttgataacc tgcacgtgca ttatctgctg   1980

ctgacaacta acggcaccgt gatggagatc gctggactgt acgaggaaag ggctcacgtg   2040

gtgctggcta tcattctgta tttcatcgcc tttgctctgg gcatttttct ggtgcataag   2100

atcgtgatgt tctttctg                                                 2118


<210> SEQ ID NO 62
<211> LENGTH: 706
<212> TYPE: PRT
<213> ORGANISM: Epstein Barr Virus

<400> SEQUENCE: 62

Met Gln Leu Leu Cys Val Phe Cys Leu Val Leu Leu Trp Glu Val Gly
1               5                   10                  15

Ala Ala Ser Leu Ser Glu Val Lys Leu His Leu Asp Ile Glu Gly His
            20                  25                  30

Ala Ser His Tyr Thr Ile Pro Trp Thr Glu Leu Met Ala Lys Val Pro
        35                  40                  45

Gly Leu Ser Pro Glu Ala Leu Trp Arg Glu Ala Asn Val Thr Glu Asp
    50                  55                  60

Leu Ala Ser Met Leu Asn Arg Tyr Lys Leu Ile Tyr Lys Thr Ser Gly
65                  70                  75                  80

Thr Leu Gly Ile Ala Leu Ala Glu Pro Val Asp Ile Pro Ala Val Ser
                85                  90                  95

Glu Gly Ser Met Gln Val Asp Ala Ser Lys Val His Pro Gly Val Ile
            100                 105                 110

Ser Gly Leu Asn Ser Pro Ala Cys Met Leu Ser Ala Pro Leu Glu Lys
        115                 120                 125

Gln Leu Phe Tyr Tyr Ile Gly Thr Met Leu Pro Asn Thr Arg Pro His
    130                 135                 140

Ser Tyr Val Phe Tyr Gln Leu Arg Cys His Leu Ser Tyr Val Ala Leu
145                 150                 155                 160

Ser Ile Asn Gly Asp Lys Phe Gln Tyr Thr Gly Ala Met Thr Ser Lys
                165                 170                 175

Phe Leu Met Gly Thr Tyr Lys Arg Val Thr Glu Lys Gly Asp Glu His
            180                 185                 190

Val Leu Ser Leu Val Phe Gly Lys Thr Lys Asp Leu Pro Asp Leu Arg
        195                 200                 205

Gly Pro Phe Ser Tyr Pro Ser Leu Thr Ser Ala Gln Ser Gly Asp Tyr
    210                 215                 220

Ser Leu Val Ile Val Thr Thr Phe Val His Tyr Ala Asn Phe His Asn
225                 230                 235                 240

Tyr Phe Val Pro Asn Leu Lys Asp Met Phe Ser Arg Ala Val Thr Met
                245                 250                 255

Thr Ala Ala Ser Tyr Ala Arg Tyr Val Leu Gln Lys Leu Val Leu Leu
            260                 265                 270

Glu Met Lys Gly Gly Cys Arg Glu Pro Glu Leu Asp Thr Glu Thr Leu
        275                 280                 285

Thr Thr Met Phe Glu Val Ser Val Ala Phe Phe Lys Val Gly His Ala
    290                 295                 300
```

-continued

```
Val Gly Glu Thr Gly Asn Gly Cys Val Asp Leu Arg Trp Leu Ala Lys
305                 310                 315                 320

Ser Phe Phe Glu Leu Thr Val Leu Lys Asp Ile Ile Gly Ile Cys Tyr
                325                 330                 335

Gly Ala Thr Val Lys Gly Met Gln Ser Tyr Gly Leu Glu Arg Leu Ala
            340                 345                 350

Ala Met Leu Met Ala Thr Val Lys Met Glu Glu Leu Gly His Leu Thr
        355                 360                 365

Thr Glu Lys Gln Glu Tyr Ala Leu Arg Leu Ala Thr Val Gly Tyr Pro
    370                 375                 380

Lys Ala Gly Val Tyr Ser Gly Leu Ile Gly Gly Ala Thr Ser Val Leu
385                 390                 395                 400

Leu Ser Ala Tyr Asn Arg His Pro Leu Phe Gln Pro Leu His Thr Val
                405                 410                 415

Met Arg Glu Thr Leu Phe Ile Gly Ser His Val Val Leu Arg Glu Leu
            420                 425                 430

Arg Leu Asn Val Thr Thr Gln Gly Pro Asn Leu Ala Leu Tyr Gln Leu
        435                 440                 445

Leu Ser Thr Ala Leu Cys Ser Ala Leu Glu Ile Gly Glu Val Leu Arg
    450                 455                 460

Gly Leu Ala Leu Gly Thr Glu Ser Gly Leu Phe Ser Pro Cys Tyr Leu
465                 470                 475                 480

Ser Leu Arg Phe Asp Leu Thr Arg Asp Lys Leu Leu Ser Met Ala Pro
                485                 490                 495

Gln Glu Ala Thr Leu Asp Gln Ala Ala Val Ser Asn Ala Val Asp Gly
            500                 505                 510

Phe Leu Gly Arg Leu Ser Leu Glu Arg Glu Asp Arg Asp Ala Trp His
        515                 520                 525

Leu Pro Ala Tyr Lys Cys Val Asp Arg Leu Asp Lys Val Leu Met Ile
    530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
                565                 570                 575

Leu Phe Leu Ser Pro Val Ile Met Asn Lys Cys Ser Gln Gly Ala Val
            580                 585                 590

Ala Gly Glu Pro Arg Gln Ile Pro Lys Ile Gln Asn Phe Thr Arg Thr
        595                 600                 605

Gln Lys Ser Cys Ile Phe Cys Gly Phe Ala Leu Leu Ser Tyr Asp Glu
    610                 615                 620

Lys Glu Gly Leu Glu Thr Thr Thr Tyr Ile Thr Ser Gln Glu Val Gln
625                 630                 635                 640

Asn Ser Ile Leu Ser Ser Asn Tyr Phe Asp Phe Asp Asn Leu His Val
                645                 650                 655

His Tyr Leu Leu Leu Thr Thr Asn Gly Thr Val Met Glu Ile Ala Gly
            660                 665                 670

Leu Tyr Glu Glu Arg Ala His Val Val Leu Ala Ile Ile Leu Tyr Phe
        675                 680                 685

Ile Ala Phe Ala Leu Gly Ile Phe Leu Val His Lys Ile Val Met Phe
    690                 695                 700

Phe Leu
705
```

<210> SEQ ID NO 63
<211> LENGTH: 2118
<212> TYPE: DNA
<213> ORGANISM: Epstein Barr Virus

<400> SEQUENCE: 63

```
cagaaagaac atcacgatct tatgcaccag aaaaatgccc agagcaaagg cgatgaaata     60
cagaatgata gccagcacca cgtgagccct ttcctcgtac agtccagcga tctccatcac    120
ggtgccgtta gttgtcagca gcagataatg cacgtgcagg ttatcaaagt cgaagtaatt    180
ggagctcagg atactgttct gcacttcctg agatgtaata taggtagttg tctccagccc    240
ttctttctca tcgtatgaca gcagggcaaa gccacagaag atgcaacttt tctgagtgcg    300
tgtgaagttc tgaatctttg ggatctgtct gggctctcca gccacagctc cctggctaca    360
cttattcata atcacaggtg acagaaacag tgaactagac agataggtag tggaagcttc    420
gtacagagcg ctgcctctca cttccctgtc ggagctaatg atgaaggtca cgttgatcag    480
gggaatgatc atcagcactt tatccaggcg gtccacgcac ttgtaagctg gcaggtgcca    540
ggcatcgcgg tcttccctct ccagggacag cctgcccagg aatccatcca cggcattgct    600
cacagcggcc tggtccaggg tagcttcctg tggggccatg ctcagcagct tatcgcgagt    660
caggtcaaac ctcagtgaca gataacaagg gctgaacagt cctgactcgg tccccagggc    720
cagtcccctc agcacttctc caatctccag agctgagcac agggcagtac tcaggagctg    780
gtacagggcc aggttgggtc cctgtgtggt cacattcagt ctcagttccc gcagcaccac    840
atgagacccg ataaacagag tctcgcgcat cactgtatgc aggggctgga acagtgggtg    900
cctattataa gcactcagca gcacagatgt ggcgcctcca atcagtccgg aatacacccc    960
ggcctttggg tatcccacgg tagccagcct cagagcgtat tcctgtttct cagttgtcag   1020
gtggcccagt tcctccatct tcacggtggc catcagcata gcggccagcc tctccaggcc   1080
atagctctgc attcctttca ctgtggcgcc gtaacagatt ccaatgatat ctttcagcac   1140
ggtcagttca aagaagctct tggccagcca tctcaggtcc acgcatccgt ttcctgtctc   1200
tcccacagcg tgtcccactt taaagaaggc cacggacacc tcgaacatgg tagtcagggt   1260
ttcagtgtcc agttcaggct cccggcaccc gcctttcatc tccagcagca ccagcttctg   1320
cagcacatat ctagcgtaag aagcggctgt catggtcacg gcccgggaaa acatatcctt   1380
cagattgggc acaaaataat tatggaagtt agcgtagtgc acgaatgtgg tcacgatcac   1440
caggctatag tcgcctgact gggcactagt cagagaaggg taggaaaagg gtcctctcag   1500
atcgggcagg tcttttgtct tcccgaacac cagagacagc acgtgttcat cgcctttctc   1560
ggtcacccgc ttgtaagttc ccatcagaaa tttggaagtc atagctcctg tatactggaa   1620
cttgtccccg ttaatagaca gggccacgta ggacagatga catctgagct gataaaacac   1680
gtagctgtgt ggccgtgtat taggcagcat ggtgccgata tagtagaaga gctgtttctc   1740
cagaggagcg ctcagcatgc aagctgggct gttcagtccg ctaatcaccc ctggatgcac   1800
cttactagca tccacctgca tgcttccttc tgacacggcg gggatgtcca ctggctcagc   1860
cagagcaatc cccagtgtgc cactggtttt atagatcagc ttgtatctgt tcagcataga   1920
ggccagatcc tcggtcacat tagcttcccg ccacagagcc tcaggagaca gtcctggcac   1980
tttagccatc agctcggtcc aagggatagt gtaatgggag gcgtggcctt caatgtccag   2040
gtgcagcttc acctcactca gagaagcggc tcccacttcc cacagcagca ccagacagaa   2100
cacgcacagg agctgcat                                                  2118
```

<210> SEQ ID NO 64
<211> LENGTH: 411
<212> TYPE: DNA
<213> ORGANISM: Epstein Barr Virus

<400> SEQUENCE: 64
atgcgggccg tgggggtgtt cctggctatc tgcctggtga ctatttttgt gctgccaacc 60
tggggaaact gggcttaccc ttgctgtcac gtgacccagc tcagggccca gcatctgctg 120
gctctggaga acatcagcga catttatctg gtgtccaatc agacatgcga tgggttcagc 180
ctggcctccc tgaacagccc caagaacgga tctaatcagc tcgtgatctc ccggtgtgct 240
aacggcctga atgtcgtgag tttctttatc tcaattctga aaaggagctc ctctgctctg 300
acaggacacc tgagggagct gctgaccaca ctggaaactc tgtacggaag tttctcagtg 360
gaagacctgt ttggcgccaa cctgaatcgg tatgcttggc atagaggcgg g 411

<210> SEQ ID NO 65
<211> LENGTH: 137
<212> TYPE: PRT
<213> ORGANISM: Epstein Barr Virus

<400> SEQUENCE: 65

Met Arg Ala Val Gly Val Phe Leu Ala Ile Cys Leu Val Thr Ile Phe
1 5 10 15

Val Leu Pro Thr Trp Gly Asn Trp Ala Tyr Pro Cys Cys His Val Thr
20 25 30

Gln Leu Arg Ala Gln His Leu Leu Ala Leu Glu Asn Ile Ser Asp Ile
35 40 45

Tyr Leu Val Ser Asn Gln Thr Cys Asp Gly Phe Ser Leu Ala Ser Leu
50 55 60

Asn Ser Pro Lys Asn Gly Ser Asn Gln Leu Val Ile Ser Arg Cys Ala
65 70 75 80

Asn Gly Leu Asn Val Val Ser Phe Phe Ile Ser Ile Leu Lys Arg Ser
85 90 95

Ser Ser Ala Leu Thr Gly His Leu Arg Glu Leu Leu Thr Thr Leu Glu
100 105 110

Thr Leu Tyr Gly Ser Phe Ser Val Glu Asp Leu Phe Gly Ala Asn Leu
115 120 125

Asn Arg Tyr Ala Trp His Arg Gly Gly
130 135

<210> SEQ ID NO 66
<211> LENGTH: 411
<212> TYPE: DNA
<213> ORGANISM: Epstein Barr Virus

<400> SEQUENCE: 66
cccgcctcta tgccaagcat accgattcag gttggcgcca aacaggtctt ccactgagaa 60
acttccgtac agagtttcca gtgtggtcag cagctccctc aggtgtcctg tcagagcaga 120
ggagctcctt ttcagaattg agataaagaa actcacgaca ttcaggccgt tagcacaccg 180
ggagatcacg agctgattag atccgttctt ggggctgttc agggaggcca ggctgaaccc 240
atcgcatgtc tgattggaca ccagataaat gtcgctgatg ttctccagag ccagcagatg 300
ctgggccctg agctgggtca cgtgacagca agggtaagcc cagtttcccc aggttggcag 360
cacaaaaata gtcaccaggc agatagccag gaacaccccc acggcccgca t 411

<210> SEQ ID NO 67
<211> LENGTH: 669
<212> TYPE: DNA
<213> ORGANISM: Epstein Barr Virus

<400> SEQUENCE: 67
atggtcagct tcaaacaagt gcgggtgccc ctgtttactg ccatcgctct ggtgattgtg 60
ctgctgctgg cctacttcct gccacctcgg gtcagaggag gaggaagagt ggccgctgcc 120
gctatcacct gggtgccaaa acctaatgtg gaagtgtggc ctgtggaccc accacctcca 180
gtgaacttta ataagacagc cgagcaggaa tatggcgata aagaagtgaa gctgcctcac 240
tggaccccaa cactgcatac attccaggtg ccacagaact acactaaagc taattgcact 300
tattgtaaca ccagggagta cacatttagt tataaggggt gctgtttcta ctttactaag 360
aaaaagcaca cctggaatgg atgcttccag gcctgtgctg aactgtatcc atgcacatac 420
ttttatggcc caactcccga catcctgccc gtggtgacca ggaacctgaa tgccattgag 480
tccctgtggg tgggagtgta cagggtggga gaaggcaact ggacctccct ggatggcggg 540
acattcaaag tgtaccagat tttggctct cattgcactt atgtgtctaa gttcagtacc 600
gtgcccgtgt cacaccatga gtgtagcttt ctgaagcctt gcctgtgtgt gtctcagaga 660
agcaactcc 669

<210> SEQ ID NO 68
<211> LENGTH: 223
<212> TYPE: PRT
<213> ORGANISM: Epstein Barr Virus

<400> SEQUENCE: 68

Met Val Ser Phe Lys Gln Val Arg Val Pro Leu Phe Thr Ala Ile Ala
1 5 10 15

Leu Val Ile Val Leu Leu Leu Ala Tyr Phe Leu Pro Pro Arg Val Arg
20 25 30

Gly Gly Gly Arg Val Ala Ala Ala Ala Ile Thr Trp Val Pro Lys Pro
35 40 45

Asn Val Glu Val Trp Pro Val Asp Pro Pro Pro Pro Val Asn Phe Asn
50 55 60

Lys Thr Ala Glu Gln Glu Tyr Gly Asp Lys Glu Val Lys Leu Pro His
65 70 75 80

Trp Thr Pro Thr Leu His Thr Phe Gln Val Pro Gln Asn Tyr Thr Lys
85 90 95

Ala Asn Cys Thr Tyr Cys Asn Thr Arg Glu Tyr Thr Phe Ser Tyr Lys
100 105 110

Gly Cys Cys Phe Tyr Phe Thr Lys Lys Lys His Thr Trp Asn Gly Cys
115 120 125

Phe Gln Ala Cys Ala Glu Leu Tyr Pro Cys Thr Tyr Phe Tyr Gly Pro
130 135 140

Thr Pro Asp Ile Leu Pro Val Val Thr Arg Asn Leu Asn Ala Ile Glu
145 150 155 160

Ser Leu Trp Val Gly Val Tyr Arg Val Gly Glu Gly Asn Trp Thr Ser
165 170 175

Leu Asp Gly Gly Thr Phe Lys Val Tyr Gln Ile Phe Gly Ser His Cys
180 185 190

Thr Tyr Val Ser Lys Phe Ser Thr Val Pro Val Ser His His Glu Cys
195 200 205

```
Ser Phe Leu Lys Pro Cys Leu Cys Val Ser Gln Arg Ser Asn Ser
    210                 215                 220

<210> SEQ ID NO 69
<211> LENGTH: 669
<212> TYPE: DNA
<213> ORGANISM: Epstein Barr Virus

<400> SEQUENCE: 69

ggagttgctt ctctgagaca cacacaggca aggcttcaga aagctacact catggtgtga     60

cacgggcacg gtactgaact tagacacata agtgcaatga gagccaaaaa tctggtacac    120

tttgaatgtc ccgccatcca gggaggtcca gttgccttct cccaccctgt acactcccac    180

ccacagggac tcaatggcat tcaggttcct ggtcaccacg ggcaggatgt cgggagttgg    240

gccataaaag tatgtgcatg gatacagttc agcacaggcc tggaagcatc cattccaggt    300

gtgctttttc ttagtaaagt agaaacagca ccccttataa ctaaatgtgt actccctggt    360

gttacaataa gtgcaattag ctttagtgta gttctgtggc acctggaatg tatgcagtgt    420

tggggtccag tgaggcagct tcacttcttt atcgccatat tcctgctcgg ctgtcttatt    480

aaagttcact ggaggtggtg ggtccacagg ccacacttcc acattaggtt ttggcaccca    540

ggtgatagcg gcagcggcca ctcttcctcc tcctctgacc cgaggtggca ggaagtaggc    600

cagcagcagc acaatcacca gagcgatggc agtaaacagg ggcacccgca cttgtttgaa    660

gctgaccat                                                             669

<210> SEQ ID NO 70
<211> LENGTH: 3093
<212> TYPE: DNA
<213> ORGANISM: Artificial Sequence
<220> FEATURE:
<223> OTHER INFORMATION: Synthetic

<400> SEQUENCE: 70

gaagccgccc tgctggtgtg ccagtacact attcagagcc tgattcatct gaccggggag     60

gaccctggat ttttcaatgt ggaaatccct gagttcccat tttaccccac ctgcaacgtc    120

tgtacagccg acgtgaacgt caccattaat ttcgatgtgg gcgggaagaa acaccagctg    180

gacctggatt ttggccagct gaccccacat acaaaagccg tgtatcagcc cagaggggct    240

ttcggaggca gcgagaacgc aacaaatctg tttctgctgg agctgctggg agcaggagaa    300

ctggctctga ccatgaggtc caagaaactg cccatcaatg tgaccacagg agaggaacag    360

caggtcagtc tggaatcagt ggacgtctac ttccaggatg tgtttggcac catgtggtgc    420

caccatgccg agatgcagaa tcctgtgtac ctgatccccg aaaccgtccc ttatattaag    480

tgggacaact gtaatagcac taacattacc gcagtggtcc gggcacaggg gctggacgtg    540

accctgccac tgtcactgcc cacaagcgcc caggatagca acttctccgt gaaaaccgag    600

atgctgggaa atgagatcga cattgaatgc atcatggagg atggagaaat tagccaggtg    660

ctgcctggcg ataacaagtt taatatcacc tgttccggct acgaatctca cgtcccaagt    720

gggggaatcc tgacatctac tagtcccgtg gccactccaa ttcccggaac cggctacgct    780

tatagcctga gactgacccc taggccagtc tcacgcttcc tgggcaacaa tagcattctg    840

tacgtgtttt attccggaaa cggaccaaag gcttctggag gggactattg catccagagt    900

aatattgtgt tctcagacga gatcccagcc agccaggata tgcccactaa cactaccgac    960

attacctacg tgggcgataa tgccacttat tccgtgccta tggtcacaag cgaagacgct   1020
```

-continued

```
aactccccaa atgtgaccgt cacagcattc tgggcctggc ccaacaatac tgagaccgat   1080

tttaagtgca aatggacact gacttcaggc acccctagcg ggtgtgaaaa catctctggc   1140

gccttcgcta gtaatcgaac ctttgatatt acagtgtccg gcctggggac tgccccaaaa   1200

accctgatca ttacccggac agctactaac gcaacaacta ccacacacaa agtgatcttc   1260

agcaaagctc ccgagtccac taccacatct cctaccctga acactaccgg gtttgccgac   1320

cccaatacaa ctaccggact gcctagctcc acccatgtgc caacaaacct gactgcacca   1380

gcatccaccg gacctacagt gtctactgcc gatgtcacca gtcccacacc tgccggaaca   1440

acttctggcg ctagtcccgt gaccccatca cccagccctt gggacaatgg gacagagagt   1500

aaggcccctg atatgacttc tagtacctca ccagtcacca caccaacccc caacgcaaca   1560

agccctactc cagccgtgac taccccccaca cctaatgcta ccagcccaac acccgcagtg   1620

acaactccta ccccaaacgc cacttcccca accctgggga agacatcacc cactagcgcc   1680

gtgaccacac ccacccctaa tgctacctct cctacactgg gaaaaacttc cccaacctct   1740

gcagtgacta ccccaacccc caacgccaca agccccactc tgggcaagac cagtcctaca   1800

tcagctgtca caactcctac cccaaatgca actgggccaa ccgtgggaga gacatccccc   1860

caggctaacg caacaaatca cactctggga ggcaccagtc ccacacctgt ggtcacctca   1920

cagcccaaga acgccacaag cgctgtgacc acaggccagc ataatatcac atcaagctcc   1980

acttctagta tgagcctgcg cccttcaagc aacccagaga cactgtcccc atctactagt   2040

gacaattcaa ccagccacat gcctctgctg acatctgcac atccaactgg gggagaaaac   2100

atcactcagg tcacccccgc ctccatttct acccaccatg tgtccacatc ctctccagca   2160

ccccgacctg gaactaccag ccaggcatcc ggaccaggaa atagttcaac cagcacaaag   2220

cctggcgagg tgaacgtcac aaaagggact ccccctcaga atgctacctc acctcaggca   2280

ccaagcggcc agaaaacagc tgtgcctact gtcacctcca caggcgggaa ggcaaactct   2340

acaactggag gcaaacacac cacagggcat ggagctcgca ctagcaccga accaactacc   2400

gactacgggg gagattccac aactccaagg cccagataca atgccaccac atatctgcca   2460

ccctctacca gctccaagct gcgacccaga tggacattca ctagtcctcc agtgactacc   2520

gcacaggcta cagtgccagt cccacctact tctcagccta gattttctaa cctgagttcc   2580

ggagagagcc aggtgaggca gaacttcaag cccgagatgg aggagaagct gaacgagcag   2640

atgaacctgg agctgtacag cagcctgctg taccagcaga tgagcgcctg gtgcagctac   2700

cacaccttcg agggcgccgc cgccttcctg aggaggcacg cccaggagga gatgacccac   2760

atgcagaggc tgttcgacta cctgaccgac accggcaacc tgcccaggat caacaccgtg   2820

gagagcccct tcgccgagta cagcagcctg gacgagctgt tccaggagac ctacaagcac   2880

gagcagctga tcacccagaa gatcaacgag ctggcccacg ccgccatgac caaccaggac   2940

taccccacct tcaacttcct gcagtggtac gtgagcgagc agcacgagga ggagaagctg   3000

ttcaagagca tcatcgacaa gctgagcctg gccggcaaga gcggcgaggg cctgtacttc   3060

atcgacaagg agctgagcac cctggacgga tcc                               3093
```

<210> SEQ ID NO 71
<211> LENGTH: 1031
<212> TYPE: PRT
<213> ORGANISM: Artificial Sequence
<220> FEATURE:
<223> OTHER INFORMATION: Synthetic

<400> SEQUENCE: 71

```
Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr Thr His
                405                 410                 415
```

```
Lys Val Ile Phe Ser Lys Ala Pro Glu Ser Thr Thr Thr Ser Pro Thr
            420                 425                 430

Leu Asn Thr Thr Gly Phe Ala Asp Pro Asn Thr Thr Thr Gly Leu Pro
        435                 440                 445

Ser Ser Thr His Val Pro Thr Asn Leu Thr Ala Pro Ala Ser Thr Gly
    450                 455                 460

Pro Thr Val Ser Thr Ala Asp Val Thr Ser Pro Thr Pro Ala Gly Thr
465                 470                 475                 480

Thr Ser Gly Ala Ser Pro Val Thr Pro Ser Pro Ser Pro Trp Asp Asn
                485                 490                 495

Gly Thr Glu Ser Lys Ala Pro Asp Met Thr Ser Ser Thr Ser Pro Val
            500                 505                 510

Thr Thr Pro Thr Pro Asn Ala Thr Ser Pro Thr Pro Ala Val Thr Thr
        515                 520                 525

Pro Thr Pro Asn Ala Thr Ser Pro Thr Pro Ala Val Thr Thr Pro Thr
    530                 535                 540

Pro Asn Ala Thr Ser Pro Thr Leu Gly Lys Thr Ser Pro Thr Ser Ala
545                 550                 555                 560

Val Thr Thr Pro Thr Pro Asn Ala Thr Ser Pro Thr Leu Gly Lys Thr
                565                 570                 575

Ser Pro Thr Ser Ala Val Thr Thr Pro Thr Pro Asn Ala Thr Ser Pro
            580                 585                 590

Thr Leu Gly Lys Thr Ser Pro Thr Ser Ala Val Thr Thr Pro Thr Pro
        595                 600                 605

Asn Ala Thr Gly Pro Thr Val Gly Glu Thr Ser Pro Gln Ala Asn Ala
    610                 615                 620

Thr Asn His Thr Leu Gly Gly Thr Ser Pro Thr Pro Val Val Thr Ser
625                 630                 635                 640

Gln Pro Lys Asn Ala Thr Ser Ala Val Thr Thr Gly Gln His Asn Ile
                645                 650                 655

Thr Ser Ser Ser Thr Ser Ser Met Ser Leu Arg Pro Ser Ser Asn Pro
            660                 665                 670

Glu Thr Leu Ser Pro Ser Thr Ser Asp Asn Ser Thr Ser His Met Pro
        675                 680                 685

Leu Leu Thr Ser Ala His Pro Thr Gly Gly Glu Asn Ile Thr Gln Val
    690                 695                 700

Thr Pro Ala Ser Ile Ser Thr His His Val Ser Thr Ser Ser Pro Ala
705                 710                 715                 720

Pro Arg Pro Gly Thr Thr Ser Gln Ala Ser Gly Pro Gly Asn Ser Ser
                725                 730                 735

Thr Ser Thr Lys Pro Gly Glu Val Asn Val Thr Lys Gly Thr Pro Pro
            740                 745                 750

Gln Asn Ala Thr Ser Pro Gln Ala Pro Ser Gly Gln Lys Thr Ala Val
        755                 760                 765

Pro Thr Val Thr Ser Thr Gly Gly Lys Ala Asn Ser Thr Thr Gly Gly
    770                 775                 780

Lys His Thr Thr Gly His Gly Ala Arg Thr Ser Thr Glu Pro Thr Thr
785                 790                 795                 800

Asp Tyr Gly Gly Asp Ser Thr Thr Pro Arg Pro Arg Tyr Asn Ala Thr
                805                 810                 815

Thr Tyr Leu Pro Pro Ser Thr Ser Ser Lys Leu Arg Pro Arg Trp Thr
            820                 825                 830
```

-continued

```
Phe Thr Ser Pro Pro Val Thr Thr Ala Gln Ala Thr Val Pro Val Pro
        835                 840                 845

Pro Thr Ser Gln Pro Arg Phe Ser Asn Leu Ser Ser Gly Glu Ser Gln
    850                 855                 860

Val Arg Gln Asn Phe Lys Pro Glu Met Glu Glu Lys Leu Asn Glu Gln
865                 870                 875                 880

Met Asn Leu Glu Leu Tyr Ser Ser Leu Leu Tyr Gln Gln Met Ser Ala
                885                 890                 895

Trp Cys Ser Tyr His Thr Phe Glu Gly Ala Ala Ala Phe Leu Arg Arg
            900                 905                 910

His Ala Gln Glu Glu Met Thr His Met Gln Arg Leu Phe Asp Tyr Leu
        915                 920                 925

Thr Asp Thr Gly Asn Leu Pro Arg Ile Asn Thr Val Glu Ser Pro Phe
    930                 935                 940

Ala Glu Tyr Ser Ser Leu Asp Glu Leu Phe Gln Glu Thr Tyr Lys His
945                 950                 955                 960

Glu Gln Leu Ile Thr Gln Lys Ile Asn Glu Leu Ala His Ala Ala Met
                965                 970                 975

Thr Asn Gln Asp Tyr Pro Thr Phe Asn Phe Leu Gln Trp Tyr Val Ser
            980                 985                 990

Glu Gln His Glu Glu Glu Lys Leu  Phe Lys Ser Ile Ile  Asp Lys Leu
        995                 1000                1005

Ser Leu  Ala Gly Lys Ser Gly  Glu Gly Leu Tyr Phe  Ile Asp Lys
    1010                 1015                 1020

Glu Leu  Ser Thr Leu Asp Gly  Ser
    1025                 1030
```

<210> SEQ ID NO 72
<211> LENGTH: 3093
<212> TYPE: DNA
<213> ORGANISM: Artificial Sequence
<220> FEATURE:
<223> OTHER INFORMATION: Synthetic

<400> SEQUENCE: 72

```
ggatccgtcc agggtgctca gctccttgtc gatgaagtac aggccctcgc cgctcttgcc     60

ggccaggctc agcttgtcga tgatgctctt gaacagcttc tcctcctcgt gctgctcgct    120

cacgtaccac tgcaggaagt tgaaggtggg gtagtcctgg ttggtcatgg cggcgtgggc    180

cagctcgttg atcttctggg tgatcagctg ctcgtgcttg taggtctcct ggaacagctc    240

gtccaggctg ctgtactcgg cgaaggggct ctccacggtg ttgatcctgg gcaggttgcc    300

ggtgtcggtc aggtagtcga acagcctctg catgtgggtc atctcctcct gggcgtgcct    360

cctcaggaag gcggcggcgc cctcgaaggt gtggtagctg caccaggcgc tcatctgctg    420

gtacagcagg ctgctgtaca gctccaggtt catctgctcg ttcagcttct cctccatctc    480

gggcttgaag ttctgcctca cctggctctc tccggaactc aggttagaaa atctaggctg    540

agaagtaggt gggactggca ctgtagcctg tgcggtagtc actggaggac tagtgaatgt    600

ccatctgggt cgcagcttgg agctggtaga gggtggcaga tatgtggtgg cattgtatct    660

gggccttgga gttgtggaat ctccccccgta gtcggtagtt ggttcggtgc tagtgcgagc    720

tccatgccct gtggtgtgtt tgcctccagt tgtagagttt gccttcccgc ctgtggaggt    780

gacagtaggc acagctgttt tctggccgct tggtgcctga ggtgaggtag cattctgagg    840

gggagtccct tttgtgacgt tcacctcgcc aggctttgtg ctggttgaac tatttcctgg    900
```

-continued

```
tccggatgcc tggctggtag ttccaggtcg gggtgctgga gaggatgtgg acacatggtg    960
ggtagaaatg gaggcggggg tgacctgagt gatgttttct cccccagttg gatgtgcaga   1020
tgtcagcaga ggcatgtggc tggttgaatt gtcactagta gatggggaca gtgtctctgg   1080
gttgcttgaa gggcgcaggc tcatactaga agtggagctt gatgtgatat tatgctggcc   1140
tgtggtcaca gcgcttgtgg cgttcttggg ctgtgaggtg accacaggtg tgggactggt   1200
gcctcccaga gtgtgatttg ttgcgttagc ctggggggat gtctctccca cggttggccc   1260
agttgcattt ggggtaggag ttgtgacagc tgatgtagga ctggtcttgc ccagagtggg   1320
gcttgtggcg ttgggggttg gggtagtcac tgcagaggtt ggggaagttt ttcccagtgt   1380
aggagaggta gcattagggg tgggtgtggt cacggcgcta gtgggtgatg tcttccccag   1440
ggttggggaa gtggcgtttg gggtaggagt tgtcactgcg ggtgttgggc tggtagcatt   1500
aggtgtgggg gtagtcacgg ctggagtagg gcttgttgcg ttgggggttg gtgtggtgac   1560
tggtgaggta ctagaagtca tatcaggggc cttactctct gtcccattgt cccaagggct   1620
gggtgatggg gtcacgggac tagcgccaga agttgttccg gcaggtgtgg gactggtgac   1680
atcggcagta gacactgtag gtccggtgga tgctggtgca gtcaggtttg ttggcacatg   1740
ggtggagcta ggcagtccgg tagttgtatt ggggtcggca aacccggtag tgttcagggt   1800
aggagatgtg gtagtggact cgggagcttt gctgaagatc actttgtgtg tggtagttgt   1860
tgcgttagta gctgtccggg taatgatcag ggtttttggg gcagtcccca ggccggacac   1920
tgtaatatca aaggttcgat tactagcgaa ggcgccagag atgttttcac acccgctagg   1980
ggtgcctgaa gtcagtgtcc atttgcactt aaaatcggtc tcagtattgt tgggccaggc   2040
ccagaatgct gtgacggtca catttgggga gttagcgtct tcgcttgtga ccataggcac   2100
ggaataagtg gcattatcgc ccacgtaggt aatgtcggta gtgttagtgg gcatatcctg   2160
gctggctggg atctcgtctg agaacacaat attactctgg atgcaatagt cccctccaga   2220
agcctttggt ccgtttccgg aataaaacac gtacagaatg ctattgttgc ccaggaagcg   2280
tgagactggc ctaggggtca gtctcaggct ataagcgtag ccggttccgg gaattggagt   2340
ggccacggga ctagtagatg tcaggattcc cccacttggg acgtgagatt cgtagccgga   2400
acaggtgata ttaaacttgt tatcgccagg cagcacctgg ctaatttctc catcctccat   2460
gatgcattca atgtcgatct catttcccag catctcggtt ttcacggaga agttgctatc   2520
ctgggcgctt gtgggcagtg acagtggcag ggtcacgtcc agcccctgtg cccggaccac   2580
tgcggtaatg ttagtgctat tacagttgtc ccacttaata taagggacgg tttcggggat   2640
caggtacaca ggattctgca tctcggcatg gtggcaccac atggtgccaa acacatcctg   2700
gaagtagacg tccactgatt ccagactgac ctgctgttcc tctcctgtgg tcacattgat   2760
gggcagtttc ttggacctca tggtcagagc cagttctcct gctcccagca gctccagcag   2820
aaacagattt gttgcgttct cgctgcctcc gaaagcccct ctgggctgat acacggcttt   2880
tgtatgtggg gtcagctggc caaaatccag gtccagctgg tgtttcttcc cgcccacatc   2940
gaaattaatg gtgacgttca cgtcggctgt acagacgttg caggtggggt aaaatgggaa   3000
ctcagggatt tccacattga aaaatccagg gtcctccccg gtcagatgaa tcaggctctg   3060
aatagtgtac tggcacacca gcagggcggc ttc                                3093
```

<210> SEQ ID NO 73
<211> LENGTH: 1923
<212> TYPE: DNA
<213> ORGANISM: Artificial Sequence -continued
<220> FEATURE:
<223> OTHER INFORMATION: Synthetic

<400> SEQUENCE: 73
gaagccgccc tgctggtgtg ccagtacact attcagagcc tgattcatct gaccggggag 60
gaccctggat ttttcaatgt ggaaatccct gagttcccat tttaccccac ctgcaacgtc 120
tgtacagccg acgtgaacgt caccattaat ttcgatgtgg gcgggaagaa acaccagctg 180
gacctggatt ttggccagct gaccccacat acaaaagccg tgtatcagcc cagaggggct 240
ttcggaggca gcgagaacgc aacaaatctg tttctgctgg agctgctggg agcaggagaa 300
ctggctctga ccatgaggtc caagaaactg cccatcaatg tgaccacagg agaggaacag 360
caggtcagtc tggaatcagt ggacgtctac ttccaggatg tgtttggcac catgtggtgc 420
caccatgccg agatgcagaa tcctgtgtac ctgatccccg aaaccgtccc ttatattaag 480
tgggacaact gtaatagcac taacattacc gcagtggtcc gggcacaggg gctggacgtg 540
accctgccac tgtcactgcc cacaagcgcc caggatagca acttctccgt gaaaaccgag 600
atgctgggaa atgagatcga cattgaatgc atcatggagg atggagaaat tagccaggtg 660
ctgcctggcg ataacaagtt taatatcacc tgttccggct acgaatctca cgtcccaagt 720
gggggaatcc tgacatctac tagtcccgtg gccactccaa ttcccggaac cggctacgct 780
tatagcctga gactgacccc taggccagtc tcacgcttcc tgggcaacaa tagcattctg 840
tacgtgtttt attccggaaa cggaccaaag gcttctggag ggactattg catccagagt 900 aatattgtgt tctcagacga gatcccagcc agccaggata tgcccactaa cactaccgac 960
attacctacg tgggcgataa tgccacttat tccgtgccta tggtcacaag cgaagacgct 1020
aactccccaa atgtgaccgt cacagcattc tgggcctggc ccaacaatac tgagaccgat 1080
tttaagtgca aatggacact gacttcaggc accccctagcg ggtgtgaaaa catctctggc 1140
gccttcgcta gtaatcgaac ctttgatatt acagtgtccg gcctggggac tgccccaaaa 1200
accctgatca ttacccggac agctactaac gcaacaacta ccacacacaa agtgatcttc 1260
agcaaagctc ccgagtccac taccacatct cctaccctga acactaccgg gtttgccgac 1320
cccaatacaa ctaccggact gcctagctcc acccatgtgc caacaaacct gactgcacca 1380
gcatccaccg gacctacagt gtctacttcc ggagagagcc aggtgaggca gaacttcaag 1440
cccgagatgg aggagaagct gaacgagcag atgaacctgg agctgtacag cagcctgctg 1500
taccagcaga tgagcgcctg gtgcagctac cacaccttcg agggcgccgc cgccttcctg 1560
aggaggcacg cccaggagga gatgacccac atgcagaggc tgttcgacta cctgaccgac 1620
accggcaacc tgcccaggat caacaccgtg gagagcccct tcgccgagta cagcagcctg 1680
gacgagctgt tccaggagac ctacaagcac gagcagctga tcacccagaa gatcaacgag 1740
ctggcccacg ccgccatgac caaccaggac taccccacct tcaacttcct gcagtggtac 1800
gtgagcgagc agcacgagga ggagaagctg ttcaagagca tcatcgacaa gctgagcctg 1860
gccggcaaga gcggcgaggg cctgtacttc atcgacaagg agctgagcac cctggacgga 1920
tcc 1923

<210> SEQ ID NO 74
<211> LENGTH: 641
<212> TYPE: PRT
<213> ORGANISM: Artificial Sequence
<220> FEATURE:
<223> OTHER INFORMATION: Synthetic

<400> SEQUENCE: 74

Glu Ala Ala Leu Leu Val Cys Gln Tyr Thr Ile Gln Ser Leu Ile His
1 5 10 15

Leu Thr Gly Glu Asp Pro Gly Phe Phe Asn Val Glu Ile Pro Glu Phe
20 25 30

Pro Phe Tyr Pro Thr Cys Asn Val Cys Thr Ala Asp Val Asn Val Thr
35 40 45

Ile Asn Phe Asp Val Gly Gly Lys Lys His Gln Leu Asp Leu Asp Phe
50 55 60

Gly Gln Leu Thr Pro His Thr Lys Ala Val Tyr Gln Pro Arg Gly Ala
65 70 75 80

Phe Gly Gly Ser Glu Asn Ala Thr Asn Leu Phe Leu Leu Glu Leu Leu
85 90 95

Gly Ala Gly Glu Leu Ala Leu Thr Met Arg Ser Lys Lys Leu Pro Ile
100 105 110

Asn Val Thr Thr Gly Glu Glu Gln Gln Val Ser Leu Glu Ser Val Asp
115 120 125

Val Tyr Phe Gln Asp Val Phe Gly Thr Met Trp Cys His His Ala Glu
130 135 140

Met Gln Asn Pro Val Tyr Leu Ile Pro Glu Thr Val Pro Tyr Ile Lys
145 150 155 160

Trp Asp Asn Cys Asn Ser Thr Asn Ile Thr Ala Val Val Arg Ala Gln
165 170 175

Gly Leu Asp Val Thr Leu Pro Leu Ser Leu Pro Thr Ser Ala Gln Asp
180 185 190

Ser Asn Phe Ser Val Lys Thr Glu Met Leu Gly Asn Glu Ile Asp Ile
195 200 205

Glu Cys Ile Met Glu Asp Gly Glu Ile Ser Gln Val Leu Pro Gly Asp
210 215 220

Asn Lys Phe Asn Ile Thr Cys Ser Gly Tyr Glu Ser His Val Pro Ser
225 230 235 240

Gly Gly Ile Leu Thr Ser Thr Ser Pro Val Ala Thr Pro Ile Pro Gly
245 250 255

Thr Gly Tyr Ala Tyr Ser Leu Arg Leu Thr Pro Arg Pro Val Ser Arg
260 265 270

Phe Leu Gly Asn Asn Ser Ile Leu Tyr Val Phe Tyr Ser Gly Asn Gly
275 280 285

Pro Lys Ala Ser Gly Gly Asp Tyr Cys Ile Gln Ser Asn Ile Val Phe
290 295 300

Ser Asp Glu Ile Pro Ala Ser Gln Asp Met Pro Thr Asn Thr Thr Asp
305 310 315 320

Ile Thr Tyr Val Gly Asp Asn Ala Thr Tyr Ser Val Pro Met Val Thr
325 330 335

Ser Glu Asp Ala Asn Ser Pro Asn Val Thr Val Thr Ala Phe Trp Ala
340 345 350

Trp Pro Asn Asn Thr Glu Thr Asp Phe Lys Cys Lys Trp Thr Leu Thr
355 360 365

Ser Gly Thr Pro Ser Gly Cys Glu Asn Ile Ser Gly Ala Phe Ala Ser
370 375 380

Asn Arg Thr Phe Asp Ile Thr Val Ser Gly Leu Gly Thr Ala Pro Lys
385 390 395 400

Thr Leu Ile Ile Thr Arg Thr Ala Thr Asn Ala Thr Thr Thr Thr His
405 410 415

```
Lys Val Ile Phe Ser Lys Ala Pro Glu Ser Thr Thr Thr Ser Pro Thr
            420                 425                 430

Leu Asn Thr Thr Gly Phe Ala Asp Pro Asn Thr Thr Thr Gly Leu Pro
        435                 440                 445

Ser Ser Thr His Val Pro Thr Asn Leu Thr Ala Pro Ala Ser Thr Gly
    450                 455                 460

Pro Thr Val Ser Thr Ser Gly Glu Ser Gln Val Arg Gln Asn Phe Lys
465                 470                 475                 480

Pro Glu Met Glu Glu Lys Leu Asn Glu Gln Met Asn Leu Glu Leu Tyr
                485                 490                 495

Ser Ser Leu Leu Tyr Gln Gln Met Ser Ala Trp Cys Ser Tyr His Thr
            500                 505                 510

Phe Glu Gly Ala Ala Ala Phe Leu Arg Arg His Ala Gln Glu Glu Met
        515                 520                 525

Thr His Met Gln Arg Leu Phe Asp Tyr Leu Thr Asp Thr Gly Asn Leu
    530                 535                 540

Pro Arg Ile Asn Thr Val Glu Ser Pro Phe Ala Glu Tyr Ser Ser Leu
545                 550                 555                 560

Asp Glu Leu Phe Gln Glu Thr Tyr Lys His Glu Gln Leu Ile Thr Gln
                565                 570                 575

Lys Ile Asn Glu Leu Ala His Ala Ala Met Thr Asn Gln Asp Tyr Pro
            580                 585                 590

Thr Phe Asn Phe Leu Gln Trp Tyr Val Ser Glu Gln His Glu Glu Glu
        595                 600                 605

Lys Leu Phe Lys Ser Ile Ile Asp Lys Leu Ser Leu Ala Gly Lys Ser
    610                 615                 620

Gly Glu Gly Leu Tyr Phe Ile Asp Lys Glu Leu Ser Thr Leu Asp Gly
625                 630                 635                 640

Ser
```

<210> SEQ ID NO 75
<211> LENGTH: 1923
<212> TYPE: DNA
<213> ORGANISM: Artificial Sequence
<220> FEATURE:
<223> OTHER INFORMATION: Synthetic

<400> SEQUENCE: 75

```
ggatccgtcc agggtgctca gctccttgtc gatgaagtac aggccctcgc cgctcttgcc      60

ggccaggctc agcttgtcga tgatgctctt gaacagcttc tcctcctcgt gctgctcgct     120

cacgtaccac tgcaggaagt tgaaggtggg gtagtcctgg ttggtcatgg cggcgtgggc     180

cagctcgttg atcttctggg tgatcagctg ctcgtgcttg taggtctcct ggaacagctc     240

gtccaggctg ctgtactcgg cgaaggggct ctccacggtg ttgatcctgg gcaggttgcc     300

ggtgtcggtc aggtagtcga acagcctctg catgtgggtc atctcctcct gggcgtgcct     360

cctcaggaag gcggcggcgc cctcgaaggt gtggtagctg caccaggcgc tcatctgctg     420

gtacagcagg ctgctgtaca gctccaggtt catctgctcg ttcagcttct cctccatctc     480

gggcttgaag ttctgcctca cctggctctc tccggaagta gacactgtag gtccggtgga     540

tgctggtgca gtcaggtttg ttggcacatg ggtggagcta ggcagtccgg tagttgtatt     600

ggggtcggca aacccggtag tgttcagggt aggagatgtg gtagtggact cgggagcttt     660

gctgaagatc actttgtgtg tggtagttgt tgcgttagta gctgtccggg taatgatcag     720
```

ggtttttggg gcagtcccca ggccggacac tgtaatatca aaggttcgat tactagcgaa 780
ggcgccagag atgttttcac acccgctagg ggtgcctgaa gtcagtgtcc atttgcactt 840
aaaatcggtc tcagtattgt tgggccaggc ccagaatgct gtgacggtca catttgggga 900
gttagcgtct tcgcttgtga ccataggcac ggaataagtg gcattatcgc ccacgtaggt 960
aatgtcggta gtgttagtgg gcatatcctg gctggctggg atctcgtctg agaacacaat 1020
attactctgg atgcaatagt cccctccaga agcctttggt ccgtttccgg aataaaacac 1080
gtacagaatg ctattgttgc ccaggaagcg tgagactggc ctaggggtca gtctcaggct 1140
ataagcgtag ccggttccgg gaattggagt ggccacggga ctagtagatg tcaggattcc 1200
cccacttggg acgtgagatt cgtagccgga acaggtgata ttaaacttgt tatcgccagg 1260
cagcacctgg ctaatttctc catcctccat gatgcattca atgtcgatct catttcccag 1320
catctcggtt ttcacggaga agttgctatc ctgggcgctt gtgggcagtg acagtggcag 1380
ggtcacgtcc agcccctgtg cccggaccac tgcggtaatg ttagtgctat tacagttgtc 1440
ccacttaata taagggacgg tttcggggat caggtacaca ggattctgca tctcggcatg 1500
gtggcaccac atggtgccaa acacatcctg gaagtagacg tccactgatt ccagactgac 1560
ctgctgttcc tctcctgtgg tcacattgat gggcagtttc ttggacctca tggtcagagc 1620
cagttctcct gctcccagca gctccagcag aaacagattt gttgcgttct cgctgcctcc 1680
gaaagcccct ctgggctgat acacggcttt tgtatgtggg gtcagctggc caaaatccag 1740
gtccagctgg tgtttcttcc cgcccacatc gaaattaatg gtgacgttca cgtcggctgt 1800
acagacgttg caggtggggt aaaatgggaa ctcagggatt tccacattga aaaatccagg 1860
gtcctccccg gtcagatgaa tcaggctctg aatagtgtac tggcacacca gcagggcggc 1920
ttc 1923

<210> SEQ ID NO 76
<211> LENGTH: 1464
<212> TYPE: DNA
<213> ORGANISM: Artificial Sequence
<220> FEATURE:
<223> OTHER INFORMATION: Synthetic

<400> SEQUENCE: 76
gaagccgccc tgctggtgtg ccagtacact attcagagcc tgattcatct gaccggggag 60
gaccctggat tttcaatgt ggaaatccct gagttcccat tttaccccac ctgcaacgtc 120
tgtacagccg acgtgaacgt caccattaat ttcgatgtgg gcgggaagaa acaccagctg 180
gacctggatt ttggccagct gaccccacat acaaaagccg tgtatcagcc cagaggggct 240
ttcggaggca gcgagaacgc aacaaatctg tttctgctgg agctgctggg agcaggagaa 300
ctggctctga ccatgaggtc caagaaactg cccatcaatg tgaccacagg agaggaacag 360
caggtcagtc tggaatcagt ggacgtctac ttccaggatg tgtttggcac catgtggtgc 420
caccatgccg agatgcagaa tcctgtgtac ctgatccccg aaaccgtccc ttatattaag 480
tgggacaact gtaatagcac taacattacc gcagtggtcc gggcacaggg gctggacgtg 540
accctgccac tgtcactgcc cacaagcgcc caggatagca acttctccgt gaaaaccgag 600
atgctgggaa atgagatcga cattgaatgc atcatggagg atggagaaat tagccaggtg 660
ctgcctggcg ataacaagtt taatatcacc tgttccggct acgaatctca cgtcccaagt 720
gggggaatcc tgacatctac tagtcccgtg gccactccaa ttcccggaac cggctacgct 780
tatagcctga gactgacccc taggccagtc tcacgcttcc tgggcaacaa tagcattctg 840

```
tacgtgtttt attccggaaa cggaccaaag gcttctggag gggactattg catccagagt     900

aatattgtgt tctcagacga gatcccagcc agccaggata tgcccacttc cggagagagc     960

caggtgaggc agaacttcaa gcccgagatg gaggagaagc tgaacgagca gatgaacctg    1020

gagctgtaca gcagcctgct gtaccagcag atgagcgcct ggtgcagcta ccacaccttc    1080

gagggcgccg ccgccttcct gaggaggcac gcccaggagg agatgaccca catgcagagg    1140

ctgttcgact acctgaccga caccggcaac ctgcccagga tcaacaccgt ggagagcccc    1200

ttcgccgagt acagcagcct ggacgagctg ttccaggaga cctacaagca cgagcagctg    1260

atcacccaga agatcaacga gctggcccac gccgccatga ccaaccagga ctaccccacc    1320

ttcaacttcc tgcagtggta cgtgagcgag cagcacgagg aggagaagct gttcaagagc    1380

atcatcgaca agctgagcct ggccggcaag agcggcgagg gcctgtactt catcgacaag    1440

gagctgagca ccctggacgg atcc                                           1464
```

```
<210> SEQ ID NO 77
<211> LENGTH: 488
<212> TYPE: PRT
<213> ORGANISM: Artificial Sequence
<220> FEATURE:
<223> OTHER INFORMATION: Synthetic

<400> SEQUENCE: 77

Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
```

```
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr Ser Gly Glu Ser
305                 310                 315                 320

Gln Val Arg Gln Asn Phe Lys Pro Glu Met Glu Glu Lys Leu Asn Glu
                325                 330                 335

Gln Met Asn Leu Glu Leu Tyr Ser Ser Leu Leu Tyr Gln Gln Met Ser
            340                 345                 350

Ala Trp Cys Ser Tyr His Thr Phe Glu Gly Ala Ala Ala Phe Leu Arg
        355                 360                 365

Arg His Ala Gln Glu Glu Met Thr His Met Gln Arg Leu Phe Asp Tyr
    370                 375                 380

Leu Thr Asp Thr Gly Asn Leu Pro Arg Ile Asn Thr Val Glu Ser Pro
385                 390                 395                 400

Phe Ala Glu Tyr Ser Ser Leu Asp Glu Leu Phe Gln Glu Thr Tyr Lys
                405                 410                 415

His Glu Gln Leu Ile Thr Gln Lys Ile Asn Glu Leu Ala His Ala Ala
            420                 425                 430

Met Thr Asn Gln Asp Tyr Pro Thr Phe Asn Phe Leu Gln Trp Tyr Val
        435                 440                 445

Ser Glu Gln His Glu Glu Glu Lys Leu Phe Lys Ser Ile Ile Asp Lys
    450                 455                 460

Leu Ser Leu Ala Gly Lys Ser Gly Glu Gly Leu Tyr Phe Ile Asp Lys
465                 470                 475                 480

Glu Leu Ser Thr Leu Asp Gly Ser
                485


<210> SEQ ID NO 78
<211> LENGTH: 1464
<212> TYPE: DNA
<213> ORGANISM: Artificial Sequence
<220> FEATURE:
<223> OTHER INFORMATION: Synthetic

<400> SEQUENCE: 78

ggatccgtcc agggtgctca gctccttgtc gatgaagtac aggccctcgc cgctcttgcc     60

ggccaggctc agcttgtcga tgatgctctt gaacagcttc tcctcctcgt gctgctcgct    120

cacgtaccac tgcaggaagt tgaaggtggg gtagtcctgg ttggtcatgg cggcgtgggc    180

cagctcgttg atcttctggg tgatcagctg ctcgtgcttg taggtctcct ggaacagctc    240

gtccaggctg ctgtactcgg cgaaggggct ctccacggtg ttgatcctgg gcaggttgcc    300

ggtgtcggtc aggtagtcga acagcctctg catgtgggtc atctcctcct gggcgtgcct    360

cctcaggaag gcggcggcgc cctcgaaggt gtggtagctg caccaggcgc tcatctgctg    420

gtacagcagg ctgctgtaca gctccaggtt catctgctcg ttcagcttct cctccatctc    480

gggcttgaag ttctgcctca cctggctctc tccggaagtg ggcatatcct ggctggctgg    540

gatctcgtct gagaacacaa tattactctg gatgcaatag tcccctccag aagcctttgg    600

tccgtttccg gaataaaaca cgtacagaat gctattgttg cccaggaagc gtgagactgg    660
```

```
cctaggggtc agtctcaggc tataagcgta gccggttccg ggaattggag tggccacggg    720

actagtagat gtcaggattc ccccacttgg gacgtgagat tcgtagccgg aacaggtgat    780

attaaacttg ttatcgccag gcagcacctg gctaatttct ccatcctcca tgatgcattc    840

aatgtcgatc tcatttccca gcatctcggt tttcacggag aagttgctat cctgggcgct    900

tgtgggcagt gacagtggca gggtcacgtc cagcccctgt gcccggacca ctgcggtaat    960

gttagtgcta ttacagttgt cccacttaat ataagggacg gtttcgggga tcaggtacac   1020

aggattctgc atctcggcat ggtggcacca catggtgcca aacacatcct ggaagtagac   1080

gtccactgat tccagactga cctgctgttc ctctcctgtg gtcacattga tgggcagttt   1140

cttggacctc atggtcagag ccagttctcc tgctcccagc agctccagca gaaacagatt   1200

tgttgcgttc tcgctgcctc cgaaagcccc tctgggctga tacacggctt ttgtatgtgg   1260

ggtcagctgg ccaaaatcca ggtccagctg gtgtttcttc ccgcccacat cgaaattaat   1320

ggtgacgttc acgtcggctg tacagacgtt gcaggtgggg taaaatggga actcagggat   1380

ttccacattg aaaaatccag ggtcctcccc ggtcagatga atcaggctct gaatagtgta   1440

ctggcacacc agcagggcgg cttc                                           1464
```

```
<210> SEQ ID NO 79
<211> LENGTH: 1788
<212> TYPE: DNA
<213> ORGANISM: Artificial Sequence
<220> FEATURE:
<223> OTHER INFORMATION: Synthetic

<400> SEQUENCE: 79
```

```
gaagccgccc tgctggtgtg ccagtacact attcagagcc tgattcatct gaccggggag     60

gaccctggat ttttcaatgt ggaaatccct gagttcccat tttaccccac ctgcaacgtc    120

tgtacagccg acgtgaacgt caccattaat ttcgatgtgg gcgggaagaa acaccagctg    180

gacctggatt ttggccagct gaccccacat acaaaagccg tgtatcagcc cagaggggct    240

ttcggaggca gcgagaacgc aacaaatctg tttctgctgg agctgctggg agcaggagaa    300

ctggctctga ccatgaggtc caagaaactg cccatcaatg tgaccacagg agaggaacag    360

caggtcagtc tggaatcagt ggacgtctac ttccaggatg tgtttggcac catgtggtgc    420

caccatgccg agatgcagaa tcctgtgtac ctgatccccg aaaccgtccc ttatattaag    480

tgggacaact gtaatagcac taacattacc gcagtggtcc gggcacaggg gctggacgtg    540

accctgccac tgtcactgcc cacaagcgcc caggatagca acttctccgt gaaaaccgag    600

atgctgggaa atgagatcga cattgaatgc atcatggagg atggagaaat tagccaggtg    660

ctgcctggcg ataacaagtt taatatcacc tgttccggct acgaatctca cgtcccaagt    720

gggggaatcc tgacatctac tagtcccgtg gccactccaa ttcccggaac cggctacgct    780

tatagcctga gactgacccc taggccagtc tcacgcttcc tgggcaacaa tagcattctg    840

tacgtgtttt attccggaaa cggaccaaag gcttctggag gggactattg catccagagt    900

aatattgtgt tctcagacga gatcccagcc agccaggata tgcccactaa cactaccgac    960

attacctacg tgggcgataa tgccacttat tccgtgccta tggtcacaag cgaagacgct   1020

aactccccaa atgtgaccgt cacagcattc tgggcctggc ccaacaatac tgagaccgat   1080

tttaagtgca aatggacact gacttcaggc accccctagcg ggtgtgaaaa catctctggc  1140

gccttcgcta gtaatcgaac ctttgatatt acagtgtccg gcctggggac tgccccaaaa   1200

accctgatca ttacccggac agctactaac gcaacaacta ccacacacaa agtgatcttc   1260
```

```
agcaaagctc cctccggaga gagccaggtg aggcagaact tcaagcccga gatggaggag   1320

aagctgaacg agcagatgaa cctggagctg tacagcagcc tgctgtacca gcagatgagc   1380

gcctggtgca gctaccacac cttcgagggc gccgccgcct tcctgaggag gcacgcccag   1440

gaggagatga cccacatgca gaggctgttc gactacctga ccgacaccgg caacctgccc   1500

aggatcaaca ccgtggagag ccccttcgcc gagtacagca gcctggacga gctgttccag   1560

gagacctaca agcacgagca gctgatcacc cagaagatca acgagctggc ccacgccgcc   1620

atgaccaacc aggactaccc caccttcaac ttcctgcagt ggtacgtgag cgagcagcac   1680

gaggaggaga agctgttcaa gagcatcatc gacaagctga gcctggccgg caagagcggc   1740

gagggcctgt acttcatcga caaggagctg agcaccctgg acggatcc                 1788
```

```
<210> SEQ ID NO 80
<211> LENGTH: 596
<212> TYPE: PRT
<213> ORGANISM: Artificial Sequence
<220> FEATURE:
<223> OTHER INFORMATION: Synthetic

<400> SEQUENCE: 80

Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270
```

```
Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr Thr His
                405                 410                 415

Lys Val Ile Phe Ser Lys Ala Pro Ser Gly Glu Ser Gln Val Arg Gln
            420                 425                 430

Asn Phe Lys Pro Glu Met Glu Glu Lys Leu Asn Glu Gln Met Asn Leu
        435                 440                 445

Glu Leu Tyr Ser Ser Leu Leu Tyr Gln Gln Met Ser Ala Trp Cys Ser
    450                 455                 460

Tyr His Thr Phe Glu Gly Ala Ala Ala Phe Leu Arg Arg His Ala Gln
465                 470                 475                 480

Glu Glu Met Thr His Met Gln Arg Leu Phe Asp Tyr Leu Thr Asp Thr
                485                 490                 495

Gly Asn Leu Pro Arg Ile Asn Thr Val Glu Ser Pro Phe Ala Glu Tyr
            500                 505                 510

Ser Ser Leu Asp Glu Leu Phe Gln Glu Thr Tyr Lys His Glu Gln Leu
        515                 520                 525

Ile Thr Gln Lys Ile Asn Glu Leu Ala His Ala Ala Met Thr Asn Gln
    530                 535                 540

Asp Tyr Pro Thr Phe Asn Phe Leu Gln Trp Tyr Val Ser Glu Gln His
545                 550                 555                 560

Glu Glu Glu Lys Leu Phe Lys Ser Ile Ile Asp Lys Leu Ser Leu Ala
                565                 570                 575

Gly Lys Ser Gly Glu Gly Leu Tyr Phe Ile Asp Lys Glu Leu Ser Thr
            580                 585                 590

Leu Asp Gly Ser
        595
```

<210> SEQ ID NO 81
<211> LENGTH: 1788
<212> TYPE: DNA
<213> ORGANISM: Artificial Sequence
<220> FEATURE:
<223> OTHER INFORMATION: Synthetic

<400> SEQUENCE: 81

```
ggatccgtcc agggtgctca gctccttgtc gatgaagtac aggccctcgc cgctcttgcc      60

ggccaggctc agcttgtcga tgatgctctt gaacagcttc tcctcctcgt gctgctcgct     120

cacgtaccac tgcaggaagt tgaaggtggg gtagtcctgg ttggtcatgg cggcgtgggc     180
```

```
cagctcgttg atcttctggg tgatcagctg ctcgtgcttg taggtctcct ggaacagctc    240
gtccaggctg ctgtactcgg cgaaggggct ctccacggtg ttgatcctgg gcaggttgcc    300
ggtgtcggtc aggtagtcga acagcctctg catgtgggtc atctcctcct gggcgtgcct    360
cctcaggaag gcggcggcgc cctcgaaggt gtggtagctg caccaggcgc tcatctgctg    420
gtacagcagg ctgctgtaca gctccaggtt catctgctcg ttcagcttct cctccatctc    480
gggcttgaag ttctgcctca cctggctctc tccggaggga gctttgctga agatcacttt    540
gtgtgtggta gttgttgcgt tagtagctgt ccgggtaatg atcagggttt ttggggcagt    600
ccccaggccg gacactgtaa tatcaaaggt tcgattacta gcgaaggcgc cagagatgtt    660
ttcacacccg ctaggggtgc ctgaagtcag tgtccatttg cacttaaaat cggtctcagt    720
attgttgggc caggcccaga atgctgtgac ggtcacattt ggggagttag cgtcttcgct    780
tgtgaccata ggcacggaat aagtggcatt atcgcccacg taggtaatgt cggtagtgtt    840
agtgggcata tcctggctgg ctgggatctc gtctgagaac acaatattac tctggatgca    900
atagtcccct ccagaagcct ttggtccgtt tccggaataa aacacgtaca gaatgctatt    960
gttgcccagg aagcgtgaga ctggcctagg ggtcagtctc aggctataag cgtagccggt   1020
tccgggaatt ggagtggcca cgggactagt agatgtcagg attcccccac ttgggacgtg   1080
agattcgtag ccggaacagg tgatattaaa cttgttatcg ccaggcagca cctggctaat   1140
ttctccatcc tccatgatgc attcaatgtc gatctcattt cccagcatct cggttttcac   1200
ggagaagttg ctatcctggg cgcttgtggg cagtgacagt ggcagggtca cgtccagccc   1260
ctgtgcccgg accactgcgg taatgttagt gctattacag ttgtcccact taatataagg   1320
gacggtttcg gggatcaggt acacaggatt ctgcatctcg gcatggtggc accacatggt   1380
gccaaacaca tcctggaagt agacgtccac tgattccaga ctgacctgct gttcctctcc   1440
tgtggtcaca ttgatgggca gtttcttgga cctcatggtc agagccagtt ctcctgctcc   1500
cagcagctcc agcagaaaca gatttgttgc gttctcgctg cctccgaaag cccctctggg   1560
ctgatacacg gcttttgtat gtggggtcag ctggccaaaa tccaggtcca gctggtgttt   1620
cttcccgccc acatcgaaat taatggtgac gttcacgtcg gctgtacaga cgttgcaggt   1680
ggggtaaaat gggaactcag ggatttccac attgaaaaat ccagggtcct ccccggtcag   1740
atgaatcagg ctctgaatag tgtactggca caccagcagg gcggcttc                1788
```

<210> SEQ ID NO 82
<211> LENGTH: 3108
<212> TYPE: DNA
<213> ORGANISM: Artificial Sequence
<220> FEATURE:
<223> OTHER INFORMATION: Synthetic

<400> SEQUENCE: 82

```
gaagccgccc tgctggtgtg ccagtacact attcagagcc tgattcatct gaccggggag     60
gaccctggat ttttcaatgt ggaaatccct gagttcccat ttaccccac ctgcaacgtc     120
tgtacagccg acgtgaacgt caccattaat ttcgatgtgg gcgggaagaa acaccagctg    180
gacctggatt ttggccagct gaccccacat acaaaagccg tgtatcagcc cagaggggct    240
ttcggaggca gcgagaacgc aacaaatctg tttctgctgg agctgctggg agcaggagaa    300
ctggctctga ccatgaggtc caagaaactg cccatcaatg tgaccacagg agaggaacag    360
caggtcagtc tggaatcagt ggacgtctac ttccaggatg tgtttggcac catgtggtgc    420
```

-continued

```
caccatgccg agatgcagaa tcctgtgtac ctgatccccg aaaccgtccc ttatattaag    480
tgggacaact gtaatagcac taacattacc gcagtggtcc gggcacaggg gctggacgtg    540
accctgccac tgtcactgcc cacaagcgcc caggatagca acttctccgt gaaaaccgag    600
atgctgggaa atgagatcga cattgaatgc atcatggagg atggagaaat tagccaggtg    660
ctgcctggcg ataacaagtt taatatcacc tgttccggct acgaatctca cgtcccaagt    720
gggggaatcc tgacatctac tagtcccgtg gccactccaa ttcccggaac cggctacgct    780
tatagcctga gactgacccc taggccagtc tcacgcttcc tgggcaacaa tagcattctg    840
tacgtgtttt attccggaaa cggaccaaag gcttctggag ggactattg catccagagt     900
aatattgtgt tctcagacga gatcccagcc agccaggata tgcccactaa cactaccgac    960
attacctacg tgggcgataa tgccacttat tccgtgccta tggtcacaag cgaagacgct   1020
aactccccaa atgtgaccgt cacagcattc tgggcctggc ccaacaatac tgagaccgat   1080
tttaagtgca aatggacact gacttcaggc accccctagcg ggtgtgaaaa catctctggc  1140
gccttcgcta gtaatcgaac ctttgatatt acagtgtccg gcctggggac tgccccaaaa   1200
accctgatca ttacccggac agctactaac gcaacaacta ccacacacaa agtgatcttc   1260
agcaaagctc ccgagtccac taccacatct cctaccctga acactaccgg gtttgccgac   1320
cccaatacaa ctaccggact gcctagctcc acccatgtgc caacaaacct gactgcacca   1380
gcatccaccg gacctacagt gtctactgcc gatgtcacca gtcccacacc tgccggaaca   1440
acttctggcg ctagtcccgt gaccccatca cccagccctt gggacaatgg gacagagagt   1500
aaggcccctg atatgacttc tagtacctca ccagtcacca caccaacccc caacgcaaca   1560
agccctactc cagccgtgac tacccccaca cctaatgcta ccagcccaac acccgcagtg   1620
acaactccta ccccaaacgc cacttcccca accctgggga agacatcacc cactagcgcc   1680
gtgaccacac ccacccctaa tgctacctct cctacactgg gaaaaacttc cccaacctct   1740
gcagtgacta ccccaacccc caacgccaca agccccactc tgggcaagac cagtcctaca   1800
tcagctgtca caactcctac cccaaatgca actgggccaa ccgtgggaga gacatccccc   1860
caggctaacg caacaaatca cactctggga ggcaccagtc ccacacctgt ggtcacctca   1920
cagcccaaga acgccacaag cgctgtgacc acaggccagc ataatatcac atcaagctcc   1980
acttctagta tgagcctgcg cccttcaagc aacccagaga cactgtcccc atctactagt   2040
gacaattcaa ccagccacat gcctctgctg acatctgcac atccaactgg gggagaaaac   2100
atcactcagg tcacccccgc ctccatttct acccaccatg tgtccacatc ctctccagca   2160
ccccgacctg gaactaccag ccaggcatcc ggaccaggaa atagttcaac cagcacaaag   2220
cctggcgagg tgaacgtcac aaaagggact ccccctcaga atgctacctc acctcaggca   2280
ccaagcggcc agaaaacagc tgtgcctact gtcacctcca caggcgggaa ggcaaactct   2340
acaactggag gcaaacacac cacagggcat ggagctcgca ctagcaccga accaactacc   2400
gactacgggg gagattccac aactccaagg cccagataca atgccaccac atatctgcca   2460
ccctctacca gctccaagct gcgacccaga tggacattca ctagtcctcc agtgactacc   2520
gcacaggcta cagtgccagt cccacctact tctcagccta gattttctaa cctgagttcc   2580
ggagagagcc aggtgaggca gcagttcagc aaggacatcg agaagctgct gaacgagcag   2640
gtgaacaagg agatgcagag cagcaacctg tacatgagca tgagcagctg gtgctacacc   2700
cacagcctgg acggcgccgg cctgttcctg ttcgaccacg ccgccgagga gtacgagcac   2760
gccaagaagc tgatcatctt cctgaacgag aacaacgtgc ccgtgcagct gaccagcatc   2820
```

agcgcccccg agcacaagtt cgagggcctg acccagatct tccagaaggc ctacgagcac 2880
gagcagcaca tcagcgagag catcaacaac atcgtggacc acgccatcaa gagcaaggac 2940
cacgccacct tcaacttcct gcagtggtac gtggccgagc agcacgagga ggaggtgctg 3000
ttcaaggaca tcctggacaa gatcgagctg atcggcaacg agaaccacgg cctgtacctg 3060
gccgaccagt acgtgaaggg catcgccaag agcaggaaga gcggatcc 3108

<210> SEQ ID NO 83
<211> LENGTH: 1036
<212> TYPE: PRT
<213> ORGANISM: Artificial Sequence
<220> FEATURE:
<223> OTHER INFORMATION: Synthetic

<400> SEQUENCE: 83

Glu Ala Ala Leu Leu Val Cys Gln Tyr Thr Ile Gln Ser Leu Ile His
1 5 10 15

Leu Thr Gly Glu Asp Pro Gly Phe Phe Asn Val Glu Ile Pro Glu Phe
20 25 30

Pro Phe Tyr Pro Thr Cys Asn Val Cys Thr Ala Asp Val Asn Val Thr
35 40 45

Ile Asn Phe Asp Val Gly Gly Lys Lys His Gln Leu Asp Leu Asp Phe
50 55 60

Gly Gln Leu Thr Pro His Thr Lys Ala Val Tyr Gln Pro Arg Gly Ala
65 70 75 80

Phe Gly Gly Ser Glu Asn Ala Thr Asn Leu Phe Leu Leu Glu Leu Leu
85 90 95

Gly Ala Gly Glu Leu Ala Leu Thr Met Arg Ser Lys Lys Leu Pro Ile
100 105 110

Asn Val Thr Thr Gly Glu Glu Gln Gln Val Ser Leu Glu Ser Val Asp
115 120 125

Val Tyr Phe Gln Asp Val Phe Gly Thr Met Trp Cys His His Ala Glu
130 135 140

Met Gln Asn Pro Val Tyr Leu Ile Pro Glu Thr Val Pro Tyr Ile Lys
145 150 155 160

Trp Asp Asn Cys Asn Ser Thr Asn Ile Thr Ala Val Val Arg Ala Gln
165 170 175

Gly Leu Asp Val Thr Leu Pro Leu Ser Leu Pro Thr Ser Ala Gln Asp
180 185 190

Ser Asn Phe Ser Val Lys Thr Glu Met Leu Gly Asn Glu Ile Asp Ile
195 200 205

Glu Cys Ile Met Glu Asp Gly Glu Ile Ser Gln Val Leu Pro Gly Asp
210 215 220

Asn Lys Phe Asn Ile Thr Cys Ser Gly Tyr Glu Ser His Val Pro Ser
225 230 235 240

Gly Gly Ile Leu Thr Ser Thr Ser Pro Val Ala Thr Pro Ile Pro Gly
245 250 255

Thr Gly Tyr Ala Tyr Ser Leu Arg Leu Thr Pro Arg Pro Val Ser Arg
260 265 270

Phe Leu Gly Asn Asn Ser Ile Leu Tyr Val Phe Tyr Ser Gly Asn Gly
275 280 285

Pro Lys Ala Ser Gly Gly Asp Tyr Cys Ile Gln Ser Asn Ile Val Phe
290 295 300

Ser Asp Glu Ile Pro Ala Ser Gln Asp Met Pro Thr Asn Thr Thr Asp

-continued 305 310 315 320

Ile Thr Tyr Val Gly Asp Asn Ala Thr Tyr Ser Val Pro Met Val Thr
325 330 335

Ser Glu Asp Ala Asn Ser Pro Asn Val Thr Val Thr Ala Phe Trp Ala
340 345 350

Trp Pro Asn Asn Thr Glu Thr Asp Phe Lys Cys Lys Trp Thr Leu Thr
355 360 365

Ser Gly Thr Pro Ser Gly Cys Glu Asn Ile Ser Gly Ala Phe Ala Ser
370 375 380

Asn Arg Thr Phe Asp Ile Thr Val Ser Gly Leu Gly Thr Ala Pro Lys
385 390 395 400

Thr Leu Ile Ile Thr Arg Thr Ala Thr Asn Ala Thr Thr Thr Thr His
405 410 415

Lys Val Ile Phe Ser Lys Ala Pro Glu Ser Thr Thr Thr Ser Pro Thr
420 425 430

Leu Asn Thr Thr Gly Phe Ala Asp Pro Asn Thr Thr Thr Gly Leu Pro
435 440 445

Ser Ser Thr His Val Pro Thr Asn Leu Thr Ala Pro Ala Ser Thr Gly
450 455 460

Pro Thr Val Ser Thr Ala Asp Val Thr Ser Pro Thr Pro Ala Gly Thr
465 470 475 480

Thr Ser Gly Ala Ser Pro Val Thr Pro Ser Pro Ser Pro Trp Asp Asn
485 490 495

Gly Thr Glu Ser Lys Ala Pro Asp Met Thr Ser Ser Thr Ser Pro Val
500 505 510

Thr Thr Pro Thr Pro Asn Ala Thr Ser Pro Thr Pro Ala Val Thr Thr
515 520 525

Pro Thr Pro Asn Ala Thr Ser Pro Thr Pro Ala Val Thr Thr Pro Thr
530 535 540

Pro Asn Ala Thr Ser Pro Thr Leu Gly Lys Thr Ser Pro Thr Ser Ala
545 550 555 560

Val Thr Thr Pro Thr Pro Asn Ala Thr Ser Pro Thr Leu Gly Lys Thr
565 570 575

Ser Pro Thr Ser Ala Val Thr Thr Pro Thr Pro Asn Ala Thr Ser Pro
580 585 590

Thr Leu Gly Lys Thr Ser Pro Thr Ser Ala Val Thr Thr Pro Thr Pro
595 600 605

Asn Ala Thr Gly Pro Thr Val Gly Glu Thr Ser Pro Gln Ala Asn Ala
610 615 620

Thr Asn His Thr Leu Gly Gly Thr Ser Pro Thr Pro Val Val Thr Ser
625 630 635 640

Gln Pro Lys Asn Ala Thr Ser Ala Val Thr Thr Gly Gln His Asn Ile
645 650 655

Thr Ser Ser Ser Thr Ser Ser Met Ser Leu Arg Pro Ser Ser Asn Pro
660 665 670

Glu Thr Leu Ser Pro Ser Thr Ser Asp Asn Ser Thr Ser His Met Pro
675 680 685

Leu Leu Thr Ser Ala His Pro Thr Gly Gly Glu Asn Ile Thr Gln Val
690 695 700

Thr Pro Ala Ser Ile Ser Thr His His Val Ser Thr Ser Ser Pro Ala
705 710 715 720

Pro Arg Pro Gly Thr Thr Ser Gln Ala Ser Gly Pro Gly Asn Ser Ser
725 730 735

```
Thr Ser Thr Lys Pro Gly Glu Val Asn Val Thr Lys Gly Thr Pro Pro
            740                 745                 750

Gln Asn Ala Thr Ser Pro Gln Ala Pro Ser Gly Gln Lys Thr Ala Val
        755                 760                 765

Pro Thr Val Thr Ser Thr Gly Gly Lys Ala Asn Ser Thr Thr Gly Gly
    770                 775                 780

Lys His Thr Thr Gly His Gly Ala Arg Thr Ser Thr Glu Pro Thr Thr
785                 790                 795                 800

Asp Tyr Gly Gly Asp Ser Thr Thr Pro Arg Pro Arg Tyr Asn Ala Thr
                805                 810                 815

Thr Tyr Leu Pro Pro Ser Thr Ser Ser Lys Leu Arg Pro Arg Trp Thr
            820                 825                 830

Phe Thr Ser Pro Pro Val Thr Thr Ala Gln Ala Thr Val Pro Val Pro
        835                 840                 845

Pro Thr Ser Gln Pro Arg Phe Ser Asn Leu Ser Ser Gly Glu Ser Gln
    850                 855                 860

Val Arg Gln Gln Phe Ser Lys Asp Ile Glu Lys Leu Leu Asn Glu Gln
865                 870                 875                 880

Val Asn Lys Glu Met Gln Ser Ser Asn Leu Tyr Met Ser Met Ser Ser
                885                 890                 895

Trp Cys Tyr Thr His Ser Leu Asp Gly Ala Gly Leu Phe Leu Phe Asp
            900                 905                 910

His Ala Ala Glu Glu Tyr Glu His Ala Lys Lys Leu Ile Ile Phe Leu
        915                 920                 925

Asn Glu Asn Asn Val Pro Val Gln Leu Thr Ser Ile Ser Ala Pro Glu
    930                 935                 940

His Lys Phe Glu Gly Leu Thr Gln Ile Phe Gln Lys Ala Tyr Glu His
945                 950                 955                 960

Glu Gln His Ile Ser Glu Ser Ile Asn Asn Ile Val Asp His Ala Ile
                965                 970                 975

Lys Ser Lys Asp His Ala Thr Phe Asn Phe Leu Gln Trp Tyr Val Ala
            980                 985                 990

Glu Gln His Glu Glu Glu Val Leu  Phe Lys Asp Ile Leu  Asp Lys Ile
        995                 1000                 1005

Glu Leu  Ile Gly Asn Glu Asn  His Gly Leu Tyr Leu  Ala Asp Gln
    1010                 1015                 1020

Tyr Val  Lys Gly Ile Ala Lys  Ser Arg Lys Ser Gly  Ser
    1025                 1030                 1035
```

<210> SEQ ID NO 84
<211> LENGTH: 3108
<212> TYPE: DNA
<213> ORGANISM: Artificial Sequence
<220> FEATURE:
<223> OTHER INFORMATION: Synthetic

<400> SEQUENCE: 84

```
ggatccgctc ttcctgctct tggcgatgcc cttcacgtac tggtcggcca ggtacaggcc      60

gtggttctcg ttgccgatca gctcgatctt gtccaggatg tccttgaaca gcacctcctc     120

ctcgtgctgc tcggccacgt accactgcag gaagttgaag gtggcgtggt ccttgctctt     180

gatggcgtgg tccacgatgt tgttgatgct ctcgctgatg tgctgctcgt gctcgtaggc     240

cttctggaag atctgggtca ggccctcgaa cttgtgctcg gggcgctga tgctggtcag      300

ctgcacgggc acgttgttct cgttcaggaa gatgatcagc ttcttggcgt gctcgtactc     360
```

-continued

```
ctcggcggcg tggtcgaaca ggaacaggcc ggcgccgtcc aggctgtggg tgtagcacca    420
gctgctcatg ctcatgtaca ggttgctgct ctgcatctcc ttgttcacct gctcgttcag    480
cagcttctcg atgtccttgc tgaactgctg cctcacctgg ctctctccgg aactcaggtt    540
agaaaatcta ggctgagaag taggtgggac tggcactgta gcctgtgcgg tagtcactgg    600
aggactagtg aatgtccatc tgggtcgcag cttggagctg gtagagggtg gcagatatgt    660
ggtggcattg tatctgggcc ttggagttgt ggaatctccc ccgtagtcgg tagttggttc    720
ggtgctagtg cgagctccat gccctgtggt gtgtttgcct ccagttgtag agtttgcctt    780
cccgcctgtg gaggtgacag taggcacagc tgttttctgg ccgcttggtg cctgaggtga    840
ggtagcattc tgagggggag tcccttttgt gacgttcacc tcgccaggct ttgtgctggt    900
tgaactattt cctggtccgg atgcctggct ggtagttcca ggtcggggtg ctggagagga    960
tgtggacaca tggtgggtag aaatggaggc gggggtgacc tgagtgatgt tttctccccc   1020
agttggatgt gcagatgtca gcagaggcat gtggctggtt gaattgtcac tagtagatgg   1080
ggacagtgtc tctgggttgc ttgaagggcg caggctcata ctagaagtgg agcttgatgt   1140
gatattatgc tggcctgtgg tcacagcgct tgtggcgttc ttgggctgtg aggtgaccac   1200
aggtgtggga ctggtgcctc ccagagtgtg atttgttgcg ttagcctggg gggatgtctc   1260
tcccacggtt ggcccagttg catttggggt aggagttgtg acagctgatg taggactggt   1320
cttgcccaga gtggggcttg tggcgttggg ggttggggta gtcactgcag aggttgggga   1380
agtttttccc agtgtaggag aggtagcatt aggggtgggt gtggtcacgg cgctagtggg   1440
tgatgtcttc cccagggttg gggaagtggc gtttggggta ggagttgtca ctgcgggtgt   1500
tgggctggta gcattaggtg tgggggtagt cacggctgga gtagggcttg ttgcgttggg   1560
ggttggtgtg gtgactggtg aggtactaga agtcatatca ggggccttac tctctgtccc   1620
attgtcccaa gggctgggtg atggggtcac gggactagcg ccagaagttg ttccggcagg   1680
tgtgggactg gtgacatcgg cagtagacac tgtaggtccg gtggatgctg gtgcagtcag   1740
gtttgttggc acatgggtgg agctaggcag tccggtagtt gtattggggt cggcaaaccc   1800
ggtagtgttc agggtaggag atgtggtagt ggactcggga gctttgctga agatcacttt   1860
gtgtgtggta gttgttgcgt tagtagctgt ccgggtaatg atcagggttt ttggggcagt   1920
ccccaggccg gacactgtaa tatcaaaggt tcgattacta gcgaaggcgc cagagatgtt   1980
ttcacacccg ctaggggtgc ctgaagtcag tgtccatttg cacttaaaat cggtctcagt   2040
attgttgggc caggcccaga atgctgtgac ggtcacattt ggggagttag cgtcttcgct   2100
tgtgaccata ggcacggaat aagtggcatt atcgcccacg taggtaatgt cggtagtgtt   2160
agtgggcata tcctggctgg ctgggatctc gtctgagaac acaatattac tctggatgca   2220
atagtcccct ccagaagcct ttggtccgtt tccggaataa aacacgtaca gaatgctatt   2280
gttgcccagg aagcgtgaga ctggcctagg ggtcagtctc aggctataag cgtagccggt   2340
tccgggaatt ggagtggcca cgggactagt agatgtcagg attcccccac ttgggacgtg   2400
agattcgtag ccggaacagg tgatattaaa cttgttatcg ccaggcagca cctggctaat   2460
ttctccatcc tccatgatgc attcaatgtc gatctcattt cccagcatct cggttttcac   2520
ggagaagttg ctatcctggg cgcttgtggg cagtgacagt ggcagggtca cgtccagccc   2580
ctgtgcccgg accactgcgg taatgttagt gctattacag ttgtcccact taatataagg   2640
gacggtttcg ggatcaggt acacaggatt ctgcatctcg gcatggtggc accacatggt   2700
```

-continued

```
gccaaacaca tcctggaagt agacgtccac tgattccaga ctgacctgct gttcctctcc   2760

tgtggtcaca ttgatgggca gtttcttgga cctcatggtc agagccagtt ctcctgctcc   2820

cagcagctcc agcagaaaca gatttgttgc gttctcgctg cctccgaaag cccctctggg   2880

ctgatacacg gcttttgtat gtggggtcag ctggccaaaa tccaggtcca gctggtgttt   2940

cttcccgccc acatcgaaat taatggtgac gttcacgtcg gctgtacaga cgttgcaggt   3000

ggggtaaaat gggaactcag ggatttccac attgaaaaat ccagggtcct ccccggtcag   3060

atgaatcagg ctctgaatag tgtactggca caccagcagg gcggcttc                3108
```

<210> SEQ ID NO 85
<211> LENGTH: 1479
<212> TYPE: DNA
<213> ORGANISM: Artificial Sequence
<220> FEATURE:
<223> OTHER INFORMATION: Synthetic

<400> SEQUENCE: 85

```
gaagccgccc tgctggtgtg ccagtacact attcagagcc tgattcatct gaccggggag     60

gaccctggat ttttcaatgt ggaaatccct gagttcccat tttaccccac ctgcaacgtc    120

tgtacagccg acgtgaacgt caccattaat ttcgatgtgg gcgggaagaa acaccagctg    180

gacctggatt ttggccagct gaccccacat acaaaagccg tgtatcagcc cagaggggct    240

ttcggaggca gcgagaacgc aacaaatctg tttctgctgg agctgctggg agcaggagaa    300

ctggctctga ccatgaggtc caagaaactg cccatcaatg tgaccacagg agaggaacag    360

caggtcagtc tggaatcagt ggacgtctac ttccaggatg tgtttggcac catgtggtgc    420

caccatgccg agatgcagaa tcctgtgtac ctgatccccg aaaccgtccc ttatattaag    480

tgggacaact gtaatagcac taacattacc gcagtggtcc gggcacaggg gctggacgtg    540

accctgccac tgtcactgcc cacaagcgcc caggatagca acttctccgt gaaaaccgag    600

atgctgggaa atgagatcga cattgaatgc atcatggagg atggagaaat tagccaggtg    660

ctgcctggcg ataacaagtt taatatcacc tgttccggct acgaatctca cgtcccaagt    720

gggggaatcc tgacatctac tagtcccgtg gccactccaa ttcccggaac cggctacgct    780

tatagcctga gactgacccc taggccagtc tcacgcttcc tgggcaacaa tagcattctg    840

tacgtgtttt attccggaaa cggaccaaag gcttctggag ggactattg catccagagt     900

aatattgtgt tctcagacga gatcccagcc agccaggata tgcccacttc cggagagagc    960

caggtgaggc agcagttcag caaggacatc gagaagctgc tgaacgagca ggtgaacaag   1020

gagatgcaga gcagcaacct gtacatgagc atgagcagct ggtgctacac ccacagcctg   1080

gacggcgccg gcctgttcct gttcgaccac gccgccgagg agtacgagca cgccaagaag   1140

ctgatcatct tcctgaacga gaacaacgtg cccgtgcagc tgaccagcat cagcgccccc   1200

gagcacaagt tcgagggcct gacccagatc ttccagaagg cctacgagca cgagcagcac   1260

atcagcgaga gcatcaacaa catcgtggac cacgccatca agagcaagga ccacgccacc   1320

ttcaacttcc tgcagtggta cgtggccgag cagcacgagg aggaggtgct gttcaaggac   1380

atcctggaca agatcgagct gatcggcaac gagaaccacg gcctgtacct ggccgaccag   1440

tacgtgaagg gcatcgccaa gagcaggaag agcggatcc                          1479
```

<210> SEQ ID NO 86
<211> LENGTH: 493
<212> TYPE: PRT
<213> ORGANISM: Artificial Sequence
<220> FEATURE:
<223> OTHER INFORMATION: Synthetic

<400> SEQUENCE: 86

```
Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr Ser Gly Glu Ser
305                 310                 315                 320

Gln Val Arg Gln Gln Phe Ser Lys Asp Ile Glu Lys Leu Leu Asn Glu
                325                 330                 335

Gln Val Asn Lys Glu Met Gln Ser Ser Asn Leu Tyr Met Ser Met Ser
            340                 345                 350

Ser Trp Cys Tyr Thr His Ser Leu Asp Gly Ala Gly Leu Phe Leu Phe
        355                 360                 365

Asp His Ala Ala Glu Glu Tyr Glu His Ala Lys Lys Leu Ile Ile Phe
    370                 375                 380

Leu Asn Glu Asn Asn Val Pro Val Gln Leu Thr Ser Ile Ser Ala Pro
385                 390                 395                 400
```

```
Glu His Lys Phe Glu Gly Leu Thr Gln Ile Phe Gln Lys Ala Tyr Glu
                405                 410                 415

His Glu Gln His Ile Ser Glu Ser Ile Asn Asn Ile Val Asp His Ala
            420                 425                 430

Ile Lys Ser Lys Asp His Ala Thr Phe Asn Phe Leu Gln Trp Tyr Val
        435                 440                 445

Ala Glu Gln His Glu Glu Glu Val Leu Phe Lys Asp Ile Leu Asp Lys
    450                 455                 460

Ile Glu Leu Ile Gly Asn Glu Asn His Gly Leu Tyr Leu Ala Asp Gln
465                 470                 475                 480

Tyr Val Lys Gly Ile Ala Lys Ser Arg Lys Ser Gly Ser
                485                 490
```

<210> SEQ ID NO 87
<211> LENGTH: 1479
<212> TYPE: DNA
<213> ORGANISM: Artificial Sequence
<220> FEATURE:
<223> OTHER INFORMATION: Synthetic

<400> SEQUENCE: 87

```
ggatccgctc ttcctgctct tggcgatgcc cttcacgtac tggtcggcca ggtacaggcc     60

gtggttctcg ttgccgatca gctcgatctt gtccaggatg tccttgaaca gcacctcctc    120

ctcgtgctgc tcggccacgt accactgcag gaagttgaag gtggcgtggt ccttgctctt    180

gatggcgtgg tccacgatgt tgttgatgct ctcgctgatg tgctgctcgt gctcgtaggc    240

cttctggaag atctgggtca ggccctcgaa cttgtgctcg ggggcgctga tgctggtcag    300

ctgcacgggc acgttgttct cgttcaggaa gatgatcagc ttcttggcgt gctcgtactc    360

ctcggcggcg tggtcgaaca ggaacaggcc ggcgccgtcc aggctgtggg tgtagcacca    420

gctgctcatg ctcatgtaca ggttgctgct ctgcatctcc ttgttcacct gctcgttcag    480

cagcttctcg atgtccttgc tgaactgctg cctcacctgg ctctctccgg aagtgggcat    540

atcctggctg gctgggatct cgtctgagaa cacaatatta ctctggatgc aatagtcccc    600

tccagaagcc tttggtccgt ttccggaata aaacacgtac agaatgctat tgttgcccag    660

gaagcgtgag actggcctag gggtcagtct caggctataa gcgtagccgg ttccgggaat    720

tggagtggcc acgggactag tagatgtcag gattccccca cttgggacgt gagattcgta    780

gccggaacag gtgatattaa acttgttatc gccaggcagc acctggctaa tttctccatc    840

ctccatgatg cattcaatgt cgatctcatt tcccagcatc tcggttttca cggagaagtt    900

gctatcctgg gcgcttgtgg gcagtgacag tggcagggtc acgtccagcc cctgtgcccg    960

gaccactgcg gtaatgttag tgctattaca gttgtcccac ttaatataag ggacggtttc   1020

ggggatcagg tacacaggat tctgcatctc ggcatggtgg caccacatgg tgccaaacac   1080

atcctggaag tagacgtcca ctgattccag actgacctgc tgttcctctc ctgtggtcac   1140

attgatgggc agtttcttgg acctcatggt cagagccagt tctcctgctc ccagcagctc   1200

cagcagaaac agatttgttg cgttctcgct gcctccgaaa gcccctctgg gctgatacac   1260

ggcttttgta tgtggggtca gctggccaaa atccaggtcc agctggtgtt tcttcccgcc   1320

cacatcgaaa ttaatggtga cgttcacgtc ggctgtacag acgttgcagg tggggtaaaa   1380

tgggaactca gggatttcca cattgaaaaa tccagggtcc tccccggtca gatgaatcag   1440

gctctgaata gtgtactggc acaccagcag ggcggcttc                          1479
```

<210> SEQ ID NO 88
<211> LENGTH: 1803
<212> TYPE: DNA
<213> ORGANISM: Artificial Sequence
<220> FEATURE:
<223> OTHER INFORMATION: Synthetic

<400> SEQUENCE: 88
gaagccgccc tgctggtgtg ccagtacact attcagagcc tgattcatct gaccggggag 60
gaccctggat ttttcaatgt ggaaatccct gagttcccat tttaccccac ctgcaacgtc 120
tgtacagccg acgtgaacgt caccattaat ttcgatgtgg gcgggaagaa acaccagctg 180
gacctggatt ttggccagct gaccccacat acaaaagccg tgtatcagcc cagaggggct 240
ttcggaggca gcgagaacgc aacaaatctg tttctgctgg agctgctggg agcaggagaa 300
ctggctctga ccatgaggtc caagaaactg cccatcaatg tgaccacagg agaggaacag 360
caggtcagtc tggaatcagt ggacgtctac ttccaggatg tgtttggcac catgtggtgc 420
caccatgccg agatgcagaa tcctgtgtac ctgatccccg aaaccgtccc ttatattaag 480
tgggacaact gtaatagcac taacattacc gcagtggtcc gggcacaggg gctggacgtg 540
accctgccac tgtcactgcc cacaagcgcc caggatagca acttctccgt gaaaaccgag 600
atgctgggaa atgagatcga cattgaatgc atcatggagg atggagaaat tagccaggtg 660
ctgcctggcg ataacaagtt taatatcacc tgttccggct acgaatctca cgtcccaagt 720
gggggaatcc tgacatctac tagtcccgtg gccactccaa ttcccggaac cggctacgct 780
tatagcctga gactgacccc taggccagtc tcacgcttcc tgggcaacaa tagcattctg 840
tacgtgtttt attccggaaa cggaccaaag gcttctggag gggactattg catccagagt 900
aatattgtgt tctcagacga gatcccagcc agccaggata tgcccactaa cactaccgac 960
attacctacg tgggcgataa tgccacttat tccgtgccta tggtcacaag cgaagacgct 1020
aactccccaa atgtgaccgt cacagcattc tgggcctggc ccaacaatac tgagaccgat 1080
tttaagtgca aatggacact gacttcaggc acccctagcg ggtgtgaaaa catctctggc 1140
gccttcgcta gtaatcgaac ctttgatatt acagtgtccg gcctggggac tgccccaaaa 1200
accctgatca ttacccggac agctactaac gcaacaacta ccacacacaa agtgatcttc 1260
agcaaagctc cctccggaga gagccaggtg aggcagcagt tcagcaagga catcgagaag 1320
ctgctgaacg agcaggtgaa caaggagatg cagagcagca acctgtacat gagcatgagc 1380
agctggtgct acacccacag cctggacggc gccggcctgt tcctgttcga ccacgccgcc 1440
gaggagtacg agcacgccaa gaagctgatc atcttcctga acgagaacaa cgtgcccgtg 1500
cagctgacca gcatcagcgc ccccgagcac aagttcgagg gcctgaccca gatcttccag 1560
aaggcctacg agcacgagca gcacatcagc gagagcatca acaacatcgt ggaccacgcc 1620
atcaagagca aggaccacgc caccttcaac ttcctgcagt ggtacgtggc cgagcagcac 1680
gaggaggagg tgctgttcaa ggacatcctg gacaagatcg agctgatcgg caacgagaac 1740
cacggcctgt acctggccga ccagtacgtg aagggcatcg ccaagagcag gaagagcgga 1800
tcc 1803

<210> SEQ ID NO 89
<211> LENGTH: 601
<212> TYPE: PRT
<213> ORGANISM: Artificial Sequence
<220> FEATURE:
<223> OTHER INFORMATION: Synthetic

<400> SEQUENCE: 89

Glu Ala Ala Leu Leu Val Cys Gln Tyr Thr Ile Gln Ser Leu Ile His
1 5 10 15

Leu Thr Gly Glu Asp Pro Gly Phe Phe Asn Val Glu Ile Pro Glu Phe
20 25 30

Pro Phe Tyr Pro Thr Cys Asn Val Cys Thr Ala Asp Val Asn Val Thr
35 40 45

Ile Asn Phe Asp Val Gly Gly Lys Lys His Gln Leu Asp Leu Asp Phe
50 55 60

Gly Gln Leu Thr Pro His Thr Lys Ala Val Tyr Gln Pro Arg Gly Ala
65 70 75 80

Phe Gly Gly Ser Glu Asn Ala Thr Asn Leu Phe Leu Leu Glu Leu Leu
85 90 95

Gly Ala Gly Glu Leu Ala Leu Thr Met Arg Ser Lys Lys Leu Pro Ile
100 105 110

Asn Val Thr Thr Gly Glu Glu Gln Gln Val Ser Leu Glu Ser Val Asp
115 120 125

Val Tyr Phe Gln Asp Val Phe Gly Thr Met Trp Cys His His Ala Glu
130 135 140

Met Gln Asn Pro Val Tyr Leu Ile Pro Glu Thr Val Pro Tyr Ile Lys
145 150 155 160

Trp Asp Asn Cys Asn Ser Thr Asn Ile Thr Ala Val Val Arg Ala Gln
165 170 175

Gly Leu Asp Val Thr Leu Pro Leu Ser Leu Pro Thr Ser Ala Gln Asp
180 185 190

Ser Asn Phe Ser Val Lys Thr Glu Met Leu Gly Asn Glu Ile Asp Ile
195 200 205

Glu Cys Ile Met Glu Asp Gly Glu Ile Ser Gln Val Leu Pro Gly Asp
210 215 220

Asn Lys Phe Asn Ile Thr Cys Ser Gly Tyr Glu Ser His Val Pro Ser
225 230 235 240

Gly Gly Ile Leu Thr Ser Thr Ser Pro Val Ala Thr Pro Ile Pro Gly
245 250 255

Thr Gly Tyr Ala Tyr Ser Leu Arg Leu Thr Pro Arg Pro Val Ser Arg
260 265 270

Phe Leu Gly Asn Asn Ser Ile Leu Tyr Val Phe Tyr Ser Gly Asn Gly
275 280 285

Pro Lys Ala Ser Gly Gly Asp Tyr Cys Ile Gln Ser Asn Ile Val Phe
290 295 300

Ser Asp Glu Ile Pro Ala Ser Gln Asp Met Pro Thr Asn Thr Thr Asp
305 310 315 320

Ile Thr Tyr Val Gly Asp Asn Ala Thr Tyr Ser Val Pro Met Val Thr
325 330 335

Ser Glu Asp Ala Asn Ser Pro Asn Val Thr Val Thr Ala Phe Trp Ala
340 345 350

Trp Pro Asn Asn Thr Glu Thr Asp Phe Lys Cys Lys Trp Thr Leu Thr
355 360 365

Ser Gly Thr Pro Ser Gly Cys Glu Asn Ile Ser Gly Ala Phe Ala Ser
370 375 380

Asn Arg Thr Phe Asp Ile Thr Val Ser Gly Leu Gly Thr Ala Pro Lys
385 390 395 400

Thr Leu Ile Ile Thr Arg Thr Ala Thr Asn Ala Thr Thr Thr Thr His

```
                405                 410                 415

Lys Val Ile Phe Ser Lys Ala Pro Ser Gly Glu Ser Gln Val Arg Gln
            420                 425                 430

Gln Phe Ser Lys Asp Ile Glu Lys Leu Leu Asn Glu Gln Val Asn Lys
        435                 440                 445

Glu Met Gln Ser Ser Asn Leu Tyr Met Ser Met Ser Ser Trp Cys Tyr
    450                 455                 460

Thr His Ser Leu Asp Gly Ala Gly Leu Phe Leu Phe Asp His Ala Ala
465                 470                 475                 480

Glu Glu Tyr Glu His Ala Lys Lys Leu Ile Ile Phe Leu Asn Glu Asn
                485                 490                 495

Asn Val Pro Val Gln Leu Thr Ser Ile Ser Ala Pro Glu His Lys Phe
            500                 505                 510

Glu Gly Leu Thr Gln Ile Phe Gln Lys Ala Tyr Glu His Glu Gln His
        515                 520                 525

Ile Ser Glu Ser Ile Asn Asn Ile Val Asp His Ala Ile Lys Ser Lys
    530                 535                 540

Asp His Ala Thr Phe Asn Phe Leu Gln Trp Tyr Val Ala Glu Gln His
545                 550                 555                 560

Glu Glu Glu Val Leu Phe Lys Asp Ile Leu Asp Lys Ile Glu Leu Ile
                565                 570                 575

Gly Asn Glu Asn His Gly Leu Tyr Leu Ala Asp Gln Tyr Val Lys Gly
            580                 585                 590

Ile Ala Lys Ser Arg Lys Ser Gly Ser
        595                 600
```

<210> SEQ ID NO 90
<211> LENGTH: 1803
<212> TYPE: DNA
<213> ORGANISM: Artificial Sequence
<220> FEATURE:
<223> OTHER INFORMATION: Synthetic

<400> SEQUENCE: 90

```
ggatccgctc ttcctgctct tggcgatgcc cttcacgtac tggtcggcca ggtacaggcc     60

gtggttctcg ttgccgatca gctcgatctt gtccaggatg tccttgaaca gcacctcctc    120

ctcgtgctgc tcggccacgt accactgcag gaagttgaag gtggcgtggt ccttgctctt    180

gatggcgtgg tccacgatgt tgttgatgct ctcgctgatg tgctgctcgt gctcgtaggc    240

cttctggaag atctgggtca ggccctcgaa cttgtgctcg ggggcgctga tgctggtcag    300

ctgcacgggc acgttgttct cgttcaggaa gatgatcagc ttcttggcgt gctcgtactc    360

ctcggcggcg tggtcgaaca ggaacaggcc ggcgccgtcc aggctgtggg tgtagcacca    420

gctgctcatg ctcatgtaca ggttgctgct ctgcatctcc ttgttcacct gctcgttcag    480

cagcttctcg atgtccttgc tgaactgctg cctcacctgg ctctctccgg agggagcttt    540

gctgaagatc actttgtgtg tggtagttgt tgcgttagta gctgtccggg taatgatcag    600

ggtttttggg gcagtcccca ggccggacac tgtaatatca aaggttcgat tactagcgaa    660

ggcgccagag atgttttcac acccgctagg ggtgcctgaa gtcagtgtcc atttgcactt    720

aaaatcggtc tcagtattgt tgggccaggc ccagaatgct gtgacggtca catttgggga    780

gttagcgtct tcgcttgtga ccataggcac ggaataagtg gcattatcgc ccacgtaggt    840

aatgtcggta gtgttagtgg gcatatcctg gctggctggg atctcgtctg agaacacaat    900

attactctgg atgcaatagt cccctccaga agcctttggt ccgtttccgg aataaaacac    960
```

```
gtacagaatg ctattgttgc ccaggaagcg tgagactggc ctaggggtca gtctcaggct   1020

ataagcgtag ccggttccgg gaattggagt ggccacggga ctagtagatg tcaggattcc   1080

cccacttggg acgtgagatt cgtagccgga acaggtgata ttaaacttgt tatcgccagg   1140

cagcacctgg ctaatttctc catcctccat gatgcattca atgtcgatct catttcccag   1200

catctcggtt ttcacggaga agttgctatc ctgggcgctt gtgggcagtg acagtggcag   1260

ggtcacgtcc agcccctgtg cccggaccac tgcggtaatg ttagtgctat tacagttgtc   1320

ccacttaata taagggacgg tttcggggat caggtacaca ggattctgca tctcggcatg   1380

gtggcaccac atggtgccaa acacatcctg gaagtagacg tccactgatt ccagactgac   1440

ctgctgttcc tctcctgtgg tcacattgat gggcagtttc ttggacctca tggtcagagc   1500

cagttctcct gctcccagca gctccagcag aaacagattt gttgcgttct cgctgcctcc   1560

gaaagcccct ctgggctgat acacggcttt tgtatgtggg gtcagctggc caaaatccag   1620

gtccagctgg tgtttcttcc cgcccacatc gaaattaatg gtgacgttca cgtcggctgt   1680

acagacgttg caggtggggt aaaatgggaa ctcagggatt tccacattga aaaatccagg   1740

gtcctccccg gtcagatgaa tcaggctctg aatagtgtac tggcacacca gcagggcggc   1800

ttc                                                                 1803
```

```
<210> SEQ ID NO 91
<211> LENGTH: 1938
<212> TYPE: DNA
<213> ORGANISM: Artificial Sequence
<220> FEATURE:
<223> OTHER INFORMATION: Synthetic

<400> SEQUENCE: 91
```

```
gaagccgccc tgctggtgtg ccagtacact attcagagcc tgattcatct gaccggggag     60

gaccctggat tttcaatgt ggaaatccct gagttcccat tttaccccac ctgcaacgtc    120

tgtacagccg acgtgaacgt caccattaat ttcgatgtgg gcgggaagaa acaccagctg    180

gacctggatt ttggccagct gaccccacat acaaaagccg tgtatcagcc cagaggggct    240

ttcggaggca gcgagaacgc aacaaatctg tttctgctgg agctgctggg agcaggagaa    300

ctggctctga ccatgaggtc caagaaactg cccatcaatg tgaccacagg agaggaacag    360

caggtcagtc tggaatcagt ggacgtctac ttccaggatg tgtttggcac catgtggtgc    420

caccatgccg agatgcagaa tcctgtgtac ctgatccccg aaaccgtccc ttatattaag    480

tgggacaact gtaatagcac taacattacc gcagtggtcc gggcacaggg gctggacgtg    540

accctgccac tgtcactgcc cacaagcgcc caggatagca acttctccgt gaaaaccgag    600

atgctgggaa atgagatcga cattgaatgc atcatggagg atggagaaat tagccaggtg    660

ctgcctggcg ataacaagtt taatatcacc tgttccggct acgaatctca cgtcccaagt    720

gggggaatcc tgacatctac tagtcccgtg gccactccaa ttcccggaac cggctacgct    780

tatagcctga gactgacccc taggccagtc tcacgcttcc tgggcaacaa tagcattctg    840

tacgtgtttt attccggaaa cggaccaaag gcttctggag gggactattg catccagagt    900

aatattgtgt tctcagacga gatcccagcc agccaggata tgcccactaa cactaccgac    960

attacctacg tgggcgataa tgccacttat tccgtgccta tggtcacaag cgaagacgct   1020

aactccccaa atgtgaccgt cacagcattc tgggcctggc ccaacaatac tgagaccgat   1080

tttaagtgca aatggacact gacttcaggc acccctagcg ggtgtgaaaa catctctggc   1140
```

```
gccttcgcta gtaatcgaac ctttgatatt acagtgtccg gcctggggac tgccccaaaa   1200

accctgatca ttacccggac agctactaac gcaacaacta ccacacacaa agtgatcttc   1260

agcaaagctc ccgagtccac taccacatct cctaccctga acactaccgg gtttgccgac   1320

cccaatacaa ctaccggact gcctagctcc acccatgtgc caacaaacct gactgcacca   1380

gcatccaccg gacctacagt gtctacttcc ggagagagcc aggtgaggca gcagttcagc   1440

aaggacatcg agaagctgct gaacgagcag gtgaacaagg agatgcagag cagcaacctg   1500

tacatgagca tgagcagctg gtgctacacc cacagcctgg acggcgccgg cctgttcctg   1560

ttcgaccacg ccgccgagga gtacgagcac gccaagaagc tgatcatctt cctgaacgag   1620

aacaacgtgc ccgtgcagct gaccagcatc agcgcccccg agcacaagtt cgagggcctg   1680

acccagatct tccagaaggc ctacgagcac gagcagcaca tcagcgagag catcaacaac   1740

atcgtggacc acgccatcaa gagcaaggac cacgccacct tcaacttcct gcagtggtac   1800

gtggccgagc agcacgagga ggaggtgctg ttcaaggaca tcctggacaa gatcgagctg   1860

atcggcaacg agaaccacgg cctgtacctg gccgaccagt acgtgaaggg catcgccaag   1920

agcaggaaga gcggatcc                                                  1938
```

```
<210> SEQ ID NO 92
<211> LENGTH: 646
<212> TYPE: PRT
<213> ORGANISM: Artificial Sequence
<220> FEATURE:
<223> OTHER INFORMATION: Synthetic

<400> SEQUENCE: 92

Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220
```

-continued

```
Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr Thr His
                405                 410                 415

Lys Val Ile Phe Ser Lys Ala Pro Glu Ser Thr Thr Thr Ser Pro Thr
            420                 425                 430

Leu Asn Thr Thr Gly Phe Ala Asp Pro Asn Thr Thr Thr Gly Leu Pro
        435                 440                 445

Ser Ser Thr His Val Pro Thr Asn Leu Thr Ala Pro Ala Ser Thr Gly
    450                 455                 460

Pro Thr Val Ser Thr Ser Gly Glu Ser Gln Val Arg Gln Gln Phe Ser
465                 470                 475                 480

Lys Asp Ile Glu Lys Leu Leu Asn Glu Gln Val Asn Lys Glu Met Gln
                485                 490                 495

Ser Ser Asn Leu Tyr Met Ser Met Ser Ser Trp Cys Tyr Thr His Ser
            500                 505                 510

Leu Asp Gly Ala Gly Leu Phe Leu Phe Asp His Ala Ala Glu Glu Tyr
        515                 520                 525

Glu His Ala Lys Lys Leu Ile Ile Phe Leu Asn Glu Asn Asn Val Pro
    530                 535                 540

Val Gln Leu Thr Ser Ile Ser Ala Pro Glu His Lys Phe Glu Gly Leu
545                 550                 555                 560

Thr Gln Ile Phe Gln Lys Ala Tyr Glu His Glu Gln His Ile Ser Glu
                565                 570                 575

Ser Ile Asn Asn Ile Val Asp His Ala Ile Lys Ser Lys Asp His Ala
            580                 585                 590

Thr Phe Asn Phe Leu Gln Trp Tyr Val Ala Glu Gln His Glu Glu Glu
        595                 600                 605

Val Leu Phe Lys Asp Ile Leu Asp Lys Ile Glu Leu Ile Gly Asn Glu
    610                 615                 620

Asn His Gly Leu Tyr Leu Ala Asp Gln Tyr Val Lys Gly Ile Ala Lys
625                 630                 635                 640
```

Ser Arg Lys Ser Gly Ser
645

<210> SEQ ID NO 93
<211> LENGTH: 1938
<212> TYPE: DNA
<213> ORGANISM: Artificial Sequence
<220> FEATURE:
<223> OTHER INFORMATION: Synthetic

<400> SEQUENCE: 93
ggatccgctc ttcctgctct tggcgatgcc cttcacgtac tggtcggcca ggtacaggcc 60
gtggttctcg ttgccgatca gctcgatctt gtccaggatg tccttgaaca gcacctcctc 120
ctcgtgctgc tcggccacgt accactgcag gaagttgaag gtggcgtggt ccttgctctt 180
gatggcgtgg tccacgatgt tgttgatgct ctcgctgatg tgctgctcgt gctcgtaggc 240
cttctggaag atctgggtca ggccctcgaa cttgtgctcg gggcgctga tgctggtcag 300 ctgcacgggc acgttgttct cgttcaggaa gatgatcagc ttcttggcgt gctcgtactc 360
ctcggcggcg tggtcgaaca ggaacaggcc ggcgccgtcc aggctgtggg tgtagcacca 420
gctgctcatg ctcatgtaca ggttgctgct ctgcatctcc ttgttcacct gctcgttcag 480
cagcttctcg atgtccttgc tgaactgctg cctcacctgg ctctctccgg aagtagacac 540
tgtaggtccg gtggatgctg gtgcagtcag gtttgttggc acatgggtgg agctaggcag 600
tccggtagtt gtattggggt cggcaaaccc ggtagtgttc agggtaggag atgtggtagt 660
ggactcggga gctttgctga agatcacttt gtgtgtggta gttgttgcgt tagtagctgt 720
ccgggtaatg atcagggttt ttggggcagt ccccaggccg gacactgtaa tatcaaaggt 780
tcgattacta gcgaaggcgc cagagatgtt ttcacacccg ctaggggtgc ctgaagtcag 840
tgtccatttg cacttaaaat cggtctcagt attgttgggc caggcccaga atgctgtgac 900
ggtcacattt ggggagttag cgtcttcgct tgtgaccata ggcacggaat aagtggcatt 960
atcgcccacg taggtaatgt cggtagtgtt agtgggcata tcctggctgg ctgggatctc 1020
gtctgagaac acaatattac tctggatgca atagtcccct ccagaagcct ttggtccgtt 1080
tccggaataa aacacgtaca gaatgctatt gttgcccagg aagcgtgaga ctggcctagg 1140
ggtcagtctc aggctataag cgtagccggt tccgggaatt ggagtggcca cgggactagt 1200
agatgtcagg attcccccac ttgggacgtg agattcgtag ccggaacagg tgatattaaa 1260
cttgttatcg ccaggcagca cctggctaat ttctccatcc tccatgatgc attcaatgtc 1320
gatctcattt cccagcatct cggttttcac ggagaagttg ctatcctggg cgcttgtggg 1380
cagtgacagt ggcagggtca cgtccagccc ctgtgcccgg accactgcgg taatgttagt 1440
gctattacag ttgtcccact taatataagg gacggtttcg gggatcaggt acacaggatt 1500
ctgcatctcg gcatggtggc accacatggt gccaaacaca tcctggaagt agacgtccac 1560
tgattccaga ctgacctgct gttcctctcc tgtggtcaca ttgatgggca gtttcttgga 1620
cctcatggtc agagccagtt ctcctgctcc cagcagctcc agcagaaaca gatttgttgc 1680
gttctcgctg cctccgaaag cccctctggg ctgatacacg gcttttgtat gtggggtcag 1740
ctggccaaaa tccaggtcca gctggtgttt cttcccgccc acatcgaaat taatggtgac 1800
gttcacgtcg gctgtacaga cgttgcaggt ggggtaaaat gggaactcag ggatttccac 1860
attgaaaaat ccagggtcct ccccggtcag atgaatcagg ctctgaatag tgtactggca 1920
caccagcagg gcggcttc 1938

<210> SEQ ID NO 94
<211> LENGTH: 3393
<212> TYPE: DNA
<213> ORGANISM: Artificial Sequence
<220> FEATURE:
<223> OTHER INFORMATION: Synthetic

<400> SEQUENCE: 94

```
atggagttcc tgaagaggag cttcgcccct ctgaccgaga agcagtggca ggagatcgac      60
aacagggcca gggagatctt caagacccag ctgtacggca ggaagttcgt ggacgtggag     120
ggcccctacg gctgggagta cgccgcccac cccctgggcg aggtggaggt gctgagcgac     180
gagaacgagg tggtgaagtg gggcctgagg aagagcctgc ccctgatcga gctgagggcc     240
accttcaccc tggacctgtg ggagctggac aacctggaga ggggcaagcc caacgtggac     300
ctgagcagcc tggaggagac cgtgaggaag gtggccgagt tcgaggacga ggtgatcttc     360
aggggctgcg agaagagcgg cgtgaagggc ctgctgagct tcgaggagag gaagatcgag     420
tgcggcagca cccccaagga cctgctggag gccatcgtga gggccctgag catcttcagc     480
aaggacggca tcgagggccc ctacaccctg gtgatcaaca ccgacaggtg gatcaacttc     540
ctgaaggagg aggccggcca ctaccccctg gagaagaggg tggaggagtg cctgaggggc     600
ggcaagatca tcaccacccc caggatcgag gacgccctgg tggtgagcga gaggggcggc     660
gacttcaagc tgatcctggg ccaggacctg agcatcggct acgaggacag ggagaaggac     720
gccgtgaggc tgttcatcac cgagaccttc accttccagg tggtgaaccc cgaggccctg     780
atcctgctga agtccggagg cggatctggc ggaggcgaag ccgccctgct ggtgtgccag     840
tacactattc agagcctgat tcatctgacc ggggaggacc ctggattttt caatgtggaa     900
atccctgagt tcccatttta ccccacctgc aacgtctgta cagccgacgt gaacgtcacc     960
attaatttcg atgtgggcgg gaagaaacac cagctggacc tggattttgg ccagctgacc    1020
ccacatacaa aagccgtgta tcagcccaga ggggctttcg gaggcagcga gaacgcaaca    1080
aatctgtttc tgctggagct gctgggagca ggagaactgg ctctgaccat gaggtccaag    1140
aaactgccca tcaatgtgac cacaggagag gaacagcagg tcagtctgga atcagtggac    1200
gtctacttcc aggatgtgtt tggcaccatg tggtgccacc atgccgagat gcagaatcct    1260
gtgtacctga tccccgaaac cgtcccttat attaagtggg acaactgtaa tagcactaac    1320
attaccgcag tggtccgggc acaggggctg gacgtgaccc tgccactgtc actgcccaca    1380
agcgcccagg atagcaactt ctccgtgaaa accgagatgc tgggaaatga gatcgacatt    1440
gaatgcatca tggaggatgg agaaattagc caggtgctgc ctggcgataa caagtttaat    1500
atcacctgtt ccggctacga atctcacgtc ccaagtgggg gaatcctgac atctactagt    1560
cccgtggcca ctccaattcc cggaaccggc tacgcttata gcctgagact gacccctagg    1620
ccagtctcac gcttcctggg caacaatagc attctgtacg tgttttattc cggaaacgga    1680
ccaaaggctt ctggagggga ctattgcatc cagagtaata ttgtgttctc agacgagatc    1740
ccagccagcc aggatatgcc cactaacact accgacatta cctacgtggg cgataatgcc    1800
acttattccg tgcctatggt cacaagcgaa gacgctaact ccccaaatgt gaccgtcaca    1860
gcattctggg cctggcccaa caatactgag accgatttta agtgcaaatg gacactgact    1920
tcaggcaccc ctagcgggtg tgaaaacatc tctggcgcct tcgctagtaa tcgaaccttt    1980
gatattacag tgtccggcct ggggactgcc ccaaaaaccc tgatcattac ccggacagct    2040
actaacgcaa caactaccac acacaaagtg atcttcagca aagctcccga gtccactacc    2100
```

```
acatctccta ccctgaacac taccgggttt gccgacccca atacaactac cggactgcct   2160

agctccaccc atgtgccaac aaacctgact gcaccagcat ccaccggacc tacagtgtct   2220

actgccgatg tcaccagtcc cacacctgcc ggaacaactt ctggcgctag tcccgtgacc   2280

ccatcaccca gcccttggga caatgggaca gagagtaagg cccctgatat gacttctagt   2340

acctcaccag tcaccacacc aacccccaac gcaacaagcc ctactccagc cgtgactacc   2400

cccacaccta atgctaccag cccaacaccc gcagtgacaa ctcctacccc aaacgccact   2460

tccccaaccc tggggaagac atcacccact agcgccgtga ccacacccac ccctaatgct   2520

acctctccta cactgggaaa aacttcccca acctctgcag tgactacccc aacccccaac   2580

gccacaagcc ccactctggg caagaccagt cctacatcag ctgtcacaac tcctacccca   2640

aatgcaactg ggccaaccgt gggagagaca tccccccagg ctaacgcaac aaatcacact   2700

ctgggaggca ccagtcccac acctgtggtc acctcacagc ccaagaacgc cacaagcgct   2760

gtgaccacag gccagcataa tatcacatca agctccactt ctagtatgag cctgcgccct   2820

tcaagcaacc cagagacact gtccccatct actagtgaca attcaaccag ccacatgcct   2880

ctgctgacat ctgcacatcc aactggggga gaaaacatca ctcaggtcac ccccgcctcc   2940

atttctaccc accatgtgtc cacatcctct ccagcacccc gacctggaac taccagccag   3000

gcatccggac caggaaatag ttcaaccagc acaaagcctg gcgaggtgaa cgtcacaaaa   3060

gggactcccc ctcagaatgc tacctcacct caggcaccaa gcggccagaa aacagctgtg   3120

cctactgtca cctccacagg cgggaaggca aactctacaa ctggaggcaa acacaccaca   3180

gggcatggag ctcgcactag caccgaacca actaccgact acgggggaga ttccacaact   3240

ccaaggccca gatacaatgc caccacatat ctgccaccct ctaccagctc caagctgcga   3300

cccagatgga cattcactag tcctccagtg actaccgcac aggctacagt gccagtccca   3360

cctacttctc agcctagatt ttctaacctg agt                                3393
```

<210> SEQ ID NO 95
<211> LENGTH: 1131
<212> TYPE: PRT
<213> ORGANISM: Artificial Sequence
<220> FEATURE:
<223> OTHER INFORMATION: Synthetic

<400> SEQUENCE: 95

```
Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125
```

-continued

```
Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
        195                 200                 205

Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Ser Gly Gly Gly Ser Gly Gly Gly
            260                 265                 270

Glu Ala Ala Leu Leu Val Cys Gln Tyr Thr Ile Gln Ser Leu Ile His
        275                 280                 285

Leu Thr Gly Glu Asp Pro Gly Phe Phe Asn Val Glu Ile Pro Glu Phe
    290                 295                 300

Pro Phe Tyr Pro Thr Cys Asn Val Cys Thr Ala Asp Val Asn Val Thr
305                 310                 315                 320

Ile Asn Phe Asp Val Gly Gly Lys Lys His Gln Leu Asp Leu Asp Phe
                325                 330                 335

Gly Gln Leu Thr Pro His Thr Lys Ala Val Tyr Gln Pro Arg Gly Ala
            340                 345                 350

Phe Gly Gly Ser Glu Asn Ala Thr Asn Leu Phe Leu Leu Glu Leu Leu
        355                 360                 365

Gly Ala Gly Glu Leu Ala Leu Thr Met Arg Ser Lys Lys Leu Pro Ile
    370                 375                 380

Asn Val Thr Thr Gly Glu Glu Gln Gln Val Ser Leu Glu Ser Val Asp
385                 390                 395                 400

Val Tyr Phe Gln Asp Val Phe Gly Thr Met Trp Cys His His Ala Glu
                405                 410                 415

Met Gln Asn Pro Val Tyr Leu Ile Pro Glu Thr Val Pro Tyr Ile Lys
            420                 425                 430

Trp Asp Asn Cys Asn Ser Thr Asn Ile Thr Ala Val Val Arg Ala Gln
        435                 440                 445

Gly Leu Asp Val Thr Leu Pro Leu Ser Leu Pro Thr Ser Ala Gln Asp
    450                 455                 460

Ser Asn Phe Ser Val Lys Thr Glu Met Leu Gly Asn Glu Ile Asp Ile
465                 470                 475                 480

Glu Cys Ile Met Glu Asp Gly Glu Ile Ser Gln Val Leu Pro Gly Asp
                485                 490                 495

Asn Lys Phe Asn Ile Thr Cys Ser Gly Tyr Glu Ser His Val Pro Ser
            500                 505                 510

Gly Gly Ile Leu Thr Ser Thr Ser Pro Val Ala Thr Pro Ile Pro Gly
        515                 520                 525

Thr Gly Tyr Ala Tyr Ser Leu Arg Leu Thr Pro Arg Pro Val Ser Arg
    530                 535                 540

Phe Leu Gly Asn Asn Ser Ile Leu Tyr Val Phe Tyr Ser Gly Asn Gly
```

-continued

```
545                 550                 555                 560

Pro Lys Ala Ser Gly Gly Asp Tyr Cys Ile Gln Ser Asn Ile Val Phe
                565                 570                 575

Ser Asp Glu Ile Pro Ala Ser Gln Asp Met Pro Thr Asn Thr Thr Asp
            580                 585                 590

Ile Thr Tyr Val Gly Asp Asn Ala Thr Tyr Ser Val Pro Met Val Thr
        595                 600                 605

Ser Glu Asp Ala Asn Ser Pro Asn Val Thr Val Thr Ala Phe Trp Ala
    610                 615                 620

Trp Pro Asn Asn Thr Glu Thr Asp Phe Lys Cys Lys Trp Thr Leu Thr
625                 630                 635                 640

Ser Gly Thr Pro Ser Gly Cys Glu Asn Ile Ser Gly Ala Phe Ala Ser
                645                 650                 655

Asn Arg Thr Phe Asp Ile Thr Val Ser Gly Leu Gly Thr Ala Pro Lys
            660                 665                 670

Thr Leu Ile Ile Thr Arg Thr Ala Thr Asn Ala Thr Thr Thr Thr His
        675                 680                 685

Lys Val Ile Phe Ser Lys Ala Pro Glu Ser Thr Thr Thr Ser Pro Thr
    690                 695                 700

Leu Asn Thr Thr Gly Phe Ala Asp Pro Asn Thr Thr Thr Gly Leu Pro
705                 710                 715                 720

Ser Ser Thr His Val Pro Thr Asn Leu Thr Ala Pro Ala Ser Thr Gly
                725                 730                 735

Pro Thr Val Ser Thr Ala Asp Val Thr Ser Pro Thr Pro Ala Gly Thr
            740                 745                 750

Thr Ser Gly Ala Ser Pro Val Thr Pro Ser Pro Ser Pro Trp Asp Asn
        755                 760                 765

Gly Thr Glu Ser Lys Ala Pro Asp Met Thr Ser Ser Thr Ser Pro Val
    770                 775                 780

Thr Thr Pro Thr Pro Asn Ala Thr Ser Pro Thr Pro Ala Val Thr Thr
785                 790                 795                 800

Pro Thr Pro Asn Ala Thr Ser Pro Thr Pro Ala Val Thr Thr Pro Thr
                805                 810                 815

Pro Asn Ala Thr Ser Pro Thr Leu Gly Lys Thr Ser Pro Thr Ser Ala
            820                 825                 830

Val Thr Thr Pro Thr Pro Asn Ala Thr Ser Pro Thr Leu Gly Lys Thr
        835                 840                 845

Ser Pro Thr Ser Ala Val Thr Thr Pro Thr Pro Asn Ala Thr Ser Pro
    850                 855                 860

Thr Leu Gly Lys Thr Ser Pro Thr Ser Ala Val Thr Thr Pro Thr Pro
865                 870                 875                 880

Asn Ala Thr Gly Pro Thr Val Gly Glu Thr Ser Pro Gln Ala Asn Ala
                885                 890                 895

Thr Asn His Thr Leu Gly Gly Thr Ser Pro Thr Pro Val Val Thr Ser
            900                 905                 910

Gln Pro Lys Asn Ala Thr Ser Ala Val Thr Thr Gly Gln His Asn Ile
        915                 920                 925

Thr Ser Ser Ser Thr Ser Ser Met Ser Leu Arg Pro Ser Ser Asn Pro
    930                 935                 940

Glu Thr Leu Ser Pro Ser Thr Ser Asp Asn Ser Thr Ser His Met Pro
945                 950                 955                 960

Leu Leu Thr Ser Ala His Pro Thr Gly Gly Glu Asn Ile Thr Gln Val
                965                 970                 975
```

```
Thr Pro Ala Ser Ile Ser Thr His His Val Ser Thr Ser Ser Pro Ala
            980                 985                 990

Pro Arg Pro Gly Thr Thr Ser Gln  Ala Ser Gly Pro Gly  Asn Ser Ser
        995                 1000                1005

Thr Ser  Thr Lys Pro Gly Glu  Val Asn Val Thr Lys  Gly Thr Pro
    1010                 1015                 1020

Pro Gln  Asn Ala Thr Ser Pro  Gln Ala Pro Ser Gly  Gln Lys Thr
    1025                 1030                 1035

Ala Val  Pro Thr Val Thr Ser  Thr Gly Gly Lys Ala  Asn Ser Thr
    1040                 1045                 1050

Thr Gly  Gly Lys His Thr Thr  Gly His Gly Ala Arg  Thr Ser Thr
    1055                 1060                 1065

Glu Pro  Thr Thr Asp Tyr Gly  Gly Asp Ser Thr Thr  Pro Arg Pro
    1070                 1075                 1080

Arg Tyr  Asn Ala Thr Thr Tyr  Leu Pro Pro Ser Thr  Ser Ser Lys
    1085                 1090                 1095

Leu Arg  Pro Arg Trp Thr Phe  Thr Ser Pro Pro Val  Thr Thr Ala
    1100                 1105                 1110

Gln Ala  Thr Val Pro Val Pro  Pro Thr Ser Gln Pro  Arg Phe Ser
    1115                 1120                 1125

Asn Leu  Ser
    1130
```

<210> SEQ ID NO 96
<211> LENGTH: 3393
<212> TYPE: DNA
<213> ORGANISM: Artificial Sequence
<220> FEATURE:
<223> OTHER INFORMATION: Synthetic

<400> SEQUENCE: 96

```
actcaggtta gaaaatctag gctgagaagt aggtgggact ggcactgtag cctgtgcggt      60

agtcactgga ggactagtga atgtccatct gggtcgcagc ttggagctgg tagagggtgg     120

cagatatgtg gtggcattgt atctgggcct tggagttgtg gaatctcccc cgtagtcggt     180

agttggttcg gtgctagtgc gagctccatg ccctgtggtg tgtttgcctc cagttgtaga     240

gtttgccttc ccgcctgtgg aggtgacagt aggcacagct gttttctggc cgcttggtgc     300

ctgaggtgag gtagcattct gagggggagt cccttttgtg acgttcacct cgccaggctt     360

tgtgctggtt gaactatttc ctggtccgga tgcctggctg gtagttccag gtcggggtgc     420

tggagaggat gtggacacat ggtgggtaga aatggaggcg ggggtgacct gagtgatgtt     480

ttctccccca gttggatgtg cagatgtcag cagaggcatg tggctggttg aattgtcact     540

agtagatggg gacagtgtct ctgggttgct tgaagggcgc aggctcatac tagaagtgga     600

gcttgatgtg atattatgct ggcctgtggt cacagcgctt gtggcgttct tgggctgtga     660

ggtgaccaca ggtgtgggac tggtgcctcc cagagtgtga tttgttgcgt tagcctgggg     720

ggatgtctct cccacggttg gcccagttgc atttggggta ggagttgtga cagctgatgt     780

aggactggtc ttgcccagag tggggcttgt ggcgttgggg gttggggtag tcactgcaga     840

ggttggggaa gtttttccca gtgtaggaga ggtagcatta ggggtgggtg tggtcacggc     900

gctagtgggt gatgtcttcc ccagggttgg ggaagtggcg tttggggtag gagttgtcac     960

tgcgggtgtt gggctggtag cattaggtgt gggggtagtc acggctggag tagggcttgt    1020

tgcgttgggg gttggtgtgg tgactggtga ggtactagaa gtcatatcag gggccttact    1080
```

```
ctctgtccca ttgtcccaag ggctgggtga tggggtcacg ggactagcgc cagaagttgt   1140
tccggcaggt gtgggactgg tgacatcggc agtagacact gtaggtccgg tggatgctgg   1200
tgcagtcagg tttgttggca catgggtgga gctaggcagt ccggtagttg tattggggtc   1260
ggcaaacccg gtagtgttca gggtaggaga tgtggtagtg gactcgggag ctttgctgaa   1320
gatcactttg tgtgtggtag ttgttgcgtt agtagctgtc cgggtaatga tcagggtttt   1380
tggggcagtc cccaggccgg acactgtaat atcaaaggtt cgattactag cgaaggcgcc   1440
agagatgttt tcacacccgc taggggtgcc tgaagtcagt gtccatttgc acttaaaatc   1500
ggtctcagta ttgttgggcc aggcccagaa tgctgtgacg gtcacatttg gggagttagc   1560
gtcttcgctt gtgaccatag gcacggaata agtggcatta tcgcccacgt aggtaatgtc   1620
ggtagtgtta gtgggcatat cctggctggc tgggatctcg tctgagaaca caatattact   1680
ctggatgcaa tagtcccctc cagaagcctt tggtccgttt ccggaataaa acacgtacag   1740
aatgctattg ttgcccagga agcgtgagac tggcctaggg gtcagtctca ggctataagc   1800
gtagccggtt ccgggaattg gagtggccac gggactagta gatgtcagga ttcccccact   1860
tgggacgtga gattcgtagc cggaacaggt gatattaaac ttgttatcgc caggcagcac   1920
ctggctaatt tctccatcct ccatgatgca ttcaatgtcg atctcatttc ccagcatctc   1980
ggttttcacg gagaagttgc tatcctgggc gcttgtgggc agtgacagtg gcagggtcac   2040
gtccagcccc tgtgcccgga ccactgcggt aatgttagtg ctattacagt tgtcccactt   2100
aatataaggg acggtttcgg ggatcaggta cacaggattc tgcatctcgg catggtggca   2160
ccacatggtg ccaaacacat cctggaagta gacgtccact gattccagac tgacctgctg   2220
ttcctctcct gtggtcacat tgatgggcag tttcttggac ctcatggtca gagccagttc   2280
tcctgctccc agcagctcca gcagaaacag atttgttgcg ttctcgctgc ctccgaaagc   2340
ccctctgggc tgatacacgg cttttgtatg tggggtcagc tggccaaaat ccaggtccag   2400
ctggtgtttc ttcccgccca catcgaaatt aatggtgacg ttcacgtcgg ctgtacagac   2460
gttgcaggtg gggtaaaatg ggaactcagg gatttccaca ttgaaaaatc cagggtcctc   2520
cccggtcaga tgaatcaggc tctgaatagt gtactggcac accagcaggg cggcttcgcc   2580
tccgccagat ccgcctccgg acttcagcag gatcagggcc tcggggttca ccacctggaa   2640
ggtgaaggtc tcggtgatga acagcctcac ggcgtccttc tccctgtcct cgtagccgat   2700
gctcaggtcc tggcccagga tcagcttgaa gtcgccgccc ctctcgctca ccaccagggc   2760
gtcctcgatc ctgggggtgg tgatgatctt gccgcccctc aggcactcct ccaccctctt   2820
ctccaggggg tagtggccgg cctcctcctt caggaagttg atccacctgt cggtgttgat   2880
caccagggtg taggggccct cgatgccgtc cttgctgaag atgctcaggg ccctcacgat   2940
ggcctccagc aggtccttgg gggtgctgcc gcactcgatc ttcctctcct cgaagctcag   3000
caggcccttc acgccgctct tctcgcagcc cctgaagatc acctcgtcct cgaactcggc   3060
caccttcctc acggtctcct ccaggctgct caggtccacg ttgggcttgc ccctctccag   3120
gttgtccagc tcccacaggt ccagggtgaa ggtggccctc agctcgatca ggggcaggct   3180
cttcctcagg ccccacttca ccacctcgtt ctcgtcgctc agcacctcca cctcgcccag   3240
ggggtgggcg gcgtactccc agccgtaggg gccctccacg tccacgaact tcctgccgta   3300
cagctgggtc ttgaagatct ccctggccct gttgtcgatc tcctgccact gcttctcggt   3360
cagaggggcg aagctcctct tcaggaactc cat                                3393
```

<210> SEQ ID NO 97
<211> LENGTH: 2223
<212> TYPE: DNA
<213> ORGANISM: Artificial Sequence
<220> FEATURE:
<223> OTHER INFORMATION: Synthetic

<400> SEQUENCE: 97
atggagttcc tgaagaggag cttcgcccct ctgaccgaga agcagtggca ggagatcgac 60
aacagggcca gggagatctt caagacccag ctgtacggca ggaagttcgt ggacgtggag 120
ggcccctacg gctgggagta cgccgcccac cccctgggcg aggtggaggt gctgagcgac 180
gagaacgagg tggtgaagtg gggcctgagg aagagcctgc ccctgatcga gctgagggcc 240
accttcaccc tggacctgtg ggagctggac aacctggaga ggggcaagcc caacgtggac 300
ctgagcagcc tggaggagac cgtgaggaag gtggccgagt tcgaggacga ggtgatcttc 360
aggggctgcg agaagagcgg cgtgaagggc ctgctgagct tcgaggagag gaagatcgag 420
tgcggcagca cccccaagga cctgctggag gccatcgtga gggccctgag catcttcagc 480
aaggacggca tcgagggccc ctacaccctg gtgatcaaca ccgacaggtg gatcaacttc 540
ctgaaggagg aggccggcca ctacccccctg gagaagaggg tggaggagtg cctgaggggc 600
ggcaagatca tcaccacccc caggatcgag gacgccctgg tggtgagcga gaggggcggc 660
gacttcaagc tgatcctggg ccaggacctg agcatcggct acgaggacag ggagaaggac 720
gccgtgaggc tgttcatcac cgagaccttc accttccagg tggtgaaccc cgaggccctg 780
atcctgctga agtccggagg cggatctggc ggaggcgaag ccgccctgct ggtgtgccag 840
tacactattc agagcctgat tcatctgacc ggggaggacc ctggattttt caatgtggaa 900
atccctgagt tcccatttta ccccacctgc aacgtctgta cagccgacgt gaacgtcacc 960
attaatttcg atgtgggcgg gaagaaacac cagctggacc tggattttgg ccagctgacc 1020
ccacatacaa aagccgtgta tcagcccaga ggggctttcg gaggcagcga gaacgcaaca 1080
aatctgtttc tgctggagct gctgggagca ggagaactgg ctctgaccat gaggtccaag 1140
aaactgccca tcaatgtgac cacaggagag gaacagcagg tcagtctgga atcagtggac 1200
gtctacttcc aggatgtgtt tggcaccatg tggtgccacc atgccgagat gcagaatcct 1260
gtgtacctga tccccgaaac cgtcccttat attaagtggg acaactgtaa tagcactaac 1320
attaccgcag tggtccgggc acaggggctg gacgtgaccc tgccactgtc actgcccaca 1380
agcgcccagg atagcaactt ctccgtgaaa accgagatgc tgggaaatga gatcgacatt 1440
gaatgcatca tggaggatgg agaaattagc caggtgctgc ctggcgataa caagtttaat 1500
atcacctgtt ccggctacga atctcacgtc ccaagtgggg gaatcctgac atctactagt 1560
cccgtggcca ctccaattcc cggaaccggc tacgcttata gcctgagact gacccctagg 1620
ccagtctcac gcttcctggg caacaatagc attctgtacg tgttttattc cggaaacgga 1680
ccaaaggctt ctggagggga ctattgcatc cagagtaata ttgtgttctc agacgagatc 1740
ccagccagcc aggatatgcc cactaacact accgacatta cctacgtggg cgataatgcc 1800
acttattccg tgcctatggt cacaagcgaa gacgctaact ccccaaatgt gaccgtcaca 1860
gcattctggg cctggcccaa caatactgag accgatttta agtgcaaatg gacactgact 1920
tcaggcaccc ctagcgggtg tgaaaacatc tctggcgcct tcgctagtaa tcgaaccttt 1980
gatattacag tgtccggcct ggggactgcc ccaaaaaccc tgatcattac ccggacagct 2040
actaacgcaa caactaccac acacaaagtg atcttcagca aagctcccga gtccactacc 2100
acatctccta ccctgaacac taccgggttt gccgacccca atacaactac cggactgcct 2160
agctccaccc atgtgccaac aaacctgact gcaccagcat ccaccggacc tacagtgtct 2220
act 2223

<210> SEQ ID NO 98
<211> LENGTH: 741
<212> TYPE: PRT
<213> ORGANISM: Artificial Sequence
<220> FEATURE:
<223> OTHER INFORMATION: Synthetic

<400> SEQUENCE: 98

Met Glu Phe Leu Lys Arg Ser Phe Ala Pro Leu Thr Glu Lys Gln Trp
1 5 10 15

Gln Glu Ile Asp Asn Arg Ala Arg Glu Ile Phe Lys Thr Gln Leu Tyr
20 25 30

Gly Arg Lys Phe Val Asp Val Glu Gly Pro Tyr Gly Trp Glu Tyr Ala
35 40 45

Ala His Pro Leu Gly Glu Val Glu Val Leu Ser Asp Glu Asn Glu Val
50 55 60

Val Lys Trp Gly Leu Arg Lys Ser Leu Pro Leu Ile Glu Leu Arg Ala
65 70 75 80

Thr Phe Thr Leu Asp Leu Trp Glu Leu Asp Asn Leu Glu Arg Gly Lys
85 90 95

Pro Asn Val Asp Leu Ser Ser Leu Glu Glu Thr Val Arg Lys Val Ala
100 105 110

Glu Phe Glu Asp Glu Val Ile Phe Arg Gly Cys Glu Lys Ser Gly Val
115 120 125

Lys Gly Leu Leu Ser Phe Glu Glu Arg Lys Ile Glu Cys Gly Ser Thr
130 135 140

Pro Lys Asp Leu Leu Glu Ala Ile Val Arg Ala Leu Ser Ile Phe Ser
145 150 155 160

Lys Asp Gly Ile Glu Gly Pro Tyr Thr Leu Val Ile Asn Thr Asp Arg
165 170 175

Trp Ile Asn Phe Leu Lys Glu Glu Ala Gly His Tyr Pro Leu Glu Lys
180 185 190

Arg Val Glu Glu Cys Leu Arg Gly Gly Lys Ile Ile Thr Thr Pro Arg
195 200 205

Ile Glu Asp Ala Leu Val Val Ser Glu Arg Gly Gly Asp Phe Lys Leu
210 215 220

Ile Leu Gly Gln Asp Leu Ser Ile Gly Tyr Glu Asp Arg Glu Lys Asp
225 230 235 240

Ala Val Arg Leu Phe Ile Thr Glu Thr Phe Thr Phe Gln Val Val Asn
245 250 255

Pro Glu Ala Leu Ile Leu Leu Lys Ser Gly Gly Gly Ser Gly Gly Gly
260 265 270

Glu Ala Ala Leu Leu Val Cys Gln Tyr Thr Ile Gln Ser Leu Ile His
275 280 285

Leu Thr Gly Glu Asp Pro Gly Phe Phe Asn Val Glu Ile Pro Glu Phe
290 295 300

Pro Phe Tyr Pro Thr Cys Asn Val Cys Thr Ala Asp Val Asn Val Thr
305 310 315 320

Ile Asn Phe Asp Val Gly Gly Lys Lys His Gln Leu Asp Leu Asp Phe
325 330 335

-continued

```
Gly Gln Leu Thr Pro His Thr Lys Ala Val Tyr Gln Pro Arg Gly Ala
            340                 345                 350

Phe Gly Gly Ser Glu Asn Ala Thr Asn Leu Phe Leu Leu Glu Leu Leu
        355                 360                 365

Gly Ala Gly Glu Leu Ala Leu Thr Met Arg Ser Lys Lys Leu Pro Ile
    370                 375                 380

Asn Val Thr Thr Gly Glu Glu Gln Gln Val Ser Leu Glu Ser Val Asp
385                 390                 395                 400

Val Tyr Phe Gln Asp Val Phe Gly Thr Met Trp Cys His His Ala Glu
                405                 410                 415

Met Gln Asn Pro Val Tyr Leu Ile Pro Glu Thr Val Pro Tyr Ile Lys
            420                 425                 430

Trp Asp Asn Cys Asn Ser Thr Asn Ile Thr Ala Val Val Arg Ala Gln
        435                 440                 445

Gly Leu Asp Val Thr Leu Pro Leu Ser Leu Pro Thr Ser Ala Gln Asp
    450                 455                 460

Ser Asn Phe Ser Val Lys Thr Glu Met Leu Gly Asn Glu Ile Asp Ile
465                 470                 475                 480

Glu Cys Ile Met Glu Asp Gly Glu Ile Ser Gln Val Leu Pro Gly Asp
                485                 490                 495

Asn Lys Phe Asn Ile Thr Cys Ser Gly Tyr Glu Ser His Val Pro Ser
            500                 505                 510

Gly Gly Ile Leu Thr Ser Thr Ser Pro Val Ala Thr Pro Ile Pro Gly
        515                 520                 525

Thr Gly Tyr Ala Tyr Ser Leu Arg Leu Thr Pro Arg Pro Val Ser Arg
    530                 535                 540

Phe Leu Gly Asn Asn Ser Ile Leu Tyr Val Phe Tyr Ser Gly Asn Gly
545                 550                 555                 560

Pro Lys Ala Ser Gly Gly Asp Tyr Cys Ile Gln Ser Asn Ile Val Phe
                565                 570                 575

Ser Asp Glu Ile Pro Ala Ser Gln Asp Met Pro Thr Asn Thr Thr Asp
            580                 585                 590

Ile Thr Tyr Val Gly Asp Asn Ala Thr Tyr Ser Val Pro Met Val Thr
        595                 600                 605

Ser Glu Asp Ala Asn Ser Pro Asn Val Thr Val Thr Ala Phe Trp Ala
    610                 615                 620

Trp Pro Asn Asn Thr Glu Thr Asp Phe Lys Cys Lys Trp Thr Leu Thr
625                 630                 635                 640

Ser Gly Thr Pro Ser Gly Cys Glu Asn Ile Ser Gly Ala Phe Ala Ser
                645                 650                 655

Asn Arg Thr Phe Asp Ile Thr Val Ser Gly Leu Gly Thr Ala Pro Lys
            660                 665                 670

Thr Leu Ile Ile Thr Arg Thr Ala Thr Asn Ala Thr Thr Thr Thr His
        675                 680                 685

Lys Val Ile Phe Ser Lys Ala Pro Glu Ser Thr Thr Thr Ser Pro Thr
    690                 695                 700

Leu Asn Thr Thr Gly Phe Ala Asp Pro Asn Thr Thr Thr Gly Leu Pro
705                 710                 715                 720

Ser Ser Thr His Val Pro Thr Asn Leu Thr Ala Pro Ala Ser Thr Gly
                725                 730                 735

Pro Thr Val Ser Thr
            740
```

<210> SEQ ID NO 99

<400> SEQUENCE: 99

000

<210> SEQ ID NO 100
<211> LENGTH: 1764
<212> TYPE: DNA
<213> ORGANISM: Artificial Sequence
<220> FEATURE:
<223> OTHER INFORMATION: Synthetic

<400> SEQUENCE: 100

```
atggagttcc tgaagaggag cttcgcccct ctgaccgaga agcagtggca ggagatcgac     60
aacagggcca gggagatctt caagacccag ctgtacggca ggaagttcgt ggacgtggag    120
ggcccctacg gctgggagta cgccgcccac cccctgggcg aggtggaggt gctgagcgac    180
gagaacgagg tggtgaagtg gggcctgagg aagagcctgc ccctgatcga gctgagggcc    240
accttcaccc tggacctgtg ggagctggac aacctggaga ggggcaagcc caacgtggac    300
ctgagcagcc tggaggagac cgtgaggaag gtggccgagt tcgaggacga ggtgatcttc    360
aggggctgcg agaagagcgg cgtgaagggc ctgctgagct tcgaggagag gaagatcgag    420
tgcggcagca cccccaagga cctgctggag gccatcgtga gggccctgag catcttcagc    480
aaggacggca tcgagggccc ctacaccctg gtgatcaaca ccgacaggtg gatcaacttc    540
ctgaaggagg aggccggcca ctacccccctg gagaagaggg tggaggagtg cctgaggggc    600
ggcaagatca tcaccacccc caggatcgag gacgccctgg tggtgagcga gaggggcggc    660
gacttcaagc tgatcctggg ccaggacctg agcatcggct acgaggacag ggagaaggac    720
gccgtgaggc tgttcatcac cgagaccttc accttccagg tggtgaaccc cgaggccctg    780
atcctgctga agtccggagg cggatctggc ggaggcgaag ccgccctgct ggtgtgccag    840
tacactattc agagcctgat tcatctgacc ggggaggacc ctggattttt caatgtggaa    900
atccctgagt tcccatttta ccccacctgc aacgtctgta cagccgacgt gaacgtcacc    960
attaatttcg atgtgggcgg gaagaaacac cagctggacc tggattttgg ccagctgacc   1020
ccacatacaa aagccgtgta tcagcccaga ggggctttcg gaggcagcga gaacgcaaca   1080
aatctgtttc tgctggagct gctgggagca ggagaactgg ctctgaccat gaggtccaag   1140
aaactgccca tcaatgtgac cacaggagag gaacagcagg tcagtctgga atcagtggac   1200
gtctacttcc aggatgtgtt tggcaccatg tggtgccacc atgccgagat gcagaatcct   1260
gtgtacctga tccccgaaac cgtcccttat attaagtggg acaactgtaa tagcactaac   1320
attaccgcag tggtccgggc acaggggctg gacgtgaccc tgccactgtc actgcccaca   1380
agcgcccagg atagcaactt ctccgtgaaa accgagatgc tgggaaatga gatcgacatt   1440
gaatgcatca tggaggatgg agaaattagc caggtgctgc ctggcgataa caagtttaat   1500
atcacctgtt ccggctacga atctcacgtc ccaagtgggg gaatcctgac atctactagt   1560
cccgtggcca ctccaattcc cggaaccggc tacgcttata gcctgagact gacccctagg   1620
ccagtctcac gcttcctggg caacaatagc attctgtacg tgttttattc cggaaacgga   1680
ccaaaggctt ctggagggga ctattgcatc cagagtaata ttgtgttctc agacgagatc   1740
ccagccagcc aggatatgcc cact                                           1764
```

<210> SEQ ID NO 101

<211> LENGTH: 588
<212> TYPE: PRT
<213> ORGANISM: Artificial Sequence
<220> FEATURE:
<223> OTHER INFORMATION: Synthetic

<400> SEQUENCE: 101

```
Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
        195                 200                 205

Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Ser Gly Gly Gly Ser Gly Gly Gly
            260                 265                 270

Glu Ala Ala Leu Leu Val Cys Gln Tyr Thr Ile Gln Ser Leu Ile His
        275                 280                 285

Leu Thr Gly Glu Asp Pro Gly Phe Phe Asn Val Glu Ile Pro Glu Phe
    290                 295                 300

Pro Phe Tyr Pro Thr Cys Asn Val Cys Thr Ala Asp Val Asn Val Thr
305                 310                 315                 320

Ile Asn Phe Asp Val Gly Gly Lys Lys His Gln Leu Asp Leu Asp Phe
                325                 330                 335

Gly Gln Leu Thr Pro His Thr Lys Ala Val Tyr Gln Pro Arg Gly Ala
            340                 345                 350

Phe Gly Gly Ser Glu Asn Ala Thr Asn Leu Phe Leu Leu Glu Leu Leu
        355                 360                 365

Gly Ala Gly Glu Leu Ala Leu Thr Met Arg Ser Lys Lys Leu Pro Ile
    370                 375                 380
```

Asn Val Thr Thr Gly Glu Glu Gln Gln Val Ser Leu Glu Ser Val Asp
385 390 395 400

Val Tyr Phe Gln Asp Val Phe Gly Thr Met Trp Cys His His Ala Glu
405 410 415

Met Gln Asn Pro Val Tyr Leu Ile Pro Glu Thr Val Pro Tyr Ile Lys
420 425 430

Trp Asp Asn Cys Asn Ser Thr Asn Ile Thr Ala Val Val Arg Ala Gln
435 440 445

Gly Leu Asp Val Thr Leu Pro Leu Ser Leu Pro Thr Ser Ala Gln Asp
450 455 460

Ser Asn Phe Ser Val Lys Thr Glu Met Leu Gly Asn Glu Ile Asp Ile
465 470 475 480

Glu Cys Ile Met Glu Asp Gly Glu Ile Ser Gln Val Leu Pro Gly Asp
485 490 495

Asn Lys Phe Asn Ile Thr Cys Ser Gly Tyr Glu Ser His Val Pro Ser
500 505 510

Gly Gly Ile Leu Thr Ser Thr Ser Pro Val Ala Thr Pro Ile Pro Gly
515 520 525

Thr Gly Tyr Ala Tyr Ser Leu Arg Leu Thr Pro Arg Pro Val Ser Arg
530 535 540

Phe Leu Gly Asn Asn Ser Ile Leu Tyr Val Phe Tyr Ser Gly Asn Gly
545 550 555 560

Pro Lys Ala Ser Gly Gly Asp Tyr Cys Ile Gln Ser Asn Ile Val Phe
565 570 575

Ser Asp Glu Ile Pro Ala Ser Gln Asp Met Pro Thr
580 585

<210> SEQ ID NO 102
<211> LENGTH: 1764
<212> TYPE: DNA
<213> ORGANISM: Artificial Sequence
<220> FEATURE:
<223> OTHER INFORMATION: Synthetic

<400> SEQUENCE: 102
agtgggcata tcctggctgg ctgggatctc gtctgagaac acaatattac tctggatgca 60
atagtcccct ccagaagcct ttggtccgtt tccggaataa aacacgtaca gaatgctatt 120
gttgcccagg aagcgtgaga ctggcctagg ggtcagtctc aggctataag cgtagccggt 180
tccgggaatt ggagtggcca cgggactagt agatgtcagg attcccccac ttgggacgtg 240
agattcgtag ccggaacagg tgatattaaa cttgttatcg ccaggcagca cctggctaat 300
ttctccatcc tccatgatgc attcaatgtc gatctcattt cccagcatct cggttttcac 360
ggagaagttg ctatcctggg cgcttgtggg cagtgacagt ggcagggtca cgtccagccc 420
ctgtgcccgg accactgcgg taatgttagt gctattacag ttgtcccact taatataagg 480
gacggtttcg gggatcaggt acacaggatt ctgcatctcg gcatggtggc accacatggt 540
gccaaacaca tcctggaagt agacgtccac tgattccaga ctgacctgct gttcctctcc 600
tgtggtcaca ttgatgggca gtttcttgga cctcatggtc agagccagtt ctcctgctcc 660
cagcagctcc agcagaaaca gatttgttgc gttctcgctg cctccgaaag cccctctggg 720
ctgatacacg gcttttgtat gtggggtcag ctggccaaaa tccaggtcca gctggtgttt 780
cttcccgccc acatcgaaat taatggtgac gttcacgtcg gctgtacaga cgttgcaggt 840
ggggtaaaat gggaactcag ggatttccac attgaaaaat ccagggtcct ccccggtcag 900

```
atgaatcagg ctctgaatag tgtactggca caccagcagg gcggcttcgc ctccgccaga    960

tccgcctccg gacttcagca ggatcagggc ctcggggttc accacctgga aggtgaaggt   1020

ctcggtgatg aacagcctca cggcgtcctt ctccctgtcc tcgtagccga tgctcaggtc   1080

ctggcccagg atcagcttga agtcgccgcc cctctcgctc accaccaggg cgtcctcgat   1140

cctgggggtg gtgatgatct tgccgcccct caggcactcc tccaccctct tctccagggg   1200

gtagtggccg gcctcctcct tcaggaagtt gatccacctg tcggtgttga tcaccagggt   1260

gtaggggccc tcgatgccgt ccttgctgaa gatgctcagg gccctcacga tggcctccag   1320

caggtccttg gggtgctgc cgcactcgat cttcctctcc tcgaagctca gcaggccctt   1380

cacgccgctc ttctcgcagc ccctgaagat cacctcgtcc tcgaactcgg ccaccttcct   1440

cacggtctcc tccaggctgc tcaggtccac gttgggcttg cccctctcca ggttgtccag   1500

ctcccacagg tccagggtga aggtggccct cagctcgatc aggggcaggc tcttcctcag   1560

gccccacttc accacctcgt tctcgtcgct cagcacctcc acctcgccca gggggtgggc   1620

ggcgtactcc cagccgtagg ggccctccac gtccacgaac ttcctgccgt acagctgggt   1680

cttgaagatc tccctggccc tgttgtcgat ctcctgccac tgcttctcgg tcagaggggc   1740

gaagctcctc ttcaggaact ccat                                           1764
```

<210> SEQ ID NO 103
<211> LENGTH: 2088
<212> TYPE: DNA
<213> ORGANISM: Artificial Sequence
<220> FEATURE:
<223> OTHER INFORMATION: Synthetic

<400> SEQUENCE: 103

```
atggagttcc tgaagaggag cttcgcccct ctgaccgaga agcagtggca ggagatcgac     60

aacagggcca gggagatctt caagacccag ctgtacggca ggaagttcgt ggacgtggag    120

ggcccctacg gctgggagta cgccgcccac cccctgggcg aggtggaggt gctgagcgac    180

gagaacgagg tggtgaagtg gggcctgagg aagagcctgc ccctgatcga gctgagggcc    240

accttcaccc tggacctgtg ggagctggac aacctggaga ggggcaagcc caacgtggac    300

ctgagcagcc tggaggagac cgtgaggaag gtggccgagt tcgaggacga ggtgatcttc    360

aggggctgcg agaagagcgg cgtgaagggc ctgctgagct tcgaggagag gaagatcgag    420

tgcggcagca cccccaagga cctgctggag gccatcgtga gggccctgag catcttcagc    480

aaggacggca tcgagggccc ctacaccctg gtgatcaaca ccgacaggtg gatcaacttc    540

ctgaaggagg aggccggcca ctacccccctg gagaagaggg tggaggagtg cctgaggggc    600

ggcaagatca tcaccacccc caggatcgag gacgccctgg tggtgagcga gaggggcggc    660

gacttcaagc tgatcctggg ccaggacctg agcatcggct acgaggacag ggagaaggac    720

gccgtgaggc tgttcatcac cgagaccttc accttccagg tggtgaaccc cgaggccctg    780

atcctgctga agtccggagg cggatctggc ggaggcgaag ccgccctgct ggtgtgccag    840

tacactattc agagcctgat tcatctgacc ggggaggacc ctggattttt caatgtggaa    900

atccctgagt tcccatttta ccccacctgc aacgtctgta cagccgacgt gaacgtcacc    960

attaatttcg atgtgggcgg gaagaaacac cagctggacc tggattttgg ccagctgacc   1020

ccacatacaa aagccgtgta tcagcccaga ggggctttcg gaggcagcga gaacgcaaca   1080

aatctgtttc tgctggagct gctgggagca ggagaactgg ctctgaccat gaggtccaag   1140
```

```
aaactgccca tcaatgtgac cacaggagag gaacagcagg tcagtctgga atcagtggac   1200

gtctacttcc aggatgtgtt tggcaccatg tggtgccacc atgccgagat gcagaatcct   1260

gtgtacctga tccccgaaac cgtcccttat attaagtggg acaactgtaa tagcactaac   1320

attaccgcag tggtccgggc acaggggctg gacgtgaccc tgccactgtc actgcccaca   1380

agcgcccagg atagcaactt ctccgtgaaa accgagatgc tgggaaatga gatcgacatt   1440

gaatgcatca tggaggatgg agaaattagc caggtgctgc ctggcgataa caagtttaat   1500

atcacctgtt ccggctacga atctcacgtc ccaagtgggg gaatcctgac atctactagt   1560

cccgtggcca ctccaattcc cggaaccggc tacgcttata gcctgagact gacccctagg   1620

ccagtctcac gcttcctggg caacaatagc attctgtacg tgttttattc cggaaacgga   1680

ccaaaggctt ctggagggga ctattgcatc cagagtaata ttgtgttctc agacgagatc   1740

ccagccagcc aggatatgcc cactaacact accgacatta cctacgtggg cgataatgcc   1800

acttattccg tgcctatggt cacaagcgaa gacgctaact ccccaaatgt gaccgtcaca   1860

gcattctggg cctggcccaa caatactgag accgatttta agtgcaaatg gacactgact   1920

tcaggcaccc ctagcgggtg tgaaaacatc tctggcgcct tcgctagtaa tcgaaccttt   1980

gatattacag tgtccggcct ggggactgcc ccaaaaaccc tgatcattac ccggacagct   2040

actaacgcaa caactaccac acacaaagtg atcttcagca aagctccc               2088


<210> SEQ ID NO 104
<211> LENGTH: 696
<212> TYPE: PRT
<213> ORGANISM: Artificial Sequence
<220> FEATURE:
<223> OTHER INFORMATION: Synthetic

<400> SEQUENCE: 104

Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
```

-continued

```
        195                 200                 205

Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Ser Gly Gly Gly Ser Gly Gly Gly
            260                 265                 270

Glu Ala Ala Leu Leu Val Cys Gln Tyr Thr Ile Gln Ser Leu Ile His
        275                 280                 285

Leu Thr Gly Glu Asp Pro Gly Phe Phe Asn Val Glu Ile Pro Glu Phe
    290                 295                 300

Pro Phe Tyr Pro Thr Cys Asn Val Cys Thr Ala Asp Val Asn Val Thr
305                 310                 315                 320

Ile Asn Phe Asp Val Gly Gly Lys Lys His Gln Leu Asp Leu Asp Phe
                325                 330                 335

Gly Gln Leu Thr Pro His Thr Lys Ala Val Tyr Gln Pro Arg Gly Ala
            340                 345                 350

Phe Gly Gly Ser Glu Asn Ala Thr Asn Leu Phe Leu Leu Glu Leu Leu
        355                 360                 365

Gly Ala Gly Glu Leu Ala Leu Thr Met Arg Ser Lys Lys Leu Pro Ile
    370                 375                 380

Asn Val Thr Thr Gly Glu Glu Gln Gln Val Ser Leu Glu Ser Val Asp
385                 390                 395                 400

Val Tyr Phe Gln Asp Val Phe Gly Thr Met Trp Cys His His Ala Glu
                405                 410                 415

Met Gln Asn Pro Val Tyr Leu Ile Pro Glu Thr Val Pro Tyr Ile Lys
            420                 425                 430

Trp Asp Asn Cys Asn Ser Thr Asn Ile Thr Ala Val Val Arg Ala Gln
        435                 440                 445

Gly Leu Asp Val Thr Leu Pro Leu Ser Leu Pro Thr Ser Ala Gln Asp
    450                 455                 460

Ser Asn Phe Ser Val Lys Thr Glu Met Leu Gly Asn Glu Ile Asp Ile
465                 470                 475                 480

Glu Cys Ile Met Glu Asp Gly Glu Ile Ser Gln Val Leu Pro Gly Asp
                485                 490                 495

Asn Lys Phe Asn Ile Thr Cys Ser Gly Tyr Glu Ser His Val Pro Ser
            500                 505                 510

Gly Gly Ile Leu Thr Ser Thr Ser Pro Val Ala Thr Pro Ile Pro Gly
        515                 520                 525

Thr Gly Tyr Ala Tyr Ser Leu Arg Leu Thr Pro Arg Pro Val Ser Arg
    530                 535                 540

Phe Leu Gly Asn Asn Ser Ile Leu Tyr Val Phe Tyr Ser Gly Asn Gly
545                 550                 555                 560

Pro Lys Ala Ser Gly Gly Asp Tyr Cys Ile Gln Ser Asn Ile Val Phe
                565                 570                 575

Ser Asp Glu Ile Pro Ala Ser Gln Asp Met Pro Thr Asn Thr Thr Asp
            580                 585                 590

Ile Thr Tyr Val Gly Asp Asn Ala Thr Tyr Ser Val Pro Met Val Thr
        595                 600                 605

Ser Glu Asp Ala Asn Ser Pro Asn Val Thr Val Thr Ala Phe Trp Ala
    610                 615                 620
```

```
Trp Pro Asn Asn Thr Glu Thr Asp Phe Lys Cys Lys Trp Thr Leu Thr
625                 630                 635                 640

Ser Gly Thr Pro Ser Gly Cys Glu Asn Ile Ser Gly Ala Phe Ala Ser
                645                 650                 655

Asn Arg Thr Phe Asp Ile Thr Val Ser Gly Leu Gly Thr Ala Pro Lys
            660                 665                 670

Thr Leu Ile Ile Thr Arg Thr Ala Thr Asn Ala Thr Thr Thr Thr His
        675                 680                 685

Lys Val Ile Phe Ser Lys Ala Pro
    690                 695


<210> SEQ ID NO 105
<211> LENGTH: 2088
<212> TYPE: DNA
<213> ORGANISM: Artificial Sequence
<220> FEATURE:
<223> OTHER INFORMATION: Synthetic

<400> SEQUENCE: 105

gggagctttg ctgaagatca ctttgtgtgt ggtagttgtt gcgttagtag ctgtccgggt     60

aatgatcagg gtttttgggg cagtccccag gccggacact gtaatatcaa aggttcgatt    120

actagcgaag gcgccagaga tgttttcaca cccgctaggg gtgcctgaag tcagtgtcca    180

tttgcactta aaatcggtct cagtattgtt gggccaggcc cagaatgctg tgacggtcac    240

atttggggag ttagcgtctt cgcttgtgac cataggcacg gaataagtgg cattatcgcc    300

cacgtaggta atgtcggtag tgttagtggg catatcctgg ctggctggga tctcgtctga    360

gaacacaata ttactctgga tgcaatagtc ccctccagaa gcctttggtc cgtttccgga    420

ataaaacacg tacagaatgc tattgttgcc caggaagcgt gagactggcc taggggtcag    480

tctcaggcta taagcgtagc cggttccggg aattggagtg gccacgggac tagtagatgt    540

caggattccc ccacttggga cgtgagattc gtagccggaa caggtgatat taaacttgtt    600

atcgccaggc agcacctggc taatttctcc atcctccatg atgcattcaa tgtcgatctc    660

atttcccagc atctcggttt tcacggagaa gttgctatcc tgggcgcttg tgggcagtga    720

cagtggcagg gtcacgtcca gcccctgtgc ccggaccact gcggtaatgt tagtgctatt    780

acagttgtcc cacttaatat aagggacggt ttcggggatc aggtacacag gattctgcat    840

ctcggcatgg tggcaccaca tggtgccaaa cacatcctgg aagtagacgt ccactgattc    900

cagactgacc tgctgttcct ctcctgtggt cacattgatg ggcagtttct tggacctcat    960

ggtcagagcc agttctcctg ctcccagcag ctccagcaga aacagatttg ttgcgttctc   1020

gctgcctccg aaagcccctc tgggctgata cacggctttt gtatgtgggg tcagctggcc   1080

aaaatccagg tccagctggt gtttcttccc gcccacatcg aaattaatgg tgacgttcac   1140

gtcggctgta cagacgttgc aggtggggta aaatgggaac tcagggattt ccacattgaa   1200

aaatccaggg tcctccccgg tcagatgaat caggctctga atagtgtact ggcacaccag   1260

cagggcggct tcgcctccgc cagatccgcc tccggacttc agcaggatca gggcctcggg   1320

gttcaccacc tggaaggtga aggtctcggt gatgaacagc ctcacggcgt ccttctccct   1380

gtcctcgtag ccgatgctca ggtcctggcc caggatcagc ttgaagtcgc cgcccctctc   1440

gctcaccacc agggcgtcct cgatcctggg ggtggtgatg atcttgccgc ccctcaggca   1500

ctcctccacc ctcttctcca gggggtagtg gccggcctcc tccttcagga agttgatcca   1560

cctgtcggtg ttgatcacca gggtgtaggg gccctcgatg ccgtccttgc tgaagatgct   1620
```

cagggccctc acgatggcct ccagcaggtc cttgggggtg ctgccgcact cgatcttcct 1680
ctcctcgaag ctcagcaggc ccttcacgcc gctcttctcg cagcccctga agatcacctc 1740
gtcctcgaac tcggccacct tcctcacggt ctcctccagg ctgctcaggt ccacgttggg 1800
cttgcccctc tccaggttgt ccagctccca caggtccagg gtgaaggtgg ccctcagctc 1860
gatcaggggc aggctcttcc tcaggcccca cttcaccacc tcgttctcgt cgctcagcac 1920
ctccacctcg cccaggggt gggcggcgta ctcccagccg taggggccct ccacgtccac 1980
gaacttcctg ccgtacagct gggtcttgaa gatctccctg gccctgttgt cgatctcctg 2040
ccactgcttc tcggtcagag gggcgaagct cctcttcagg aactccat 2088

<210> SEQ ID NO 106
<211> LENGTH: 6005
<212> TYPE: DNA
<213> ORGANISM: Artificial Sequence
<220> FEATURE:
<223> OTHER INFORMATION: Synthetic

<400> SEQUENCE: 106
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
gggaacttcc atagcccata tatggagttc cgcgttacat aacttacggg aatttccaaa 420
cctggctgac cgcccaacga cccccgccca ttgacgtcaa taatgacgta tgttcccata 480
gtaacgccaa tagggaactt ccattgacgt caatgggtgg agtatttacg gtaaactgcc 540
cacttgggaa tttccaagtg tatcatatgc caagtacgcc ccctattgac gtcaatgacg 600
ggaacttcca taagcttgca ttatgcccag tacatgacct tatgggaatt tcctacttgg 660
cagtacatct acgtattagt catcgctatt accatggtga tgcggttttg gcagtacatc 720
aatgggcgtg gatagcggtt tgactcacgg gaacttccaa gtctccaccc cattgacgtc 780
aatgggagtt tgttttgact caccaaaatc aacgggaatt cccaaaatgt cgtaacaact 840
ccgccccatt gacgcaaatg ggcggtaggc gtgtacggtg ggaggtctat ataagcagag 900
ctcgtttagt gaaccgtcag atcgcctgga gacgccatcc acgctgtttt gacctccata 960
gaagacaccg ggaccgatcc agcctccatc ggctcgcatc tctccttcac gcgcccgccg 1020
ccctacctga ggccgccatc cacgccggtt gagtcgcgtt ctgccgcctc ccgcctgtgg 1080
tgcctcctga actgcgtccg ccgtctaggt aagtttaaag ctcaggtcga gaccgggcct 1140
ttgtccggcg ctcccttgga gcctacctag actcagccgg ctctccacgc tttgcctgac 1200
cctgcttgct caactctagt taacggtgga gggcagtgta gtctgagcag tactcgttgc 1260
tgccgcgcgc gccaccagac ataatagctg acagactaac agactgttcc tttccatggg 1320 tctttctgc agtcaccgtc gtcgacacgt gtgatcagat atcgcggccg ctctagagat 1380
atcgccacca tggacagcaa gggcagcagc cagaagggca gcagactgct gctgctgctg 1440
gtggtgagca acctgctgct gcctcagggc gtgctagccg aagccgccct gctggtgtgc 1500
cagtacacta ttcagagcct gattcatctg accggggagg accctggatt tttcaatgtg 1560

```
gaaatccctg agttcccatt ttaccccacc tgcaacgtct gtacagccga cgtgaacgtc   1620
accattaatt tcgatgtggg cgggaagaaa caccagctgg acctggattt tggccagctg   1680
accccacata caaaagccgt gtatcagccc agaggggctt tcggaggcag cgagaacgca   1740
acaaatctgt ttctgctgga gctgctggga gcaggagaac tggctctgac catgaggtcc   1800
aagaaactgc ccatcaatgt gaccacagga gaggaacagc aggtcagtct ggaatcagtg   1860
gacgtctact tccaggatgt gtttggcacc atgtggtgcc accatgccga gatgcagaat   1920
cctgtgtacc tgatccccga aaccgtccct tatattaagt gggacaactg taatagcact   1980
aacattaccg cagtggtccg ggcacagggg ctggacgtga ccctgccact gtcactgccc   2040
acaagcgccc aggatagcaa cttctccgtg aaaaccgaga tgctgggaaa tgagatcgac   2100
attgaatgca tcatggagga tggagaaatt agccaggtgc tgcctggcga taacaagttt   2160
aatatcacct gttccggcta cgaatctcac gtcccaagtg gggaatcct gacatctact   2220
agtcccgtgg ccactccaat tcccggaacc ggctacgctt atagcctgag actgacccct   2280
aggccagtct cacgcttcct gggcaacaat agcattctgt acgtgtttta ttccggaaac   2340
ggaccaaagg cttctggagg ggactattgc atccagagta atattgtgtt ctcagacgag   2400
atcccagcca gccaggatat gcccacttcc ggagagagcc aggtgaggca gaacttcaag   2460
cccgagatgg aggagaagct gaacgagcag atgaacctgg agctgtacag cagcctgctg   2520
taccagcaga tgagcgcctg gtgcagctac cacaccttcg agggcgccgc cgccttcctg   2580
aggaggcacg cccaggagga gatgacccac atgcagaggc tgttcgacta cctgaccgac   2640
accggcaacc tgcccaggat caacaccgtg gagagcccct tcgccgagta cagcagcctg   2700
gacgagctgt tccaggagac ctacaagcac gagcagctga tcacccagaa gatcaacgag   2760
ctggcccacg ccgccatgac caaccaggac taccccacct tcaacttcct gcagtggtac   2820
gtgagcgagc agcacgagga ggagaagctg ttcaagagca tcatcgacaa gctgagcctg   2880
gccggcaaga gcggcgaggg cctgtacttc atcgacaagg agctgagcac cctggacgga   2940
tcctagcatc atcatcatca ttagtctgga agggcgaatt gatccagatc tgctgtgcct   3000
tctagttgcc agccatctgt tgtttgcccc tcccccgtgc cttccttgac cctggaaggt   3060
gccactccca ctgtcctttc ctaataaaat gaggaaattg catcgcattg tctgagtagg   3120
tgtcattcta ttctgggggg tggggtgggg caggacagca agggggagga ttgggaagac   3180
aatagcaggc atgctgggga tgcggtgggc tctatgggta cccaggtgct gaagaattga   3240
cccggttcct cctgggccag aaagaagcag gcacatcccc ttctctgtga cacaccctgt   3300
ccacgcccct ggttcttagt tccagcccca ctcataggac actcatagct caggagggct   3360
ccgccttcaa tcccacccgc taaagtactt ggagcggtct ctccctccct catcagccca   3420
ccaaaccaaa cctagcctcc aagagtggga agaaattaaa gcaagatagg ctattaagtg   3480
cagagggaga gaaaatgcct ccaacatgtg aggaagtaat gagagaaatc atagaatttt   3540
aaggccatga tttaaggcca tcatggcctt aatcttccgc ttcctcgctc actgactcgc   3600
tgcgctcggt cgttcggctg cggcgagcgg tatcagctca ctcaaaggcg gtaatacggt   3660
tatccacaga atcaggggat aacgcaggaa agaacatgtg agcaaaaggc cagcaaaagg   3720
ccaggaaccg taaaaaggcc gcgttgctgg cgtttttcca taggctccgc ccccctgacg   3780
agcatcacaa aaatcgacgc tcaagtcaga ggtggcgaaa cccgacagga ctataaagat   3840
accaggcgtt tccccctgga agctccctcg tgcgctctcc tgttccgacc ctgccgctta   3900
ccggatacct gtccgccttt ctcccttcgg gaagcgtggc gctttctcat agctcacgct   3960
```

```
gtaggtatct cagttcggtg taggtcgttc gctccaagct gggctgtgtg cacgaacccc   4020

ccgttcagcc cgaccgctgc gccttatccg gtaactatcg tcttgagtcc aacccggtaa   4080

gacacgactt atcgccactg gcagcagcca ctggtaacag gattagcaga gcgaggtatg   4140

taggcggtgc tacagagttc ttgaagtggt ggcctaacta cggctacact agaagaacag   4200

tatttggtat ctgcgctctg ctgaagccag ttaccttcgg aaaaagagtt ggtagctctt   4260

gatccggcaa acaaaccacc gctggtagcg gtggtttttt tgtttgcaag cagcagatta   4320

cgcgcagaaa aaaaggatct caagaagatc ctttgatctt ttctacgggg tctgacgctc   4380

agtggaacga aaactcacgt taagggattt tggtcatgag attatcaaaa aggatcttca   4440

cctagatcct tttaaattaa aaatgaagtt ttaaatcaat ctaaagtata tatgagtaaa   4500

cttggtctga cagttaccaa tgcttaatca gtgaggcacc tatctcagcg atctgtctat   4560

ttcgttcatc catagttgcc tgactcgggg ggggggggcg ctgaggtctg cctcgtgaag   4620

aaggtgttgc tgactcatac caggcctgaa tcgccccatc atccagccag aaagtgaggg   4680

agccacggtt gatgagagct ttgttgtagg tggaccagtt ggtgattttg aacttttgct   4740

ttgccacgga acggtctgcg ttgtcgggaa gatgcgtgat ctgatccttc aactcagcaa   4800

aagttcgatt tattcaacaa agccgccgtc ccgtcaagtc agcgtaatgc tctgccagtg   4860

ttacaaccaa ttaaccaatt ctgattagaa aaactcatcg agcatcaaat gaaactgcaa   4920

tttattcata tcaggattat caataccata tttttgaaaa agccgtttct gtaatgaagg   4980

agaaaactca ccgaggcagt tccataggat ggcaagatcc tggtatcggt ctgcgattcc   5040

gactcgtcca acatcaatac aacctattaa tttcccctcg tcaaaaataa ggttatcaag   5100

tgagaaatca ccatgagtga cgactgaatc cggtgagaat ggcaaaagct tatgcatttc   5160

tttccagact tgttcaacag gccagccatt acgctcgtca tcaaaatcac tcgcatcaac   5220

caaaccgtta ttcattcgtg attgcgcctg agcgagacga aatacgcgat cgctgttaaa   5280

aggacaatta caaacaggaa tcgaatgcaa ccggcgcagg aacactgcca gcgcatcaac   5340

aatattttca cctgaatcag gatattcttc taatacctgg aatgctgttt tcccggggat   5400

cgcagtggtg agtaaccatg catcatcagg agtacggata aaatgcttga tggtcggaag   5460

aggcataaat tccgtcagcc agtttagtct gaccatctca tctgtaacat cattggcaac   5520

gctacctttg ccatgtttca gaaacaactc tggcgcatcg ggcttcccat acaatcgata   5580

gattgtcgca cctgattgcc cgacattatc gcgagcccat ttatacccat ataaatcagc   5640

atccatgttg gaatttaatc gcggcctcga gcaagacgtt tcccgttgaa tatggctcat   5700

aacacccctt gtattactgt ttatgtaagc agacagtttt attgttcatg atgatatatt   5760

tttatcttgt gcaatgtaac atcagagatt ttgagacaca acgtggcttt cccccccccc   5820

ccattattga agcatttatc agggttattg tctcatgagc ggatacatat ttgaatgtat   5880

ttagaaaaat aaacaaatag gggttccgcg cacatttccc cgaaaagtgc cacctgacgt   5940

ctaagaaacc attattatca tgacattaac ctataaaaat aggcgtatca cgaggccctt   6000

tcgtc                                                               6005
```

<210> SEQ ID NO 107
<211> LENGTH: 6329
<212> TYPE: DNA
<213> ORGANISM: Artificial Sequence
<220> FEATURE:
<223> OTHER INFORMATION: Synthetic

<400> SEQUENCE: 107

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
gggaacttcc atagcccata tatggagttc cgcgttacat aacttacggg aatttccaaa    420
cctggctgac cgcccaacga cccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg gatagcggtt tgactcacgg gaacttccaa gtctccaccc cattgacgtc    780
aatgggagtt tgttttgact caccaaaatc aacgggaatt cccaaaatgt cgtaacaact    840
ccgccccatt gacgcaaatg ggcggtaggc gtgtacggtg ggaggtctat ataagcagag    900
ctcgtttagt gaaccgtcag atcgcctgga gacgccatcc acgctgtttt gacctccata    960
gaagacaccg ggaccgatcc agcctccatc ggctcgcatc tctccttcac gcgcccgccg   1020
ccctacctga ggccgccatc cacgccggtt gagtcgcgtt ctgccgcctc ccgcctgtgg   1080
tgcctcctga actgcgtccg ccgtctaggt aagtttaaag ctcaggtcga gaccgggcct   1140
ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagagat   1380
atcgccacca tggacagcaa gggcagcagc cagaagggca gcagactgct gctgctgctg   1440
gtggtgagca acctgctgct gcctcagggc gtgctagccg aagccgccct gctggtgtgc   1500
cagtacacta ttcagagcct gattcatctg accggggagg accctggatt tttcaatgtg   1560
gaaatccctg agttcccatt ttaccccacc tgcaacgtct gtacagccga cgtgaacgtc   1620
accattaatt tcgatgtggg cggggaagaaa caccagctgg acctggattt tggccagctg   1680
accccacata caaaagccgt gtatcagccc agaggggctt tcggaggcag cgagaacgca   1740
acaaatctgt ttctgctgga gctgctggga gcaggagaac tggctctgac catgaggtcc   1800
aagaaactgc ccatcaatgt gaccacagga gaggaacagc aggtcagtct ggaatcagtg   1860
gacgtctact tccaggatgt gtttggcacc atgtggtgcc accatgccga gatgcagaat   1920
cctgtgtacc tgatccccga aaccgtccct tatattaagt gggacaactg taatagcact   1980
aacattaccg cagtggtccg ggcacagggg ctggacgtga ccctgccact gtcactgccc   2040
acaagcgccc aggatagcaa cttctccgtg aaaaccgaga tgctgggaaa tgagatcgac   2100
attgaatgca tcatggagga tggagaaatt agccaggtgc tgcctggcga taacaagttt   2160
aatatcacct gttccggcta cgaatctcac gtcccaagtg ggggaatcct gacatctact   2220
agtcccgtgg ccactccaat tcccggaacc ggctacgctt atagcctgag actgacccct   2280
aggccagtct cacgcttcct gggcaacaat agcattctgt acgtgtttta ttccggaaac   2340
```

```
ggaccaaagg cttctggagg ggactattgc atccagagta atattgtgtt ctcagacgag   2400
atcccagcca gccaggatat gcccactaac actaccgaca ttacctacgt gggcgataat   2460
gccacttatt ccgtgcctat ggtcacaagc gaagacgcta actccccaaa tgtgaccgtc   2520
acagcattct gggcctggcc caacaatact gagaccgatt ttaagtgcaa atggacactg   2580
acttcaggca cccctagcgg gtgtgaaaac atctctggcg ccttcgctag taatcgaacc   2640
tttgatatta cagtgtccgg cctggggact gccccaaaaa ccctgatcat tacccggaca   2700
gctactaacg caacaactac cacacacaaa gtgatcttca gcaaagctcc ctccggagag   2760
agccaggtga ggcagaactt caagcccgag atggaggaga agctgaacga gcagatgaac   2820
ctggagctgt acagcagcct gctgtaccag cagatgagcg cctggtgcag ctaccacacc   2880
ttcgagggcg ccgccgcctt cctgaggagg cacgcccagg aggagatgac ccacatgcag   2940
aggctgttcg actacctgac cgacaccggc aacctgccca ggatcaacac cgtggagagc   3000
cccttcgccg agtacagcag cctggacgag ctgttccagg agacctacaa gcacgagcag   3060
ctgatcaccc agaagatcaa cgagctggcc cacgccgcca tgaccaacca ggactacccc   3120
accttcaact tcctgcagtg gtacgtgagc gagcagcacg aggaggagaa gctgttcaag   3180
agcatcatcg acaagctgag cctggccggc aagagcggcg agggcctgta cttcatcgac   3240
aaggagctga gcaccctgga cggatcctag catcatcatc atcattagtc tggaagggcg   3300
aattgatcca gatctgctgt gccttctagt tgccagccat ctgttgtttg cccctccccc   3360
gtgccttcct tgaccctgga aggtgccact cccactgtcc tttcctaata aaatgaggaa   3420
attgcatcgc attgtctgag taggtgtcat tctattctgg ggggtggggt ggggcaggac   3480
agcaaggggg aggattggga agacaatagc aggcatgctg gggatgcggt gggctctatg   3540
ggtacccagg tgctgaagaa ttgacccggt tcctcctggg ccagaaagaa gcaggcacat   3600
ccccttctct gtgacacacc ctgtccacgc ccctggttct tagttccagc cccactcata   3660
ggacactcat agctcaggag ggctccgcct tcaatcccac ccgctaaagt acttggagcg   3720
gtctctccct ccctcatcag cccaccaaac caaacctagc ctccaagagt gggaagaaat   3780
taaagcaaga taggctatta agtgcagagg gagagaaaat gcctccaaca tgtgaggaag   3840
taatgagaga aatcatagaa ttttaaggcc atgatttaag gccatcatgg ccttaatctt   3900
ccgcttcctc gctcactgac tcgctgcgct cggtcgttcg gctgcggcga gcggtatcag   3960
ctcactcaaa ggcggtaata cggttatcca cagaatcagg ggataacgca ggaaagaaca   4020
tgtgagcaaa aggccagcaa aaggccagga accgtaaaaa ggccgcgttg ctggcgtttt   4080
tccataggct ccgcccccct gacgagcatc acaaaaatcg acgctcaagt cagaggtggc   4140
gaaacccgac aggactataa agataccagg cgtttccccc tggaagctcc ctcgtgcgct   4200
ctcctgttcc gaccctgccg cttaccggat acctgtccgc ctttctccct tcgggaagcg   4260
tggcgctttc tcatagctca cgctgtaggt atctcagttc ggtgtaggtc gttcgctcca   4320
agctgggctg tgtgcacgaa ccccccgttc agcccgaccg ctgcgcctta tccggtaact   4380
atcgtcttga gtccaacccg gtaagacacg acttatcgcc actggcagca gccactggta   4440
acaggattag cagagcgagg tatgtaggcg gtgctacaga gttcttgaag tggtggccta   4500
actacggcta cactagaaga acagtatttg gtatctgcgc tctgctgaag ccagttacct   4560
tcggaaaaag agttggtagc tcttgatccg gcaaacaaac caccgctggt agcggtggtt   4620
tttttgtttg caagcagcag attacgcgca gaaaaaaagg atctcaagaa gatcctttga   4680
```

-continued

```
tcttttctac ggggtctgac gctcagtgga acgaaaactc acgttaaggg attttggtca   4740

tgagattatc aaaaaggatc ttcacctaga tccttttaaa ttaaaaatga agttttaaat   4800

caatctaaag tatatatgag taaacttggt ctgacagtta ccaatgctta atcagtgagg   4860

cacctatctc agcgatctgt ctatttcgtt catccatagt tgcctgactc gggggggggg   4920

ggcgctgagg tctgcctcgt gaagaaggtg ttgctgactc ataccaggcc tgaatcgccc   4980

catcatccag ccagaaagtg agggagccac ggttgatgag agctttgttg taggtggacc   5040

agttggtgat tttgaacttt tgctttgcca cggaacggtc tgcgttgtcg ggaagatgcg   5100

tgatctgatc cttcaactca gcaaaagttc gatttattca acaaagccgc cgtcccgtca   5160

agtcagcgta atgctctgcc agtgttacaa ccaattaacc aattctgatt agaaaaactc   5220

atcgagcatc aaatgaaact gcaatttatt catatcagga ttatcaatac catatttttg   5280

aaaaagccgt ttctgtaatg aaggagaaaa ctcaccgagg cagttccata ggatggcaag   5340

atcctggtat cggtctgcga ttccgactcg tccaacatca atacaaccta ttaatttccc   5400

ctcgtcaaaa ataaggttat caagtgagaa atcaccatga gtgacgactg aatccggtga   5460

gaatggcaaa agcttatgca tttctttcca gacttgttca acaggccagc cattacgctc   5520

gtcatcaaaa tcactcgcat caaccaaacc gttattcatt cgtgattgcg cctgagcgag   5580

acgaaatacg cgatcgctgt taaaaggaca attacaaaca ggaatcgaat gcaaccggcg   5640

caggaacact gccagcgcat caacaatatt ttcacctgaa tcaggatatt cttctaatac   5700

ctggaatgct gttttcccgg ggatcgcagt ggtgagtaac catgcatcat caggagtacg   5760

gataaaatgc ttgatggtcg gaagaggcat aaattccgtc agccagttta gtctgaccat   5820

ctcatctgta acatcattgg caacgctacc tttgccatgt ttcagaaaca actctggcgc   5880

atcgggcttc ccatacaatc gatagattgt cgcacctgat tgcccgacat tatcgcgagc   5940

ccatttatac ccatataaat cagcatccat gttggaattt aatcgcggcc tcgagcaaga   6000

cgtttcccgt tgaatatggc tcataacacc ccttgtatta ctgtttatgt aagcagacag   6060

ttttattgtt catgatgata tatttttatc ttgtgcaatg taacatcaga gatttgaga   6120

cacaacgtgg ctttcccccc ccccccatta ttgaagcatt tatcagggtt attgtctcat   6180

gagcggatac atatttgaat gtatttagaa aaataaacaa ataggggttc cgcgcacatt   6240

tccccgaaaa gtgccacctg acgtctaaga aaccattatt atcatgacat taacctataa   6300

aaataggcgt atcacgaggc cctttcgtc                                     6329
```

<210> SEQ ID NO 108
<211> LENGTH: 6464
<212> TYPE: DNA
<213> ORGANISM: Artificial Sequence
<220> FEATURE:
<223> OTHER INFORMATION: Synthetic

<400> SEQUENCE: 108

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360

gggaacttcc atagcccata tatggagttc cgcgttacat aacttacggg aatttccaaa    420
```

```
cctggctgac cgcccaacga cccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg gatagcggtt tgactcacgg gaacttccaa gtctccaccc cattgacgtc    780
aatgggagtt tgttttgact caccaaaatc aacgggaatt cccaaaatgt cgtaacaact    840
ccgccccatt gacgcaaatg ggcggtaggc gtgtacggtg ggaggtctat ataagcagag    900
ctcgtttagt gaaccgtcag atcgcctgga gacgccatcc acgctgtttt gacctccata    960
gaagacaccg ggaccgatcc agcctccatc ggctcgcatc tctccttcac gcgcccgccg   1020
ccctacctga ggccgccatc cacgccggtt gagtcgcgtt ctgccgcctc ccgcctgtgg   1080
tgcctcctga actgcgtccg ccgtctaggt aagtttaaag ctcaggtcga gaccgggcct   1140
ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagagat   1380
atcgccacca tggacagcaa gggcagcagc cagaagggca gcagactgct gctgctgctg   1440
gtggtgagca acctgctgct gcctcagggc gtgctagccg aagccgccct gctggtgtgc   1500
cagtacacta ttcagagcct gattcatctg accggggagg accctggatt tttcaatgtg   1560
gaaatccctg agttcccatt ttaccccacc tgcaacgtct gtacagccga cgtgaacgtc   1620
accattaatt tcgatgtggg cgggaagaaa caccagctgg acctggattt tggccagctg   1680
accccacata caaaagccgt gtatcagccc agaggggctt tcggaggcag cgagaacgca   1740
acaaatctgt ttctgctgga gctgctggga gcaggagaac tggctctgac catgaggtcc   1800
aagaaactgc ccatcaatgt gaccacagga gaggaacagc aggtcagtct ggaatcagtg   1860
gacgtctact tccaggatgt gtttggcacc atgtggtgcc accatgccga gatgcagaat   1920
cctgtgtacc tgatccccga aaccgtccct tatattaagt gggacaactg taatagcact   1980
aacattaccg cagtggtccg ggcacagggg ctggacgtga ccctgccact gtcactgccc   2040
acaagcgccc aggatagcaa cttctccgtg aaaaccgaga tgctgggaaa tgagatcgac   2100
attgaatgca tcatggagga tggagaaatt agccaggtgc tgcctggcga taacaagttt   2160
aatatcacct gttccggcta cgaatctcac gtcccaagtg ggggaatcct gacatctact   2220
agtcccgtgg ccactccaat tcccggaacc ggctacgctt atagcctgag actgacccct   2280
aggccagtct cacgcttcct gggcaacaat agcattctgt acgtgtttta ttccggaaac   2340
ggaccaaagg cttctggagg ggactattgc atccagagta atattgtgtt ctcagacgag   2400
atcccagcca gccaggatat gcccactaac actaccgaca ttacctacgt gggcgataat   2460
gccacttatt ccgtgcctat ggtcacaagc gaagacgcta actccccaaa tgtgaccgtc   2520
acagcattct gggcctggcc caacaatact gagaccgatt ttaagtgcaa atggacactg   2580
acttcaggca cccctagcgg gtgtgaaaac atctctggcg ccttcgctag taatcgaacc   2640
tttgatatta cagtgtccgg cctggggact gccccaaaaa ccctgatcat tacccggaca   2700
gctactaacg caacaactac cacacacaaa gtgatcttca gcaaagctcc cgagtccact   2760
```

-continued

```
accacatctc ctaccctgaa cactaccggg tttgccgacc ccaatacaac taccggactg   2820
cctagctcca cccatgtgcc aacaaacctg actgcaccag catccaccgg acctacagtg   2880
tctacttccg gagagagcca ggtgaggcag aacttcaagc ccgagatgga ggagaagctg   2940
aacgagcaga tgaacctgga gctgtacagc agcctgctgt accagcagat gagcgcctgg   3000
tgcagctacc acaccttcga gggcgccgcc gccttcctga ggaggcacgc ccaggaggag   3060
atgacccaca tgcagaggct gttcgactac ctgaccgaca ccggcaacct gcccaggatc   3120
aacaccgtgg agagcccctt cgccgagtac agcagcctgg acgagctgtt ccaggagacc   3180
tacaagcacg agcagctgat cacccagaag atcaacgagc tggcccacgc cgccatgacc   3240
aaccaggact accccacctt caacttcctg cagtggtacg tgagcgagca gcacgaggag   3300
gagaagctgt tcaagagcat catcgacaag ctgagcctgg ccggcaagag cggcgagggc   3360
ctgtacttca tcgacaagga gctgagcacc ctggacggat cctagcatca tcatcatcat   3420
tagtctggaa gggcgaattg atccagatct gctgtgcctt ctagttgcca gccatctgtt   3480
gtttgcccct cccccgtgcc ttccttgacc ctggaaggtg ccactcccac tgtcctttcc   3540
taataaaatg aggaaattgc atcgcattgt ctgagtaggt gtcattctat tctggggggt   3600
ggggtggggc aggacagcaa gggggaggat tgggaagaca atagcaggca tgctggggat   3660
gcggtgggct ctatgggtac ccaggtgctg aagaattgac ccggttcctc ctgggccaga   3720
aagaagcagg cacatcccct tctctgtgac acaccctgtc cacgcccctg gttcttagtt   3780
ccagccccac tcataggaca ctcatagctc aggagggctc cgccttcaat cccacccgct   3840
aaagtacttg gagcggtctc tccctccctc atcagcccac caaaccaaac ctagcctcca   3900
agagtgggaa gaaattaaag caagataggc tattaagtgc agagggagag aaaatgcctc   3960
caacatgtga ggaagtaatg agagaaatca tagaatttta aggccatgat ttaaggccat   4020
catggcctta atcttccgct tcctcgctca ctgactcgct gcgctcggtc gttcggctgc   4080
ggcgagcggt atcagctcac tcaaaggcgg taatacggtt atccacagaa tcaggggata   4140
acgcaggaaa gaacatgtga gcaaaaggcc agcaaaaggc caggaaccgt aaaaaggccg   4200
cgttgctggc gtttttccat aggctccgcc cccctgacga gcatcacaaa aatcgacgct   4260
caagtcagag gtggcgaaac ccgacaggac tataaagata ccaggcgttt ccccctggaa   4320
gctccctcgt gcgctctcct gttccgaccc tgccgcttac cggatacctg tccgcctttc   4380
tcccttcggg aagcgtggcg ctttctcata gctcacgctg taggtatctc agttcggtgt   4440
aggtcgttcg ctccaagctg ggctgtgtgc acgaaccccc cgttcagccc gaccgctgcg   4500
ccttatccgg taactatcgt cttgagtcca acccggtaag acacgactta tcgccactgg   4560
cagcagccac tggtaacagg attagcagag cgaggtatgt aggcggtgct acagagttct   4620
tgaagtggtg gcctaactac ggctacacta gaagaacagt atttggtatc tgcgctctgc   4680
tgaagccagt taccttcgga aaaagagttg gtagctcttg atccggcaaa caaaccaccg   4740
ctggtagcgg tggttttttt gtttgcaagc agcagattac gcgcagaaaa aaaggatctc   4800
aagaagatcc tttgatcttt tctacggggt ctgacgctca gtggaacgaa aactcacgtt   4860
aagggatttt ggtcatgaga ttatcaaaaa ggatcttcac ctagatcctt ttaaattaaa   4920
aatgaagttt taaatcaatc taaagtatat atgagtaaac ttggtctgac agttaccaat   4980
gcttaatcag tgaggcacct atctcagcga tctgtctatt tcgttcatcc atagttgcct   5040
gactcggggg gggggggcgc tgaggtctgc ctcgtgaaga aggtgttgct gactcatacc   5100
aggcctgaat cgccccatca tccagccaga aagtgaggga gccacggttg atgagagctt   5160
```

tgttgtaggt ggaccagttg gtgattttga acttttgctt tgccacggaa cggtctgcgt 5220
tgtcgggaag atgcgtgatc tgatccttca actcagcaaa agttcgattt attcaacaaa 5280
gccgccgtcc cgtcaagtca gcgtaatgct ctgccagtgt tacaaccaat taaccaattc 5340
tgattagaaa aactcatcga gcatcaaatg aaactgcaat ttattcatat caggattatc 5400
aataccatat ttttgaaaaa gccgtttctg taatgaagga gaaaactcac cgaggcagtt 5460
ccataggatg gcaagatcct ggtatcggtc tgcgattccg actcgtccaa catcaataca 5520
acctattaat ttcccctcgt caaaaataag gttatcaagt gagaaatcac catgagtgac 5580
gactgaatcc ggtgagaatg gcaaaagctt atgcatttct ttccagactt gttcaacagg 5640
ccagccatta cgctcgtcat caaaatcact cgcatcaacc aaaccgttat tcattcgtga 5700
ttgcgcctga gcgagacgaa atacgcgatc gctgttaaaa ggacaattac aaacaggaat 5760
cgaatgcaac cggcgcagga acactgccag cgcatcaaca atattttcac ctgaatcagg 5820
atattcttct aatacctgga atgctgtttt cccggggatc gcagtggtga gtaaccatgc 5880
atcatcagga gtacggataa aatgcttgat ggtcggaaga ggcataaatt ccgtcagcca 5940
gtttagtctg accatctcat ctgtaacatc attggcaacg ctacctttgc catgtttcag 6000
aaacaactct ggcgcatcgg gcttcccata caatcgatag attgtcgcac ctgattgccc 6060
gacattatcg cgagcccatt tatacccata taaatcagca tccatgttgg aatttaatcg 6120
cggcctcgag caagacgttt cccgttgaat atggctcata acaccccttg tattactgtt 6180
tatgtaagca gacagtttta ttgttcatga tgatatattt ttatcttgtg caatgtaaca 6240
tcagagattt tgagacacaa cgtggctttc cccccccccc cattattgaa gcatttatca 6300
gggttattgt ctcatgagcg gatacatatt tgaatgtatt tagaaaaata aacaaatagg 6360
ggttccgcgc acatttcccc gaaaagtgcc acctgacgtc taagaaacca ttattatcat 6420
gacattaacc tataaaaata ggcgtatcac gaggcccttt cgtc 6464

<210> SEQ ID NO 109
<211> LENGTH: 7634
<212> TYPE: DNA
<213> ORGANISM: Artificial Sequence
<220> FEATURE:
<223> OTHER INFORMATION: Synthetic

<400> SEQUENCE: 109
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
gggaacttcc atagcccata tatggagttc cgcgttacat aacttacggg aatttccaaa 420
cctggctgac cgcccaacga cccccgccca ttgacgtcaa taatgacgta tgttcccata 480
gtaacgccaa tagggaactt ccattgacgt caatgggtgg agtatttacg gtaaactgcc 540
cacttgggaa tttccaagtg tatcatatgc caagtacgcc ccctattgac gtcaatgacg 600
ggaacttcca taagcttgca ttatgcccag tacatgacct tatgggaatt tcctacttgg 660
cagtacatct acgtattagt catcgctatt accatggtga tgcggttttg gcagtacatc 720

```
aatgggcgtg gatagcggtt tgactcacgg gaacttccaa gtctccaccc cattgacgtc    780
aatgggagtt tgttttgact caccaaaatc aacgggaatt cccaaaatgt cgtaacaact    840
ccgccccatt gacgcaaatg ggcggtaggc gtgtacggtg ggaggtctat ataagcagag    900
ctcgtttagt gaaccgtcag atcgcctgga gacgccatcc acgctgtttt gacctccata    960
gaagacaccg ggaccgatcc agcctccatc ggctcgcatc tctccttcac gcgcccgccg   1020
ccctacctga ggccgccatc cacgccggtt gagtcgcgtt ctgccgcctc ccgcctgtgg   1080
tgcctcctga actgcgtccg ccgtctaggt aagtttaaag ctcaggtcga gaccgggcct   1140
ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagagat   1380
atcgccacca tggacagcaa gggcagcagc cagaagggca gcagactgct gctgctgctg   1440
gtggtgagca acctgctgct gcctcagggc gtgctagccg aagccgccct gctggtgtgc   1500
cagtacacta ttcagagcct gattcatctg accggggagg accctggatt tttcaatgtg   1560
gaaatccctg agttcccatt ttaccccacc tgcaacgtct gtacagccga cgtgaacgtc   1620
accattaatt tcgatgtggg cgggaagaaa caccagctgg acctggattt tggccagctg   1680
accccacata caaaagccgt gtatcagccc agaggggctt tcggaggcag cgagaacgca   1740
acaaatctgt ttctgctgga gctgctggga gcaggagaac tggctctgac catgaggtcc   1800
aagaaactgc ccatcaatgt gaccacagga gaggaacagc aggtcagtct ggaatcagtg   1860
gacgtctact tccaggatgt gtttggcacc atgtggtgcc accatgccga gatgcagaat   1920
cctgtgtacc tgatccccga aaccgtccct tatattaagt gggacaactg taatagcact   1980
aacattaccg cagtggtccg ggcacagggg ctggacgtga ccctgccact gtcactgccc   2040
acaagcgccc aggatagcaa cttctccgtg aaaaccgaga tgctgggaaa tgagatcgac   2100
attgaatgca tcatggagga tggagaaatt agccaggtgc tgcctggcga taacaagttt   2160
aatatcacct gttccggcta cgaatctcac gtcccaagtg ggggaatcct gacatctact   2220
agtcccgtgg ccactccaat tcccggaacc ggctacgctt atagcctgag actgacccct   2280
aggccagtct cacgcttcct gggcaacaat agcattctgt acgtgtttta ttccggaaac   2340
ggaccaaagg cttctggagg ggactattgc atccagagta atattgtgtt ctcagacgag   2400
atcccagcca gccaggatat gcccactaac actaccgaca ttacctacgt gggcgataat   2460
gccacttatt ccgtgcctat ggtcacaagc gaagacgcta actccccaaa tgtgaccgtc   2520
acagcattct gggcctggcc caacaatact gagaccgatt ttaagtgcaa atggacactg   2580
acttcaggca cccctagcgg gtgtgaaaac atctctggcg ccttcgctag taatcgaacc   2640
tttgatatta cagtgtccgg cctggggact gccccaaaaa ccctgatcat tacccggaca   2700
gctactaacg caacaactac cacacacaaa gtgatcttca gcaaagctcc cgagtccact   2760
accacatctc ctaccctgaa cactaccggg tttgccgacc ccaatacaac taccggactg   2820
cctagctcca cccatgtgcc aacaaacctg actgcaccag catccaccgg acctacagtg   2880
tctactgccg atgtcaccag tcccacacct gccggaacaa cttctggcgc tagtcccgtg   2940
accccatcac ccagcccttg ggacaatggg acagagagta aggcccctga tatgacttct   3000
agtacctcac cagtcaccac accaaccccc aacgcaacaa gccctactcc agccgtgact   3060
acccccacac ctaatgctac cagcccaaca cccgcagtga caactcctac cccaaacgcc   3120
```

-continued

```
acttccccaa ccctggggaa gacatcaccc actagcgccg tgaccacacc caccccctaat   3180
gctacctctc ctacactggg aaaaacttcc ccaacctctg cagtgactac cccaaccccc   3240
aacgccacaa gccccactct gggcaagacc agtcctacat cagctgtcac aactcctacc   3300
ccaaatgcaa ctgggccaac cgtgggagag acatccccccc aggctaacgc aacaaatcac   3360
actctgggag gcaccagtcc cacacctgtg gtcacctcac agcccaagaa cgccacaagc   3420
gctgtgacca caggccagca taatatcaca tcaagctcca cttctagtat gagcctgcgc   3480
ccttcaagca acccagagac actgtcccca tctactagtg acaattcaac cagccacatg   3540
cctctgctga catctgcaca tccaactggg ggagaaaaca tcactcaggt cacccccgcc   3600
tccatttcta cccaccatgt gtccacatcc tctccagcac cccgacctgg aactaccagc   3660
caggcatccg gaccaggaaa tagttcaacc agcacaaagc ctggcgaggt gaacgtcaca   3720
aaagggactc cccctcagaa tgctacctca cctcaggcac caagcggcca gaaaacagct   3780
gtgcctactg tcacctccac aggcgggaag gcaaactcta caactggagg caaacacacc   3840
acagggcatg gagctcgcac tagcaccgaa ccaactaccg actacggggg agattccaca   3900
actccaaggc ccagatacaa tgccaccaca tatctgccac cctctaccag ctccaagctg   3960
cgacccagat ggacattcac tagtcctcca gtgactaccg cacaggctac agtgccagtc   4020
ccacctactt ctcagcctag attttctaac ctgagttccg gagagagcca ggtgaggcag   4080
aacttcaagc ccgagatgga ggagaagctg aacgagcaga tgaacctgga gctgtacagc   4140
agcctgctgt accagcagat gagcgcctgg tgcagctacc acaccttcga gggcgccgcc   4200
gccttcctga ggaggcacgc ccaggaggag atgacccaca tgcagaggct gttcgactac   4260
ctgaccgaca ccggcaacct gcccaggatc aacaccgtgg agagccccctt cgccgagtac   4320
agcagcctgg acgagctgtt ccaggagacc tacaagcacg agcagctgat cacccagaag   4380
atcaacgagc tggcccacgc cgccatgacc aaccaggact accccacctt caacttcctg   4440
cagtggtacg tgagcgagca gcacgaggag gagaagctgt tcaagagcat catcgacaag   4500
ctgagcctgg ccggcaagag cggcgagggc ctgtacttca tcgacaagga gctgagcacc   4560
ctggacggat cctagcatca tcatcatcat tagtctggaa gggcgaattg atccagatct   4620
gctgtgcctt ctagttgcca gccatctgtt gtttgcccct cccccgtgcc ttccttgacc   4680
ctggaaggtg ccactcccac tgtcctttcc taataaaatg aggaaattgc atcgcattgt   4740
ctgagtaggt gtcattctat tctggggggt ggggtggggc aggacagcaa gggggaggat   4800
tgggaagaca atagcaggca tgctggggat gcggtgggct ctatgggtac ccaggtgctg   4860
aagaattgac ccggttcctc ctgggccaga aagaagcagg cacatcccct tctctgtgac   4920
acaccctgtc cacgcccctg gttcttagtt ccagccccac tcataggaca ctcatagctc   4980
aggagggctc cgccttcaat cccacccgct aaagtacttg gagcggtctc tccctccctc   5040
atcagcccac caaaccaaac ctagcctcca agagtgggaa gaaattaaag caagataggc   5100
tattaagtgc agagggagag aaaatgcctc caacatgtga ggaagtaatg agagaaatca   5160
tagaatttta aggccatgat ttaaggccat catggcctta atcttccgct tcctcgctca   5220
ctgactcgct gcgctcggtc gttcggctgc ggcgagcggt atcagctcac tcaaaggcgg   5280
taatacggtt atccacagaa tcaggggata acgcaggaaa gaacatgtga gcaaaaggcc   5340
agcaaaaggc caggaaccgt aaaaaggccg cgttgctggc gtttttccat aggctccgcc   5400
cccctgacga gcatcacaaa aatcgacgct caagtcagag gtggcgaaac ccgacaggac   5460
```

-continued

```
tataaagata ccaggcgttt cccccctggaa gctccctcgt gcgctctcct gttccgaccc   5520
tgccgcttac cggatacctg tccgcctttc tcccttcggg aagcgtggcg ctttctcata   5580
gctcacgctg taggtatctc agttcggtgt aggtcgttcg ctccaagctg ggctgtgtgc   5640
acgaaccccc cgttcagccc gaccgctgcg ccttatccgg taactatcgt cttgagtcca   5700
acccggtaag acacgactta tcgccactgg cagcagccac tggtaacagg attagcagag   5760
cgaggtatgt aggcggtgct acagagttct tgaagtggtg gcctaactac ggctacacta   5820
gaagaacagt atttggtatc tgcgctctgc tgaagccagt taccttcgga aaaagagttg   5880
gtagctcttg atccggcaaa caaaccaccg ctggtagcgg tggttttttt gtttgcaagc   5940
agcagattac gcgcagaaaa aaaggatctc aagaagatcc tttgatcttt tctacggggt   6000
ctgacgctca gtggaacgaa aactcacgtt aagggatttt ggtcatgaga ttatcaaaaa   6060
ggatcttcac ctagatcctt ttaaattaaa aatgaagttt taaatcaatc taaagtatat   6120
atgagtaaac ttggtctgac agttaccaat gcttaatcag tgaggcacct atctcagcga   6180
tctgtctatt tcgttcatcc atagttgcct gactcggggg gggggggcgc tgaggtctgc   6240
ctcgtgaaga aggtgttgct gactcatacc aggcctgaat cgccccatca tccagccaga   6300
aagtgaggga gccacggttg atgagagctt tgttgtaggt ggaccagttg gtgattttga   6360
acttttgctt tgccacggaa cggtctgcgt tgtcgggaag atgcgtgatc tgatccttca   6420
actcagcaaa agttcgattt attcaacaaa gccgccgtcc cgtcaagtca gcgtaatgct   6480
ctgccagtgt tacaaccaat taaccaattc tgattagaaa aactcatcga gcatcaaatg   6540
aaactgcaat ttattcatat caggattatc aataccatat ttttgaaaaa gccgtttctg   6600
taatgaagga gaaaactcac cgaggcagtt ccataggatg gcaagatcct ggtatcggtc   6660
tgcgattccg actcgtccaa catcaataca acctattaat ttcccctcgt caaaaataag   6720
gttatcaagt gagaaatcac catgagtgac gactgaatcc ggtgagaatg gcaaaagctt   6780
atgcatttct ttccagactt gttcaacagg ccagccatta cgctcgtcat caaaatcact   6840
cgcatcaacc aaaccgttat tcattcgtga ttgcgcctga gcgagacgaa atacgcgatc   6900
gctgttaaaa ggacaattac aaacaggaat cgaatgcaac cggcgcagga acactgccag   6960
cgcatcaaca atattttcac ctgaatcagg atattcttct aatacctgga atgctgtttt   7020
cccggggatc gcagtggtga gtaaccatgc atcatcagga gtacggataa aatgcttgat   7080
ggtcggaaga ggcataaatt ccgtcagcca gtttagtctg accatctcat ctgtaacatc   7140
attggcaacg ctacctttgc catgtttcag aaacaactct ggcgcatcgg gcttcccata   7200
caatcgatag attgtcgcac ctgattgccc gacattatcg cgagcccatt tatacccata   7260
taaatcagca tccatgttgg aatttaatcg cggcctcgag caagacgttt cccgttgaat   7320
atggctcata acaccccttg tattactgtt tatgtaagca gacagtttta ttgttcatga   7380
tgatatattt ttatcttgtg caatgtaaca tcagagattt tgagacacaa cgtggctttc   7440
cccccccccc cattattgaa gcatttatca gggttattgt ctcatgagcg gatacatatt   7500
tgaatgtatt tagaaaaata aacaaatagg ggttccgcgc acatttcccc gaaaagtgcc   7560
acctgacgtc taagaaacca ttattatcat gacattaacc tataaaaata ggcgtatcac   7620
gaggcccttt cgtc                                                      7634
```

<210> SEQ ID NO 110
<211> LENGTH: 6020
<212> TYPE: DNA
<213> ORGANISM: Artificial Sequence
<220> FEATURE:
<223> OTHER INFORMATION: Synthetic

<400> SEQUENCE: 110
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
gggaacttcc atagcccata tatggagttc cgcgttacat aacttacggg aatttccaaa 420
cctggctgac cgcccaacga cccccgccca ttgacgtcaa taatgacgta tgttcccata 480
gtaacgccaa tagggaactt ccattgacgt caatgggtgg agtatttacg gtaaactgcc 540
cacttgggaa tttccaagtg tatcatatgc caagtacgcc ccctattgac gtcaatgacg 600
ggaacttcca taagcttgca ttatgcccag tacatgacct tatgggaatt tcctacttgg 660
cagtacatct acgtattagt catcgctatt accatggtga tgcggttttg gcagtacatc 720
aatgggcgtg gatagcggtt tgactcacgg gaacttccaa gtctccaccc cattgacgtc 780
aatgggagtt tgttttgact caccaaaatc aacgggaatt cccaaaatgt cgtaacaact 840
ccgccccatt gacgcaaatg ggcggtaggc gtgtacggtg ggaggtctat ataagcagag 900
ctcgtttagt gaaccgtcag atcgcctgga gacgccatcc acgctgtttt gacctccata 960
gaagacaccg ggaccgatcc agcctccatc ggctcgcatc tctccttcac gcgcccgccg 1020
ccctacctga ggccgccatc cacgccggtt gagtcgcgtt ctgccgcctc ccgcctgtgg 1080
tgcctcctga actgcgtccg ccgtctaggt aagtttaaag ctcaggtcga gaccgggcct 1140
ttgtccggcg ctcccttgga gcctacctag actcagccgg ctctccacgc tttgcctgac 1200
cctgcttgct caactctagt taacggtgga gggcagtgta gtctgagcag tactcgttgc 1260
tgccgcgcgc gccaccagac ataatagctg acagactaac agactgttcc tttccatggg 1320
tcttttctgc agtcaccgtc gtcgacacgt gtgatcagat atcgcggccg ctctagagat 1380
atcgccacca tggacagcaa gggcagcagc cagaagggca gcagactgct gctgctgctg 1440
gtggtgagca acctgctgct gcctcagggc gtgctagccg aagccgccct gctggtgtgc 1500
cagtacacta ttcagagcct gattcatctg accggggagg accctggatt tttcaatgtg 1560
gaaatccctg agttcccatt ttaccccacc tgcaacgtct gtacagccga cgtgaacgtc 1620
accattaatt tcgatgtggg cgggaagaaa caccagctgg acctggattt tggccagctg 1680
accccacata caaaagccgt gtatcagccc agaggggctt tcggaggcag cgagaacgca 1740
acaaatctgt ttctgctgga gctgctggga gcaggagaac tggctctgac catgaggtcc 1800 aagaaaactgc ccatcaatgt gaccacagga gaggaacagc aggtcagtct ggaatcagtg 1860
gacgtctact tccaggatgt gtttggcacc atgtggtgcc accatgccga gatgcagaat 1920
cctgtgtacc tgatccccga aaccgtccct tatattaagt gggacaactg taatagcact 1980
aacattaccg cagtggtccg ggcacagggg ctggacgtga ccctgccact gtcactgccc 2040
acaagcgccc aggatagcaa cttctccgtg aaaaccgaga tgctgggaaa tgagatcgac 2100
attgaatgca tcatggagga tggagaaatt agccaggtgc tgcctggcga taacaagttt 2160
aatatcacct gttccggcta cgaatctcac gtcccaagtg gggaatcct gacatctact 2220

-continued agtcccgtgg ccactccaat tcccggaacc ggctacgctt atagcctgag actgacccct 2280
aggccagtct cacgcttcct gggcaacaat agcattctgt acgtgtttta ttccggaaac 2340
ggaccaaagg cttctggagg ggactattgc atccagagta atattgtgtt ctcagacgag 2400
atcccagcca gccaggatat gcccacttcc ggagagagcc aggtgaggca gcagttcagc 2460
aaggacatcg agaagctgct gaacgagcag gtgaacaagg agatgcagag cagcaacctg 2520
tacatgagca tgagcagctg gtgctacacc cacagcctgg acggcgccgg cctgttcctg 2580
ttcgaccacg ccgccgagga gtacgagcac gccaagaagc tgatcatctt cctgaacgag 2640
aacaacgtgc ccgtgcagct gaccagcatc agcgcccccg agcacaagtt cgagggcctg 2700
acccagatct tccagaaggc ctacgagcac gagcagcaca tcagcgagag catcaacaac 2760
atcgtggacc acgccatcaa gagcaaggac cacgccacct tcaacttcct gcagtggtac 2820
gtggccgagc agcacgagga ggaggtgctg ttcaaggaca tcctggacaa gatcgagctg 2880
atcggcaacg agaaccacgg cctgtacctg gccgaccagt acgtgaaggg catcgccaag 2940
agcaggaaga gcggatccta gcatcatcat catcattagt ctggaagggc gaattgatcc 3000
agatctgctg tgccttctag ttgccagcca tctgttgttt gcccctcccc cgtgccttcc 3060
ttgaccctgg aaggtgccac tcccactgtc ctttcctaat aaaatgagga aattgcatcg 3120
cattgtctga gtaggtgtca ttctattctg gggggtgggg tggggcagga cagcaagggg 3180
gaggattggg aagacaatag caggcatgct ggggatgcgg tgggctctat gggtacccag 3240
gtgctgaaga attgacccgg ttcctcctgg gccagaaaga agcaggcaca tccccttctc 3300
tgtgacacac cctgtccacg cccctggttc ttagttccag ccccactcat aggacactca 3360
tagctcagga gggctccgcc ttcaatccca cccgctaaag tacttggagc ggtctctccc 3420
tccctcatca gcccaccaaa ccaaacctag cctccaagag tgggaagaaa ttaaagcaag 3480
ataggctatt aagtgcagag ggagagaaaa tgcctccaac atgtgaggaa gtaatgagag 3540
aaatcataga attttaaggc catgatttaa ggccatcatg gccttaatct tccgcttcct 3600
cgctcactga ctcgctgcgc tcggtcgttc ggctgcggcg agcggtatca gctcactcaa 3660
aggcggtaat acggttatcc acagaatcag gggataacgc aggaaagaac atgtgagcaa 3720
aaggccagca aaaggccagg aaccgtaaaa aggccgcgtt gctggcgttt ttccataggc 3780
tccgcccccc tgacgagcat cacaaaaatc gacgctcaag tcagaggtgg cgaaacccga 3840
caggactata aagataccag gcgtttcccc ctggaagctc cctcgtgcgc tctcctgttc 3900
cgaccctgcc gcttaccgga tacctgtccg cctttctccc ttcgggaagc gtggcgcttt 3960
ctcatagctc acgctgtagg tatctcagtt cggtgtaggt cgttcgctcc aagctgggct 4020
gtgtgcacga accccccgtt cagcccgacc gctgcgcctt atccggtaac tatcgtcttg 4080
agtccaaccc ggtaagacac gacttatcgc cactggcagc agccactggt aacaggatta 4140
gcagagcgag gtatgtaggc ggtgctacag agttcttgaa gtggtggcct aactacggct 4200
acactagaag aacagtattt ggtatctgcg ctctgctgaa gccagttacc ttcggaaaaa 4260
gagttggtag ctcttgatcc ggcaaacaaa ccaccgctgg tagcggtggt ttttttgttt 4320
gcaagcagca gattacgcgc agaaaaaaag gatctcaaga agatcctttg atcttttcta 4380
cggggtctga cgctcagtgg aacgaaaact cacgttaagg gattttggtc atgagattat 4440
caaaaaggat cttcacctag atccttttaa attaaaaatg aagttttaaa tcaatctaaa 4500
gtatatatga gtaaacttgg tctgacagtt accaatgctt aatcagtgag gcacctatct 4560
cagcgatctg tctatttcgt tcatccatag ttgcctgact cggggggggg gggcgctgag 4620
gtctgcctcg tgaagaaggt gttgctgact cataccaggc ctgaatcgcc ccatcatcca 4680
gccagaaagt gagggagcca cggttgatga gagctttgtt gtaggtggac cagttggtga 4740
ttttgaactt ttgctttgcc acggaacggt ctgcgttgtc gggaagatgc gtgatctgat 4800
ccttcaactc agcaaaagtt cgatttattc aacaaagccg ccgtcccgtc aagtcagcgt 4860
aatgctctgc cagtgttaca accaattaac caattctgat tagaaaaact catcgagcat 4920
caaatgaaac tgcaatttat tcatatcagg attatcaata ccatattttt gaaaaagccg 4980
tttctgtaat gaaggagaaa actcaccgag gcagttccat aggatggcaa gatcctggta 5040
tcggtctgcg attccgactc gtccaacatc aatacaacct attaatttcc cctcgtcaaa 5100
aataaggtta tcaagtgaga aatcaccatg agtgacgact gaatccggtg agaatggcaa 5160
aagcttatgc atttctttcc agacttgttc aacaggccag ccattacgct cgtcatcaaa 5220
atcactcgca tcaaccaaac cgttattcat tcgtgattgc gcctgagcga gacgaaatac 5280
gcgatcgctg ttaaaaggac aattacaaac aggaatcgaa tgcaaccggc gcaggaacac 5340
tgccagcgca tcaacaatat tttcacctga atcaggatat tcttctaata cctggaatgc 5400
tgttttcccg gggatcgcag tggtgagtaa ccatgcatca tcaggagtac ggataaaatg 5460
cttgatggtc ggaagaggca taaattccgt cagccagttt agtctgacca tctcatctgt 5520
aacatcattg gcaacgctac ctttgccatg tttcagaaac aactctggcg catcgggctt 5580
cccatacaat cgatagattg tcgcacctga ttgcccgaca ttatcgcgag cccatttata 5640
cccatataaa tcagcatcca tgttggaatt taatcgcggc ctcgagcaag acgtttcccg 5700
ttgaatatgg ctcataacac cccttgtatt actgtttatg taagcagaca gttttattgt 5760
tcatgatgat atatttttat cttgtgcaat gtaacatcag agattttgag acacaacgtg 5820
gctttccccc cccccccatt attgaagcat ttatcagggt tattgtctca tgagcggata 5880
catatttgaa tgtatttaga aaaataaaca aataggggtt ccgcgcacat ttccccgaaa 5940
agtgccacct gacgtctaag aaaccattat tatcatgaca ttaacctata aaaataggcg 6000
tatcacgagg ccctttcgtc 6020

<210> SEQ ID NO 111
<211> LENGTH: 6344
<212> TYPE: DNA
<213> ORGANISM: Artificial Sequence
<220> FEATURE:
<223> OTHER INFORMATION: Synthetic

<400> SEQUENCE: 111
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
gggaacttcc atagcccata tatggagttc cgcgttacat aacttacggg aatttccaaa 420
cctggctgac cgcccaacga cccccgccca ttgacgtcaa taatgacgta tgttcccata 480
gtaacgccaa tagggaactt ccattgacgt caatgggtgg agtatttacg gtaaactgcc 540
cacttgggaa tttccaagtg tatcatatgc caagtacgcc ccctattgac gtcaatgacg 600

-continued

```
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg gatagcggtt tgactcacgg gaacttccaa gtctccaccc cattgacgtc    780
aatgggagtt tgttttgact caccaaaatc aacgggaatt cccaaaatgt cgtaacaact    840
ccgccccatt gacgcaaatg ggcggtaggc gtgtacggtg ggaggtctat ataagcagag    900
ctcgtttagt gaaccgtcag atcgcctgga gacgccatcc acgctgtttt gacctccata    960
gaagacaccg ggaccgatcc agcctccatc ggctcgcatc tctccttcac gcgcccgccg   1020
ccctacctga ggccgccatc cacgccggtt gagtcgcgtt ctgccgcctc ccgcctgtgg   1080
tgcctcctga actgcgtccg ccgtctaggt aagtttaaag ctcaggtcga gaccgggcct   1140
ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagagat   1380
atcgccacca tggacagcaa gggcagcagc cagaagggca gcagactgct gctgctgctg   1440
gtggtgagca acctgctgct gcctcagggc gtgctagccg aagccgccct gctggtgtgc   1500
cagtacacta ttcagagcct gattcatctg accggggagg accctggatt tttcaatgtg   1560
gaaatccctg agttcccatt ttaccccacc tgcaacgtct gtacagccga cgtgaacgtc   1620
accattaatt tcgatgtggg cgggaagaaa caccagctgg acctggattt tggccagctg   1680
accccacata caaaagccgt gtatcagccc agaggggctt tcggaggcag cgagaacgca   1740
acaaatctgt ttctgctgga gctgctggga gcaggagaac tggctctgac catgaggtcc   1800
aagaaactgc ccatcaatgt gaccacagga gaggaacagc aggtcagtct ggaatcagtg   1860
gacgtctact tccaggatgt gtttggcacc atgtggtgcc accatgccga gatgcagaat   1920
cctgtgtacc tgatccccga aaccgtccct tatattaagt gggacaactg taatagcact   1980
aacattaccg cagtggtccg ggcacagggg ctggacgtga ccctgccact gtcactgccc   2040
acaagcgccc aggatagcaa cttctccgtg aaaaccgaga tgctgggaaa tgagatcgac   2100
attgaatgca tcatggagga tggagaaatt agccaggtgc tgcctggcga taacaagttt   2160
aatatcacct gttccggcta cgaatctcac gtcccaagtg gggaatcct gacatctact    2220
agtcccgtgg ccactccaat tcccggaacc ggctacgctt atagcctgag actgacccct   2280
aggccagtct cacgcttcct gggcaacaat agcattctgt acgtgtttta ttccggaaac   2340
ggaccaaagg cttctggagg ggactattgc atccagagta atattgtgtt ctcagacgag   2400
atcccagcca gccaggatat gcccactaac actaccgaca ttacctacgt gggcgataat   2460
gccacttatt ccgtgcctat ggtcacaagc gaagacgcta actccccaaa tgtgaccgtc   2520
acagcattct gggcctggcc caacaatact gagaccgatt ttaagtgcaa atggacactg   2580
acttcaggca cccctagcgg gtgtgaaaac atctctggcg ccttcgctag taatcgaacc   2640
tttgatatta cagtgtccgg cctggggact gccccaaaaa ccctgatcat tacccggaca   2700
gctactaacg caacaactac cacacacaaa gtgatcttca gcaaagctcc ctccggagag   2760
agccaggtga ggcagcagtt cagcaaggac atcgagaagc tgctgaacga gcaggtgaac   2820
aaggagatgc agagcagcaa cctgtacatg agcatgagca gctggtgcta cacccacagc   2880
ctggacggcg ccggcctgtt cctgttcgac cacgccgccg aggagtacga gcacgccaag   2940
aagctgatca tcttcctgaa cgagaacaac gtgcccgtgc agctgaccag catcagcgcc   3000
```

```
cccgagcaca agttcgaggg cctgacccag atcttccaga aggcctacga gcacgagcag   3060
cacatcagcg agagcatcaa caacatcgtg gaccacgcca tcaagagcaa ggaccacgcc   3120
accttcaact tcctgcagtg gtacgtggcc gagcagcacg aggaggaggt gctgttcaag   3180
gacatcctgg acaagatcga gctgatcggc aacgagaacc acggcctgta cctggccgac   3240
cagtacgtga agggcatcgc caagagcagg aagagcggat cctagcatca tcatcatcat   3300
tagtctggaa gggcgaattg atccagatct gctgtgcctt ctagttgcca gccatctgtt   3360
gtttgcccct cccccgtgcc ttccttgacc ctggaaggtg ccactcccac tgtcctttcc   3420
taataaaatg aggaaattgc atcgcattgt ctgagtaggt gtcattctat tctggggggt   3480
ggggtggggc aggacagcaa gggggaggat tgggaagaca atagcaggca tgctggggat   3540
gcggtgggct ctatgggtac ccaggtgctg aagaattgac ccggttcctc ctgggccaga   3600
aagaagcagg cacatcccct tctctgtgac acaccctgtc cacgcccctg gttcttagtt   3660
ccagccccac tcataggaca ctcatagctc aggagggctc cgccttcaat cccacccgct   3720
aaagtacttg gagcggtctc tccctccctc atcagcccac caaaccaaac ctagcctcca   3780
agagtgggaa gaaattaaag caagataggc tattaagtgc agagggagag aaaatgcctc   3840
caacatgtga ggaagtaatg agagaaatca tagaatttta aggccatgat ttaaggccat   3900
catggcctta atcttccgct tcctcgctca ctgactcgct gcgctcggtc gttcggctgc   3960
ggcgagcggt atcagctcac tcaaaggcgg taatacggtt atccacagaa tcaggggata   4020
acgcaggaaa gaacatgtga gcaaaaggcc agcaaaaggc caggaaccgt aaaaaggccg   4080
cgttgctggc gtttttccat aggctccgcc cccctgacga gcatcacaaa aatcgacgct   4140
caagtcagag gtggcgaaac ccgacaggac tataaagata ccaggcgttt ccccctggaa   4200
gctccctcgt gcgctctcct gttccgaccc tgccgcttac cggatacctg tccgcctttc   4260
tcccttcggg aagcgtggcg ctttctcata gctcacgctg taggtatctc agttcggtgt   4320
aggtcgttcg ctccaagctg ggctgtgtgc acgaaccccc cgttcagccc gaccgctgcg   4380
ccttatccgg taactatcgt cttgagtcca acccggtaag acacgactta tcgccactgg   4440
cagcagccac tggtaacagg attagcagag cgaggtatgt aggcggtgct acagagttct   4500
tgaagtggtg gcctaactac ggctacacta gaagaacagt atttggtatc tgcgctctgc   4560
tgaagccagt taccttcgga aaaagagttg gtagctcttg atccggcaaa caaaccaccg   4620
ctggtagcgg tggttttttt gtttgcaagc agcagattac gcgcagaaaa aaaggatctc   4680
aagaagatcc tttgatcttt tctacggggt ctgacgctca gtggaacgaa aactcacgtt   4740
aagggatttt ggtcatgaga ttatcaaaaa ggatcttcac ctagatcctt ttaaattaaa   4800
aatgaagttt taaatcaatc taaagtatat atgagtaaac ttggtctgac agttaccaat   4860
gcttaatcag tgaggcacct atctcagcga tctgtctatt tcgttcatcc atagttgcct   4920
gactcggggg gggggggcgc tgaggtctgc ctcgtgaaga aggtgttgct gactcatacc   4980
aggcctgaat cgccccatca tccagccaga aagtgaggga gccacggttg atgagagctt   5040
tgttgtaggt ggaccagttg gtgattttga acttttgctt tgccacggaa cggtctgcgt   5100
tgtcgggaag atgcgtgatc tgatccttca actcagcaaa agttcgattt attcaacaaa   5160
gccgccgtcc cgtcaagtca gcgtaatgct ctgccagtgt tacaaccaat taaccaattc   5220
tgattagaaa aactcatcga gcatcaaatg aaactgcaat ttattcatat caggattatc   5280
aataccatat ttttgaaaaa gccgtttctg taatgaagga gaaaactcac cgaggcagtt   5340
```

ccataggatg gcaagatcct ggtatcggtc tgcgattccg actcgtccaa catcaataca 5400
acctattaat ttcccctcgt caaaaataag gttatcaagt gagaaatcac catgagtgac 5460
gactgaatcc ggtgagaatg gcaaaagctt atgcatttct ttccagactt gttcaacagg 5520
ccagccatta cgctcgtcat caaaatcact cgcatcaacc aaaccgttat tcattcgtga 5580
ttgcgcctga gcgagacgaa atacgcgatc gctgttaaaa ggacaattac aaacaggaat 5640
cgaatgcaac cggcgcagga acactgccag cgcatcaaca atattttcac ctgaatcagg 5700
atattcttct aatacctgga atgctgtttt cccggggatc gcagtggtga gtaaccatgc 5760
atcatcagga gtacggataa aatgcttgat ggtcggaaga ggcataaatt ccgtcagcca 5820
gtttagtctg accatctcat ctgtaacatc attggcaacg ctacctttgc catgtttcag 5880
aaacaactct ggcgcatcgg gcttcccata caatcgatag attgtcgcac ctgattgccc 5940
gacattatcg cgagcccatt tatacccata taaatcagca tccatgttgg aatttaatcg 6000
cggcctcgag caagacgttt cccgttgaat atggctcata acaccccttg tattactgtt 6060
tatgtaagca gacagtttta ttgttcatga tgatatattt ttatcttgtg caatgtaaca 6120
tcagagattt tgagacacaa cgtggctttc cccccccccc cattattgaa gcatttatca 6180
gggttattgt ctcatgagcg gatacatatt tgaatgtatt tagaaaaata aacaaatagg 6240
ggttccgcgc acatttcccc gaaaagtgcc acctgacgtc taagaaacca ttattatcat 6300
gacattaacc tataaaaata ggcgtatcac gaggcccttt cgtc 6344

<210> SEQ ID NO 112
<211> LENGTH: 6479
<212> TYPE: DNA
<213> ORGANISM: Artificial Sequence
<220> FEATURE:
<223> OTHER INFORMATION: Synthetic

<400> SEQUENCE: 112
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
gggaacttcc atagcccata tatggagttc cgcgttacat aacttacggg aatttccaaa 420
cctggctgac cgcccaacga cccccgccca ttgacgtcaa taatgacgta tgttcccata 480
gtaacgccaa tagggaactt ccattgacgt caatgggtgg agtatttacg gtaaactgcc 540
cacttgggaa tttccaagtg tatcatatgc caagtacgcc ccctattgac gtcaatgacg 600
ggaacttcca taagcttgca ttatgcccag tacatgacct tatgggaatt tcctacttgg 660
cagtacatct acgtattagt catcgctatt accatggtga tgcggttttg gcagtacatc 720
aatgggcgtg gatagcggtt tgactcacgg gaacttccaa gtctccaccc cattgacgtc 780
aatgggagtt tgttttgact caccaaaatc aacgggaatt cccaaaatgt cgtaacaact 840
ccgccccatt gacgcaaatg ggcggtaggc gtgtacggtg ggaggtctat ataagcagag 900
ctcgtttagt gaaccgtcag atcgcctgga gacgccatcc acgctgtttt gacctccata 960
gaagacaccg ggaccgatcc agcctccatc ggctcgcatc tctccttcac gcgcccgccg 1020
ccctacctga ggccgccatc cacgccggtt gagtcgcgtt ctgccgcctc ccgcctgtgg 1080

```
tgcctcctga actgcgtccg ccgtctaggt aagtttaaag ctcaggtcga gaccgggcct   1140
ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagagat   1380
atcgccacca tggacagcaa gggcagcagc cagaagggca gcagactgct gctgctgctg   1440
gtggtgagca acctgctgct gcctcagggc gtgctagccg aagccgccct gctggtgtgc   1500
cagtacacta ttcagagcct gattcatctg accggggagg accctggatt tttcaatgtg   1560
gaaatccctg agttcccatt ttaccccacc tgcaacgtct gtacagccga cgtgaacgtc   1620
accattaatt tcgatgtggg cgggaagaaa caccagctgg acctggattt tggccagctg   1680
accccacata caaaagccgt gtatcagccc agaggggctt tcggaggcag cgagaacgca   1740
acaaatctgt ttctgctgga gctgctggga gcaggagaac tggctctgac catgaggtcc   1800
aagaaactgc ccatcaatgt gaccacagga gaggaacagc aggtcagtct ggaatcagtg   1860
gacgtctact tccaggatgt gtttggcacc atgtggtgcc accatgccga gatgcagaat   1920
cctgtgtacc tgatccccga aaccgtccct tatattaagt gggacaactg taatagcact   1980
aacattaccg cagtggtccg ggcacagggg ctggacgtga ccctgccact gtcactgccc   2040
acaagcgccc aggatagcaa cttctccgtg aaaaccgaga tgctgggaaa tgagatcgac   2100
attgaatgca tcatggagga tggagaaatt agccaggtgc tgcctggcga taacaagttt   2160
aatatcacct gttccggcta cgaatctcac gtcccaagtg gggaatcct gacatctact   2220
agtcccgtgg ccactccaat tcccggaacc ggctacgctt atagcctgag actgacccct   2280
aggccagtct cacgcttcct gggcaacaat agcattctgt acgtgtttta ttccggaaac   2340
ggaccaaagg cttctggagg ggactattgc atccagagta atattgtgtt ctcagacgag   2400
atcccagcca gccaggatat gcccactaac actaccgaca ttacctacgt gggcgataat   2460
gccacttatt ccgtgcctat ggtcacaagc gaagacgcta actccccaaa tgtgaccgtc   2520
acagcattct gggcctggcc caacaatact gagaccgatt ttaagtgcaa atggacactg   2580
acttcaggca cccctagcgg gtgtgaaaac atctctggcg ccttcgctag taatcgaacc   2640
tttgatatta cagtgtccgg cctggggact gccccaaaaa ccctgatcat tacccggaca   2700
gctactaacg caacaactac cacacacaaa gtgatcttca gcaaagctcc cgagtccact   2760
accacatctc ctaccctgaa cactaccggg tttgccgacc ccaatacaac taccggactg   2820
cctagctcca cccatgtgcc aacaaacctg actgcaccag catccaccgg acctacagtg   2880
tctacttccg gagagagcca ggtgaggcag cagttcagca aggacatcga gaagctgctg   2940
aacgagcagg tgaacaagga gatgcagagc agcaacctgt acatgagcat gagcagctgg   3000
tgctacaccc acagcctgga cggcgccggc ctgttcctgt tcgaccacgc cgccgaggag   3060
tacgagcacg ccaagaagct gatcatcttc ctgaacgaga acaacgtgcc cgtgcagctg   3120
accagcatca gcgcccccga gcacaagttc gagggcctga cccagatctt ccagaaggcc   3180
tacgagcacg agcagcacat cagcgagagc atcaacaaca tcgtggacca cgccatcaag   3240
agcaaggacc acgccacctt caacttcctg cagtggtacg tggccgagca gcacgaggag   3300
gaggtgctgt tcaaggacat cctggacaag atcgagctga tcggcaacga gaaccacggc   3360
ctgtacctgg ccgaccagta cgtgaagggc atcgccaaga gcaggaagag cggatcctag   3420
```

```
catcatcatc atcattagtc tggaagggcg aattgatcca gatctgctgt gccttctagt   3480
tgccagccat ctgttgtttg cccctccccc gtgccttcct tgaccctgga aggtgccact   3540
cccactgtcc tttcctaata aaatgaggaa attgcatcgc attgtctgag taggtgtcat   3600
tctattctgg ggggtggggt ggggcaggac agcaaggggg aggattggga agacaatagc   3660
aggcatgctg gggatgcggt gggctctatg ggtacccagg tgctgaagaa ttgacccggt   3720
tcctcctggg ccagaaagaa gcaggcacat ccccttctct gtgacacacc ctgtccacgc   3780
ccctggttct tagttccagc cccactcata ggacactcat agctcaggag ggctccgcct   3840
tcaatcccac ccgctaaagt acttggagcg gtctctccct ccctcatcag cccaccaaac   3900
caaacctagc ctccaagagt gggaagaaat taaagcaaga taggctatta agtgcagagg   3960
gagagaaaat gcctccaaca tgtgaggaag taatgagaga aatcatagaa ttttaaggcc   4020
atgatttaag gccatcatgg ccttaatctt ccgcttcctc gctcactgac tcgctgcgct   4080
cggtcgttcg gctgcggcga gcggtatcag ctcactcaaa ggcggtaata cggttatcca   4140
cagaatcagg ggataacgca ggaaagaaca tgtgagcaaa aggccagcaa aaggccagga   4200
accgtaaaaa ggccgcgttg ctggcgtttt tccataggct ccgcccccct gacgagcatc   4260
acaaaaatcg acgctcaagt cagaggtggc gaaacccgac aggactataa agataccagg   4320
cgtttccccc tggaagctcc ctcgtgcgct ctcctgttcc gaccctgccg cttaccggat   4380
acctgtccgc ctttctccct tcgggaagcg tggcgctttc tcatagctca cgctgtaggt   4440
atctcagttc ggtgtaggtc gttcgctcca agctgggctg tgtgcacgaa ccccccgttc   4500
agcccgaccg ctgcgcctta tccggtaact atcgtcttga gtccaacccg gtaagacacg   4560
acttatcgcc actggcagca gccactggta acaggattag cagagcgagg tatgtaggcg   4620
gtgctacaga gttcttgaag tggtggccta actacggcta cactagaaga acagtatttg   4680
gtatctgcgc tctgctgaag ccagttacct tcggaaaaag agttggtagc tcttgatccg   4740
gcaaacaaac caccgctggt agcggtggtt tttttgtttg caagcagcag attacgcgca   4800
gaaaaaaagg atctcaagaa gatcctttga tcttttctac ggggtctgac gctcagtgga   4860
acgaaaactc acgttaaggg attttggtca tgagattatc aaaaaggatc ttcacctaga   4920
tccttttaaa ttaaaaatga agttttaaat caatctaaag tatatatgag taaacttggt   4980
ctgacagtta ccaatgctta atcagtgagg cacctatctc agcgatctgt ctatttcgtt   5040
catccatagt tgcctgactc gggggggggg ggcgctgagg tctgcctcgt gaagaaggtg   5100
ttgctgactc ataccaggcc tgaatcgccc catcatccag ccagaaagtg agggagccac   5160
ggttgatgag agctttgttg taggtggacc agttggtgat tttgaacttt tgctttgcca   5220
cggaacggtc tgcgttgtcg ggaagatgcg tgatctgatc cttcaactca gcaaaagttc   5280
gatttattca acaaagccgc cgtcccgtca agtcagcgta atgctctgcc agtgttacaa   5340
ccaattaacc aattctgatt agaaaaactc atcgagcatc aaatgaaact gcaatttatt   5400
catatcagga ttatcaatac catatttttg aaaaagccgt ttctgtaatg aaggagaaaa   5460
ctcaccgagg cagttccata ggatggcaag atcctggtat cggtctgcga ttccgactcg   5520
tccaacatca atacaaccta ttaatttccc ctcgtcaaaa ataaggttat caagtgagaa   5580
atcaccatga gtgacgactg aatccggtga gaatggcaaa agcttatgca tttctttcca   5640
gacttgttca acaggccagc cattacgctc gtcatcaaaa tcactcgcat caaccaaacc   5700
gttattcatt cgtgattgcg cctgagcgag acgaaatacg cgatcgctgt taaaaggaca   5760
attacaaaca ggaatcgaat gcaaccggcg caggaacact gccagcgcat caacaatatt   5820
```

ttcacctgaa tcaggatatt cttctaatac ctggaatgct gttttcccgg ggatcgcagt 5880
ggtgagtaac catgcatcat caggagtacg gataaaatgc ttgatggtcg gaagaggcat 5940
aaattccgtc agccagttta gtctgaccat ctcatctgta acatcattgg caacgctacc 6000
tttgccatgt ttcagaaaca actctggcgc atcgggcttc ccatacaatc gatagattgt 6060
cgcacctgat tgcccgacat tatcgcgagc ccatttatac ccatataaat cagcatccat 6120
gttggaattt aatcgcggcc tcgagcaaga cgtttcccgt tgaatatggc tcataacacc 6180
ccttgtatta ctgtttatgt aagcagacag ttttattgtt catgatgata tatttttatc 6240
ttgtgcaatg taacatcaga gattttgaga cacaacgtgg ctttcccccc ccccccatta 6300
ttgaagcatt tatcagggtt attgtctcat gagcggatac atatttgaat gtatttagaa 6360
aaataaacaa ataggggttc cgcgcacatt tccccgaaaa gtgccacctg acgtctaaga 6420
aaccattatt atcatgacat taacctataa aaataggcgt atcacgaggc cctttcgtc 6479

<210> SEQ ID NO 113
<211> LENGTH: 7649
<212> TYPE: DNA
<213> ORGANISM: Artificial Sequence
<220> FEATURE:
<223> OTHER INFORMATION: Synthetic

<400> SEQUENCE: 113
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
gggaacttcc atagcccata tatggagttc cgcgttacat aacttacggg aatttccaaa 420
cctggctgac cgcccaacga cccccgccca ttgacgtcaa taatgacgta tgttcccata 480
gtaacgccaa tagggaactt ccattgacgt caatgggtgg agtatttacg gtaaactgcc 540
cacttgggaa tttccaagtg tatcatatgc caagtacgcc ccctattgac gtcaatgacg 600
ggaacttcca taagcttgca ttatgcccag tacatgacct tatgggaatt tcctacttgg 660
cagtacatct acgtattagt catcgctatt accatggtga tgcggttttg gcagtacatc 720
aatgggcgtg gatagcggtt tgactcacgg gaacttccaa gtctccaccc cattgacgtc 780
aatgggagtt tgttttgact caccaaaatc aacgggaatt cccaaaatgt cgtaacaact 840
ccgccccatt gacgcaaatg ggcggtaggc gtgtacggtg ggaggtctat ataagcagag 900
ctcgtttagt gaaccgtcag atcgcctgga gacgccatcc acgctgtttt gacctccata 960
gaagacaccg ggaccgatcc agcctccatc ggctcgcatc tctccttcac gcgcccgccg 1020
ccctacctga ggccgccatc cacgccggtt gagtcgcgtt ctgccgcctc ccgcctgtgg 1080
tgcctcctga actgcgtccg ccgtctaggt aagtttaaag ctcaggtcga gaccgggcct 1140
ttgtccggcg ctcccttgga gcctacctag actcagccgg ctctccacgc tttgcctgac 1200
cctgcttgct caactctagt taacggtgga gggcagtgta gtctgagcag tactcgttgc 1260
tgccgcgcgc gccaccagac ataatagctg acagactaac agactgttcc tttccatggg 1320
tcttttctgc agtcaccgtc gtcgacacgt gtgatcagat atcgcggccg ctctagagat 1380

-continued

```
atcgccacca tggacagcaa gggcagcagc cagaagggca gcagactgct gctgctgctg   1440
gtggtgagca acctgctgct gcctcagggc gtgctagccg aagccgccct gctggtgtgc   1500
cagtacacta ttcagagcct gattcatctg accggggagg accctggatt tttcaatgtg   1560
gaaatccctg agttcccatt ttaccccacc tgcaacgtct gtacagccga cgtgaacgtc   1620
accattaatt tcgatgtggg cgggaagaaa caccagctgg acctggattt tggccagctg   1680
accccacata caaaagccgt gtatcagccc agaggggctt tcggaggcag cgagaacgca   1740
acaaatctgt ttctgctgga gctgctggga gcaggagaac tggctctgac catgaggtcc   1800
aagaaactgc ccatcaatgt gaccacagga gaggaacagc aggtcagtct ggaatcagtg   1860
gacgtctact tccaggatgt gtttggcacc atgtggtgcc accatgccga gatgcagaat   1920
cctgtgtacc tgatccccga aaccgtccct tatattaagt gggacaactg taatagcact   1980
aacattaccg cagtggtccg ggcacagggg ctggacgtga ccctgccact gtcactgccc   2040
acaagcgccc aggatagcaa cttctccgtg aaaaccgaga tgctgggaaa tgagatcgac   2100
attgaatgca tcatggagga tggagaaatt agccaggtgc tgcctggcga taacaagttt   2160
aatatcacct gttccggcta cgaatctcac gtcccaagtg gggaatcct gacatctact    2220
agtcccgtgg ccactccaat tcccggaacc ggctacgctt atagcctgag actgacccct   2280
aggccagtct cacgcttcct gggcaacaat agcattctgt acgtgtttta ttccggaaac   2340
ggaccaaagg cttctggagg ggactattgc atccagagta atattgtgtt ctcagacgag   2400
atcccagcca gccaggatat gcccactaac actaccgaca ttacctacgt gggcgataat   2460
gccacttatt ccgtgcctat ggtcacaagc gaagacgcta actccccaaa tgtgaccgtc   2520
acagcattct gggcctggcc caacaatact gagaccgatt ttaagtgcaa atggacactg   2580
acttcaggca cccctagcgg gtgtgaaaac atctctggcg ccttcgctag taatcgaacc   2640
tttgatatta cagtgtccgg cctggggact gccccaaaaa ccctgatcat tacccggaca   2700
gctactaacg caacaactac cacacacaaa gtgatcttca gcaaagctcc cgagtccact   2760
accacatctc ctaccctgaa cactaccggg tttgccgacc ccaatacaac taccggactg   2820
cctagctcca cccatgtgcc aacaaacctg actgcaccag catccaccgg acctacagtg   2880
tctactgccg atgtcaccag tcccacacct gccggaacaa cttctggcgc tagtcccgtg   2940
accccatcac ccagcccttg ggacaatggg acagagagta aggcccctga tatgacttct   3000
agtacctcac cagtcaccac accaaccccc aacgcaacaa gccctactcc agccgtgact   3060
acccccacac ctaatgctac cagcccaaca cccgcagtga caactcctac cccaaacgcc   3120
acttccccaa ccctggggaa gacatcaccc actagcgccg tgaccacacc cacccctaat   3180
gctacctctc ctacactggg aaaaacttcc ccaacctctg cagtgactac cccaacccc    3240
aacgccacaa gccccactct gggcaagacc agtcctacat cagctgtcac aactcctacc   3300
ccaaatgcaa ctgggccaac cgtgggagag acatccccc aggctaacgc aacaaatcac    3360
actctgggag gcaccagtcc cacacctgtg gtcacctcac agcccaagaa cgccacaagc   3420
gctgtgacca caggccagca taatatcaca tcaagctcca cttctagtat gagcctgcgc   3480
ccttcaagca acccagagac actgtcccca tctactagtg acaattcaac cagccacatg   3540
cctctgctga catctgcaca tccaactggg ggagaaaaca tcactcaggt cacccccgcc   3600
tccatttcta cccaccatgt gtccacatcc tctccagcac cccgacctgg aactaccagc   3660
caggcatccg gaccaggaaa tagttcaacc agcacaaagc ctggcgaggt gaacgtcaca   3720
aaagggactc cccctcagaa tgctacctca cctcaggcac caagcggcca gaaaacagct   3780
```

```
gtgcctactg tcacctccac aggcgggaag gcaaactcta caactggagg caaacacacc   3840
acagggcatg gagctcgcac tagcaccgaa ccaactaccg actacggggg agattccaca   3900
actccaaggc ccagatacaa tgccaccaca tatctgccac cctctaccag ctccaagctg   3960
cgacccagat ggacattcac tagtcctcca gtgactaccg cacaggctac agtgccagtc   4020
ccacctactt ctcagcctag attttctaac ctgagttccg gagagagcca ggtgaggcag   4080
cagttcagca aggacatcga gaagctgctg aacgagcagg tgaacaagga gatgcagagc   4140
agcaacctgt acatgagcat gagcagctgg tgctacaccc acagcctgga cggcgccggc   4200
ctgttcctgt tcgaccacgc cgccgaggag tacgagcacg ccaagaagct gatcatcttc   4260
ctgaacgaga acaacgtgcc cgtgcagctg accagcatca gcgcccccga gcacaagttc   4320
gagggcctga cccagatctt ccagaaggcc tacgagcacg agcagcacat cagcgagagc   4380
atcaacaaca tcgtggacca cgccatcaag agcaaggacc acgccacctt caacttcctg   4440
cagtggtacg tggccgagca gcacgaggag gaggtgctgt tcaaggacat cctggacaag   4500
atcgagctga tcggcaacga gaaccacggc ctgtacctgg ccgaccagta cgtgaagggc   4560
atcgccaaga gcaggaagag cggatcctag catcatcatc atcattagtc tggaagggcg   4620
aattgatcca gatctgctgt gccttctagt tgccagccat ctgttgtttg cccctccccc   4680
gtgccttcct tgaccctgga aggtgccact cccactgtcc tttcctaata aaatgaggaa   4740
attgcatcgc attgtctgag taggtgtcat tctattctgg ggggtggggt ggggcaggac   4800
agcaaggggg aggattggga agacaatagc aggcatgctg gggatgcggt gggctctatg   4860
ggtacccagg tgctgaagaa ttgacccggt tcctcctggg ccagaaagaa gcaggcacat   4920
ccccttctct gtgacacacc ctgtccacgc ccctggttct tagttccagc cccactcata   4980
ggacactcat agctcaggag ggctccgcct tcaatcccac ccgctaaagt acttggagcg   5040
gtctctccct ccctcatcag cccaccaaac caaacctagc ctccaagagt gggaagaaat   5100
taaagcaaga taggctatta agtgcagagg gagagaaaat gcctccaaca tgtgaggaag   5160
taatgagaga aatcatagaa ttttaaggcc atgatttaag gccatcatgg ccttaatctt   5220
ccgcttcctc gctcactgac tcgctgcgct cggtcgttcg gctgcggcga gcggtatcag   5280
ctcactcaaa ggcggtaata cggttatcca cagaatcagg ggataacgca ggaaagaaca   5340
tgtgagcaaa aggccagcaa aaggccagga accgtaaaaa ggccgcgttg ctggcgtttt   5400
tccataggct ccgcccccct gacgagcatc acaaaaatcg acgctcaagt cagaggtggc   5460
gaaacccgac aggactataa agataccagg cgtttccccc tggaagctcc ctcgtgcgct   5520
ctcctgttcc gaccctgccg cttaccggat acctgtccgc ctttctccct tcgggaagcg   5580
tggcgctttc tcatagctca cgctgtaggt atctcagttc ggtgtaggtc gttcgctcca   5640
agctgggctg tgtgcacgaa ccccccgttc agcccgaccg ctgcgcctta tccggtaact   5700
atcgtcttga gtccaacccg gtaagacacg acttatcgcc actggcagca gccactggta   5760
acaggattag cagagcgagg tatgtaggcg gtgctacaga gttcttgaag tggtggccta   5820
actacggcta cactagaaga acagtatttg gtatctgcgc tctgctgaag ccagttacct   5880
tcggaaaaag agttggtagc tcttgatccg gcaaacaaac caccgctggt agcggtggtt   5940
tttttgtttg caagcagcag attacgcgca gaaaaaaagg atctcaagaa gatcctttga   6000
tcttttctac ggggtctgac gctcagtgga acgaaaactc acgttaaggg attttggtca   6060
tgagattatc aaaaaggatc ttcacctaga tccttttaaa ttaaaaatga agttttaaat   6120
```

caatctaaag tatatatgag taaacttggt ctgacagtta ccaatgctta atcagtgagg 6180
cacctatctc agcgatctgt ctatttcgtt catccatagt tgcctgactc gggggggggg 6240
ggcgctgagg tctgcctcgt gaagaaggtg ttgctgactc ataccaggcc tgaatcgccc 6300
catcatccag ccagaaagtg agggagccac ggttgatgag agctttgttg taggtggacc 6360
agttggtgat tttgaacttt tgctttgcca cggaacggtc tgcgttgtcg ggaagatgcg 6420
tgatctgatc cttcaactca gcaaaagttc gatttattca acaaagccgc cgtcccgtca 6480
agtcagcgta atgctctgcc agtgttacaa ccaattaacc aattctgatt agaaaaactc 6540
atcgagcatc aaatgaaact gcaatttatt catatcagga ttatcaatac catatttttg 6600
aaaaagccgt ttctgtaatg aaggagaaaa ctcaccgagg cagttccata ggatggcaag 6660
atcctggtat cggtctgcga ttccgactcg tccaacatca atacaaccta ttaatttccc 6720
ctcgtcaaaa ataaggttat caagtgagaa atcaccatga gtgacgactg aatccggtga 6780
gaatggcaaa agcttatgca tttctttcca gacttgttca acaggccagc cattacgctc 6840
gtcatcaaaa tcactcgcat caaccaaacc gttattcatt cgtgattgcg cctgagcgag 6900
acgaaatacg cgatcgctgt taaaaggaca attacaaaca ggaatcgaat gcaaccggcg 6960
caggaacact gccagcgcat caacaatatt ttcacctgaa tcaggatatt cttctaatac 7020
ctggaatgct gttttcccgg ggatcgcagt ggtgagtaac catgcatcat caggagtacg 7080
gataaaatgc ttgatggtcg gaagaggcat aaattccgtc agccagttta gtctgaccat 7140
ctcatctgta acatcattgg caacgctacc tttgccatgt ttcagaaaca actctggcgc 7200
atcgggcttc ccatacaatc gatagattgt cgcacctgat tgcccgacat tatcgcgagc 7260
ccatttatac ccatataaat cagcatccat gttggaattt aatcgcggcc tcgagcaaga 7320
cgtttcccgt tgaatatggc tcataacacc ccttgtatta ctgtttatgt aagcagacag 7380
ttttattgtt catgatgata tatttttatc ttgtgcaatg taacatcaga gattttgaga 7440
cacaacgtgg ctttcccccc ccccccatta ttgaagcatt tatcagggtt attgtctcat 7500
gagcggatac atatttgaat gtatttagaa aaataaacaa ataggggttc cgcgcacatt 7560
tccccgaaaa gtgccacctg acgtctaaga aaccattatt atcatgacat taacctataa 7620
aaataggcgt atcacgaggc cctttcgtc 7649

<210> SEQ ID NO 114
<211> LENGTH: 6291
<212> TYPE: DNA
<213> ORGANISM: Artificial Sequence
<220> FEATURE:
<223> OTHER INFORMATION: Synthetic

<400> SEQUENCE: 114
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
gggaacttcc atagcccata tatggagttc cgcgttacat aacttacggg aatttccaaa 420
cctggctgac cgcccaacga cccccgccca ttgacgtcaa taatgacgta tgttcccata 480
gtaacgccaa tagggaactt ccattgacgt caatgggtgg agtatttacg gtaaactgcc 540

```
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg gatagcggtt tgactcacgg gaacttccaa gtctccaccc cattgacgtc    780
aatgggagtt tgttttgact caccaaaatc aacgggaatt cccaaaatgt cgtaacaact    840
ccgccccatt gacgcaaatg ggcggtaggc gtgtacggtg ggaggtctat ataagcagag    900
ctcgtttagt gaaccgtcag atcgcctgga gacgccatcc acgctgtttt gacctccata    960
gaagacaccg ggaccgatcc agcctccatc ggctcgcatc tctccttcac gcgcccgccg   1020
ccctacctga ggccgccatc cacgccggtt gagtcgcgtt ctgccgcctc ccgcctgtgg   1080
tgcctcctga actgcgtccg ccgtctaggt aagtttaaag ctcaggtcga gaccgggcct   1140
ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagacac   1380
catgcccatg ggcagcctgc agcccctggc caccctgtac ctgctgggca tgctggtggc   1440
tagcgtgctg gccatggagt tcctgaagag gagcttcgcc cctctgaccg agaagcagtg   1500
gcaggagatc gacaacaggg ccagggagat cttcaagacc cagctgtacg gcaggaagtt   1560
cgtggacgtg gagggcccct acggctggga gtacgccgcc cacccccctgg gcgaggtgga   1620
ggtgctgagc gacgagaacg aggtggtgaa gtggggcctg aggaagagcc tgcccctgat   1680
cgagctgagg gccaccttca ccctggacct gtgggagctg gacaacctgg agaggggcaa   1740
gcccaacgtg gacctgagca gcctggagga gaccgtgagg aaggtggccg agttcgagga   1800
cgaggtgatc ttcagggggct gcgagaagag cggcgtgaag ggcctgctga gcttcgagga   1860
gaggaagatc gagtgcggca gcaccccccaa ggacctgctg gaggccatcg tgagggccct   1920
gagcatcttc agcaaggacg gcatcgaggg ccccctacacc ctggtgatca acaccgacag   1980
gtggatcaac ttcctgaagg aggaggccgg ccactacccc ctggagaaga gggtggagga   2040
gtgcctgagg ggcggcaaga tcatcaccac ccccaggatc gaggacgccc tggtggtgag   2100
cgagaggggc ggcgacttca agctgatcct gggccaggac ctgagcatcg gctacgagga   2160
cagggagaag gacgccgtga ggctgttcat caccgagacc ttcaccttcc aggtggtgaa   2220
ccccgaggcc ctgatcctgc tgaagtccgg aggcggatct ggcggaggcg aagccgccct   2280
gctggtgtgc cagtacacta ttcagagcct gattcatctg accggggagg accctggatt   2340
tttcaatgtg gaaatccctg agttcccatt ttaccccacc tgcaacgtct gtacagccga   2400
cgtgaacgtc accattaatt tcgatgtggg cgggaagaaa caccagctgg acctggattt   2460
tggccagctg accccacata caaaagccgt gtatcagccc agaggggctt tcggaggcag   2520
cgagaacgca acaaatctgt ttctgctgga gctgctggga gcaggagaac tggctctgac   2580
catgaggtcc aagaaactgc ccatcaatgt gaccacagga gaggaacagc aggtcagtct   2640
ggaatcagtg gacgtctact tccaggatgt gtttggcacc atgtggtgcc accatgccga   2700
gatgcagaat cctgtgtacc tgatccccga aaccgtccct tatattaagt gggacaactg   2760
taatagcact aacattaccg cagtggtccg ggcacagggg ctggacgtga ccctgccact   2820
gtcactgccc acaagcgccc aggatagcaa cttctccgtg aaaaccgaga tgctgggaaa   2880
```

-continued

```
tgagatcgac attgaatgca tcatggagga tggagaaatt agccaggtgc tgcctggcga   2940
taacaagttt aatatcacct gttccggcta cgaatctcac gtcccaagtg ggggaatcct   3000
gacatctact agtcccgtgg ccactccaat tcccggaacc ggctacgctt atagcctgag   3060
actgacccct aggccagtct cacgcttcct gggcaacaat agcattctgt acgtgtttta   3120
ttccggaaac ggaccaaagg cttctggagg ggactattgc atccagagta atattgtgtt   3180
ctcagacgag atcccagcca gccaggatat gcccacttga tgaggatccc atcatcatca   3240
tcatcattag tctggaaggg cgaattgatc cagatctgct gtgccttcta gttgccagcc   3300
atctgttgtt tgcccctccc ccgtgccttc cttgaccctg gaaggtgcca ctcccactgt   3360
cctttcctaa taaaatgagg aaattgcatc gcattgtctg agtaggtgtc attctattct   3420
ggggggtggg gtggggcagg acagcaaggg ggaggattgg gaagacaata gcaggcatgc   3480
tggggatgcg gtgggctcta tgggtaccca ggtgctgaag aattgacccg gttcctcctg   3540
ggccagaaag aagcaggcac atccccttct ctgtgacaca ccctgtccac gcccctggtt   3600
cttagttcca gccccactca taggacactc atagctcagg agggctccgc cttcaatccc   3660
acccgctaaa gtacttggag cggtctctcc ctccctcatc agcccaccaa accaaaccta   3720
gcctccaaga gtgggaagaa attaaagcaa gataggctat taagtgcaga gggagagaaa   3780
atgcctccaa catgtgagga agtaatgaga gaaatcatag aattttaagg ccatgattta   3840
aggccatcat ggccttaatc ttccgcttcc tcgctcactg actcgctgcg ctcggtcgtt   3900
cggctgcggc gagcggtatc agctcactca aaggcggtaa tacggttatc cacagaatca   3960
ggggataacg caggaaagaa catgtgagca aaaggccagc aaaaggccag gaaccgtaaa   4020
aaggccgcgt tgctggcgtt tttccatagg ctccgccccc ctgacgagca tcacaaaaat   4080
cgacgctcaa gtcagaggtg gcgaaacccg acaggactat aaagatacca ggcgtttccc   4140
cctggaagct ccctcgtgcg ctctcctgtt ccgaccctgc cgcttaccgg atacctgtcc   4200
gcctttctcc cttcgggaag cgtggcgctt tctcatagct cacgctgtag gtatctcagt   4260
tcggtgtagg tcgttcgctc caagctgggc tgtgtgcacg aaccccccgt tcagcccgac   4320
cgctgcgcct tatccggtaa ctatcgtctt gagtccaacc cggtaagaca cgacttatcg   4380
ccactggcag cagccactgg taacaggatt agcagagcga ggtatgtagg cggtgctaca   4440
gagttcttga agtggtggcc taactacggc tacactagaa gaacagtatt tggtatctgc   4500
gctctgctga agccagttac cttcggaaaa agagttggta gctcttgatc cggcaaacaa   4560
accaccgctg gtagcggtgg tttttttgtt tgcaagcagc agattacgcg cagaaaaaaa   4620
ggatctcaag aagatccttt gatcttttct acggggtctg acgctcagtg gaacgaaaac   4680
tcacgttaag ggattttggt catgagatta tcaaaaagga tcttcaccta gatcctttta   4740
aattaaaaat gaagttttaa atcaatctaa agtatatatg agtaaacttg gtctgacagt   4800
taccaatgct taatcagtga ggcacctatc tcagcgatct gtctatttcg ttcatccata   4860
gttgcctgac tcgggggggg ggggcgctga ggtctgcctc gtgaagaagg tgttgctgac   4920
tcataccagg cctgaatcgc cccatcatcc agccagaaag tgagggagcc acggttgatg   4980
agagctttgt tgtaggtgga ccagttggtg attttgaact tttgctttgc cacggaacgg   5040
tctgcgttgt cgggaagatg cgtgatctga tccttcaact cagcaaaagt tcgatttatt   5100
caacaaagcc gccgtcccgt caagtcagcg taatgctctg ccagtgttac aaccaattaa   5160
ccaattctga ttagaaaaac tcatcgagca tcaaatgaaa ctgcaattta ttcatatcag   5220
gattatcaat accatatttt tgaaaaagcc gtttctgtaa tgaaggagaa aactcaccga   5280
```

```
ggcagttcca taggatggca agatcctggt atcggtctgc gattccgact cgtccaacat   5340

caatacaacc tattaatttc ccctcgtcaa aaataaggtt atcaagtgag aaatcaccat   5400

gagtgacgac tgaatccggt gagaatggca aaagcttatg catttctttc cagacttgtt   5460

caacaggcca gccattacgc tcgtcatcaa aatcactcgc atcaaccaaa ccgttattca   5520

ttcgtgattg cgcctgagcg agacgaaata cgcgatcgct gttaaaagga caattacaaa   5580

caggaatcga atgcaaccgg cgcaggaaca ctgccagcgc atcaacaata ttttcacctg   5640

aatcaggata ttcttctaat acctggaatg ctgttttccc ggggatcgca gtggtgagta   5700

accatgcatc atcaggagta cggataaaat gcttgatggt cggaagaggc ataaattccg   5760

tcagccagtt tagtctgacc atctcatctg taacatcatt ggcaacgcta cctttgccat   5820

gtttcagaaa caactctggc gcatcgggct tcccatacaa tcgatagatt gtcgcacctg   5880

attgcccgac attatcgcga gcccatttat acccatataa atcagcatcc atgttggaat   5940

ttaatcgcgg cctcgagcaa gacgtttccc gttgaatatg gctcataaca ccccttgtat   6000

tactgtttat gtaagcagac agttttattg ttcatgatga tatattttta tcttgtgcaa   6060

tgtaacatca gagattttga gacacaacgt ggctttcccc cccccccccat tattgaagca   6120

tttatcaggg ttattgtctc atgagcggat acatatttga atgtatttag aaaaataaac   6180

aaataggggt tccgcgcaca tttccccgaa aagtgccacc tgacgtctaa gaaaccatta   6240

ttatcatgac attaacctat aaaaataggc gtatcacgag gccctttcgt c            6291
```

<210> SEQ ID NO 115
<211> LENGTH: 6615
<212> TYPE: DNA
<213> ORGANISM: Artificial Sequence
<220> FEATURE:
<223> OTHER INFORMATION: Synthetic

<400> SEQUENCE: 115

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360

gggaacttcc atagcccata tatggagttc cgcgttacat aacttacggg aatttccaaa    420

cctggctgac cgcccaacga cccccgccca ttgacgtcaa taatgacgta tgttcccata    480

gtaacgccaa tagggaactt ccattgacgt caatgggtgg agtatttacg gtaaactgcc    540

cacttgggaa tttccaagtg tatcatatgc caagtacgcc ccctattgac gtcaatgacg    600

ggaacttcca taagcttgca ttatgcccag tacatgacct tatgggaatt tcctacttgg    660

cagtacatct acgtattagt catcgctatt accatggtga tgcggttttg gcagtacatc    720

aatgggcgtg gatagcggtt tgactcacgg gaacttccaa gtctccaccc cattgacgtc    780

aatgggagtt tgttttgact caccaaaatc aacgggaatt cccaaaatgt cgtaacaact    840

ccgccccatt gacgcaaatg ggcggtaggc gtgtacggtg ggaggtctat ataagcagag    900

ctcgtttagt gaaccgtcag atcgcctgga gacgccatcc acgctgtttt gacctccata    960

gaagacaccg ggaccgatcc agcctccatc ggctcgcatc tctccttcac gcgcccgccg   1020
```

```
ccctacctga ggccgccatc cacgccggtt gagtcgcgtt ctgccgcctc ccgcctgtgg   1080
tgcctcctga actgcgtccg ccgtctaggt aagtttaaag ctcaggtcga gaccgggcct   1140
ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagacac   1380
catgcccatg ggcagcctgc agcccctggc caccctgtac ctgctgggca tgctggtggc   1440
tagcgtgctg gccatggagt tcctgaagag gagcttcgcc cctctgaccg agaagcagtg   1500
gcaggagatc gacaacaggg ccagggagat cttcaagacc cagctgtacg gcaggaagtt   1560
cgtggacgtg gagggcccct acggctggga gtacgccgcc cacccccctgg gcgaggtgga   1620
ggtgctgagc gacgagaacg aggtggtgaa gtggggcctg aggaagagcc tgcccctgat   1680
cgagctgagg gccaccttca ccctggacct gtgggagctg gacaacctgg agaggggcaa   1740
gcccaacgtg gacctgagca gcctggagga gaccgtgagg aaggtggccg agttcgagga   1800
cgaggtgatc ttcaggggct gcgagaagag cggcgtgaag ggcctgctga gcttcgagga   1860
gaggaagatc gagtgcggca gcaccccccaa ggacctgctg gaggccatcg tgagggccct   1920
gagcatcttc agcaaggacg gcatcgaggg cccctacacc ctggtgatca acaccgacag   1980
gtggatcaac ttcctgaagg aggaggccgg ccactacccc ctggagaaga gggtggagga   2040
gtgcctgagg ggcggcaaga tcatcaccac ccccaggatc gaggacgccc tggtggtgag   2100
cgagaggggc ggcgacttca agctgatcct gggccaggac ctgagcatcg gctacgagga   2160
cagggagaag gacgccgtga ggctgttcat caccgagacc ttcaccttcc aggtggtgaa   2220
ccccgaggcc ctgatcctgc tgaagtccgg aggcggatct ggcggaggcg aagccgccct   2280
gctggtgtgc cagtacacta ttcagagcct gattcatctg accggggagg accctggatt   2340
tttcaatgtg gaaatccctg agttcccatt ttaccccacc tgcaacgtct gtacagccga   2400
cgtgaacgtc accattaatt tcgatgtggg cgggaagaaa caccagctgg acctggattt   2460
tggccagctg accccacata caaaagccgt gtatcagccc agaggggctt tcggaggcag   2520
cgagaacgca acaaatctgt ttctgctgga gctgctggga gcaggagaac tggctctgac   2580
catgaggtcc aagaaactgc ccatcaatgt gaccacagga gaggaacagc aggtcagtct   2640
ggaatcagtg gacgtctact tccaggatgt gtttggcacc atgtggtgcc accatgccga   2700
gatgcagaat cctgtgtacc tgatccccga aaccgtccct tatattaagt gggacaactg   2760
taatagcact aacattaccg cagtggtccg ggcacagggg ctggacgtga ccctgccact   2820
gtcactgccc acaagcgccc aggatagcaa cttctccgtg aaaaccgaga tgctgggaaa   2880
tgagatcgac attgaatgca tcatggagga tggagaaatt agccaggtgc tgcctggcga   2940
taacaagttt aatatcacct gttccggcta cgaatctcac gtcccaagtg gggggaatcct   3000
gacatctact agtcccgtgg ccactccaat tcccggaacc ggctacgctt atagcctgag   3060
actgacccct aggccagtct cacgcttcct gggcaacaat agcattctgt acgtgtttta   3120
ttccggaaac ggaccaaagg cttctggagg ggactattgc atccagagta atattgtgtt   3180
ctcagacgag atcccagcca gccaggatat gcccactaac actaccgaca ttacctacgt   3240
gggcgataat gccacttatt ccgtgcctat ggtcacaagc gaagacgcta actccccaaa   3300
tgtgaccgtc acagcattct gggcctggcc caacaatact gagaccgatt ttaagtgcaa   3360
atggacactg acttcaggca cccctagcgg gtgtgaaaac atctctggcg ccttcgctag   3420
```

taatcgaacc tttgatatta cagtgtccgg cctggggact gccccaaaaa ccctgatcat 3480
tacccggaca gctactaacg caacaactac cacacacaaa gtgatcttca gcaaagctcc 3540
ctgatgagga tcccatcatc atcatcatca ttagtctgga agggcgaatt gatccagatc 3600
tgctgtgcct tctagttgcc agccatctgt tgtttgcccc tcccccgtgc cttccttgac 3660
cctggaaggt gccactccca ctgtcctttc ctaataaaat gaggaaattg catcgcattg 3720
tctgagtagg tgtcattcta ttctgggggg tggggtgggg caggacagca agggggagga 3780
ttgggaagac aatagcaggc atgctgggga tgcggtgggc tctatgggta cccaggtgct 3840
gaagaattga cccggttcct cctgggccag aaagaagcag gcacatcccc ttctctgtga 3900
cacaccctgt ccacgcccct ggttcttagt tccagcccca ctcataggac actcatagct 3960
caggagggct ccgccttcaa tcccacccgc taaagtactt ggagcggtct ctccctccct 4020
catcagccca ccaaaccaaa cctagcctcc aagagtggga agaaattaaa gcaagatagg 4080
ctattaagtg cagagggaga gaaaatgcct ccaacatgtg aggaagtaat gagagaaatc 4140
atagaatttt aaggccatga tttaaggcca tcatggcctt aatcttccgc ttcctcgctc 4200
actgactcgc tgcgctcggt cgttcggctg cggcgagcgg tatcagctca ctcaaaggcg 4260
gtaatacggt tatccacaga atcaggggat aacgcaggaa agaacatgtg agcaaaaggc 4320
cagcaaaagg ccaggaaccg taaaaaggcc gcgttgctgg cgtttttcca taggctccgc 4380
ccccctgacg agcatcacaa aaatcgacgc tcaagtcaga ggtggcgaaa cccgacagga 4440
ctataaagat accaggcgtt tccccctgga agctccctcg tgcgctctcc tgttccgacc 4500
ctgccgctta ccggatacct gtccgccttt ctcccttcgg gaagcgtggc gctttctcat 4560
agctcacgct gtaggtatct cagttcggtg taggtcgttc gctccaagct gggctgtgtg 4620
cacgaacccc ccgttcagcc cgaccgctgc gccttatccg gtaactatcg tcttgagtcc 4680
aacccggtaa gacacgactt atcgccactg gcagcagcca ctggtaacag gattagcaga 4740
gcgaggtatg taggcggtgc tacagagttc ttgaagtggt ggcctaacta cggctacact 4800
agaagaacag tatttggtat ctgcgctctg ctgaagccag ttaccttcgg aaaaagagtt 4860
ggtagctctt gatccggcaa acaaaccacc gctggtagcg gtggtttttt tgtttgcaag 4920
cagcagatta cgcgcagaaa aaaaggatct caagaagatc ctttgatctt ttctacgggg 4980
tctgacgctc agtggaacga aaactcacgt taagggattt tggtcatgag attatcaaaa 5040
aggatcttca cctagatcct tttaaattaa aaatgaagtt ttaaatcaat ctaaagtata 5100
tatgagtaaa cttggtctga cagttaccaa tgcttaatca gtgaggcacc tatctcagcg 5160
atctgtctat ttcgttcatc catagttgcc tgactcgggg gggggggggcg ctgaggtctg 5220 cctcgtgaag aaggtgttgc tgactcatac caggcctgaa tcgccccatc atccagccag 5280
aaagtgaggg agccacggtt gatgagagct ttgttgtagg tggaccagtt ggtgattttg 5340
aacttttgct ttgccacgga acggtctgcg ttgtcgggaa gatgcgtgat ctgatccttc 5400
aactcagcaa aagttcgatt tattcaacaa agccgccgtc ccgtcaagtc agcgtaatgc 5460
tctgccagtg ttacaaccaa ttaaccaatt ctgattagaa aaactcatcg agcatcaaat 5520
gaaactgcaa tttattcata tcaggattat caataccata tttttgaaaa agccgtttct 5580
gtaatgaagg agaaaactca ccgaggcagt tccataggat ggcaagatcc tggtatcggt 5640
ctgcgattcc gactcgtcca acatcaatac aacctattaa tttcccctcg tcaaaaataa 5700
ggttatcaag tgagaaatca ccatgagtga cgactgaatc cggtgagaat ggcaaaagct 5760

-continued tatgcatttc tttccagact tgttcaacag gccagccatt acgctcgtca tcaaaatcac 5820
tcgcatcaac caaaccgtta ttcattcgtg attgcgcctg agcgagacga aatacgcgat 5880
cgctgttaaa aggacaatta caaacaggaa tcgaatgcaa ccggcgcagg aacactgcca 5940
gcgcatcaac aatattttca cctgaatcag gatattcttc taatacctgg aatgctgttt 6000
tcccggggat cgcagtggtg agtaaccatg catcatcagg agtacggata aaatgcttga 6060
tggtcggaag aggcataaat tccgtcagcc agtttagtct gaccatctca tctgtaacat 6120
cattggcaac gctacctttg ccatgtttca gaaacaactc tggcgcatcg ggcttcccat 6180
acaatcgata gattgtcgca cctgattgcc cgacattatc gcgagcccat ttatacccat 6240
ataaatcagc atccatgttg gaatttaatc gcggcctcga gcaagacgtt tcccgttgaa 6300
tatggctcat aacacccctt gtattactgt ttatgtaagc agacagtttt attgttcatg 6360
atgatatatt tttatcttgt gcaatgtaac atcagagatt ttgagacaca acgtggcttt 6420
cccccccccc ccattattga agcatttatc agggttattg tctcatgagc ggatacatat 6480
ttgaatgtat ttagaaaaat aaacaaatag gggttccgcg cacatttccc cgaaaagtgc 6540
cacctgacgt ctaagaaacc attattatca tgacattaac ctataaaaat aggcgtatca 6600
cgaggccctt tcgtc 6615

<210> SEQ ID NO 116
<211> LENGTH: 6750
<212> TYPE: DNA
<213> ORGANISM: Artificial Sequence
<220> FEATURE:
<223> OTHER INFORMATION: Synthetic

<400> SEQUENCE: 116
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
gggaacttcc atagcccata tatggagttc cgcgttacat aacttacggg aatttccaaa 420
cctggctgac cgcccaacga cccccgccca ttgacgtcaa taatgacgta tgttcccata 480
gtaacgccaa tagggaactt ccattgacgt caatgggtgg agtatttacg gtaaactgcc 540
cacttgggaa tttccaagtg tatcatatgc caagtacgcc ccctattgac gtcaatgacg 600
ggaacttcca taagcttgca ttatgcccag tacatgacct tatgggaatt tcctacttgg 660
cagtacatct acgtattagt catcgctatt accatggtga tgcggttttg gcagtacatc 720
aatgggcgtg gatagcggtt tgactcacgg gaacttccaa gtctccaccc cattgacgtc 780
aatgggagtt tgttttgact caccaaaatc aacgggaatt cccaaaatgt cgtaacaact 840
ccgccccatt gacgcaaatg ggcggtaggc gtgtacggtg ggaggtctat ataagcagag 900
ctcgtttagt gaaccgtcag atcgcctgga gacgccatcc acgctgtttt gacctccata 960
gaagacaccg ggaccgatcc agcctccatc ggctcgcatc tctccttcac gcgcccgccg 1020
ccctacctga ggccgccatc cacgccggtt gagtcgcgtt ctgccgcctc ccgcctgtgg 1080
tgcctcctga actgcgtccg ccgtctaggt aagtttaaag ctcaggtcga gaccgggcct 1140
ttgtccggcg ctcccttgga gcctacctag actcagccgg ctctccacgc tttgcctgac 1200

-continued

```
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagacac   1380
catgcccatg ggcagcctgc agcccctggc caccctgtac ctgctgggca tgctggtggc   1440
tagcgtgctg gccatggagt tcctgaagag gagcttcgcc cctctgaccg agaagcagtg   1500
gcaggagatc gacaacaggg ccagggagat cttcaagacc cagctgtacg gcaggaagtt   1560
cgtggacgtg gagggcccct acggctggga gtacgccgcc cacccccctgg gcgaggtgga   1620
ggtgctgagc gacgagaacg aggtggtgaa gtggggcctg aggaagagcc tgcccctgat   1680
cgagctgagg gccaccttca ccctggacct gtgggagctg gacaacctgg agaggggcaa   1740
gcccaacgtg gacctgagca gcctggagga gaccgtgagg aaggtggccg agttcgagga   1800
cgaggtgatc ttcaggggct gcgagaagag cggcgtgaag ggcctgctga gcttcgagga   1860
gaggaagatc gagtgcggca gcacccccaa ggacctgctg gaggccatcg tgagggccct   1920
gagcatcttc agcaaggacg gcatcgaggg cccctacacc ctggtgatca acaccgacag   1980
gtggatcaac ttcctgaagg aggaggccgg ccactacccc ctggagaaga gggtggagga   2040
gtgcctgagg ggcggcaaga tcatcaccac ccccaggatc gaggacgccc tggtggtgag   2100
cgagaggggc ggcgacttca agctgatcct gggccaggac ctgagcatcg gctacgagga   2160
cagggagaag gacgccgtga ggctgttcat caccgagacc ttcaccttcc aggtggtgaa   2220
ccccgaggcc ctgatcctgc tgaagtccgg aggcggatct ggcggaggcg aagccgccct   2280
gctggtgtgc cagtacacta ttcagagcct gattcatctg accggggagg accctggatt   2340
tttcaatgtg gaaatccctg agttcccatt ttaccccacc tgcaacgtct gtacagccga   2400
cgtgaacgtc accattaatt tcgatgtggg cgggaagaaa caccagctgg acctggattt   2460
tggccagctg accccacata caaaagccgt gtatcagccc agaggggctt tcggaggcag   2520
cgagaacgca acaaatctgt ttctgctgga gctgctggga gcaggagaac tggctctgac   2580
catgaggtcc aagaaactgc ccatcaatgt gaccacagga gaggaacagc aggtcagtct   2640
ggaatcagtg gacgtctact tccaggatgt gtttggcacc atgtggtgcc accatgccga   2700
gatgcagaat cctgtgtacc tgatccccga aaccgtccct tatattaagt gggacaactg   2760
taatagcact aacattaccg cagtggtccg ggcacagggg ctggacgtga ccctgccact   2820
gtcactgccc acaagcgccc aggatagcaa cttctccgtg aaaaccgaga tgctgggaaa   2880
tgagatcgac attgaatgca tcatggagga tggagaaatt agccaggtgc tgcctggcga   2940
taacaagttt aatatcacct gttccggcta cgaatctcac gtcccaagtg ggggaatcct   3000
gacatctact agtcccgtgg ccactccaat tcccggaacc ggctacgctt atagcctgag   3060
actgacccct aggccagtct cacgcttcct gggcaacaat agcattctgt acgtgtttta   3120
ttccggaaac ggaccaaagg cttctggagg ggactattgc atccagagta atattgtgtt   3180
ctcagacgag atcccagcca gccaggatat gcccactaac actaccgaca ttacctacgt   3240
gggcgataat gccacttatt ccgtgcctat ggtcacaagc gaagacgcta actccccaaa   3300
tgtgaccgtc acagcattct gggcctggcc caacaatact gagaccgatt ttaagtgcaa   3360
atggacactg acttcaggca cccctagcgg gtgtgaaaac atctctggcg ccttcgctag   3420
taatcgaacc tttgatatta cagtgtccgg cctggggact gccccaaaaa ccctgatcat   3480
tacccggaca gctactaacg caacaactac cacacacaaa gtgatcttca gcaaagctcc   3540
```

cgagtccact accacatctc ctaccctgaa cactaccggg tttgccgacc ccaatacaac 3600
taccggactg cctagctcca cccatgtgcc aacaaacctg actgcaccag catccaccgg 3660
acctacagtg tctacttgat gaggatccca tcatcatcat catcattagt ctggaagggc 3720
gaattgatcc agatctgctg tgccttctag ttgccagcca tctgttgttt gcccctcccc 3780
cgtgccttcc ttgaccctgg aaggtgccac tcccactgtc ctttcctaat aaaatgagga 3840
aattgcatcg cattgtctga gtaggtgtca ttctattctg gggggtgggg tggggcagga 3900
cagcaagggg gaggattggg aagacaatag caggcatgct ggggatgcgg tgggctctat 3960
gggtacccag gtgctgaaga attgacccgg ttcctcctgg gccagaaaga agcaggcaca 4020
tccccttctc tgtgacacac cctgtccacg cccctggttc ttagttccag ccccactcat 4080
aggacactca tagctcagga gggctccgcc ttcaatccca cccgctaaag tacttggagc 4140
ggtctctccc tccctcatca gcccaccaaa ccaaacctag cctccaagag tgggaagaaa 4200
ttaaagcaag ataggctatt aagtgcagag ggagagaaaa tgcctccaac atgtgaggaa 4260
gtaatgagag aaatcataga attttaaggc catgatttaa ggccatcatg gccttaatct 4320
tccgcttcct cgctcactga ctcgctgcgc tcggtcgttc ggctgcggcg agcggtatca 4380
gctcactcaa aggcggtaat acggttatcc acagaatcag gggataacgc aggaaagaac 4440
atgtgagcaa aaggccagca aaaggccagg aaccgtaaaa aggccgcgtt gctggcgttt 4500
ttccataggc tccgcccccc tgacgagcat cacaaaaatc gacgctcaag tcagaggtgg 4560
cgaaacccga caggactata aagataccag gcgtttcccc ctggaagctc cctcgtgcgc 4620
tctcctgttc cgaccctgcc gcttaccgga tacctgtccg cctttctccc ttcgggaagc 4680
gtggcgcttt ctcatagctc acgctgtagg tatctcagtt cggtgtaggt cgttcgctcc 4740
aagctgggct gtgtgcacga accccccgtt cagcccgacc gctgcgcctt atccggtaac 4800
tatcgtcttg agtccaaccc ggtaagacac gacttatcgc cactggcagc agccactggt 4860
aacaggatta gcagagcgag gtatgtaggc ggtgctacag agttcttgaa gtggtggcct 4920
aactacggct acactagaag aacagtattt ggtatctgcg ctctgctgaa gccagttacc 4980
ttcggaaaaa gagttggtag ctcttgatcc ggcaaacaaa ccaccgctgg tagcggtggt 5040 tttttgttt gcaagcagca gattacgcgc agaaaaaaag gatctcaaga agatcctttg 5100
atcttttcta cggggtctga cgctcagtgg aacgaaaact cacgttaagg gattttggtc 5160
atgagattat caaaaaggat cttcacctag atccttttaa attaaaaatg aagttttaaa 5220
tcaatctaaa gtatatatga gtaaacttgg tctgacagtt accaatgctt aatcagtgag 5280
gcacctatct cagcgatctg tctatttcgt tcatccatag ttgcctgact cggggggggg 5340
gggcgctgag gtctgcctcg tgaagaaggt gttgctgact cataccaggc ctgaatcgcc 5400
ccatcatcca gccagaaagt gagggagcca cggttgatga gagctttgtt gtaggtggac 5460
cagttggtga ttttgaactt ttgctttgcc acggaacggt ctgcgttgtc gggaagatgc 5520
gtgatctgat ccttcaactc agcaaaagtt cgatttattc aacaaagccg ccgtcccgtc 5580
aagtcagcgt aatgctctgc cagtgttaca accaattaac caattctgat tagaaaaact 5640
catcgagcat caaatgaaac tgcaatttat tcatatcagg attatcaata ccatattttt 5700
gaaaaagccg tttctgtaat gaaggagaaa actcaccgag gcagttccat aggatggcaa 5760
gatcctggta tcggtctgcg attccgactc gtccaacatc aatacaacct attaatttcc 5820
cctcgtcaaa aataaggtta tcaagtgaga aatcaccatg agtgacgact gaatccggtg 5880
agaatggcaa aagcttatgc atttctttcc agacttgttc aacaggccag ccattacgct 5940
cgtcatcaaa atcactcgca tcaaccaaac cgttattcat tcgtgattgc gcctgagcga 6000
gacgaaatac gcgatcgctg ttaaaaggac aattacaaac aggaatcgaa tgcaaccggc 6060
gcaggaacac tgccagcgca tcaacaatat tttcacctga atcaggatat tcttctaata 6120
cctggaatgc tgttttcccg gggatcgcag tggtgagtaa ccatgcatca tcaggagtac 6180
ggataaaatg cttgatggtc ggaagaggca taaattccgt cagccagttt agtctgacca 6240
tctcatctgt aacatcattg gcaacgctac ctttgccatg tttcagaaac aactctggcg 6300
catcgggctt cccatacaat cgatagattg tcgcacctga ttgcccgaca ttatcgcgag 6360
cccatttata cccatataaa tcagcatcca tgttggaatt taatcgcggc ctcgagcaag 6420
acgtttcccg ttgaatatgg ctcataacac cccttgtatt actgtttatg taagcagaca 6480
gttttattgt tcatgatgat atatttttat cttgtgcaat gtaacatcag agattttgag 6540
acacaacgtg gctttccccc cccccccatt attgaagcat ttatcagggt tattgtctca 6600
tgagcggata catatttgaa tgtatttaga aaaataaaca aataggggtt ccgcgcacat 6660
ttccccgaaa agtgccacct gacgtctaag aaaccattat tatcatgaca ttaacctata 6720
aaaataggcg tatcacgagg ccctttcgtc 6750

<210> SEQ ID NO 117
<211> LENGTH: 7920
<212> TYPE: DNA
<213> ORGANISM: Artificial Sequence
<220> FEATURE:
<223> OTHER INFORMATION: Synthetic

<400> SEQUENCE: 117
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
gggaacttcc atagcccata tatggagttc cgcgttacat aacttacggg aatttccaaa 420
cctggctgac cgcccaacga cccccgccca ttgacgtcaa taatgacgta tgttcccata 480
gtaacgccaa tagggaactt ccattgacgt caatgggtgg agtatttacg gtaaactgcc 540
cacttgggaa tttccaagtg tatcatatgc caagtacgcc ccctattgac gtcaatgacg 600
ggaacttcca taagcttgca ttatgcccag tacatgacct tatgggaatt tcctacttgg 660
cagtacatct acgtattagt catcgctatt accatggtga tgcggttttg gcagtacatc 720
aatgggcgtg gatagcggtt tgactcacgg gaacttccaa gtctccaccc cattgacgtc 780
aatgggagtt tgttttgact caccaaaatc aacgggaatt cccaaaatgt cgtaacaact 840
ccgccccatt gacgcaaatg ggcggtaggc gtgtacggtg ggaggtctat ataagcagag 900
ctcgtttagt gaaccgtcag atcgcctgga gacgccatcc acgctgtttt gacctccata 960
gaagacaccg ggaccgatcc agcctccatc ggctcgcatc tctccttcac gcgcccgccg 1020
ccctacctga ggccgccatc cacgccggtt gagtcgcgtt ctgccgcctc ccgcctgtgg 1080
tgcctcctga actgcgtccg ccgtctaggt aagtttaaag ctcaggtcga gaccgggcct 1140
ttgtccggcg ctcccttgga gcctacctag actcagccgg ctctccacgc tttgcctgac 1200

-continued

```
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagacac   1380
catgcccatg ggcagcctgc agcccctggc caccctgtac ctgctgggca tgctggtggc   1440
tagcgtgctg gccatggagt tcctgaagag gagcttcgcc cctctgaccg agaagcagtg   1500
gcaggagatc gacaacaggg ccagggagat cttcaagacc cagctgtacg gcaggaagtt   1560
cgtggacgtg gagggcccct acggctggga gtacgccgcc cacccccctgg gcgaggtgga   1620
ggtgctgagc gacgagaacg aggtggtgaa gtggggcctg aggaagagcc tgcccctgat   1680
cgagctgagg gccaccttca ccctggacct gtgggagctg gacaacctgg agaggggcaa   1740
gcccaacgtg gacctgagca gcctggagga gaccgtgagg aaggtggccg agttcgagga   1800
cgaggtgatc ttcaggggct gcgagaagag cggcgtgaag ggcctgctga gcttcgagga   1860
gaggaagatc gagtgcggca gcacccccaa ggacctgctg gaggccatcg tgagggccct   1920
gagcatcttc agcaaggacg gcatcgaggg cccctacacc ctggtgatca acaccgacag   1980
gtggatcaac ttcctgaagg aggaggccgg ccactacccc ctggagaaga gggtggagga   2040
gtgcctgagg ggcggcaaga tcatcaccac ccccaggatc gaggacgccc tggtggtgag   2100
cgagaggggc ggcgacttca agctgatcct gggccaggac ctgagcatcg gctacgagga   2160
cagggagaag gacgccgtga ggctgttcat caccgagacc ttcaccttcc aggtggtgaa   2220
ccccgaggcc ctgatcctgc tgaagtccgg aggcggatct ggcggaggcg aagccgccct   2280
gctggtgtgc cagtacacta ttcagagcct gattcatctg accggggagg accctggatt   2340
tttcaatgtg gaaatccctg agttcccatt ttaccccacc tgcaacgtct gtacagccga   2400
cgtgaacgtc accattaatt tcgatgtggg cgggaagaaa caccagctgg acctggattt   2460
tggccagctg accccacata caaaagccgt gtatcagccc agaggggctt tcggaggcag   2520
cgagaacgca acaaatctgt ttctgctgga gctgctggga gcaggagaac tggctctgac   2580
catgaggtcc aagaaactgc ccatcaatgt gaccacagga gaggaacagc aggtcagtct   2640
ggaatcagtg gacgtctact tccaggatgt gtttggcacc atgtggtgcc accatgccga   2700
gatgcagaat cctgtgtacc tgatccccga aaccgtccct tatattaagt gggacaactg   2760
taatagcact aacattaccg cagtggtccg ggcacagggg ctggacgtga ccctgccact   2820
gtcactgccc acaagcgccc aggatagcaa cttctccgtg aaaaccgaga tgctgggaaa   2880
tgagatcgac attgaatgca tcatggagga tggagaaatt agccaggtgc tgcctggcga   2940
taacaagttt aatatcacct gttccggcta cgaatctcac gtcccaagtg ggggaatcct   3000
gacatctact agtcccgtgg ccactccaat tcccggaacc ggctacgctt atagcctgag   3060
actgacccct aggccagtct cacgcttcct gggcaacaat agcattctgt acgtgtttta   3120
ttccggaaac ggaccaaagg cttctggagg ggactattgc atccagagta atattgtgtt   3180
ctcagacgag atcccagcca gccaggatat gcccactaac actaccgaca ttacctacgt   3240
gggcgataat gccacttatt ccgtgcctat ggtcacaagc gaagacgcta actccccaaa   3300
tgtgaccgtc acagcattct gggcctggcc caacaatact gagaccgatt ttaagtgcaa   3360
atggacactg acttcaggca cccctagcgg gtgtgaaaac atctctggcg ccttcgctag   3420
taatcgaacc tttgatatta cagtgtccgg cctggggact gccccaaaaa ccctgatcat   3480
tacccggaca gctactaacg caacaactac cacacacaaa gtgatcttca gcaaagctcc   3540
cgagtccact accacatctc ctaccctgaa cactaccggg tttgccgacc ccaatacaac   3600
```

```
taccggactg cctagctcca cccatgtgcc aacaaacctg actgcaccag catccaccgg   3660
acctacagtg tctactgccg atgtcaccag tcccacacct gccggaacaa cttctggcgc   3720
tagtcccgtg accccatcac ccagcccttg ggacaatggg acagagagta aggcccctga   3780
tatgacttct agtacctcac cagtcaccac accaaccccc aacgcaacaa gccctactcc   3840
agccgtgact acccccacac ctaatgctac cagcccaaca cccgcagtga caactcctac   3900
cccaaacgcc acttccccaa ccctggggaa gacatcaccc actagcgccg tgaccacacc   3960
cacccctaat gctacctctc ctacactggg aaaaacttcc ccaacctctg cagtgactac   4020
cccaaccccc aacgccacaa gccccactct gggcaagacc agtcctacat cagctgtcac   4080
aactcctacc ccaaatgcaa ctgggccaac cgtgggagag acatcccccc aggctaacgc   4140
aacaaatcac actctgggag gcaccagtcc cacacctgtg gtcacctcac agcccaagaa   4200
cgccacaagc gctgtgacca caggccagca taatatcaca tcaagctcca cttctagtat   4260
gagcctgcgc ccttcaagca acccagagac actgtcccca tctactagtg acaattcaac   4320
cagccacatg cctctgctga catctgcaca tccaactggg ggagaaaaca tcactcaggt   4380
cacccccgcc tccatttcta cccaccatgt gtccacatcc tctccagcac cccgacctgg   4440
aactaccagc caggcatccg gaccaggaaa tagttcaacc agcacaaagc ctggcgaggt   4500
gaacgtcaca aaagggactc cccctcagaa tgctacctca cctcaggcac caagcggcca   4560
gaaaacagct gtgcctactg tcacctccac aggcgggaag gcaaactcta caactggagg   4620
caaacacacc acagggcatg gagctcgcac tagcaccgaa ccaactaccg actacggggg   4680
agattccaca actccaaggc ccagatacaa tgccaccaca tatctgccac cctctaccag   4740
ctccaagctg cgacccagat ggacattcac tagtcctcca gtgactaccg cacaggctac   4800
agtgccagtc ccacctactt ctcagcctag attttctaac ctgagttgat gaggatccca   4860
tcatcatcat catcattagt ctggaagggc gaattgatcc agatctgctg tgccttctag   4920
ttgccagcca tctgttgttt gcccctcccc cgtgccttcc ttgaccctgg aaggtgccac   4980
tcccactgtc ctttcctaat aaaatgagga aattgcatcg cattgtctga gtaggtgtca   5040
ttctattctg gggggtgggg tggggcagga cagcaagggg gaggattggg aagacaatag   5100
caggcatgct ggggatgcgg tgggctctat gggtacccag gtgctgaaga attgacccgg   5160
ttcctcctgg gccagaaaga agcaggcaca tccccttctc tgtgacacac cctgtccacg   5220
cccctggttc ttagttccag ccccactcat aggacactca tagctcagga gggctccgcc   5280
ttcaatccca cccgctaaag tacttggagc ggtctctccc tccctcatca gcccaccaaa   5340
ccaaacctag cctccaagag tgggaagaaa ttaaagcaag ataggctatt aagtgcagag   5400
ggagagaaaa tgcctccaac atgtgaggaa gtaatgagag aaatcataga attttaaggc   5460
catgatttaa ggccatcatg gccttaatct tccgcttcct cgctcactga ctcgctgcgc   5520
tcggtcgttc ggctgcggcg agcggtatca gctcactcaa aggcggtaat acggttatcc   5580
acagaatcag gggataacgc aggaaagaac atgtgagcaa aaggccagca aaaggccagg   5640
aaccgtaaaa aggccgcgtt gctggcgttt ttccataggc tccgcccccc tgacgagcat   5700
cacaaaaatc gacgctcaag tcagaggtgg cgaaacccga caggactata aagataccag   5760
gcgtttcccc ctggaagctc cctcgtgcgc tctcctgttc cgaccctgcc gcttaccgga   5820
tacctgtccg cctttctccc ttcgggaagc gtggcgcttt ctcatagctc acgctgtagg   5880
tatctcagtt cggtgtaggt cgttcgctcc aagctgggct gtgtgcacga acccccgtt   5940
```

cagcccgacc gctgcgcctt atccggtaac tatcgtcttg agtccaaccc ggtaagacac 6000
gacttatcgc cactggcagc agccactggt aacaggatta gcagagcgag gtatgtaggc 6060
ggtgctacag agttcttgaa gtggtggcct aactacggct acactagaag aacagtattt 6120
ggtatctgcg ctctgctgaa gccagttacc ttcggaaaaa gagttggtag ctcttgatcc 6180
ggcaaacaaa ccaccgctgg tagcggtggt ttttttgttt gcaagcagca gattacgcgc 6240
agaaaaaaag gatctcaaga agatcctttg atcttttcta cggggtctga cgctcagtgg 6300
aacgaaaact cacgttaagg gattttggtc atgagattat caaaaaggat cttcacctag 6360
atccttttaa attaaaaatg aagttttaaa tcaatctaaa gtatatatga gtaaacttgg 6420
tctgacagtt accaatgctt aatcagtgag gcacctatct cagcgatctg tctatttcgt 6480
tcatccatag ttgcctgact cggggggggg gggcgctgag gtctgcctcg tgaagaaggt 6540
gttgctgact cataccaggc ctgaatcgcc ccatcatcca gccagaaagt gagggagcca 6600
cggttgatga gagctttgtt gtaggtggac cagttggtga ttttgaactt ttgctttgcc 6660
acggaacggt ctgcgttgtc gggaagatgc gtgatctgat ccttcaactc agcaaaagtt 6720
cgatttattc aacaaagccg ccgtcccgtc aagtcagcgt aatgctctgc cagtgttaca 6780
accaattaac caattctgat tagaaaaact catcgagcat caaatgaaac tgcaatttat 6840
tcatatcagg attatcaata ccatattttt gaaaaagccg tttctgtaat gaaggagaaa 6900
actcaccgag gcagttccat aggatggcaa gatcctggta tcggtctgcg attccgactc 6960
gtccaacatc aatacaacct attaatttcc cctcgtcaaa aataaggtta tcaagtgaga 7020
aatcaccatg agtgacgact gaatccggtg agaatggcaa aagcttatgc atttctttcc 7080
agacttgttc aacaggccag ccattacgct cgtcatcaaa atcactcgca tcaaccaaac 7140
cgttattcat tcgtgattgc gcctgagcga gacgaaatac gcgatcgctg ttaaaaggac 7200
aattacaaac aggaatcgaa tgcaaccggc gcaggaacac tgccagcgca tcaacaatat 7260
tttcacctga atcaggatat tcttctaata cctggaatgc tgttttcccg gggatcgcag 7320
tggtgagtaa ccatgcatca tcaggagtac ggataaaatg cttgatggtc ggaagaggca 7380
taaattccgt cagccagttt agtctgacca tctcatctgt aacatcattg gcaacgctac 7440
ctttgccatg tttcagaaac aactctggcg catcgggctt cccatacaat cgatagattg 7500
tcgcacctga ttgcccgaca ttatcgcgag cccatttata cccatataaa tcagcatcca 7560
tgttggaatt taatcgcggc ctcgagcaag acgtttcccg ttgaatatgg ctcataacac 7620
cccttgtatt actgtttatg taagcagaca gttttattgt tcatgatgat atatttttat 7680
cttgtgcaat gtaacatcag agattttgag acacaacgtg gctttccccc cccccccatt 7740
attgaagcat ttatcagggt tattgtctca tgagcggata catatttgaa tgtatttaga 7800
aaaataaaca aataggggtt ccgcgcacat ttccccgaaa agtgccacct gacgtctaag 7860
aaaccattat tatcatgaca ttaacctata aaaataggcg tatcacgagg ccctttcgtc 7920

<210> SEQ ID NO 118
<211> LENGTH: 5031
<212> TYPE: DNA
<213> ORGANISM: Artificial Sequence
<220> FEATURE:
<223> OTHER INFORMATION: Synthetic

<400> SEQUENCE: 118
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120

```
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
gggaacttcc atagcccata tatggagttc cgcgttacat aacttacggg aatttccaaa    420
cctggctgac cgcccaacga cccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg gatagcggtt tgactcacgg gaacttccaa gtctccaccc cattgacgtc    780
aatgggagtt tgttttgact caccaaaatc aacgggaatt cccaaaatgt cgtaacaact    840
ccgccccatt gacgcaaatg ggcggtaggc gtgtacggtg ggaggtctat ataagcagag    900
ctcgtttagt gaaccgtcag atcgcctgga gacgccatcc acgctgtttt gacctccata    960
gaagacaccg ggaccgatcc agcctccatc ggctcgcatc tctccttcac gcgcccgccg   1020
ccctacctga ggccgccatc cacgccggtt gagtcgcgtt ctgccgcctc ccgcctgtgg   1080
tgcctcctga actgcgtccg ccgtctaggt aagtttaaag ctcaggtcga gaccgggcct   1140
ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagacac   1380
catgcccatg ggcagcctgc agcccctggc caccctgtac ctgctgggca tgctggtggc   1440
tagcgtgctg gcctccggag agagccaggt gaggcagaac ttcaagcccg agatggagga   1500
gaagctgaac gagcagatga acctggagct gtacagcagc ctgctgtacc agcagatgag   1560
cgcctggtgc agctaccaca ccttcgaggg cgccgccgcc ttcctgagga ggcacgccca   1620
ggaggagatg acccacatgc agaggctgtt cgactacctg accgacaccg gcaacctgcc   1680
caggatcaac accgtggaga gccccttcgc cgagtacagc agcctggacg agctgttcca   1740
ggagacctac aagcacgagc agctgatcac ccagaagatc aacgagctgg cccacgccgc   1800
catgaccaac caggactacc ccaccttcaa cttcctgcag tggtacgtga gcgagcagca   1860
cgaggaggag aagctgttca agagcatcat cgacaagctg agcctggccg gcaagagcgg   1920
cgagggcctg tacttcatcg acaaggagct gagcaccctg gacggatcct agcatcatca   1980
tcatcattag tctggaaggg cgaattgatc cagatctgct gtgccttcta gttgccagcc   2040
atctgttgtt tgcccctccc ccgtgccttc cttgaccctg gaaggtgcca ctcccactgt   2100
cctttcctaa taaaatgagg aaattgcatc gcattgtctg agtaggtgtc attctattct   2160
ggggggtggg gtggggcagg acagcaaggg ggaggattgg gaagacaata gcaggcatgc   2220
tggggatgcg gtgggctcta tgggtaccca ggtgctgaag aattgacccg gttcctcctg   2280
ggccagaaag aagcaggcac atccccttct ctgtgacaca ccctgtccac gcccctggtt   2340
cttagttcca gccccactca taggacactc atagctcagg agggctccgc cttcaatccc   2400
acccgctaaa gtacttggag cggtctctcc ctccctcatc agcccaccaa accaaaccta   2460
```

-continued

```
gcctccaaga gtgggaagaa attaaagcaa gataggctat taagtgcaga gggagagaaa   2520
atgcctccaa catgtgagga agtaatgaga gaaatcatag aattttaagg ccatgattta   2580
aggccatcat ggccttaatc ttccgcttcc tcgctcactg actcgctgcg ctcggtcgtt   2640
cggctgcggc gagcggtatc agctcactca aaggcggtaa tacggttatc cacagaatca   2700
ggggataacg caggaaagaa catgtgagca aaaggccagc aaaaggccag gaaccgtaaa   2760
aaggccgcgt tgctggcgtt tttccatagg ctccgccccc ctgacgagca tcacaaaaat   2820
cgacgctcaa gtcagaggtg gcgaaacccg acaggactat aaagatacca ggcgtttccc   2880
cctggaagct ccctcgtgcg ctctcctgtt ccgaccctgc cgcttaccgg atacctgtcc   2940
gcctttctcc cttcgggaag cgtggcgctt tctcatagct cacgctgtag gtatctcagt   3000
tcggtgtagg tcgttcgctc caagctgggc tgtgtgcacg aaccccccgt tcagcccgac   3060
cgctgcgcct tatccggtaa ctatcgtctt gagtccaacc cggtaagaca cgacttatcg   3120
ccactggcag cagccactgg taacaggatt agcagagcga ggtatgtagg cggtgctaca   3180
gagttcttga agtggtggcc taactacggc tacactagaa gaacagtatt tggtatctgc   3240
gctctgctga agccagttac cttcggaaaa agagttggta gctcttgatc cggcaaacaa   3300
accaccgctg gtagcggtgg tttttttgtt tgcaagcagc agattacgcg cagaaaaaaa   3360
ggatctcaag aagatccttt gatcttttct acggggtctg acgctcagtg gaacgaaaac   3420
tcacgttaag ggattttggt catgagatta tcaaaaagga tcttcaccta gatcctttta   3480
aattaaaaat gaagttttaa atcaatctaa agtatatatg agtaaacttg gtctgacagt   3540
taccaatgct taatcagtga ggcacctatc tcagcgatct gtctatttcg ttcatccata   3600
gttgcctgac tcgggggggg ggggcgctga ggtctgcctc gtgaagaagg tgttgctgac   3660
tcataccagg cctgaatcgc cccatcatcc agccagaaag tgagggagcc acggttgatg   3720
agagctttgt tgtaggtgga ccagttggtg attttgaact tttgctttgc cacggaacgg   3780
tctgcgttgt cgggaagatg cgtgatctga tccttcaact cagcaaaagt tcgatttatt   3840
caacaaagcc gccgtcccgt caagtcagcg taatgctctg ccagtgttac aaccaattaa   3900
ccaattctga ttagaaaaac tcatcgagca tcaaatgaaa ctgcaattta ttcatatcag   3960
gattatcaat accatatttt tgaaaaagcc gtttctgtaa tgaaggagaa aactcaccga   4020
ggcagttcca taggatggca agatcctggt atcggtctgc gattccgact cgtccaacat   4080
caatacaacc tattaatttc ccctcgtcaa aaataaggtt atcaagtgag aaatcaccat   4140
gagtgacgac tgaatccggt gagaatggca aaagcttatg catttctttc cagacttgtt   4200
caacaggcca gccattacgc tcgtcatcaa aatcactcgc atcaaccaaa ccgttattca   4260
ttcgtgattg cgcctgagcg agacgaaata cgcgatcgct gttaaaagga caattacaaa   4320
caggaatcga atgcaaccgg cgcaggaaca ctgccagcgc atcaacaata ttttcacctg   4380
aatcaggata ttcttctaat acctggaatg ctgttttccc ggggatcgca gtggtgagta   4440
accatgcatc atcaggagta cggataaaat gcttgatggt cggaagaggc ataaattccg   4500
tcagccagtt tagtctgacc atctcatctg taacatcatt ggcaacgcta cctttgccat   4560
gtttcagaaa caactctggc gcatcgggct tcccatacaa tcgatagatt gtcgcacctg   4620
attgcccgac attatcgcga gcccatttat acccatataa atcagcatcc atgttggaat   4680
ttaatcgcgg cctcgagcaa gacgtttccc gttgaatatg gctcataaca ccccttgtat   4740
tactgtttat gtaagcagac agttttattg ttcatgatga tatattttta tcttgtgcaa   4800
tgtaacatca gagattttga gacacaacgt ggctttcccc ccccccccat tattgaagca   4860
```

tttatcaggg ttattgtctc atgagcggat acatatttga atgtatttag aaaaataaac 4920
aaataggggt tccgcgcaca tttccccgaa aagtgccacc tgacgtctaa gaaaccatta 4980
ttatcatgac attaacctat aaaaataggc gtatcacgag gccctttcgt c 5031

<210> SEQ ID NO 119
<211> LENGTH: 5046
<212> TYPE: DNA
<213> ORGANISM: Artificial Sequence
<220> FEATURE:
<223> OTHER INFORMATION: Synthetic

<400> SEQUENCE: 119
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
gggaacttcc atagcccata tatggagttc cgcgttacat aacttacggg aatttccaaa 420
cctggctgac cgcccaacga cccccgccca ttgacgtcaa taatgacgta tgttcccata 480
gtaacgccaa tagggaactt ccattgacgt caatgggtgg agtatttacg gtaaactgcc 540
cacttgggaa tttccaagtg tatcatatgc caagtacgcc ccctattgac gtcaatgacg 600
ggaacttcca taagcttgca ttatgcccag tacatgacct tatgggaatt tcctacttgg 660
cagtacatct acgtattagt catcgctatt accatggtga tgcggttttg gcagtacatc 720
aatgggcgtg gatagcggtt tgactcacgg gaacttccaa gtctccaccc cattgacgtc 780
aatgggagtt tgttttgact caccaaaatc aacgggaatt cccaaaatgt cgtaacaact 840
ccgccccatt gacgcaaatg ggcggtaggc gtgtacggtg ggaggtctat ataagcagag 900
ctcgtttagt gaaccgtcag atcgcctgga gacgccatcc acgctgtttt gacctccata 960
gaagacaccg ggaccgatcc agcctccatc ggctcgcatc tctccttcac gcgcccgccg 1020
ccctacctga ggccgccatc cacgccggtt gagtcgcgtt ctgccgcctc ccgcctgtgg 1080
tgcctcctga actgcgtccg ccgtctaggt aagtttaaag ctcaggtcga gaccgggcct 1140
ttgtccggcg ctcccttgga gcctacctag actcagccgg ctctccacgc tttgcctgac 1200
cctgcttgct caactctagt taacggtgga gggcagtgta gtctgagcag tactcgttgc 1260
tgccgcgcgc gccaccagac ataatagctg acagactaac agactgttcc tttccatggg 1320
tcttttctgc agtcaccgtc gtcgacacgt gtgatcagat atcgcggccg ctctagacac 1380
catgcccatg ggcagcctgc agcccctggc caccctgtac ctgctgggca tgctggtggc 1440
tagcgtgctg gcctccggag agagccaggt gaggcagcag ttcagcaagg acatcgagaa 1500
gctgctgaac gagcaggtga acaaggagat gcagagcagc aacctgtaca tgagcatgag 1560
cagctggtgc tacacccaca gcctggacgg cgccggcctg ttcctgttcg accacgccgc 1620
cgaggagtac gagcacgcca agaagctgat catcttcctg aacgagaaca acgtgcccgt 1680
gcagctgacc agcatcagcg cccccgagca caagttcgag ggcctgaccc agatcttcca 1740
gaaggcctac gagcacgagc agcacatcag cgagagcatc aacaacatcg tggaccacgc 1800
catcaagagc aaggaccacg ccaccttcaa cttcctgcag tggtacgtgg ccgagcagca 1860

```
cgaggaggag gtgctgttca aggacatcct ggacaagatc gagctgatcg gcaacgagaa   1920
ccacggcctg tacctggccg accagtacgt gaagggcatc gccaagagca ggaagagcgg   1980
atcctagcat catcatcatc attagtctgg aagggcgaat tgatccagat ctgctgtgcc   2040
ttctagttgc cagccatctg ttgtttgccc ctcccccgtg ccttccttga ccctggaagg   2100
tgccactccc actgtccttt cctaataaaa tgaggaaatt gcatcgcatt gtctgagtag   2160
gtgtcattct attctggggg gtggggtggg gcaggacagc aagggggagg attgggaaga   2220
caatagcagg catgctgggg atgcggtggg ctctatgggt acccaggtgc tgaagaattg   2280
acccggttcc tcctgggcca gaaagaagca ggcacatccc cttctctgtg acacaccctg   2340
tccacgcccc tggttcttag ttccagcccc actcatagga cactcatagc tcaggagggc   2400
tccgccttca atcccacccg ctaaagtact tggagcggtc tctccctccc tcatcagccc   2460
accaaaccaa acctagcctc caagagtggg aagaaattaa agcaagatag gctattaagt   2520
gcagagggag agaaaatgcc tccaacatgt gaggaagtaa tgagagaaat catagaattt   2580
taaggccatg atttaaggcc atcatggcct taatcttccg cttcctcgct cactgactcg   2640
ctgcgctcgg tcgttcggct gcggcgagcg gtatcagctc actcaaaggc ggtaatacgg   2700
ttatccacag aatcagggga taacgcagga aagaacatgt gagcaaaagg ccagcaaaag   2760
gccaggaacc gtaaaaaggc cgcgttgctg gcgtttttcc ataggctccg cccccctgac   2820
gagcatcaca aaaatcgacg ctcaagtcag aggtggcgaa acccgacagg actataaaga   2880
taccaggcgt ttccccctgg aagctccctc gtgcgctctc ctgttccgac cctgccgctt   2940
accggatacc tgtccgcctt tctcccttcg ggaagcgtgg cgctttctca tagctcacgc   3000
tgtaggtatc tcagttcggt gtaggtcgtt cgctccaagc tgggctgtgt gcacgaaccc   3060
cccgttcagc ccgaccgctg cgccttatcc ggtaactatc gtcttgagtc caacccggta   3120
agacacgact tatcgccact ggcagcagcc actggtaaca ggattagcag agcgaggtat   3180
gtaggcggtg ctacagagtt cttgaagtgg tggcctaact acggctacac tagaagaaca   3240
gtatttggta tctgcgctct gctgaagcca gttaccttcg gaaaaagagt tggtagctct   3300
tgatccggca aacaaaccac cgctggtagc ggtggttttt ttgtttgcaa gcagcagatt   3360
acgcgcagaa aaaaaggatc tcaagaagat cctttgatct tttctacggg gtctgacgct   3420
cagtggaacg aaaactcacg ttaagggatt ttggtcatga gattatcaaa aaggatcttc   3480
acctagatcc ttttaaatta aaaatgaagt tttaaatcaa tctaaagtat atatgagtaa   3540
acttggtctg acagttacca atgcttaatc agtgaggcac ctatctcagc gatctgtcta   3600
tttcgttcat ccatagttgc ctgactcggg gggggggggc gctgaggtct gcctcgtgaa   3660
gaaggtgttg ctgactcata ccaggcctga atcgccccat catccagcca gaaagtgagg   3720
gagccacggt tgatgagagc tttgttgtag gtggaccagt tggtgatttt gaacttttgc   3780
tttgccacgg aacggtctgc gttgtcggga agatgcgtga tctgatcctt caactcagca   3840
aaagttcgat ttattcaaca aagccgccgt cccgtcaagt cagcgtaatg ctctgccagt   3900
gttacaacca attaaccaat tctgattaga aaaactcatc gagcatcaaa tgaaactgca   3960
atttattcat atcaggatta tcaataccat atttttgaaa aagccgtttc tgtaatgaag   4020
gagaaaactc accgaggcag ttccatagga tggcaagatc ctggtatcgg tctgcgattc   4080
cgactcgtcc aacatcaata caacctatta atttcccctc gtcaaaaata aggttatcaa   4140
gtgagaaatc accatgagtg acgactgaat ccggtgagaa tggcaaaagc ttatgcattt   4200
ctttccagac ttgttcaaca ggccagccat tacgctcgtc atcaaaatca ctcgcatcaa   4260
```

ccaaaccgtt attcattcgt gattgcgcct gagcgagacg aaatacgcga tcgctgttaa 4320
aaggacaatt acaaacagga atcgaatgca accggcgcag gaacactgcc agcgcatcaa 4380
caatattttc acctgaatca ggatattctt ctaatacctg gaatgctgtt ttcccgggga 4440
tcgcagtggt gagtaaccat gcatcatcag gagtacggat aaaatgcttg atggtcggaa 4500
gaggcataaa ttccgtcagc cagtttagtc tgaccatctc atctgtaaca tcattggcaa 4560
cgctaccttt gccatgtttc agaaacaact ctggcgcatc gggcttccca tacaatcgat 4620
agattgtcgc acctgattgc ccgacattat cgcgagccca tttataccca tataaatcag 4680
catccatgtt ggaatttaat cgcggcctcg agcaagacgt ttcccgttga atatggctca 4740
taacacccct tgtattactg tttatgtaag cagacagttt tattgttcat gatgatatat 4800
ttttatcttg tgcaatgtaa catcagagat tttgagacac aacgtggctt tcccccccc 4860 cccattattg aagcatttat cagggttatt gtctcatgag cggatacata tttgaatgta 4920
tttagaaaaa taaacaaata ggggttccgc gcacatttcc ccgaaaagtg ccacctgacg 4980
tctaagaaac cattattatc atgacattaa cctataaaaa taggcgtatc acgaggccct 5040
ttcgtc 5046

<210> SEQ ID NO 120
<211> LENGTH: 5322
<212> TYPE: DNA
<213> ORGANISM: Artificial Sequence
<220> FEATURE:
<223> OTHER INFORMATION: Synthetic

<400> SEQUENCE: 120
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
gggaacttcc atagcccata tatggagttc cgcgttacat aacttacggg aatttccaaa 420
cctggctgac cgcccaacga cccccgccca ttgacgtcaa taatgacgta tgttcccata 480
gtaacgccaa tagggaactt ccattgacgt caatgggtgg agtatttacg gtaaactgcc 540
cacttgggaa tttccaagtg tatcatatgc caagtacgcc ccctattgac gtcaatgacg 600
ggaacttcca taagcttgca ttatgcccag tacatgacct tatgggaatt tcctacttgg 660
cagtacatct acgtattagt catcgctatt accatggtga tgcggttttg gcagtacatc 720
aatgggcgtg gatagcggtt tgactcacgg gaacttccaa gtctccaccc cattgacgtc 780
aatgggagtt tgttttgact caccaaaatc aacgggaatt cccaaaatgt cgtaacaact 840
ccgccccatt gacgcaaatg ggcggtaggc gtgtacggtg ggaggtctat ataagcagag 900
ctcgtttagt gaaccgtcag atcgcctgga gacgccatcc acgctgtttt gacctccata 960
gaagacaccg ggaccgatcc agcctccatc ggctcgcatc tctccttcac gcgcccgccg 1020
ccctacctga ggccgccatc cacgccggtt gagtcgcgtt ctgccgcctc ccgcctgtgg 1080
tgcctcctga actgcgtccg ccgtctaggt aagtttaaag ctcaggtcga gaccgggcct 1140
ttgtccggcg ctcccttgga gcctacctag actcagccgg ctctccacgc tttgcctgac 1200

-continued

```
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagacac   1380
catgcccatg ggcagcctgc agcccctggc caccctgtac ctgctgggca tgctggtggc   1440
tagcgtgctg gccatggagt tcctgaagag gagcttcgcc cctctgaccg agaagcagtg   1500
gcaggagatc gacaacaggg ccagggagat cttcaagacc cagctgtacg gcaggaagtt   1560
cgtggacgtg gagggcccct acggctggga gtacgccgcc cacccccctgg gcgaggtgga   1620
ggtgctgagc gacgagaacg aggtggtgaa gtggggcctg aggaagagcc tgcccctgat   1680
cgagctgagg gccaccttca ccctggacct gtgggagctg gacaacctgg agaggggcaa   1740
gcccaacgtg gacctgagca gcctggagga gaccgtgagg aaggtggccg agttcgagga   1800
cgaggtgatc ttcaggggct gcgagaagag cggcgtgaag ggcctgctga gcttcgagga   1860
gaggaagatc gagtgcggca gcacccccaa ggacctgctg gaggccatcg tgagggccct   1920
gagcatcttc agcaaggacg gcatcgaggg cccctacacc ctggtgatca acaccgacag   1980
gtggatcaac ttcctgaagg aggaggccgg ccactacccc ctggagaaga gggtggagga   2040
gtgcctgagg ggcggcaaga tcatcaccac ccccaggatc gaggacgccc tggtggtgag   2100
cgagaggggc ggcgacttca agctgatcct gggccaggac ctgagcatcg gctacgagga   2160
cagggagaag gacgccgtga ggctgttcat caccgagacc ttcaccttcc aggtggtgaa   2220
ccccgaggcc ctgatcctgc tgaagtccgg aggcggatcc catcatcatc atcatcatta   2280
gtctggaagg gcgaattgat ccagatctgc tgtgccttct agttgccagc catctgttgt   2340
ttgcccctcc cccgtgcctt ccttgaccct ggaaggtgcc actcccactg tcctttccta   2400
ataaaatgag gaaattgcat cgcattgtct gagtaggtgt cattctattc tggggggtgg   2460
ggtggggcag gacagcaagg gggaggattg ggaagacaat agcaggcatg ctggggatgc   2520
ggtgggctct atgggtaccc aggtgctgaa gaattgaccc ggttcctcct gggccagaaa   2580
gaagcaggca catccccttc tctgtgacac accctgtcca cgcccctggt tcttagttcc   2640
agccccactc ataggacact catagctcag gagggctccg ccttcaatcc cacccgctaa   2700
agtacttgga gcggtctctc cctccctcat cagcccacca aaccaaacct agcctccaag   2760
agtgggaaga aattaaagca agataggcta ttaagtgcag agggagagaa aatgcctcca   2820
acatgtgagg aagtaatgag agaaatcata gaattttaag gccatgattt aaggccatca   2880
tggccttaat cttccgcttc ctcgctcact gactcgctgc gctcggtcgt tcggctgcgg   2940
cgagcggtat cagctcactc aaaggcggta atacggttat ccacagaatc aggggataac   3000
gcaggaaaga acatgtgagc aaaaggccag caaaaggcca ggaaccgtaa aaaggccgcg   3060
ttgctggcgt ttttccatag gctccgcccc cctgacgagc atcacaaaaa tcgacgctca   3120
agtcagaggt ggcgaaaccc gacaggacta taaagatacc aggcgtttcc ccctggaagc   3180
tccctcgtgc gctctcctgt tccgaccctg ccgcttaccg gatacctgtc cgcctttctc   3240
ccttcgggaa gcgtggcgct ttctcatagc tcacgctgta ggtatctcag ttcggtgtag   3300
gtcgttcgct ccaagctggg ctgtgtgcac gaaccccccg ttcagcccga ccgctgcgcc   3360
ttatccggta actatcgtct tgagtccaac ccggtaagac acgacttatc gccactggca   3420
gcagccactg gtaacaggat tagcagagcg aggtatgtag gcggtgctac agagttcttg   3480
aagtggtggc ctaactacgg ctacactaga agaacagtat ttggtatctg cgctctgctg   3540
aagccagtta ccttcggaaa aagagttggt agctcttgat ccggcaaaca aaccaccgct   3600
```

```
ggtagcggtg gtttttttgt ttgcaagcag cagattacgc gcagaaaaaa aggatctcaa   3660

gaagatcctt tgatcttttc tacggggtct gacgctcagt ggaacgaaaa ctcacgttaa   3720

gggattttgg tcatgagatt atcaaaaagg atcttcacct agatcctttt aaattaaaaa   3780

tgaagtttta aatcaatcta aagtatatat gagtaaactt ggtctgacag ttaccaatgc   3840

ttaatcagtg aggcacctat ctcagcgatc tgtctatttc gttcatccat agttgcctga   3900

ctcggggggg gggggcgctg aggtctgcct cgtgaagaag gtgttgctga ctcataccag   3960

gcctgaatcg ccccatcatc cagccagaaa gtgagggagc cacggttgat gagagctttg   4020

ttgtaggtgg accagttggt gattttgaac ttttgctttg ccacggaacg gtctgcgttg   4080

tcgggaagat gcgtgatctg atccttcaac tcagcaaaag ttcgatttat tcaacaaagc   4140

cgccgtcccg tcaagtcagc gtaatgctct gccagtgtta caaccaatta accaattctg   4200

attagaaaaa ctcatcgagc atcaaatgaa actgcaattt attcatatca ggattatcaa   4260

taccatattt ttgaaaaagc cgtttctgta atgaaggaga aaactcaccg aggcagttcc   4320

ataggatggc aagatcctgg tatcggtctg cgattccgac tcgtccaaca tcaatacaac   4380

ctattaattt cccctcgtca aaaataaggt tatcaagtga gaaatcacca tgagtgacga   4440

ctgaatccgg tgagaatggc aaaagcttat gcatttcttt ccagacttgt tcaacaggcc   4500

agccattacg ctcgtcatca aaatcactcg catcaaccaa accgttattc attcgtgatt   4560

gcgcctgagc gagacgaaat acgcgatcgc tgttaaaagg acaattacaa acaggaatcg   4620

aatgcaaccg gcgcaggaac actgccagcg catcaacaat attttcacct gaatcaggat   4680

attcttctaa tacctggaat gctgttttcc cggggatcgc agtggtgagt aaccatgcat   4740

catcaggagt acggataaaa tgcttgatgg tcggaagagg cataaattcc gtcagccagt   4800

ttagtctgac catctcatct gtaacatcat tggcaacgct acctttgcca tgtttcagaa   4860

acaactctgg cgcatcgggc ttcccataca atcgatagat tgtcgcacct gattgcccga   4920

cattatcgcg agcccattta tacccatata aatcagcatc catgttggaa tttaatcgcg   4980

gcctcgagca agacgtttcc cgttgaatat ggctcataac accccttgta ttactgttta   5040

tgtaagcaga cagttttatt gttcatgatg atatattttt atcttgtgca atgtaacatc   5100

agagattttg agacacaacg tggctttccc ccccccccca ttattgaagc atttatcagg   5160

gttattgtct catgagcgga tacatatttg aatgtattta gaaaaataaa caaatagggg   5220

ttccgcgcac atttccccga aaagtgccac ctgacgtcta agaaaccatt attatcatga   5280

cattaaccta taaaaatagg cgtatcacga ggccctttcg tc                      5322
```

<210> SEQ ID NO 121
<211> LENGTH: 7135
<212> TYPE: DNA
<213> ORGANISM: Artificial Sequence
<220> FEATURE:
<223> OTHER INFORMATION: Synthetic

<400> SEQUENCE: 121

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300
```

-continued

```
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
accatggaag ccgccctgct ggtgtgccag tacactattc agagcctgat tcatctgacc   1440
ggggaggacc ctggattttt caatgtggaa atccctgagt tcccatttta ccccacctgc   1500
aacgtctgta cagccgacgt gaacgtcacc attaatttcg atgtgggcgg gaagaaacac   1560
cagctggacc tggattttgg ccagctgacc ccacatacaa aagccgtgta tcagcccaga   1620
ggggctttcg gaggcagcga gaacgcaaca aatctgtttc tgctggagct gctgggagca   1680
ggagaactgg ctctgaccat gaggtccaag aaactgccca tcaatgtgac cacaggagag   1740
gaacagcagg tcagtctgga atcagtggac gtctacttcc aggatgtgtt tggcaccatg   1800
tggtgccacc atgccgagat gcagaatcct gtgtacctga tccccgaaac cgtcccttat   1860
attaagtggg acaactgtaa tagcactaac attaccgcag tggtccgggc acaggggctg   1920
gacgtgaccc tgccactgtc actgcccaca agcgcccagg atagcaactt ctccgtgaaa   1980
accgagatgc tgggaaatga gatcgacatt gaatgcatca tggaggatgg agaaattagc   2040
caggtgctgc ctggcgataa caagtttaat atcacctgtt ccggctacga atctcacgtc   2100
ccaagtgggg gaatcctgac atctactagt cccgtggcca ctccaattcc cggaaccggc   2160
tacgcttata gcctgagact gacccctagg ccagtctcac gcttcctggg caacaatagc   2220
attctgtacg tgttttattc cggaaacgga ccaaaggctt ctggagggga ctattgcatc   2280
cagagtaata ttgtgttctc agacgagatc ccagccagcc aggatatgcc cactaacact   2340
accgacatta cctacgtggg cgataatgcc acttattccg tgcctatggt cacaagcgaa   2400
gacgctaact ccccaaatgt gaccgtcaca gcattctggg cctggcccaa caatactgag   2460
accgatttta agtgcaaatg gacactgact tcaggcaccc ctagcgggtg tgaaaacatc   2520
tctggcgcct tcgctagtaa tcgaaccttt gatattacag tgtccggcct ggggactgcc   2580
ccaaaaaccc tgatcattac ccggacagct actaacgcaa caactaccac acacaaagtg   2640
atcttcagca aagctcccga gtccactacc acatctccta ccctgaacac taccgggttt   2700
```

gccgacccca atacaactac cggactgcct agctccaccc atgtgccaac aaacctgact 2760
gcaccagcat ccaccggacc tacagtgtct actgccgatg tcaccagtcc cacacctgcc 2820
ggaacaactt ctggcgctag tcccgtgacc ccatcaccca gcccttggga caatgggaca 2880
gagagtaagg cccctgatat gacttctagt acctcaccag tcaccacacc aacccccaac 2940
gcaacaagcc ctactccagc cgtgactacc cccacaccta atgctaccag cccaacaccc 3000
gcagtgacaa ctcctacccc aaacgccact tccccaaccc tggggaagac atcacccact 3060
agcgccgtga ccacacccac ccctaatgct acctctccta cactgggaaa aacttcccca 3120
acctctgcag tgactacccc aacccccaac gccacaagcc ccactctggg caagaccagt 3180
cctacatcag ctgtcacaac tcctacccca aatgcaactg ggccaaccgt gggagagaca 3240
tccccccagg ctaacgcaac aaatcacact ctgggaggca ccagtcccac acctgtggtc 3300
acctcacagc ccaagaacgc cacaagcgct gtgaccacag gccagcataa tatcacatca 3360
agctccactt ctagtatgag cctgcgccct tcaagcaacc cagagacact gtccccatct 3420
actagtgaca attcaaccag ccacatgcct ctgctgacat ctgcacatcc aactggggga 3480
gaaaacatca ctcaggtcac ccccgcctcc atttctaccc accatgtgtc cacatcctct 3540
ccagcacccc gacctggaac taccagccag gcatccggac caggaaatag ttcaaccagc 3600
acaaagcctg gcgaggtgaa cgtcacaaaa gggactcccc ctcagaatgc tacctcacct 3660
caggcaccaa gcggccagaa aacagctgtg cctactgtca cctccacagg cgggaaggca 3720
aactctacaa ctggaggcaa acacaccaca gggcatggag ctcgcactag caccgaacca 3780
actaccgact acgggggaga ttccacaact ccaaggccca gatacaatgc caccacatat 3840
ctgccaccct ctaccagctc caagctgcga cccagatgga cattcactag tcctccagtg 3900
actaccgcac aggctacagt gccagtccca cctacttctc agcctagatt ttctaacctg 3960
agtatgctgg tgctgcagtg ggcaagcctg gcagtcctga ccctgctgct gctgctggtc 4020
atggctgact gtgcattccg gagaaacctg tccacttcac acacttacac caccccccct 4080
tacgatgacg cagagactta tgtctgatag gatccagatc tgctgtgcct tctagttgcc 4140
agccatctgt tgtttgcccc tcccccgtgc cttccttgac cctggaaggt gccactccca 4200
ctgtcctttc ctaataaaat gaggaaattg catcgcattg tctgagtagg tgtcattcta 4260
ttctgggggg tggggtgggg caggacagca agggggagga ttgggaagac aatagcaggc 4320
atgctgggga tgcggtgggc tctatgggta cccaggtgct gaagaattga cccggttcct 4380
cctgggccag aaagaagcag gcacatcccc ttctctgtga cacaccctgt ccacgcccct 4440
ggttcttagt tccagcccca ctcataggac actcatagct caggagggct ccgccttcaa 4500
tcccacccgc taaagtactt ggagcggtct ctccctccct catcagccca ccaaaccaaa 4560
cctagcctcc aagagtggga agaaattaaa gcaagatagg ctattaagtg cagagggaga 4620
gaaaatgcct ccaacatgtg aggaagtaat gagagaaatc atagaatttt aaggccatga 4680
tttaaggcca tcatggcctt aatcttccgc ttcctcgctc actgactcgc tgcgctcggt 4740
cgttcggctg cggcgagcgg tatcagctca ctcaaaggcg gtaatacggt tatccacaga 4800
atcaggggat aacgcaggaa agaacatgtg agcaaaaggc cagcaaaagg ccaggaaccg 4860
taaaaaggcc gcgttgctgg cgtttttcca taggctccgc ccccctgacg agcatcacaa 4920
aaatcgacgc tcaagtcaga ggtggcgaaa cccgacagga ctataaagat accaggcgtt 4980
tccccctgga agctccctcg tgcgctctcc tgttccgacc ctgccgctta ccggatacct 5040

```
gtccgccttt ctcccttcgg gaagcgtggc gctttctcat agctcacgct gtaggtatct   5100
cagttcggtg taggtcgttc gctccaagct gggctgtgtg cacgaacccc ccgttcagcc   5160
cgaccgctgc gccttatccg gtaactatcg tcttgagtcc aacccggtaa gacacgactt   5220
atcgccactg gcagcagcca ctggtaacag gattagcaga gcgaggtatg taggcggtgc   5280
tacagagttc ttgaagtggt ggcctaacta cggctacact agaagaacag tatttggtat   5340
ctgcgctctg ctgaagccag ttaccttcgg aaaaagagtt ggtagctctt gatccggcaa   5400
acaaaccacc gctggtagcg gtggtttttt tgtttgcaag cagcagatta cgcgcagaaa   5460
aaaaggatct caagaagatc ctttgatctt ttctacgggg tctgacgctc agtggaacga   5520
aaactcacgt taagggattt tggtcatgag attatcaaaa aggatcttca cctagatcct   5580
tttaaattaa aaatgaagtt ttaaatcaat ctaaagtata tatgagtaaa cttggtctga   5640
cagttaccaa tgcttaatca gtgaggcacc tatctcagcg atctgtctat ttcgttcatc   5700
catagttgcc tgactcgggg ggggggggcg ctgaggtctg cctcgtgaag aaggtgttgc   5760
tgactcatac caggcctgaa tcgccccatc atccagccag aaagtgaggg agccacggtt   5820
gatgagagct ttgttgtagg tggaccagtt ggtgattttg aacttttgct ttgccacgga   5880
acggtctgcg ttgtcgggaa gatgcgtgat ctgatccttc aactcagcaa aagttcgatt   5940
tattcaacaa agccgccgtc ccgtcaagtc agcgtaatgc tctgccagtg ttacaaccaa   6000
ttaaccaatt ctgattagaa aaactcatcg agcatcaaat gaaactgcaa tttattcata   6060
tcaggattat caataccata tttttgaaaa agccgtttct gtaatgaagg agaaaactca   6120
ccgaggcagt tccataggat ggcaagatcc tggtatcggt ctgcgattcc gactcgtcca   6180
acatcaatac aacctattaa tttcccctcg tcaaaaataa ggttatcaag tgagaaatca   6240
ccatgagtga cgactgaatc cggtgagaat ggcaaaagct tatgcatttc tttccagact   6300
tgttcaacag gccagccatt acgctcgtca tcaaaatcac tcgcatcaac caaaccgtta   6360
ttcattcgtg attgcgcctg agcgagacga aatacgcgat cgctgttaaa aggacaatta   6420
caaacaggaa tcgaatgcaa ccggcgcagg aacactgcca gcgcatcaac aatattttca   6480
cctgaatcag gatattcttc taatacctgg aatgctgttt tcccggggat cgcagtggtg   6540
agtaaccatg catcatcagg agtacggata aaatgcttga tggtcggaag aggcataaat   6600
tccgtcagcc agtttagtct gaccatctca tctgtaacat cattggcaac gctacctttg   6660
ccatgtttca gaaacaactc tggcgcatcg ggcttcccat acaatcgata gattgtcgca   6720
cctgattgcc cgacattatc gcgagcccat ttatacccat ataaatcagc atccatgttg   6780
gaatttaatc gcggcctcga gcaagacgtt tcccgttgaa tatggctcat aacacccctt   6840
gtattactgt ttatgtaagc agacagtttt attgttcatg atgatatatt tttatcttgt   6900
gcaatgtaac atcagagatt ttgagacaca acgtggcttt cccccccccc ccattattga   6960
agcatttatc agggttattg tctcatgagc ggatacatat ttgaatgtat ttagaaaaat   7020
aaacaaatag gggttccgcg cacatttccc cgaaaagtgc cacctgacgt ctaagaaacc   7080
attattatca tgacattaac ctataaaaat aggcgtatca cgaggccctt tcgtc        7135
```

<210> SEQ ID NO 122
<211> LENGTH: 7148
<212> TYPE: DNA
<213> ORGANISM: Artificial Sequence
<220> FEATURE:
<223> OTHER INFORMATION: Synthetic

<400> SEQUENCE: 122

-continued

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
gggaacttcc atagcccata tatggagttc cgcgttacat aacttacggg aatttccaaa    420
cctggctgac cgcccaacga cccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg gatagcggtt tgactcacgg gaacttccaa gtctccaccc cattgacgtc    780
aatgggagtt tgttttgact caccaaaatc aacgggaatt cccaaaatgt cgtaacaact    840
ccgccccatt gacgcaaatg ggcggtaggc gtgtacggtg ggaggtctat ataagcagag    900
ctcgtttagt gaaccgtcag atcgcctgga gacgccatcc acgctgtttt gacctccata    960
gaagacaccg ggaccgatcc agcctccatc ggctcgcatc tctccttcac gcgcccgccg   1020
ccctacctga ggccgccatc cacgccggtt gagtcgcgtt ctgccgcctc ccgcctgtgg   1080
tgcctcctga actgcgtccg ccgtctaggt aagtttaaag ctcaggtcga gaccgggcct   1140
ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagagat   1380
atcgccacca tggacagcaa gggcagcagc cagaagggca gcagactgct gctgctgctg   1440
gtggtgagca acctgctgct gcctcagggc gtgctagccg aagccgccct gctggtgtgc   1500
cagtacacta ttcagagcct gattcatctg accggggagg accctggatt tttcaatgtg   1560
gaaatccctg agttcccatt ttaccccacc tgcaacgtct gtacagccga cgtgaacgtc   1620
accattaatt tcgatgtggg cgggaagaaa caccagctgg acctggattt tggccagctg   1680
accccacata caaaagccgt gtatcagccc agaggggctt tcggaggcag cgagaacgca   1740
acaaatctgt ttctgctgga gctgctggga gcaggagaac tggctctgac catgaggtcc   1800
aagaaactgc ccatcaatgt gaccacagga gaggaacagc aggtcagtct ggaatcagtg   1860
gacgtctact tccaggatgt gtttggcacc atgtggtgcc accatgccga gatgcagaat   1920
cctgtgtacc tgatccccga aaccgtccct tatattaagt gggacaactg taatagcact   1980
aacattaccg cagtggtccg ggcacagggg ctggacgtga ccctgccact gtcactgccc   2040
acaagcgccc aggatagcaa cttctccgtg aaaaccgaga tgctgggaaa tgagatcgac   2100
attgaatgca tcatggagga tggagaaatt agccaggtgc tgcctggcga taacaagttt   2160
aatatcacct gttccggcta cgaatctcac gtcccaagtg ggggaatcct gacatctact   2220
agtcccgtgg ccactccaat tcccggaacc ggctacgctt atagcctgag actgacccct   2280
aggccagtct cacgcttcct gggcaacaat agcattctgt acgtgtttta ttccggaaac   2340
```

-continued

```
ggaccaaagg cttctggagg ggactattgc atccagagta atattgtgtt ctcagacgag   2400
atcccagcca gccaggatat gcccactaac actaccgaca ttacctacgt gggcgataat   2460
gccacttatt ccgtgcctat ggtcacaagc gaagacgcta actccccaaa tgtgaccgtc   2520
acagcattct gggcctggcc caacaatact gagaccgatt ttaagtgcaa atggacactg   2580
acttcaggca cccctagcgg gtgtgaaaac atctctggcg ccttcgctag taatcgaacc   2640
tttgatatta cagtgtccgg cctggggact gccccaaaaa ccctgatcat tacccggaca   2700
gctactaacg caacaactac cacacacaaa gtgatcttca gcaaagctcc cgagtccact   2760
accacatctc ctaccctgaa cactaccggg tttgccgacc ccaatacaac taccggactg   2820
cctagctcca cccatgtgcc aacaaacctg actgcaccag catccaccgg acctacagtg   2880
tctactgccg atgtcaccag tcccacacct gccggaacaa cttctggcgc tagtcccgtg   2940
accccatcac ccagcccttg ggacaatggg acagagagta aggcccctga tatgacttct   3000
agtacctcac cagtcaccac accaaccccc aacgcaacaa gccctactcc agccgtgact   3060
acccccacac ctaatgctac cagcccaaca cccgcagtga caactcctac cccaaacgcc   3120
acttccccaa ccctggggaa gacatcaccc actagcgccg tgaccacacc caccccctaat   3180
gctacctctc ctacactggg aaaaacttcc ccaacctctg cagtgactac cccaaccccc   3240
aacgccacaa gccccactct gggcaagacc agtcctacat cagctgtcac aactcctacc   3300
ccaaatgcaa ctgggccaac cgtgggagag acatcccccc aggctaacgc aacaaatcac   3360
actctgggag gcaccagtcc cacacctgtg gtcacctcac agcccaagaa cgccacaagc   3420
gctgtgacca caggccagca taatatcaca tcaagctcca cttctagtat gagcctgcgc   3480
ccttcaagca acccagagac actgtcccca tctactagtg acaattcaac cagccacatg   3540
cctctgctga catctgcaca tccaactggg ggagaaaaca tcactcaggt cacccccgcc   3600
tccatttcta cccaccatgt gtccacatcc tctccagcac cccgacctgg aactaccagc   3660
caggcatccg gaccaggaaa tagttcaacc agcacaaagc ctggcgaggt gaacgtcaca   3720
aaagggactc cccctcagaa tgctacctca cctcaggcac caagcggcca gaaaacagct   3780
gtgcctactg tcacctccac aggcgggaag gcaaactcta caactggagg caaacacacc   3840
acagggcatg gagctcgcac tagcaccgaa ccaactaccg actacggggg agattccaca   3900
actccaaggc ccagatacaa tgccaccaca tatctgccac cctctaccag ctccaagctg   3960
cgacccagat ggacattcac tagtcctcca gtgactaccg cacaggctac agtgccagtc   4020
ccacctactt ctcagcctag attttctaac ctgagtcacc accaccacca ccactgatga   4080
ggatcctagc atcatcatca tcattagtct ggaagggcga attgatccag atctgctgtg   4140
ccttctagtt gccagccatc tgttgtttgc ccctcccccg tgccttcctt gaccctggaa   4200
ggtgccactc ccactgtcct ttcctaataa aatgaggaaa ttgcatcgca ttgtctgagt   4260
aggtgtcatt ctattctggg gggtggggtg gggcaggaca gcaaggggga ggattgggaa   4320
gacaatagca ggcatgctgg ggatgcggtg ggctctatgg gtacccaggt gctgaagaat   4380
tgacccggtt cctcctgggc cagaaagaag caggcacatc cccttctctg tgacacaccc   4440
tgtccacgcc cctggttctt agttccagcc ccactcatag gacactcata gctcaggagg   4500
gctccgcctt caatcccacc cgctaaagta cttggagcgg tctctccctc cctcatcagc   4560
ccaccaaacc aaacctagcc tccaagagtg ggaagaaatt aaagcaagat aggctattaa   4620
gtgcagaggg agagaaaatg cctccaacat gtgaggaagt aatgagagaa atcatagaat   4680
tttaaggcca tgatttaagg ccatcatggc cttaatcttc cgcttcctcg ctcactgact   4740
```

cgctgcgctc ggtcgttcgg ctgcggcgag cggtatcagc tcactcaaag gcggtaatac 4800
ggttatccac agaatcaggg gataacgcag gaaagaacat gtgagcaaaa ggccagcaaa 4860
aggccaggaa ccgtaaaaag gccgcgttgc tggcgttttt ccataggctc cgcccccctg 4920
acgagcatca caaaaatcga cgctcaagtc agaggtggcg aaacccgaca ggactataaa 4980
gataccaggc gtttccccct ggaagctccc tcgtgcgctc tcctgttccg accctgccgc 5040
ttaccggata cctgtccgcc tttctccctt cgggaagcgt ggcgctttct catagctcac 5100
gctgtaggta tctcagttcg gtgtaggtcg ttcgctccaa gctgggctgt gtgcacgaac 5160
cccccgttca gcccgaccgc tgcgccttat ccggtaacta tcgtcttgag tccaacccgg 5220
taagacacga cttatcgcca ctggcagcag ccactggtaa caggattagc agagcgaggt 5280
atgtaggcgg tgctacagag ttcttgaagt ggtggcctaa ctacggctac actagaagaa 5340
cagtatttgg tatctgcgct ctgctgaagc cagttacctt cggaaaaaga gttggtagct 5400
cttgatccgg caaacaaacc accgctggta gcggtggttt ttttgtttgc aagcagcaga 5460
ttacgcgcag aaaaaaagga tctcaagaag atcctttgat cttttctacg gggtctgacg 5520
ctcagtggaa cgaaaactca cgttaaggga ttttggtcat gagattatca aaaaggatct 5580
tcacctagat ccttttaaat taaaaatgaa gttttaaatc aatctaaagt atatatgagt 5640
aaacttggtc tgacagttac caatgcttaa tcagtgaggc acctatctca gcgatctgtc 5700
tatttcgttc atccatagtt gcctgactcg gggggggggg gcgctgaggt ctgcctcgtg 5760
aagaaggtgt tgctgactca taccaggcct gaatcgcccc atcatccagc cagaaagtga 5820
gggagccacg gttgatgaga gctttgttgt aggtggacca gttggtgatt ttgaactttt 5880
gctttgccac ggaacggtct gcgttgtcgg gaagatgcgt gatctgatcc ttcaactcag 5940
caaaagttcg atttattcaa caaagccgcc gtcccgtcaa gtcagcgtaa tgctctgcca 6000
gtgttacaac caattaacca attctgatta gaaaaactca tcgagcatca aatgaaactg 6060
caatttattc atatcaggat tatcaatacc atatttttga aaaagccgtt tctgtaatga 6120
aggagaaaac tcaccgaggc agttccatag gatggcaaga tcctggtatc ggtctgcgat 6180
tccgactcgt ccaacatcaa tacaacctat taatttcccc tcgtcaaaaa taaggttatc 6240
aagtgagaaa tcaccatgag tgacgactga atccggtgag aatggcaaaa gcttatgcat 6300
ttctttccag acttgttcaa caggccagcc attacgctcg tcatcaaaat cactcgcatc 6360
aaccaaaccg ttattcattc gtgattgcgc ctgagcgaga cgaaatacgc gatcgctgtt 6420
aaaaggacaa ttacaaacag gaatcgaatg caaccggcgc aggaacactg ccagcgcatc 6480
aacaatattt tcacctgaat caggatattc ttctaatacc tggaatgctg ttttcccggg 6540
gatcgcagtg gtgagtaacc atgcatcatc aggagtacgg ataaaatgct tgatggtcgg 6600
aagaggcata aattccgtca gccagtttag tctgaccatc tcatctgtaa catcattggc 6660
aacgctacct ttgccatgtt tcagaaacaa ctctggcgca tcgggcttcc catacaatcg 6720
atagattgtc gcacctgatt gcccgacatt atcgcgagcc catttatacc catataaatc 6780
agcatccatg ttggaattta atcgcggcct cgagcaagac gtttcccgtt gaatatggct 6840
cataacaccc cttgtattac tgtttatgta agcagacagt tttattgttc atgatgatat 6900
atttttatct tgtgcaatgt aacatcagag attttgagac acaacgtggc tttccccccc 6960
cccccattat tgaagcattt atcagggtta ttgtctcatg agcggataca tatttgaatg 7020
tatttagaaa aataaacaaa taggggttcc gcgcacattt ccccgaaaag tgccacctga 7080
cgtctaagaa accattatta tcatgacatt aacctataaa aataggcgta tcacgaggcc 7140
ctttcgtc 7148

<210> SEQ ID NO 123
<211> LENGTH: 5843
<212> TYPE: DNA
<213> ORGANISM: Artificial Sequence
<220> FEATURE:
<223> OTHER INFORMATION: Synthetic

<400> SEQUENCE: 123
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
gggaacttcc atagcccata tatggagttc cgcgttacat aacttacggg aatttccaaa 420
cctggctgac cgcccaacga cccccgccca ttgacgtcaa taatgacgta tgttcccata 480
gtaacgccaa tagggaactt ccattgacgt caatgggtgg agtatttacg gtaaactgcc 540
cacttgggaa tttccaagtg tatcatatgc caagtacgcc ccctattgac gtcaatgacg 600
ggaacttcca taagcttgca ttatgcccag tacatgacct tatgggaatt tcctacttgg 660
cagtacatct acgtattagt catcgctatt accatggtga tgcggttttg gcagtacatc 720
aatgggcgtg gatagcggtt tgactcacgg gaacttccaa gtctccaccc cattgacgtc 780
aatgggagtt tgttttgact caccaaaatc aacgggaatt cccaaaatgt cgtaacaact 840
ccgccccatt gacgcaaatg ggcggtaggc gtgtacggtg ggaggtctat ataagcagag 900
ctcgtttagt gaaccgtcag atcgcctgga gacgccatcc acgctgtttt gacctccata 960
gaagacaccg ggaccgatcc agcctccatc ggctcgcatc tctccttcac gcgcccgccg 1020
ccctacctga ggccgccatc cacgccggtt gagtcgcgtt ctgccgcctc ccgcctgtgg 1080
tgcctcctga actgcgtccg ccgtctaggt aagtttaaag ctcaggtcga gaccgggcct 1140
ttgtccggcg ctcccttgga gcctacctag actcagccgg ctctccacgc tttgcctgac 1200
cctgcttgct caactctagt taacggtgga gggcagtgta gtctgagcag tactcgttgc 1260
tgccgcgcgc gccaccagac ataatagctg acagactaac agactgttcc tttccatggg 1320
tcttttctgc agtcaccgtc gtcgacacgt gtgatcagat atcgcggccg ctctagagat 1380
atcgccacca tggacagcaa gggcagcagc cagaagggca gcagactgct gctgctgctg 1440
gtggtgagca acctgctgct gcctcagggc gtgctagccg aagccgccct gctggtgtgc 1500
cagtacacta ttcagagcct gattcatctg accggggagg accctggatt tttcaatgtg 1560
gaaatccctg agttcccatt ttaccccacc tgcaacgtct gtacagccga cgtgaacgtc 1620
accattaatt tcgatgtggg cgggaagaaa caccagctgg acctggattt tggccagctg 1680
accccacata caaaagccgt gtatcagccc agaggggctt tcggaggcag cgagaacgca 1740
acaaatctgt ttctgctgga gctgctggga gcaggagaac tggctctgac catgaggtcc 1800
aagaaactgc ccatcaatgt gaccacagga gaggaacagc aggtcagtct ggaatcagtg 1860
gacgtctact tccaggatgt gtttggcacc atgtggtgcc accatgccga gatgcagaat 1920
cctgtgtacc tgatccccga aaccgtccct tatattaagt gggacaactg taatagcact 1980

```
aacattaccg cagtggtccg ggcacagggg ctggacgtga ccctgccact gtcactgccc   2040
acaagcgccc aggatagcaa cttctccgtg aaaaccgaga tgctgggaaa tgagatcgac   2100
attgaatgca tcatggagga tggagaaatt agccaggtgc tgcctggcga taacaagttt   2160
aatatcacct gttccggcta cgaatctcac gtcccaagtg ggggaatcct gacatctact   2220
agtcccgtgg ccactccaat tcccggaacc ggctacgctt atagcctgag actgacccct   2280
aggccagtct cacgcttcct gggcaacaat agcattctgt acgtgtttta ttccggaaac   2340
ggaccaaagg cttctggagg ggactattgc atccagagta atattgtgtt ctcagacgag   2400
atcccagcca gccaggatat gcccactaac actaccgaca ttacctacgt gggcgataat   2460
gccacttatt ccgtgcctat ggtcacaagc gaagacgcta actccccaaa tgtgaccgtc   2520
acagcattct gggcctggcc caacaatact gagaccgatt ttaagtgcaa atggacactg   2580
acttcaggca cccctagcgg gtgtgaaaac atctctggcg ccttcgctag taatcgaacc   2640
tttgatatta cagtgtccgg cctggggact gccccaaaaa ccctgatcat tacccggaca   2700
gctactaacg caacaactac cacacacaaa gtgatcttca gcaaagctcc ccaccaccac   2760
caccaccact gatgaggatc ctagcatcat catcatcatt agtctggaag ggcgaattga   2820
tccagatctg ctgtgccttc tagttgccag ccatctgttg tttgcccctc ccccgtgcct   2880
tccttgaccc tggaaggtgc cactcccact gtcctttcct aataaaatga ggaaattgca   2940
tcgcattgtc tgagtaggtg tcattctatt ctggggggtg gggtggggca ggacagcaag   3000
ggggaggatt gggaagacaa tagcaggcat gctggggatg cggtgggctc tatgggtacc   3060
caggtgctga agaattgacc cggttcctcc tgggccagaa agaagcaggc acatcccctt   3120
ctctgtgaca caccctgtcc acgcccctgg ttcttagttc cagccccact cataggacac   3180
tcatagctca ggagggctcc gccttcaatc ccacccgcta aagtacttgg agcggtctct   3240
ccctccctca tcagcccacc aaaccaaacc tagcctccaa gagtgggaag aaattaaagc   3300
aagataggct attaagtgca gagggagaga aaatgcctcc aacatgtgag gaagtaatga   3360
gagaaatcat agaattttaa ggccatgatt taaggccatc atggccttaa tcttccgctt   3420
cctcgctcac tgactcgctg cgctcggtcg ttcggctgcg gcgagcggta tcagctcact   3480
caaaggcggt aatacggtta tccacagaat caggggataa cgcaggaaag aacatgtgag   3540
caaaaggcca gcaaaaggcc aggaaccgta aaaaggccgc gttgctggcg tttttccata   3600
ggctccgccc ccctgacgag catcacaaaa atcgacgctc aagtcagagg tggcgaaacc   3660
cgacaggact ataaagatac caggcgtttc cccctggaag ctccctcgtg cgctctcctg   3720
ttccgaccct gccgcttacc ggatacctgt ccgcctttct cccttcggga agcgtggcgc   3780
tttctcatag ctcacgctgt aggtatctca gttcggtgta ggtcgttcgc tccaagctgg   3840
gctgtgtgca cgaacccccc gttcagcccg accgctgcgc cttatccggt aactatcgtc   3900
ttgagtccaa cccggtaaga cacgacttat cgccactggc agcagccact ggtaacagga   3960
ttagcagagc gaggtatgta ggcggtgcta cagagttctt gaagtggtgg cctaactacg   4020
gctacactag aagaacagta tttggtatct gcgctctgct gaagccagtt accttcggaa   4080
aaagagttgg tagctcttga tccggcaaac aaaccaccgc tggtagcggt ggtttttttg   4140
tttgcaagca gcagattacg cgcagaaaaa aaggatctca agaagatcct ttgatctttt   4200
ctacggggtc tgacgctcag tggaacgaaa actcacgtta agggattttg gtcatgagat   4260
tatcaaaaag gatcttcacc tagatccttt taaattaaaa atgaagtttt aaatcaatct   4320
```

aaagtatata tgagtaaact tggtctgaca gttaccaatg cttaatcagt gaggcaccta 4380
tctcagcgat ctgtctattt cgttcatcca tagttgcctg actcgggggg ggggggcgct 4440
gaggtctgcc tcgtgaagaa ggtgttgctg actcatacca ggcctgaatc gccccatcat 4500
ccagccagaa agtgagggag ccacggttga tgagagcttt gttgtaggtg gaccagttgg 4560
tgattttgaa cttttgcttt gccacggaac ggtctgcgtt gtcgggaaga tgcgtgatct 4620
gatccttcaa ctcagcaaaa gttcgattta ttcaacaaag ccgccgtccc gtcaagtcag 4680
cgtaatgctc tgccagtgtt acaaccaatt aaccaattct gattagaaaa actcatcgag 4740
catcaaatga aactgcaatt tattcatatc aggattatca ataccatatt tttgaaaaag 4800
ccgtttctgt aatgaaggag aaaactcacc gaggcagttc cataggatgg caagatcctg 4860
gtatcggtct gcgattccga ctcgtccaac atcaatacaa cctattaatt tcccctcgtc 4920
aaaaataagg ttatcaagtg agaaatcacc atgagtgacg actgaatccg gtgagaatgg 4980
caaaagctta tgcatttctt tccagacttg ttcaacaggc cagccattac gctcgtcatc 5040
aaaatcactc gcatcaacca aaccgttatt cattcgtgat tgcgcctgag cgagacgaaa 5100
tacgcgatcg ctgttaaaag gacaattaca aacaggaatc gaatgcaacc ggcgcaggaa 5160
cactgccagc gcatcaacaa tattttcacc tgaatcagga tattcttcta atacctggaa 5220
tgctgttttc ccggggatcg cagtggtgag taaccatgca tcatcaggag tacggataaa 5280
atgcttgatg gtcggaagag gcataaattc cgtcagccag tttagtctga ccatctcatc 5340
tgtaacatca ttggcaacgc tacctttgcc atgtttcaga aacaactctg gcgcatcggg 5400
cttcccatac aatcgataga ttgtcgcacc tgattgcccg acattatcgc gagcccattt 5460
atacccatat aaatcagcat ccatgttgga atttaatcgc ggcctcgagc aagacgtttc 5520
ccgttgaata tggctcataa caccccttgt attactgttt atgtaagcag acagttttat 5580
tgttcatgat gatatatttt tatcttgtgc aatgtaacat cagagatttt gagacacaac 5640
gtggctttcc cccccccccc attattgaag catttatcag ggttattgtc tcatgagcgg 5700
atacatattt gaatgtattt agaaaaataa acaaataggg gttccgcgca catttccccg 5760
aaaagtgcca cctgacgtct aagaaaccat tattatcatg acattaacct ataaaaatag 5820
gcgtatcacg aggccctttc gtc 5843

<210> SEQ ID NO 124
<211> LENGTH: 6533
<212> TYPE: DNA
<213> ORGANISM: Artificial Sequence
<220> FEATURE:
<223> OTHER INFORMATION: Synthetic

<400> SEQUENCE: 124
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540

-continued

```
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgcttctaga   1380
caccatgcag ctcctgtgcg tgttctgtct ggtgctgctg tgggaagtgg gagccgcttc   1440
tctgagtgag gtgaagctgc acctggacat tgaaggccac gcctcccatt acactatccc   1500
ttggaccgag ctgatggcta aagtgccagg actgtctcct gaggctctgt ggcgggaagc   1560
taatgtgacc gaggatctgg cctctatgct gaacagatac aagctgatct ataaaaccag   1620
tggcacactg ggattgctc tggctgagcc agtggacatc cccgccgtgt cagaaggaag    1680
catgcaggtg gatgctagta aggtgcatcc aggggtgatt agcggactga acagcccagc   1740
ttgcatgctg agcgctcctc tggagaaaca gctcttctac tatatcggca ccatgctgcc   1800
taatacacgg ccacacagct acgtgtttta tcagctcaga tgtcatctgt cctacgtggc   1860
cctgtctatt aacggggaca agttccagta tacaggagct atgacttcca aatttctgat   1920
gggaacttac aagcgggtga ccgagaaagg cgatgaacac gtgctgtctc tggtgttcgg   1980
gaagacaaaa gacctgcccg atctgagagg accctttttcc taccccttctc tgactagtgc 2040
ccagtcaggc gactatagcc tggtgatcgt gaccacattc gtgcactacg ctaacttcca   2100
taattatttt gtgcccaatc tgaaggatat gttttcccgg gccgtgacca tgacagccgc   2160
ttcttacgct agatatgtgc tgcagaagct ggtgctgctg gagatgaaag gcgggtgccg   2220
ggagcctgaa ctggacactg aaaccctgac taccatgttc gaggtgtccg tggccttctt   2280
taaagtggga cacgctgtgg gagagacagg aaacggatgc gtggacctga gatggctggc   2340
caagagcttc tttgaactga ccgtgctgaa agatatcatt ggaatctgtt acggcgccac   2400
agtgaaagga atgcagagct atggcctgga gaggctggcc gctatgctga tggccaccgt   2460
gaagatggag gaactgggcc acctgacaac tgagaaacag gaatacgctc tgaggctggc   2520
taccgtggga tacccaaagg ccggggtgta ttccggactg attggaggcg ccacatctgt   2580
gctgctgagt gcttataata ggcacccact gttccagccc ctgcatacag tgatgcgcga   2640
gactctgttt atcgggtctc atgtggtgct gcgggaactg agactgaatg tgaccacaca   2700
gggacccaac ctggccctgt accagctcct gagtactgcc ctgtgctcag ctctggagat   2760
tggagaagtg ctgaggggac tggccctggg gaccgagtca ggactgttca gcccttgtta   2820
tctgtcactg aggtttgacc tgactcgcga taagctgctg agcatggccc cacaggaagc   2880
```

-continued

```
taccctggac caggccgctg tgagcaatgc cgtggatgga ttcctgggca ggctgtccct   2940
ggagagggaa gaccgcgatg cctggcacct gccagcttac aagtgcgtgg accgcctgga   3000
taaagtgctg atgatcattc ccctgatcaa cgtgaccttc atcattagct ccgacaggga   3060
agtgagaggc agcgctctgt acgaagcttc cactacctat ctgtctagtt cactgtttct   3120
gtcacctgtg attatgaata agtgtagcca gggagctgtg gctggagagc ccagacagat   3180
cccaaagatt cagaacttca cacgcactca gaaaagttgc atcttctgtg gctttgccct   3240
gctgtcatac gatgagaaag aagggctgga gacaactacc tatattacat ctcaggaagt   3300
gcagaacagt atcctgagct ccaattactt cgactttgat aacctgcacg tgcattatct   3360
gctgctgaca actaacggca ccgtgatgga gatcgctgga ctgtacgagg aaagggctca   3420
cgtggtgctg gctatcattc tgtatttcat cgcctttgct ctgggcattt ttctggtgca   3480
taagatcgtg atgttctttc tgtgatagga tccagatctg ctgtgccttc tagttgccag   3540
ccatctgttg tttgcccctc ccccgtgcct tccttgaccc tggaaggtgc cactcccact   3600
gtcctttcct aataaaatga ggaaattgca tcgcattgtc tgagtaggtg tcattctatt   3660
ctggggggtg gggtggggca ggacagcaag ggggaggatt gggaagacaa tagcaggcat   3720
gctggggatg cggtgggctc tatgggtacc caggtgctga agaattgacc cggttcctcc   3780
tgggccagaa agaagcaggc acatcccctt ctctgtgaca caccctgtcc acgcccctgg   3840
ttcttagttc cagccccact cataggacac tcatagctca ggagggctcc gccttcaatc   3900
ccacccgcta aagtacttgg agcggtctct ccctccctca tcagcccacc aaaccaaacc   3960
tagcctccaa gagtgggaag aaattaaagc aagataggct attaagtgca gagggagaga   4020
aaatgcctcc aacatgtgag gaagtaatga gagaaatcat agaattttaa ggccatgatt   4080
taaggccatc atggccttaa tcttccgctt cctcgctcac tgactcgctg cgctcggtcg   4140
ttcggctgcg gcgagcggta tcagctcact caaaggcggt aatacggtta tccacagaat   4200
caggggataa cgcaggaaag aacatgtgag caaaaggcca gcaaaaggcc aggaaccgta   4260
aaaaggccgc gttgctggcg tttttccata ggctccgccc ccctgacgag catcacaaaa   4320
atcgacgctc aagtcagagg tggcgaaacc cgacaggact ataaagatac caggcgtttc   4380
cccctggaag ctccctcgtg cgctctcctg ttccgaccct gccgcttacc ggatacctgt   4440
ccgcctttct cccttcggga agcgtggcgc tttctcatag ctcacgctgt aggtatctca   4500
gttcggtgta ggtcgttcgc tccaagctgg gctgtgtgca cgaacccccc gttcagcccg   4560
accgctgcgc cttatccggt aactatcgtc ttgagtccaa cccggtaaga cacgacttat   4620
cgccactggc agcagccact ggtaacagga ttagcagagc gaggtatgta ggcggtgcta   4680
cagagttctt gaagtggtgg cctaactacg gctacactag aagaacagta tttggtatct   4740
gcgctctgct gaagccagtt accttcggaa aaagagttgg tagctcttga tccggcaaac   4800
aaaccaccgc tggtagcggt ggtttttttg tttgcaagca gcagattacg cgcagaaaaa   4860
aaggatctca agaagatcct ttgatctttt ctacggggtc tgacgctcag tggaacgaaa   4920
actcacgtta agggattttg gtcatgagat tatcaaaaag gatcttcacc tagatccttt   4980
taaattaaaa atgaagtttt aaatcaatct aaagtatata tgagtaaact tggtctgaca   5040
gttaccaatg cttaatcagt gaggcaccta tctcagcgat ctgtctattt cgttcatcca   5100
tagttgcctg actcgggggg ggggggcgct gaggtctgcc tcgtgaagaa ggtgttgctg   5160
actcatacca ggcctgaatc gccccatcat ccagccagaa agtgagggag ccacggttga   5220
tgagagcttt gttgtaggtg gaccagttgg tgattttgaa cttttgcttt gccacggaac   5280
```

```
ggtctgcgtt gtcgggaaga tgcgtgatct gatccttcaa ctcagcaaaa gttcgattta   5340
ttcaacaaag ccgccgtccc gtcaagtcag cgtaatgctc tgccagtgtt acaaccaatt   5400
aaccaattct gattagaaaa actcatcgag catcaaatga aactgcaatt tattcatatc   5460
aggattatca ataccatatt tttgaaaaag ccgtttctgt aatgaaggag aaaactcacc   5520
gaggcagttc cataggatgg caagatcctg gtatcggtct gcgattccga ctcgtccaac   5580
atcaatacaa cctattaatt tcccctcgtc aaaaataagg ttatcaagtg agaaatcacc   5640
atgagtgacg actgaatccg gtgagaatgg caaaagctta tgcatttctt tccagacttg   5700
ttcaacaggc cagccattac gctcgtcatc aaaatcactc gcatcaacca aaccgttatt   5760
cattcgtgat tgcgcctgag cgagacgaaa tacgcgatcg ctgttaaaag gacaattaca   5820
aacaggaatc gaatgcaacc ggcgcaggaa cactgccagc gcatcaacaa tattttcacc   5880
tgaatcagga tattcttcta atacctggaa tgctgttttc ccggggatcg cagtggtgag   5940
taaccatgca tcatcaggag tacggataaa atgcttgatg gtcggaagag gcataaattc   6000
cgtcagccag tttagtctga ccatctcatc tgtaacatca ttggcaacgc tacctttgcc   6060
atgtttcaga aacaactctg gcgcatcggg cttcccatac aatcgataga ttgtcgcacc   6120
tgattgcccg acattatcgc gagcccattt atacccatat aaatcagcat ccatgttgga   6180
atttaatcgc ggcctcgagc aagacgtttc ccgttgaata tggctcataa cacccccttgt   6240
attactgttt atgtaagcag acagttttat tgttcatgat gatatatttt tatcttgtgc   6300
aatgtaacat cagagatttt gagacacaac gtggctttcc cccccccccc attattgaag   6360
catttatcag ggttattgtc tcatgagcgg atacatattt gaatgtattt agaaaaataa   6420
acaaataggg gttccgcgca catttccccg aaaagtgcca cctgacgtct aagaaaccat   6480
tattatcatg acattaacct ataaaaatag gcgtatcacg aggccctttc gtc          6533
```

<210> SEQ ID NO 125
<211> LENGTH: 4826
<212> TYPE: DNA
<213> ORGANISM: Artificial Sequence
<220> FEATURE:
<223> OTHER INFORMATION: Synthetic

<400> SEQUENCE: 125

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
```

-continued

```
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgcttctaga   1380
caccatgcgg gccgtggggg tgttcctggc tatctgcctg gtgactattt ttgtgctgcc   1440
aacctgggga aactgggctt accccttgctg tcacgtgacc cagctcaggg cccagcatct   1500
gctggctctg gagaacatca gcgacattta tctggtgtcc aatcagacat gcgatgggtt   1560
cagcctggcc tccctgaaca gccccaagaa cggatctaat cagctcgtga tctcccggtg   1620
tgctaacggc ctgaatgtcg tgagtttctt tatctcaatt ctgaaaagga gctcctctgc   1680
tctgacagga cacctgaggg agctgctgac cacactggaa actctgtacg gaagtttctc   1740
agtggaagac ctgtttggcg ccaacctgaa tcggtatgct tggcatagag gcgggtgata   1800
ggatccagat ctgctgtgcc ttctagttgc cagccatctg ttgtttgccc ctcccccgtg   1860
ccttccttga ccctggaagg tgccactccc actgtccttt cctaataaaa tgaggaaatt   1920
gcatcgcatt gtctgagtag gtgtcattct attctggggg gtggggtggg gcaggacagc   1980
aagggggagg attgggaaga caatagcagg catgctgggg atgcggtggg ctctatgggt   2040
acccaggtgc tgaagaattg acccggttcc tcctgggcca gaaagaagca ggcacatccc   2100
cttctctgtg acacaccctg tccacgcccc tggttcttag ttccagcccc actcatagga   2160
cactcatagc tcaggagggc tccgccttca atcccacccg ctaaagtact tggagcggtc   2220
tctccctccc tcatcagccc accaaaccaa acctagcctc caagagtggg aagaaattaa   2280
agcaagatag gctattaagt gcagagggag agaaaatgcc tccaacatgt gaggaagtaa   2340
tgagagaaat catagaattt taaggccatg atttaaggcc atcatggcct taatcttccg   2400
cttcctcgct cactgactcg ctgcgctcgg tcgttcggct gcggcgagcg gtatcagctc   2460
actcaaaggc ggtaatacgg ttatccacag aatcagggga taacgcagga aagaacatgt   2520
gagcaaaagg ccagcaaaag gccaggaacc gtaaaaaggc cgcgttgctg gcgtttttcc   2580
ataggctccg cccccctgac gagcatcaca aaaatcgacg ctcaagtcag aggtggcgaa   2640
acccgacagg actataaaga taccaggcgt ttccccctgg aagctccctc gtgcgctctc   2700
ctgttccgac cctgccgctt accggatacc tgtccgcctt tctcccttcg ggaagcgtgg   2760
cgctttctca tagctcacgc tgtaggtatc tcagttcggt gtaggtcgtt cgctccaagc   2820
tgggctgtgt gcacgaaccc cccgttcagc ccgaccgctg cgccttatcc ggtaactatc   2880
gtcttgagtc caacccggta agacacgact tatcgccact ggcagcagcc actggtaaca   2940
ggattagcag agcgaggtat gtaggcggtg ctacagagtt cttgaagtgg tggcctaact   3000
acggctacac tagaagaaca gtatttggta tctgcgctct gctgaagcca gttaccttcg   3060
gaaaaagagt tggtagctct tgatccggca aacaaaccac cgctggtagc ggtggttttt   3120
ttgtttgcaa gcagcagatt acgcgcagaa aaaaaggatc tcaagaagat cctttgatct   3180
```

tttctacggg gtctgacgct cagtggaacg aaaactcacg ttaagggatt ttggtcatga 3240
gattatcaaa aaggatcttc acctagatcc ttttaaatta aaaatgaagt tttaaatcaa 3300
tctaaagtat atatgagtaa acttggtctg acagttacca atgcttaatc agtgaggcac 3360
ctatctcagc gatctgtcta tttcgttcat ccatagttgc ctgactcggg gggggggggc 3420
gctgaggtct gcctcgtgaa gaaggtgttg ctgactcata ccaggcctga atcgccccat 3480
catccagcca gaaagtgagg gagccacggt tgatgagagc tttgttgtag gtggaccagt 3540
tggtgatttt gaacttttgc tttgccacgg aacggtctgc gttgtcggga agatgcgtga 3600
tctgatcctt caactcagca aaagttcgat ttattcaaca aagccgccgt cccgtcaagt 3660
cagcgtaatg ctctgccagt gttacaacca attaaccaat tctgattaga aaaactcatc 3720
gagcatcaaa tgaaactgca atttattcat atcaggatta tcaataccat atttttgaaa 3780
aagccgtttc tgtaatgaag gagaaaactc accgaggcag ttccatagga tggcaagatc 3840
ctggtatcgg tctgcgattc cgactcgtcc aacatcaata caacctatta atttcccctc 3900
gtcaaaaata aggttatcaa gtgagaaatc accatgagtg acgactgaat ccggtgagaa 3960
tggcaaaagc ttatgcattt ctttccagac ttgttcaaca ggccagccat tacgctcgtc 4020
atcaaaatca ctcgcatcaa ccaaaccgtt attcattcgt gattgcgcct gagcgagacg 4080
aaatacgcga tcgctgttaa aaggacaatt acaaacagga atcgaatgca accggcgcag 4140
gaacactgcc agcgcatcaa caatattttc acctgaatca ggatattctt ctaatacctg 4200
gaatgctgtt ttcccgggga tcgcagtggt gagtaaccat gcatcatcag gagtacggat 4260
aaaatgcttg atggtcggaa gaggcataaa ttccgtcagc cagtttagtc tgaccatctc 4320
atctgtaaca tcattggcaa cgctaccttt gccatgtttc agaaacaact ctggcgcatc 4380
gggcttccca tacaatcgat agattgtcgc acctgattgc ccgacattat cgcgagccca 4440
tttataccca tataaatcag catccatgtt ggaatttaat cgcggcctcg agcaagacgt 4500
ttcccgttga atatggctca taacacccct tgtattactg tttatgtaag cagacagttt 4560
tattgttcat gatgatatat ttttatcttg tgcaatgtaa catcagagat tttgagacac 4620
aacgtggctt tcccccccccc cccattattg aagcatttat cagggttatt gtctcatgag 4680
cggatacata tttgaatgta tttagaaaaa taaacaaata ggggttccgc gcacatttcc 4740
ccgaaaagtg ccacctgacg tctaagaaac cattattatc atgacattaa cctataaaaa 4800
taggcgtatc acgaggccct ttcgtc 4826

<210> SEQ ID NO 126
<211> LENGTH: 5084
<212> TYPE: DNA
<213> ORGANISM: Artificial Sequence
<220> FEATURE:
<223> OTHER INFORMATION: Synthetic

<400> SEQUENCE: 126
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360

-continued

```
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgcttctaga   1380
caccatggtc agcttcaaac aagtgcgggt gcccctgttt actgccatcg ctctggtgat   1440
tgtgctgctg ctggcctact tcctgccacc tcgggtcaga ggaggaggaa gagtggccgc   1500
tgccgctatc acctgggtgc caaaacctaa tgtggaagtg tggcctgtgg acccaccacc   1560
tccagtgaac tttaataaga cagccgagca ggaatatggc gataaagaag tgaagctgcc   1620
tcactggacc ccaacactgc atacattcca ggtgccacag aactacacta aagctaattg   1680
cacttattgt aacaccaggg agtacacatt tagttataag ggtgctgtt tctactttac    1740
taagaaaaag cacacctgga atggatgctt ccaggcctgt gctgaactgt atccatgcac   1800
atacttttat ggcccaactc ccgacatcct gcccgtggtg accaggaacc tgaatgccat   1860
tgagtccctg tgggtgggag tgtacagggt gggagaaggc aactggacct ccctggatgg   1920
cgggacattc aaagtgtacc agatttttgg ctctcattgc acttatgtgt ctaagttcag   1980
taccgtgccc gtgtcacacc atgagtgtag ctttctgaag ccttgcctgt gtgtgtctca   2040
gagaagcaac tcctgatagg atccagatct gctgtgcctt ctagttgcca gccatctgtt   2100
gtttgcccct cccccgtgcc ttccttgacc ctggaaggtg ccactcccac tgtcctttcc   2160
taataaaatg aggaaattgc atcgcattgt ctgagtaggt gtcattctat tctggggggt   2220
ggggtggggc aggacagcaa gggggaggat tgggaagaca atagcaggca tgctggggat   2280
gcggtgggct ctatgggtac ccaggtgctg aagaattgac ccggttcctc ctgggccaga   2340
aagaagcagg cacatcccct tctctgtgac acaccctgtc cacgcccctg gttcttagtt   2400
ccagccccac tcataggaca ctcatagctc aggagggctc cgccttcaat cccacccgct   2460
aaagtacttg gagcggtctc tccctccctc atcagcccac caaaccaaac ctagcctcca   2520
agagtgggaa gaaattaaag caagataggc tattaagtgc agagggagag aaaatgcctc   2580
caacatgtga ggaagtaatg agagaaatca tagaatttta aggccatgat ttaaggccat   2640
catggcctta atcttccgct tcctcgctca ctgactcgct gcgctcggtc gttcggctgc   2700
ggcgagcggt atcagctcac tcaaaggcgg taatacggtt atccacagaa tcaggggata   2760
```

-continued

```
acgcaggaaa gaacatgtga gcaaaaggcc agcaaaaggc caggaaccgt aaaaaggccg   2820
cgttgctggc gtttttccat aggctccgcc cccctgacga gcatcacaaa aatcgacgct   2880
caagtcagag gtggcgaaac ccgacaggac tataaagata ccaggcgttt ccccctggaa   2940
gctccctcgt gcgctctcct gttccgaccc tgccgcttac cggatacctg tccgcctttc   3000
tcccttcggg aagcgtggcg ctttctcata gctcacgctg taggtatctc agttcggtgt   3060
aggtcgttcg ctccaagctg ggctgtgtgc acgaaccccc cgttcagccc gaccgctgcg   3120
ccttatccgg taactatcgt cttgagtcca acccggtaag acacgactta tcgccactgg   3180
cagcagccac tggtaacagg attagcagag cgaggtatgt aggcggtgct acagagttct   3240
tgaagtggtg gcctaactac ggctacacta gaagaacagt atttggtatc tgcgctctgc   3300
tgaagccagt taccttcgga aaaagagttg gtagctcttg atccggcaaa caaaccaccg   3360
ctggtagcgg tggttttttt gtttgcaagc agcagattac gcgcagaaaa aaaggatctc   3420
aagaagatcc tttgatcttt tctacggggt ctgacgctca gtggaacgaa aactcacgtt   3480
aagggatttt ggtcatgaga ttatcaaaaa ggatcttcac ctagatcctt ttaaattaaa   3540
aatgaagttt taaatcaatc taaagtatat atgagtaaac ttggtctgac agttaccaat   3600
gcttaatcag tgaggcacct atctcagcga tctgtctatt tcgttcatcc atagttgcct   3660
gactcggggg gggggggcgc tgaggtctgc ctcgtgaaga aggtgttgct gactcatacc   3720
aggcctgaat cgccccatca tccagccaga aagtgaggga gccacggttg atgagagctt   3780
tgttgtaggt ggaccagttg gtgattttga acttttgctt tgccacggaa cggtctgcgt   3840
tgtcgggaag atgcgtgatc tgatccttca actcagcaaa agttcgattt attcaacaaa   3900
gccgccgtcc cgtcaagtca gcgtaatgct ctgccagtgt tacaaccaat taaccaattc   3960
tgattagaaa aactcatcga gcatcaaatg aaactgcaat ttattcatat caggattatc   4020
aataccatat ttttgaaaaa gccgtttctg taatgaagga gaaaactcac cgaggcagtt   4080
ccataggatg gcaagatcct ggtatcggtc tgcgattccg actcgtccaa catcaataca   4140
acctattaat ttcccctcgt caaaaataag gttatcaagt gagaaatcac catgagtgac   4200
gactgaatcc ggtgagaatg gcaaaagctt atgcatttct ttccagactt gttcaacagg   4260
ccagccatta cgctcgtcat caaaatcact cgcatcaacc aaaccgttat tcattcgtga   4320
ttgcgcctga gcgagacgaa atacgcgatc gctgttaaaa ggacaattac aaacaggaat   4380
cgaatgcaac cggcgcagga acactgccag cgcatcaaca atattttcac ctgaatcagg   4440
atattcttct aatacctgga atgctgtttt cccggggatc gcagtggtga gtaaccatgc   4500
atcatcagga gtacggataa aatgcttgat ggtcggaaga ggcataaatt ccgtcagcca   4560
gtttagtctg accatctcat ctgtaacatc attggcaacg ctacctttgc catgtttcag   4620
aaacaactct ggcgcatcgg gcttcccata caatcgatag attgtcgcac ctgattgccc   4680
gacattatcg cgagcccatt tatacccata taaatcagca tccatgttgg aatttaatcg   4740
cggcctcgag caagacgttt cccgttgaat atggctcata acaccccttg tattactgtt   4800
tatgtaagca gacagtttta ttgttcatga tgatatattt ttatcttgtg caatgtaaca   4860
tcagagattt tgagacacaa cgtggctttc cccccccccc cattattgaa gcatttatca   4920
gggttattgt ctcatgagcg gatacatatt tgaatgtatt tagaaaaata aacaaatagg   4980
ggttccgcgc acatttcccc gaaaagtgcc acctgacgtc taagaaacca ttattatcat   5040
gacattaacc tataaaaata ggcgtatcac gaggcccttt cgtc                    5084
```

<210> SEQ ID NO 127
<211> LENGTH: 2580
<212> TYPE: DNA
<213> ORGANISM: Artificial Sequence
<220> FEATURE:
<223> OTHER INFORMATION: Synthetic

<400> SEQUENCE: 127
atgcagctcc tgtgcgtgtt ctgtctggtg ctgctgtggg aagtgggagc cgcttctctg 60
agtgaggtga agctgcacct ggacattgaa ggccacgcct cccattacac tatcccttgg 120
accgagctga tggctaaagt gccaggactg tctcctgagg ctctgtggcg ggaagctaat 180
gtgaccgagg atctggcctc tatgctgaac agatacaagc tgatctataa aaccagtggc 240
acactgggga ttgctctggc tgagccagtg gacatccccg ccgtgtcaga aggaagcatg 300
caggtggatg ctagtaaggt gcatccaggg gtgattagcg gactgaacag cccagcttgc 360
atgctgagcg ctcctctgga gaaacagctc ttctactata tcggcaccat gctgcctaat 420
acacggccac acagctacgt gttttatcag ctcagatgtc atctgtccta cgtggccctg 480
tctattaacg gggacaagtt ccagtataca ggagctatga cttccaaatt tctgatggga 540
acttacaagc gggtgaccga gaaaggcgat gaacacgtgc tgtctctggt gttcgggaag 600
acaaaagacc tgcccgatct gagaggaccc ttttcctacc cttctctgac tagtgcccag 660
tcaggcgact atagcctggt gatcgtgacc acattcgtgc actacgctaa cttccataat 720
tattttgtgc ccaatctgaa ggatatgttt tcccgggccg tgaccatgac agccgcttct 780
tacgctagat atgtgctgca gaagctggtg ctgctggaga tgaaaggcgg gtgccgggag 840
cctgaactgg acactgaaac cctgactacc atgttcgagg tgtccgtggc cttctttaaa 900
gtgggacacg ctgtgggaga gacaggaaac ggatgcgtgg acctgagatg gctggccaag 960
agcttctttg aactgaccgt gctgaaagat atcattggaa tctgttacgg cgccacagtg 1020
aaaggaatgc agagctatgg cctggagagg ctggccgcta tgctgatggc caccgtgaag 1080
atggaggaac tgggccacct gacaactgag aaacaggaat acgctctgag gctggctacc 1140
gtgggatacc caaaggccgg ggtgtattcc ggactgattg gaggcgccac atctgtgctg 1200
ctgagtgctt ataataggca cccactgttc cagcccctgc atacagtgat gcgcgagact 1260
ctgtttatcg ggtctcatgt ggtgctgcgg gaactgagac tgaatgtgac cacacaggga 1320
cccaacctgg ccctgtacca gctcctgagt actgccctgt gctcagctct ggagattgga 1380
gaagtgctga ggggactggc cctggggacc gagtcaggac tgttcagccc ttgttatctg 1440
tcactgaggt ttgacctgac tcgcgataag ctgctgagca tggccccaca ggaagctacc 1500
ctggaccagg ccgctgtgag caatgccgtg gatggattcc tgggcaggct gtccctggag 1560
agggaagacc gcgatgcctg gcacctgcca gcttacaagt gcgtggaccg cctggataaa 1620
gtgctgatga tcattcccct gatcaacgtg accttcatca ttagctccga cagggaagtg 1680
agaggcagcg ctctgtacga agcttccact acctatctgt ctagttcact gtttctgtca 1740
cctgtgatta tgaataagtg tagccaggga gctgtggctg gagagcccag acagatccca 1800
aagattcaga acttcacacg cactcagaaa agttgcatct tctgtggctt tgccctgctg 1860
tcatacgatg agaaagaagg gctggagaca actacctata ttacatctca ggaagtgcag 1920
aacagtatcc tgagctccaa ttacttcgac tttgataacc tgcacgtgca ttatctgctg 1980
ctgacaacta acggcaccgt gatggagatc gctggactgt acgaggaaag ggctcactct 2040
ggcggctccg gagagagcca ggtgaggcag cagttcagca aggacatcga gaagctgctg 2100
aacgagcagg tgaacaagga gatgcagagc agcaacctgt acatgagcat gagcagctgg 2160
tgctacaccc acagcctgga cggcgccggc ctgttcctgt tcgaccacgc cgccgaggag 2220
tacgagcacg ccaagaagct gatcatcttc ctgaacgaga acaacgtgcc cgtgcagctg 2280
accagcatca gcgcccccga gcacaagttc gagggcctga cccagatctt ccagaaggcc 2340
tacgagcacg agcagcacat cagcgagagc atcaacaaca tcgtggacca cgccatcaag 2400
agcaaggacc acgccacctt caacttcctg cagtggtacg tggccgagca gcacgaggag 2460
gaggtgctgt tcaaggacat cctggacaag atcgagctga tcggcaacga gaaccacggc 2520
ctgtacctgg ccgaccagta cgtgaagggc atcgccaaga gcaggaagag cggatcctag 2580

<210> SEQ ID NO 128
<211> LENGTH: 859
<212> TYPE: PRT
<213> ORGANISM: Artificial Sequence
<220> FEATURE:
<223> OTHER INFORMATION: Synthetic

<400> SEQUENCE: 128

Met Gln Leu Leu Cys Val Phe Cys Leu Val Leu Leu Trp Glu Val Gly
1 5 10 15

Ala Ala Ser Leu Ser Glu Val Lys Leu His Leu Asp Ile Glu Gly His
20 25 30

Ala Ser His Tyr Thr Ile Pro Trp Thr Glu Leu Met Ala Lys Val Pro
35 40 45

Gly Leu Ser Pro Glu Ala Leu Trp Arg Glu Ala Asn Val Thr Glu Asp
50 55 60

Leu Ala Ser Met Leu Asn Arg Tyr Lys Leu Ile Tyr Lys Thr Ser Gly
65 70 75 80

Thr Leu Gly Ile Ala Leu Ala Glu Pro Val Asp Ile Pro Ala Val Ser
85 90 95

Glu Gly Ser Met Gln Val Asp Ala Ser Lys Val His Pro Gly Val Ile
100 105 110

Ser Gly Leu Asn Ser Pro Ala Cys Met Leu Ser Ala Pro Leu Glu Lys
115 120 125

Gln Leu Phe Tyr Tyr Ile Gly Thr Met Leu Pro Asn Thr Arg Pro His
130 135 140

Ser Tyr Val Phe Tyr Gln Leu Arg Cys His Leu Ser Tyr Val Ala Leu
145 150 155 160

Ser Ile Asn Gly Asp Lys Phe Gln Tyr Thr Gly Ala Met Thr Ser Lys
165 170 175

Phe Leu Met Gly Thr Tyr Lys Arg Val Thr Glu Lys Gly Asp Glu His
180 185 190

Val Leu Ser Leu Val Phe Gly Lys Thr Lys Asp Leu Pro Asp Leu Arg
195 200 205

Gly Pro Phe Ser Tyr Pro Ser Leu Thr Ser Ala Gln Ser Gly Asp Tyr
210 215 220

Ser Leu Val Ile Val Thr Thr Phe Val His Tyr Ala Asn Phe His Asn
225 230 235 240

Tyr Phe Val Pro Asn Leu Lys Asp Met Phe Ser Arg Ala Val Thr Met
245 250 255

Thr Ala Ala Ser Tyr Ala Arg Tyr Val Leu Gln Lys Leu Val Leu Leu
260 265 270

Glu Met Lys Gly Gly Cys Arg Glu Pro Glu Leu Asp Thr Glu Thr Leu

-continued

```
        275                 280                 285

Thr Thr Met Phe Glu Val Ser Val Ala Phe Phe Lys Val Gly His Ala
    290                 295                 300

Val Gly Glu Thr Gly Asn Gly Cys Val Asp Leu Arg Trp Leu Ala Lys
305                 310                 315                 320

Ser Phe Phe Glu Leu Thr Val Leu Lys Asp Ile Ile Gly Ile Cys Tyr
                325                 330                 335

Gly Ala Thr Val Lys Gly Met Gln Ser Tyr Gly Leu Glu Arg Leu Ala
            340                 345                 350

Ala Met Leu Met Ala Thr Val Lys Met Glu Glu Leu Gly His Leu Thr
        355                 360                 365

Thr Glu Lys Gln Glu Tyr Ala Leu Arg Leu Ala Thr Val Gly Tyr Pro
    370                 375                 380

Lys Ala Gly Val Tyr Ser Gly Leu Ile Gly Gly Ala Thr Ser Val Leu
385                 390                 395                 400

Leu Ser Ala Tyr Asn Arg His Pro Leu Phe Gln Pro Leu His Thr Val
                405                 410                 415

Met Arg Glu Thr Leu Phe Ile Gly Ser His Val Val Leu Arg Glu Leu
            420                 425                 430

Arg Leu Asn Val Thr Thr Gln Gly Pro Asn Leu Ala Leu Tyr Gln Leu
        435                 440                 445

Leu Ser Thr Ala Leu Cys Ser Ala Leu Glu Ile Gly Glu Val Leu Arg
    450                 455                 460

Gly Leu Ala Leu Gly Thr Glu Ser Gly Leu Phe Ser Pro Cys Tyr Leu
465                 470                 475                 480

Ser Leu Arg Phe Asp Leu Thr Arg Asp Lys Leu Leu Ser Met Ala Pro
                485                 490                 495

Gln Glu Ala Thr Leu Asp Gln Ala Ala Val Ser Asn Ala Val Asp Gly
            500                 505                 510

Phe Leu Gly Arg Leu Ser Leu Glu Arg Glu Asp Arg Asp Ala Trp His
        515                 520                 525

Leu Pro Ala Tyr Lys Cys Val Asp Arg Leu Asp Lys Val Leu Met Ile
    530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
                565                 570                 575

Leu Phe Leu Ser Pro Val Ile Met Asn Lys Cys Ser Gln Gly Ala Val
            580                 585                 590

Ala Gly Glu Pro Arg Gln Ile Pro Lys Ile Gln Asn Phe Thr Arg Thr
        595                 600                 605

Gln Lys Ser Cys Ile Phe Cys Gly Phe Ala Leu Leu Ser Tyr Asp Glu
    610                 615                 620

Lys Glu Gly Leu Glu Thr Thr Thr Tyr Ile Thr Ser Gln Glu Val Gln
625                 630                 635                 640

Asn Ser Ile Leu Ser Ser Asn Tyr Phe Asp Phe Asp Asn Leu His Val
                645                 650                 655

His Tyr Leu Leu Leu Thr Thr Asn Gly Thr Val Met Glu Ile Ala Gly
            660                 665                 670

Leu Tyr Glu Glu Arg Ala His Ser Gly Gly Ser Gly Glu Ser Gln Val
        675                 680                 685

Arg Gln Gln Phe Ser Lys Asp Ile Glu Lys Leu Leu Asn Glu Gln Val
    690                 695                 700
```

Asn Lys Glu Met Gln Ser Ser Asn Leu Tyr Met Ser Met Ser Ser Trp
705 710 715 720

Cys Tyr Thr His Ser Leu Asp Gly Ala Gly Leu Phe Leu Phe Asp His
725 730 735

Ala Ala Glu Glu Tyr Glu His Ala Lys Lys Leu Ile Ile Phe Leu Asn
740 745 750

Glu Asn Asn Val Pro Val Gln Leu Thr Ser Ile Ser Ala Pro Glu His
755 760 765

Lys Phe Glu Gly Leu Thr Gln Ile Phe Gln Lys Ala Tyr Glu His Glu
770 775 780

Gln His Ile Ser Glu Ser Ile Asn Asn Ile Val Asp His Ala Ile Lys
785 790 795 800

Ser Lys Asp His Ala Thr Phe Asn Phe Leu Gln Trp Tyr Val Ala Glu
805 810 815

Gln His Glu Glu Glu Val Leu Phe Lys Asp Ile Leu Asp Lys Ile Glu
820 825 830

Leu Ile Gly Asn Glu Asn His Gly Leu Tyr Leu Ala Asp Gln Tyr Val
835 840 845

Lys Gly Ile Ala Lys Ser Arg Lys Ser Gly Ser
850 855

<210> SEQ ID NO 129
<211> LENGTH: 645
<212> TYPE: DNA
<213> ORGANISM: Artificial Sequence
<220> FEATURE:
<223> OTHER INFORMATION: Synthetic

<400> SEQUENCE: 129
atgcccatgg gcagcctgca gcccctggcc accctgtacc tgctgggcat gctggtggct 60
agcgtgctgg ccggaggaag agtggccgct gccgctatca cctgggtgcc aaaacctaat 120
gtggaagtgt ggcctgtgga cccaccacct ccagtgaact ttaataagac agccgagcag 180
gaatatggcg ataaagaagt gaagctgcct cactggaccc caacactgca tacattccag 240
gtgccacaga actacactaa agctaattgc acttattgta acaccaggga gtacacattt 300
agttataagg ggtgctgttt ctactttact aagaaaaagc acacctggaa tggatgcttc 360
caggcctgtg ctgaactgta tccatgcaca tacttttatg gcccaactcc cgacatcctg 420
cccgtggtga ccaggaacct gaatgccatt gagtccctgt gggtgggagt gtacagggtg 480
ggagaaggca actggacctc cctggatggc gggacattca aagtgtacca gatttttggc 540
tctcattgca cttatgtgtc taagttcagt accgtgcccg tgtcacacca tgagtgtagc 600
tttctgaagc cttgcctgtg tgtgtctcag agaagcaact cctga 645

<210> SEQ ID NO 130
<211> LENGTH: 214
<212> TYPE: PRT
<213> ORGANISM: Artificial Sequence
<220> FEATURE:
<223> OTHER INFORMATION: Synthetic

<400> SEQUENCE: 130

Met Pro Met Gly Ser Leu Gln Pro Leu Ala Thr Leu Tyr Leu Leu Gly
1 5 10 15

Met Leu Val Ala Ser Val Leu Ala Gly Gly Arg Val Ala Ala Ala Ala
20 25 30

-continued

```
Ile Thr Trp Val Pro Lys Pro Asn Val Glu Val Trp Pro Val Asp Pro
        35                  40                  45

Pro Pro Pro Val Asn Phe Asn Lys Thr Ala Glu Gln Glu Tyr Gly Asp
    50                  55                  60

Lys Glu Val Lys Leu Pro His Trp Thr Pro Thr Leu His Thr Phe Gln
65                  70                  75                  80

Val Pro Gln Asn Tyr Thr Lys Ala Asn Cys Thr Tyr Cys Asn Thr Arg
                85                  90                  95

Glu Tyr Thr Phe Ser Tyr Lys Gly Cys Cys Phe Tyr Phe Thr Lys Lys
            100                 105                 110

Lys His Thr Trp Asn Gly Cys Phe Gln Ala Cys Ala Glu Leu Tyr Pro
        115                 120                 125

Cys Thr Tyr Phe Tyr Gly Pro Thr Pro Asp Ile Leu Pro Val Val Thr
    130                 135                 140

Arg Asn Leu Asn Ala Ile Glu Ser Leu Trp Val Gly Val Tyr Arg Val
145                 150                 155                 160

Gly Glu Gly Asn Trp Thr Ser Leu Asp Gly Gly Thr Phe Lys Val Tyr
                165                 170                 175

Gln Ile Phe Gly Ser His Cys Thr Tyr Val Ser Lys Phe Ser Thr Val
            180                 185                 190

Pro Val Ser His His Glu Cys Ser Phe Leu Lys Pro Cys Leu Cys Val
        195                 200                 205

Ser Gln Arg Ser Asn Ser
    210
```

<210> SEQ ID NO 131
<211> LENGTH: 414
<212> TYPE: DNA
<213> ORGANISM: Epstein Barr Virus

<400> SEQUENCE: 131

```
atgcgggccg tgggggtgtt cctggctatc tgcctggtga ctatttttgt gctgccaacc      60

tggggaaact gggcttaccc ttgctgtcac gtgacccagc tcagggccca gcatctgctg     120

gctctggaga acatcagcga catttatctg gtgtccaatc agacatgcga tgggttcagc     180

ctggcctccc tgaacagccc caagaacgga tctaatcagc tcgtgatctc ccggtgtgct     240

aacggcctga atgtcgtgag tttctttatc tcaattctga aaaggagctc ctctgctctg     300

acaggacacc tgagggagct gctgaccaca ctggaaactc tgtacggaag tttctcagtg     360

gaagacctgt ttggcgccaa cctgaatcgg tatgcttggc atagaggcgg gtga           414
```

<210> SEQ ID NO 132
<211> LENGTH: 137
<212> TYPE: PRT
<213> ORGANISM: Epstein Barr Virus

<400> SEQUENCE: 132

```
Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
```

-continued

```
65                  70                  75                  80

Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly
    130                 135


<210> SEQ ID NO 133
<211> LENGTH: 1458
<212> TYPE: DNA
<213> ORGANISM: Artificial Sequence
<220> FEATURE:
<223> OTHER INFORMATION: Synthetic

<400> SEQUENCE: 133

atgcccatgg gcagcctgca gcccctggcc accctgtacc tgctgggcat gctggtggct     60

agcatggagt tcctgaagag gagcttcgcc cctctgaccg agaagcagtg gcaggagatc    120

gacaacaggg ccagggagat cttcaagacc cagctgtacg gcaggaagtt cgtggacgtg    180

gagggcccct acggctggga gtacgccgcc cacccccctgg gcgaggtgga ggtgctgagc    240

gacgagaacg aggtggtgaa gtggggcctg aggaagagcc tgcccctgat cgagctgagg    300

gccaccttca ccctggacct gtgggagctg gacaacctgg agaggggcaa gcccaacgtg    360

gacctgagca gcctggagga gaccgtgagg aaggtggccg agttcgagga cgaggtgatc    420

ttcaggggct gcgagaagag cggcgtgaag ggcctgctga gcttcgagga gaggaagatc    480

gagtgcggca gcacccccaa ggacctgctg gaggccatcg tgagggccct gagcatcttc    540

agcaaggacg gcatcgaggg cccctacacc ctggtgatca acaccgacag gtggatcaac    600

ttcctgaagg aggaggccgg ccactacccc ctggagaaga gggtggagga gtgcctgagg    660

ggcggcaaga tcatcaccac ccccaggatc gaggacgccc tggtggtgag cgagaggggc    720

ggcgacttca agctgatcct gggccaggac ctgagcatcg gctacgagga cagggagaag    780

gacgccgtga ggctgttcat caccgagacc ttcaccttcc aggtggtgaa ccccgaggcc    840

ctgatcctgc tgaagtccgg atctggcggc ggtagcggcg gtggcggagg aagagtggcc    900

gctgccgcta tcacctgggt gccaaaacct aatgtggaag tgtggcctgt ggacccacca    960

cctccagtga actttaataa gacagccgag caggaatatg gcgataaaga agtgaagctg   1020

cctcactgga ccccaacact gcatacattc caggtgccac agaactacac taaagctaat   1080

tgcacttatt gtaacaccag ggagtacaca tttagttata aggggtgctg tttctacttt   1140

actaagaaaa agcacacctg gaatggatgc ttccaggcct gtgctgaact gtatccatgc   1200

acatactttt atggcccaac tcccgacatc ctgcccgtgg tgaccaggaa cctgaatgcc   1260

attgagtccc tgtgggtggg agtgtacagg gtgggagaag gcaactggac ctccctggat   1320

ggcgggacat tcaaagtgta ccagattttt ggctctcatt gcacttatgt gtctaagttc   1380

agtaccgtgc ccgtgtcaca ccatgagtgt agctttctga agccttgcct gtgtgtgtct   1440

cagagaagca actcctga                                                 1458


<210> SEQ ID NO 134
<211> LENGTH: 485
<212> TYPE: PRT
<213> ORGANISM: Artificial Sequence
```

<220> FEATURE:
<223> OTHER INFORMATION: Synthetic

<400> SEQUENCE: 134

```
Met Pro Met Gly Ser Leu Gln Pro Leu Ala Thr Leu Tyr Leu Leu Gly
1               5                   10                  15

Met Leu Val Ala Ser Met Glu Phe Leu Lys Arg Ser Phe Ala Pro Leu
            20                  25                  30

Thr Glu Lys Gln Trp Gln Glu Ile Asp Asn Arg Ala Arg Glu Ile Phe
        35                  40                  45

Lys Thr Gln Leu Tyr Gly Arg Lys Phe Val Asp Val Glu Gly Pro Tyr
    50                  55                  60

Gly Trp Glu Tyr Ala Ala His Pro Leu Gly Glu Val Glu Val Leu Ser
65                  70                  75                  80

Asp Glu Asn Glu Val Val Lys Trp Gly Leu Arg Lys Ser Leu Pro Leu
                85                  90                  95

Ile Glu Leu Arg Ala Thr Phe Thr Leu Asp Leu Trp Glu Leu Asp Asn
            100                 105                 110

Leu Glu Arg Gly Lys Pro Asn Val Asp Leu Ser Ser Leu Glu Glu Thr
        115                 120                 125

Val Arg Lys Val Ala Glu Phe Glu Asp Glu Val Ile Phe Arg Gly Cys
    130                 135                 140

Glu Lys Ser Gly Val Lys Gly Leu Leu Ser Phe Glu Glu Arg Lys Ile
145                 150                 155                 160

Glu Cys Gly Ser Thr Pro Lys Asp Leu Leu Glu Ala Ile Val Arg Ala
                165                 170                 175

Leu Ser Ile Phe Ser Lys Asp Gly Ile Glu Gly Pro Tyr Thr Leu Val
            180                 185                 190

Ile Asn Thr Asp Arg Trp Ile Asn Phe Leu Lys Glu Glu Ala Gly His
        195                 200                 205

Tyr Pro Leu Glu Lys Arg Val Glu Glu Cys Leu Arg Gly Gly Lys Ile
    210                 215                 220

Ile Thr Thr Pro Arg Ile Glu Asp Ala Leu Val Val Ser Glu Arg Gly
225                 230                 235                 240

Gly Asp Phe Lys Leu Ile Leu Gly Gln Asp Leu Ser Ile Gly Tyr Glu
                245                 250                 255

Asp Arg Glu Lys Asp Ala Val Arg Leu Phe Ile Thr Glu Thr Phe Thr
            260                 265                 270

Phe Gln Val Val Asn Pro Glu Ala Leu Ile Leu Leu Lys Ser Gly Ser
        275                 280                 285

Gly Gly Gly Ser Gly Gly Gly Gly Gly Arg Val Ala Ala Ala Ala Ile
    290                 295                 300

Thr Trp Val Pro Lys Pro Asn Val Glu Val Trp Pro Val Asp Pro Pro
305                 310                 315                 320

Pro Pro Val Asn Phe Asn Lys Thr Ala Glu Gln Glu Tyr Gly Asp Lys
                325                 330                 335

Glu Val Lys Leu Pro His Trp Thr Pro Thr Leu His Thr Phe Gln Val
            340                 345                 350

Pro Gln Asn Tyr Thr Lys Ala Asn Cys Thr Tyr Cys Asn Thr Arg Glu
        355                 360                 365

Tyr Thr Phe Ser Tyr Lys Gly Cys Cys Phe Tyr Phe Thr Lys Lys Lys
    370                 375                 380

His Thr Trp Asn Gly Cys Phe Gln Ala Cys Ala Glu Leu Tyr Pro Cys
385                 390                 395                 400
```

```
Thr Tyr Phe Tyr Gly Pro Thr Pro Asp Ile Leu Pro Val Val Thr Arg
                405                 410                 415

Asn Leu Asn Ala Ile Glu Ser Leu Trp Val Gly Val Tyr Arg Val Gly
            420                 425                 430

Glu Gly Asn Trp Thr Ser Leu Asp Gly Gly Thr Phe Lys Val Tyr Gln
        435                 440                 445

Ile Phe Gly Ser His Cys Thr Tyr Val Ser Lys Phe Ser Thr Val Pro
    450                 455                 460

Val Ser His His Glu Cys Ser Phe Leu Lys Pro Cys Leu Cys Val Ser
465                 470                 475                 480

Gln Arg Ser Asn Ser
                485


<210> SEQ ID NO 135
<211> LENGTH: 2040
<212> TYPE: DNA
<213> ORGANISM: Artificial Sequence
<220> FEATURE:
<223> OTHER INFORMATION: Synthetic

<400> SEQUENCE: 135

atgcagctcc tgtgcgtgtt ctgtctggtg ctgctgtggg aagtgggagc cgcttctctg      60

agtgaggtga agctgcacct ggacattgaa ggccacgcct cccattacac tatcccttgg     120

accgagctga tggctaaagt gccaggactg tctcctgagg ctctgtggcg ggaagctaat     180

gtgaccgagg atctggcctc tatgctgaac agatacaagc tgatctataa aaccagtggc     240

acactgggga ttgctctggc tgagccagtg gacatccccg ccgtgtcaga aggaagcatg     300

caggtggatg ctagtaaggt gcatccaggg gtgattagcg gactgaacag cccagcttgc     360

atgctgagcg ctcctctgga gaaacagctc ttctactata tcggcaccat gctgcctaat     420

acacggccac acagctacgt gttttatcag ctcagatgtc atctgtccta cgtggccctg     480

tctattaacg gggacaagtt ccagtataca ggagctatga cttccaaatt tctgatggga     540

acttacaagc gggtgaccga gaaaggcgat gaacacgtgc tgtctctggt gttcgggaag     600

acaaaagacc tgcccgatct gagaggaccc ttttcctacc cttctctgac tagtgcccag     660

tcaggcgact atagcctggt gatcgtgacc acattcgtgc actacgctaa cttccataat     720

tattttgtgc ccaatctgaa ggatatgttt tcccgggccg tgaccatgac agccgcttct     780

tacgctagat atgtgctgca gaagctggtg ctgctggaga tgaaaggcgg gtgccgggag     840

cctgaactgg acactgaaac cctgactacc atgttcgagg tgtccgtggc cttctttaaa     900

gtgggacacg ctgtgggaga gacaggaaac ggatgcgtgg acctgagatg gctggccaag     960

agcttctttg aactgaccgt gctgaaagat atcattggaa tctgttacgg cgccacagtg    1020

aaaggaatgc agagctatgg cctggagagg ctggccgcta tgctgatggc caccgtgaag    1080

atggaggaac tgggccacct gacaactgag aaacaggaat acgctctgag gctggctacc    1140

gtgggatacc caaaggccgg ggtgtattcc ggactgattg gaggcgccac atctgtgctg    1200

ctgagtgctt ataataggca cccactgttc cagcccctgc atacagtgat gcgcgagact    1260

ctgtttatcg ggtctcatgt ggtgctgcgg gaactgagac tgaatgtgac cacacaggga    1320

cccaacctgg ccctgtacca gctcctgagt actgccctgt gctcagctct ggagattgga    1380

gaagtgctga ggggactggc cctggggacc gagtcaggac tgttcagccc ttgttatctg    1440

tcactgaggt ttgacctgac tcgcgataag ctgctgagca tggccccaca ggaagctacc    1500
```

```
ctggaccagg ccgctgtgag caatgccgtg gatggattcc tgggcaggct gtccctggag   1560

agggaagacc gcgatgcctg gcacctgcca gcttacaagt gcgtggaccg cctggataaa   1620

gtgctgatga tcattcccct gatcaacgtg accttcatca ttagctccga cagggaagtg   1680

agaggcagcg ctctgtacga agcttccact acctatctgt ctagttcact gtttctgtca   1740

cctgtgatta tgaataagtg tagccaggga gctgtggctg gagagcccag acagatccca   1800

aagattcaga acttcacacg cactcagaaa agttgcatct tctgtggctt tgccctgctg   1860

tcatacgatg agaaagaagg gctggagaca actacctata ttacatctca ggaagtgcag   1920

aacagtatcc tgagctccaa ttacttcgac tttgataacc tgcacgtgca ttatctgctg   1980

ctgacaacta acggcaccgt gatggagatc gctggactgt acgaggaaag ggctcactga   2040
```

```
<210> SEQ ID NO 136
<211> LENGTH: 679
<212> TYPE: PRT
<213> ORGANISM: Artificial Sequence
<220> FEATURE:
<223> OTHER INFORMATION: Synthetic

<400> SEQUENCE: 136

Met Gln Leu Leu Cys Val Phe Cys Leu Val Leu Leu Trp Glu Val Gly
1               5                   10                  15

Ala Ala Ser Leu Ser Glu Val Lys Leu His Leu Asp Ile Glu Gly His
            20                  25                  30

Ala Ser His Tyr Thr Ile Pro Trp Thr Glu Leu Met Ala Lys Val Pro
        35                  40                  45

Gly Leu Ser Pro Glu Ala Leu Trp Arg Glu Ala Asn Val Thr Glu Asp
    50                  55                  60

Leu Ala Ser Met Leu Asn Arg Tyr Lys Leu Ile Tyr Lys Thr Ser Gly
65                  70                  75                  80

Thr Leu Gly Ile Ala Leu Ala Glu Pro Val Asp Ile Pro Ala Val Ser
                85                  90                  95

Glu Gly Ser Met Gln Val Asp Ala Ser Lys Val His Pro Gly Val Ile
            100                 105                 110

Ser Gly Leu Asn Ser Pro Ala Cys Met Leu Ser Ala Pro Leu Glu Lys
        115                 120                 125

Gln Leu Phe Tyr Tyr Ile Gly Thr Met Leu Pro Asn Thr Arg Pro His
    130                 135                 140

Ser Tyr Val Phe Tyr Gln Leu Arg Cys His Leu Ser Tyr Val Ala Leu
145                 150                 155                 160

Ser Ile Asn Gly Asp Lys Phe Gln Tyr Thr Gly Ala Met Thr Ser Lys
                165                 170                 175

Phe Leu Met Gly Thr Tyr Lys Arg Val Thr Glu Lys Gly Asp Glu His
            180                 185                 190

Val Leu Ser Leu Val Phe Gly Lys Thr Lys Asp Leu Pro Asp Leu Arg
        195                 200                 205

Gly Pro Phe Ser Tyr Pro Ser Leu Thr Ser Ala Gln Ser Gly Asp Tyr
    210                 215                 220

Ser Leu Val Ile Val Thr Thr Phe Val His Tyr Ala Asn Phe His Asn
225                 230                 235                 240

Tyr Phe Val Pro Asn Leu Lys Asp Met Phe Ser Arg Ala Val Thr Met
                245                 250                 255

Thr Ala Ala Ser Tyr Ala Arg Tyr Val Leu Gln Lys Leu Val Leu Leu
            260                 265                 270
```

```
Glu Met Lys Gly Gly Cys Arg Glu Pro Glu Leu Asp Thr Glu Thr Leu
        275                 280                 285

Thr Thr Met Phe Glu Val Ser Val Ala Phe Phe Lys Val Gly His Ala
    290                 295                 300

Val Gly Glu Thr Gly Asn Gly Cys Val Asp Leu Arg Trp Leu Ala Lys
305                 310                 315                 320

Ser Phe Phe Glu Leu Thr Val Leu Lys Asp Ile Ile Gly Ile Cys Tyr
            325                 330                 335

Gly Ala Thr Val Lys Gly Met Gln Ser Tyr Gly Leu Glu Arg Leu Ala
            340                 345                 350

Ala Met Leu Met Ala Thr Val Lys Met Glu Glu Leu Gly His Leu Thr
        355                 360                 365

Thr Glu Lys Gln Glu Tyr Ala Leu Arg Leu Ala Thr Val Gly Tyr Pro
    370                 375                 380

Lys Ala Gly Val Tyr Ser Gly Leu Ile Gly Gly Ala Thr Ser Val Leu
385                 390                 395                 400

Leu Ser Ala Tyr Asn Arg His Pro Leu Phe Gln Pro Leu His Thr Val
            405                 410                 415

Met Arg Glu Thr Leu Phe Ile Gly Ser His Val Val Leu Arg Glu Leu
            420                 425                 430

Arg Leu Asn Val Thr Thr Gln Gly Pro Asn Leu Ala Leu Tyr Gln Leu
        435                 440                 445

Leu Ser Thr Ala Leu Cys Ser Ala Leu Glu Ile Gly Glu Val Leu Arg
    450                 455                 460

Gly Leu Ala Leu Gly Thr Glu Ser Gly Leu Phe Ser Pro Cys Tyr Leu
465                 470                 475                 480

Ser Leu Arg Phe Asp Leu Thr Arg Asp Lys Leu Leu Ser Met Ala Pro
            485                 490                 495

Gln Glu Ala Thr Leu Asp Gln Ala Ala Val Ser Asn Ala Val Asp Gly
            500                 505                 510

Phe Leu Gly Arg Leu Ser Leu Glu Arg Glu Asp Arg Asp Ala Trp His
        515                 520                 525

Leu Pro Ala Tyr Lys Cys Val Asp Arg Leu Asp Lys Val Leu Met Ile
    530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
            565                 570                 575

Leu Phe Leu Ser Pro Val Ile Met Asn Lys Cys Ser Gln Gly Ala Val
            580                 585                 590

Ala Gly Glu Pro Arg Gln Ile Pro Lys Ile Gln Asn Phe Thr Arg Thr
        595                 600                 605

Gln Lys Ser Cys Ile Phe Cys Gly Phe Ala Leu Leu Ser Tyr Asp Glu
    610                 615                 620

Lys Glu Gly Leu Glu Thr Thr Thr Tyr Ile Thr Ser Gln Glu Val Gln
625                 630                 635                 640

Asn Ser Ile Leu Ser Ser Asn Tyr Phe Asp Phe Asp Asn Leu His Val
            645                 650                 655

His Tyr Leu Leu Leu Thr Thr Asn Gly Thr Val Met Glu Ile Ala Gly
            660                 665                 670

Leu Tyr Glu Glu Arg Ala His
        675
```

<210> SEQ ID NO 137
<211> LENGTH: 84
<212> TYPE: DNA
<213> ORGANISM: Picornavirus

<400> SEQUENCE: 137
agcgggtccg gagctccagt gaaacagacc ctgaactttg acctgctgaa gctggcaggg 60
gatgtggaga gcaatcctgg ccca 84

<210> SEQ ID NO 138
<211> LENGTH: 28
<212> TYPE: PRT
<213> ORGANISM: Picornavirus

<400> SEQUENCE: 138

Ser Gly Ser Gly Ala Pro Val Lys Gln Thr Leu Asn Phe Asp Leu Leu
1 5 10 15

Lys Leu Ala Gly Asp Val Glu Ser Asn Pro Gly Pro
20 25

<210> SEQ ID NO 139
<211> LENGTH: 72
<212> TYPE: DNA
<213> ORGANISM: Homo sapiens

<400> SEQUENCE: 139
atgccaatgg gcagcctgca gccactggca actctgtacc tgctgggaat gctggtggca 60
tccgtcctgg ca 72

<210> SEQ ID NO 140
<211> LENGTH: 24
<212> TYPE: PRT
<213> ORGANISM: Homo sapiens

<400> SEQUENCE: 140

Met Pro Met Gly Ser Leu Gln Pro Leu Ala Thr Leu Tyr Leu Leu Gly
1 5 10 15

Met Leu Val Ala Ser Val Leu Ala
20

<210> SEQ ID NO 141
<211> LENGTH: 3087
<212> TYPE: DNA
<213> ORGANISM: Artificial Sequence
<220> FEATURE:
<223> OTHER INFORMATION: NAM encoding ferritin-gH-F2A-gL

<400> SEQUENCE: 141
atgcagctgc tgtgtgtgtt ctgtctggtc ctgctgtggg aagtcggagc cgcctctctg 60
agcgaagtga aactgcacct ggatattgaa gggcacgcct ctcattacac catcccttgg 120
acagagctga tggctaaggt gcctggactg agtccagaag ctctgtggcg cgaggcaaac 180
gtgaccgaag acctggcctc catgctgaat cgatacaaac tgatctacaa gacatctggg 240
actctgggaa tcgccctggc tgaacccgtg gacattcctg ctgtcagtga gggctcaatg 300
caggtggatg caagcaaagt gcacccagga gtcatctctg gcctgaacag tcccgcctgc 360
atgctgtccg ctcctctgga gaagcagctg ttctactata ttgggacaat gctgccaaac 420
actagacccc acagctacgt gttttatcag ctgaggtgtc atctgagcta cgtcgcactg 480
tccatcaatg gagacaaatt ccagtatact ggcgccatga cctctaagtt tctgatggga 540

-continued

```
acctacaaaa gggtgacaga aaagggcgat gagcacgtgc tgagcctggt cttcggcaaa    600
accaaggacc tgcccgatct gcgcgggcct tttagctacc catccctgac atctgcccag    660
agtggcgact atagcctggt catcgtcacc acattcgtgc actacgctaa cttccataat    720
tattttgtcc ctaacctgaa ggatatgttt tccagggcag tgactatgac cgccgcttct    780
tacgcccgct atgtgctgca gaaactggtc ctgctggaga tgaagggagg atgccgagaa    840
ccagagctgg acacagaaac tctgactacc atgttcgagg tgtccgtcgc tttctttaaa    900
gtggggcacg cagtcggaga aacaggcaat gggtgcgtgg acctgagatg gctggccaaa    960
agcttctttg agctgaccgt gctgaaggat atcattggca tctgttacgg ggctacagtc   1020
aagggcatgc agtcctatgg gctggagcgg ctggcagcca tgctgatggc caccgtgaaa   1080
atggaggaac tgggacacct gacaactgaa aagcaggagt acgccctgag actggctact   1140
gtgggctacc caaaggccgg agtctatagc ggactgatcg gaggagcaac ctcagtgctg   1200
ctgagcgctt ataaccgaca cccccctgttc cagcctctgc atactgtgat gcgggaaacc   1260
ctgtttattg gctcccatgt ggtcctgcga gagctgcggc tgaacgtgac cacacagggg   1320
cccaatctgg ctctgtacca gctgctgtct acagcactgt gcagtgccct ggaaatcgga   1380
gaggtgctga ggggactggc actgggaact gaatccggac tgttctctcc ctgttatctg   1440
agtctgaggt ttgacctgac tcgcgataag ctgctgtcaa tggctcctca ggaggcaacc   1500
ctggaccagg ctgcagtgtc aaacgcagtc gatggcttcc tgggacgact gagcctggaa   1560
agagaggaca gggatgcatg gcacctgcct gcctacaaat gcgtggacag actggataag   1620
gtcctgatga tcattccact gatcaatgtg accttcatca ttagctccga ccgagaagtc   1680
cgaggctccg cactgtacga ggcttctact acctatctgt ctagttcact gtttctgtca   1740
cccgtgatca tgaacaaatg tagccaggga gcagtcgcag gagagccacg acagatcccc   1800
aaaattcaga atttcacccg aacacagaag tcttgcattt tctgtggatt tgccctgctg   1860
agttacgatg aaaaggaggg cctggaaaca actacctata tcacaagtca ggaggtgcag   1920
aattcaattc tgagctccaa ctacttcgac tttgataatc tgcacgtgca ttatctgctg   1980
ctgacaacta acgggaccgt catggaaatc gcaggactgt acgaggaaag agcacactca   2040
ggaggaagcg gagagtccca ggtgaggcag cagttctcta aagacattga gaagctgctg   2100
aacgaacaag tgaataagga gatgcagtct agtaacctgt acatgagtat gtcaagctgg   2160
tgctataccc actcactgga cggagcaggc ctgttcctgt ttgatcacgc cgctgaggaa   2220
tacgaacatg ccaagaaact gatcattttt ctgaacgaga acaacgtgcc tgtccagctg   2280
acatcaatca gcgctccaga acataaattc gagggcctga ctcagatctt tcagaaggca   2340
tacgaacacg agcagcatat ttccgaatct atcaacaata ttgtggacca cgccatcaag   2400
agcaaggatc atgcaacctt caattttctg cagtggtacg tggccgagca gcacgaggaa   2460
gaggtcctgt tcaaagacat cctggataag atcgaactga ttggaaacga gaatcatggc   2520
ctgtacctgg ccgatcagta tgtgaaaggc attgctaaat ctcgaaagag tgggtcacgg   2580
aagcgaagaa gcgggtccgg agctccagtg aaacagaccc tgaactttga cctgctgaag   2640
ctggcagggg atgtggagag caatcctggc ccaatgaggg ccgtgggggt cttcctggct   2700
atctgtctgg tgaccatttt tgtcctgcca acatggggaa actgggccta cccatgctgt   2760
cacgtgaccc agctgcgagc tcagcatctg ctggcactgg agaacatcag cgacatctac   2820
ctggtgagca atcagacatg cgatgggttc tctctggcca gtctgaattc acctaaaaac   2880
ggatctaatc agctggtcat cagtaggtgt gctaacggcc tgaatgtggt cagtttcttt   2940
```

atctcaattc tgaagcggtc ctctagtgcc ctgacaggcc acctgagaga actgctgacc 3000
acactggaga ctctgtacgg gtctttcagt gtggaggacc tgtttggagc aaacctgaat 3060
cgctatgcat ggcatcgagg aggatga 3087

<210> SEQ ID NO 142
<211> LENGTH: 1028
<212> TYPE: PRT
<213> ORGANISM: Artificial Sequence
<220> FEATURE:
<223> OTHER INFORMATION: Protein encoded by SEQ ID NO:141 (ferritin-gH-F2A-gL)

<400> SEQUENCE: 142

Met Gln Leu Leu Cys Val Phe Cys Leu Val Leu Leu Trp Glu Val Gly
1 5 10 15

Ala Ala Ser Leu Ser Glu Val Lys Leu His Leu Asp Ile Glu Gly His
20 25 30

Ala Ser His Tyr Thr Ile Pro Trp Thr Glu Leu Met Ala Lys Val Pro
35 40 45

Gly Leu Ser Pro Glu Ala Leu Trp Arg Glu Ala Asn Val Thr Glu Asp
50 55 60

Leu Ala Ser Met Leu Asn Arg Tyr Lys Leu Ile Tyr Lys Thr Ser Gly
65 70 75 80

Thr Leu Gly Ile Ala Leu Ala Glu Pro Val Asp Ile Pro Ala Val Ser
85 90 95

Glu Gly Ser Met Gln Val Asp Ala Ser Lys Val His Pro Gly Val Ile
100 105 110

Ser Gly Leu Asn Ser Pro Ala Cys Met Leu Ser Ala Pro Leu Glu Lys
115 120 125

Gln Leu Phe Tyr Tyr Ile Gly Thr Met Leu Pro Asn Thr Arg Pro His
130 135 140

Ser Tyr Val Phe Tyr Gln Leu Arg Cys His Leu Ser Tyr Val Ala Leu
145 150 155 160

Ser Ile Asn Gly Asp Lys Phe Gln Tyr Thr Gly Ala Met Thr Ser Lys
165 170 175

Phe Leu Met Gly Thr Tyr Lys Arg Val Thr Glu Lys Gly Asp Glu His
180 185 190

Val Leu Ser Leu Val Phe Gly Lys Thr Lys Asp Leu Pro Asp Leu Arg
195 200 205

Gly Pro Phe Ser Tyr Pro Ser Leu Thr Ser Ala Gln Ser Gly Asp Tyr
210 215 220

Ser Leu Val Ile Val Thr Thr Phe Val His Tyr Ala Asn Phe His Asn
225 230 235 240

Tyr Phe Val Pro Asn Leu Lys Asp Met Phe Ser Arg Ala Val Thr Met
245 250 255

Thr Ala Ala Ser Tyr Ala Arg Tyr Val Leu Gln Lys Leu Val Leu Leu
260 265 270

Glu Met Lys Gly Gly Cys Arg Glu Pro Glu Leu Asp Thr Glu Thr Leu
275 280 285

Thr Thr Met Phe Glu Val Ser Val Ala Phe Phe Lys Val Gly His Ala
290 295 300

Val Gly Glu Thr Gly Asn Gly Cys Val Asp Leu Arg Trp Leu Ala Lys
305 310 315 320

Ser Phe Phe Glu Leu Thr Val Leu Lys Asp Ile Ile Gly Ile Cys Tyr

-continued

```
                325                 330                 335

Gly Ala Thr Val Lys Gly Met Gln Ser Tyr Gly Leu Glu Arg Leu Ala
            340                 345                 350

Ala Met Leu Met Ala Thr Val Lys Met Glu Glu Leu Gly His Leu Thr
        355                 360                 365

Thr Glu Lys Gln Glu Tyr Ala Leu Arg Leu Ala Thr Val Gly Tyr Pro
    370                 375                 380

Lys Ala Gly Val Tyr Ser Gly Leu Ile Gly Gly Ala Thr Ser Val Leu
385                 390                 395                 400

Leu Ser Ala Tyr Asn Arg His Pro Leu Phe Gln Pro Leu His Thr Val
                405                 410                 415

Met Arg Glu Thr Leu Phe Ile Gly Ser His Val Val Leu Arg Glu Leu
            420                 425                 430

Arg Leu Asn Val Thr Thr Gln Gly Pro Asn Leu Ala Leu Tyr Gln Leu
        435                 440                 445

Leu Ser Thr Ala Leu Cys Ser Ala Leu Glu Ile Gly Glu Val Leu Arg
    450                 455                 460

Gly Leu Ala Leu Gly Thr Glu Ser Gly Leu Phe Ser Pro Cys Tyr Leu
465                 470                 475                 480

Ser Leu Arg Phe Asp Leu Thr Arg Asp Lys Leu Leu Ser Met Ala Pro
                485                 490                 495

Gln Glu Ala Thr Leu Asp Gln Ala Ala Val Ser Asn Ala Val Asp Gly
            500                 505                 510

Phe Leu Gly Arg Leu Ser Leu Glu Arg Glu Asp Arg Asp Ala Trp His
        515                 520                 525

Leu Pro Ala Tyr Lys Cys Val Asp Arg Leu Asp Lys Val Leu Met Ile
    530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
                565                 570                 575

Leu Phe Leu Ser Pro Val Ile Met Asn Lys Cys Ser Gln Gly Ala Val
            580                 585                 590

Ala Gly Glu Pro Arg Gln Ile Pro Lys Ile Gln Asn Phe Thr Arg Thr
        595                 600                 605

Gln Lys Ser Cys Ile Phe Cys Gly Phe Ala Leu Leu Ser Tyr Asp Glu
    610                 615                 620

Lys Glu Gly Leu Glu Thr Thr Thr Tyr Ile Thr Ser Gln Glu Val Gln
625                 630                 635                 640

Asn Ser Ile Leu Ser Ser Asn Tyr Phe Asp Phe Asp Asn Leu His Val
                645                 650                 655

His Tyr Leu Leu Leu Thr Thr Asn Gly Thr Val Met Glu Ile Ala Gly
            660                 665                 670

Leu Tyr Glu Glu Arg Ala His Ser Gly Gly Ser Gly Glu Ser Gln Val
        675                 680                 685

Arg Gln Gln Phe Ser Lys Asp Ile Glu Lys Leu Leu Asn Glu Gln Val
    690                 695                 700

Asn Lys Glu Met Gln Ser Ser Asn Leu Tyr Met Ser Met Ser Ser Trp
705                 710                 715                 720

Cys Tyr Thr His Ser Leu Asp Gly Ala Gly Leu Phe Leu Phe Asp His
                725                 730                 735

Ala Ala Glu Glu Tyr Glu His Ala Lys Lys Leu Ile Ile Phe Leu Asn
            740                 745                 750
```

Glu Asn Asn Val Pro Val Gln Leu Thr Ser Ile Ser Ala Pro Glu His
755 760 765

Lys Phe Glu Gly Leu Thr Gln Ile Phe Gln Lys Ala Tyr Glu His Glu
770 775 780

Gln His Ile Ser Glu Ser Ile Asn Asn Ile Val Asp His Ala Ile Lys
785 790 795 800

Ser Lys Asp His Ala Thr Phe Asn Phe Leu Gln Trp Tyr Val Ala Glu
805 810 815

Gln His Glu Glu Glu Val Leu Phe Lys Asp Ile Leu Asp Lys Ile Glu
820 825 830

Leu Ile Gly Asn Glu Asn His Gly Leu Tyr Leu Ala Asp Gln Tyr Val
835 840 845

Lys Gly Ile Ala Lys Ser Arg Lys Ser Gly Ser Arg Lys Arg Arg Ser
850 855 860

Gly Ser Gly Ala Pro Val Lys Gln Thr Leu Asn Phe Asp Leu Leu Lys
865 870 875 880

Leu Ala Gly Asp Val Glu Ser Asn Pro Gly Pro Met Arg Ala Val Gly
885 890 895

Val Phe Leu Ala Ile Cys Leu Val Thr Ile Phe Val Leu Pro Thr Trp
900 905 910

Gly Asn Trp Ala Tyr Pro Cys Cys His Val Thr Gln Leu Arg Ala Gln
915 920 925

His Leu Leu Ala Leu Glu Asn Ile Ser Asp Ile Tyr Leu Val Ser Asn
930 935 940

Gln Thr Cys Asp Gly Phe Ser Leu Ala Ser Leu Asn Ser Pro Lys Asn
945 950 955 960

Gly Ser Asn Gln Leu Val Ile Ser Arg Cys Ala Asn Gly Leu Asn Val
965 970 975

Val Ser Phe Phe Ile Ser Ile Leu Lys Arg Ser Ser Ser Ala Leu Thr
980 985 990

Gly His Leu Arg Glu Leu Leu Thr Thr Leu Glu Thr Leu Tyr Gly Ser
995 1000 1005

Phe Ser Val Glu Asp Leu Phe Gly Ala Asn Leu Asn Arg Tyr Ala
1010 1015 1020

Trp His Arg Gly Gly
1025

<210> SEQ ID NO 143
<211> LENGTH: 3825
<212> TYPE: DNA
<213> ORGANISM: Artificial Sequence
<220> FEATURE:
<223> OTHER INFORMATION: NAM encoding ferritin-gH-F2A-gL-F2A-gp42

<400> SEQUENCE: 143
atgcagctgc tgtgtgtgtt ctgtctggtc ctgctgtggg aagtcggagc cgcctctctg 60
agcgaagtga aactgcacct ggatattgaa gggcacgcct ctcattacac catcccttgg 120
acagagctga tggctaaggt gcctggactg agtccagaag ctctgtggcg cgaggcaaac 180
gtgaccgaag acctggcctc catgctgaat cgatacaaac tgatctacaa gacatctggg 240
actctgggaa tcgccctggc tgaacccgtg gacattcctg ctgtcagtga gggctcaatg 300
caggtggatg caagcaaagt gcacccagga gtcatctctg gcctgaacag tcccgcctgc 360
atgctgtccg ctcctctgga gaagcagctg ttctactata ttgggacaat gctgccaaac 420

```
actagacccc acagctacgt gttttatcag ctgaggtgtc atctgagcta cgtcgcactg    480
tccatcaatg gagacaaatt ccagtatact ggcgccatga cctctaagtt tctgatggga    540
acctacaaaa gggtgacaga aaagggcgat gagcacgtgc tgagcctggt cttcggcaaa    600
accaaggacc tgcccgatct gcgcgggcct tttagctacc catccctgac atctgcccag    660
agtggcgact atagcctggt catcgtcacc acattcgtgc actacgctaa cttccataat    720
tattttgtcc ctaacctgaa ggatatgttt tccagggcag tgactatgac cgccgcttct    780
tacgcccgct atgtgctgca gaaactggtc ctgctggaga tgaagggagg atgccgagaa    840
ccagagctgg acacagaaac tctgactacc atgttcgagg tgtccgtcgc tttctttaaa    900
gtggggcacg cagtcggaga aacaggcaat gggtgcgtgg acctgagatg gctggccaaa    960
agcttctttg agctgaccgt gctgaaggat atcattggca tctgttacgg ggctacagtc   1020
aagggcatgc agtcctatgg gctggagcgg ctggcagcca tgctgatggc caccgtgaaa   1080
atggaggaac tgggacacct gacaactgaa aagcaggagt acgccctgag actggctact   1140
gtgggctacc caaaggccgg agtctatagc ggactgatcg gaggagcaac ctcagtgctg   1200
ctgagcgctt ataaccgaca ccccctgttc cagcctctgc atactgtgat gcgggaaacc   1260
ctgtttattg gctcccatgt ggtcctgcga gagctgcggc tgaacgtgac cacacagggg   1320
cccaatctgg ctctgtacca gctgctgtct acagcactgt gcagtgccct ggaaatcgga   1380
gaggtgctga ggggactggc actgggaact gaatccggac tgttctctcc ctgttatctg   1440
agtctgaggt ttgacctgac tcgcgataag ctgctgtcaa tggctcctca ggaggcaacc   1500
ctggaccagg ctgcagtgtc aaacgcagtc gatggcttcc tgggacgact gagcctggaa   1560
agagaggaca gggatgcatg gcacctgcct gcctacaaat gcgtggacag actggataag   1620
gtcctgatga tcattccact gatcaatgtg accttcatca ttagctccga ccgagaagtc   1680
cgaggctccg cactgtacga ggcttctact acctatctgt ctagttcact gtttctgtca   1740
cccgtgatca tgaacaaatg tagccaggga gcagtcgcag gagagccacg acagatcccc   1800
aaaattcaga atttcacccg aacacagaag tcttgcattt tctgtggatt tgccctgctg   1860
agttacgatg aaaaggaggg cctggaaaca actacctata tcacaagtca ggaggtgcag   1920
aattcaattc tgagctccaa ctacttcgac tttgataatc tgcacgtgca ttatctgctg   1980
ctgacaacta acgggaccgt catggaaatc gcaggactgt acgaggaaag agcacactca   2040
ggaggaagcg gagagtccca ggtgaggcag cagttctcta aagacattga gaagctgctg   2100
aacgaacaag tgaataagga gatgcagtct agtaacctgt acatgagtat gtcaagctgg   2160
tgctataccc actcactgga cggagcaggc ctgttcctgt ttgatcacgc cgctgaggaa   2220
tacgaacatg ccaagaaact gatcattttt ctgaacgaga acaacgtgcc tgtccagctg   2280
acatcaatca gcgctccaga acataaattc gagggcctga ctcagatctt tcagaaggca   2340
tacgaacacg agcagcatat ttccgaatct atcaacaata ttgtggacca cgccatcaag   2400
agcaaggatc atgcaacctt caattttctg cagtggtacg tggccgagca gcacgaggaa   2460
gaggtcctgt tcaaagacat cctggataag atcgaactga ttggaaacga gaatcatggc   2520
ctgtacctgg ccgatcagta tgtgaaaggc attgctaaat ctcgaaagag tgggtcacgg   2580
aagcgaagaa gcgggtccgg agctccagtg aaacagaccc tgaactttga cctgctgaag   2640
ctggcagggg atgtggagag caatcctggc ccaatgaggg ccgtgggggt cttcctggct   2700
atctgtctgg tgaccatttt tgtcctgcca acatggggaa actgggccta cccatgctgt   2760
cacgtgaccc agctgcgagc tcagcatctg ctggcactgg agaacatcag cgacatctac   2820
```

```
ctggtgagca atcagacatg cgatgggttc tctctggcca gtctgaattc acctaaaaac   2880

ggatctaatc agctggtcat cagtaggtgt gctaacggcc tgaatgtggt cagtttcttt   2940

atctcaattc tgaagcggtc ctctagtgcc ctgacaggcc acctgagaga actgctgacc   3000

acactggaga ctctgtacgg gtctttcagt gtggaggacc tgtttggagc aaacctgaat   3060

cgctatgcat ggcatcgagg aggaagaaag aggcgatcag gcagcggagc acctgtcaaa   3120

cagaccctga acttcgacct gctgaagctg gctggagatg tggagagcaa tcccgggcct   3180

atgccaatgg gcagcctgca gccactggca actctgtacc tgctgggaat gctggtggca   3240

tccgtcctgg caggaggacg agtggcagca gctgcaatca catgggtccc caaacctaac   3300

gtggaagtct ggccagtgga ccccccctcca ccagtcaact ttaataagac cgccgaacag   3360

gagtatggcg ataaagaggt gaagctgcct cactggactc caaccctgca tactttccag   3420

gtgcctcaga actacaccaa agccaattgc acatattgta acactagaga gtacaccttt   3480

tcttataagg ggtgctgttt ctactttaca aagaaaaagc acacttggaa cggatgcttc   3540

caggcttgtg cagagctgta tccatgcact tacttttatg gaccaacccc agacatcctg   3600

ccagtggtca ccaggaacct gaatgccatt gaaagcctgt gggtgggagt ctaccgagtg   3660

ggagagggca attggacaag cctggatggg ggaactttca aagtgtacca gatctttggc   3720

tcccattgca cctatgtcag caagttctcc acagtgcccg tctcacacca tgagtgtagc   3780

tttctgaagc cttgcctgtg tgtgagccag cggtccaact cttga                   3825
```

<210> SEQ ID NO 144
<211> LENGTH: 1274
<212> TYPE: PRT
<213> ORGANISM: Artificial Sequence
<220> FEATURE:
<223> OTHER INFORMATION: Protein encoded by SEQ ID NO:143 (ferritin-gH-F2A-gL-F2A-gp42)

<400> SEQUENCE: 144

```
Met Gln Leu Leu Cys Val Phe Cys Leu Val Leu Leu Trp Glu Val Gly
1               5                   10                  15

Ala Ala Ser Leu Ser Glu Val Lys Leu His Leu Asp Ile Glu Gly His
            20                  25                  30

Ala Ser His Tyr Thr Ile Pro Trp Thr Glu Leu Met Ala Lys Val Pro
        35                  40                  45

Gly Leu Ser Pro Glu Ala Leu Trp Arg Glu Ala Asn Val Thr Glu Asp
    50                  55                  60

Leu Ala Ser Met Leu Asn Arg Tyr Lys Leu Ile Tyr Lys Thr Ser Gly
65                  70                  75                  80

Thr Leu Gly Ile Ala Leu Ala Glu Pro Val Asp Ile Pro Ala Val Ser
                85                  90                  95

Glu Gly Ser Met Gln Val Asp Ala Ser Lys Val His Pro Gly Val Ile
            100                 105                 110

Ser Gly Leu Asn Ser Pro Ala Cys Met Leu Ser Ala Pro Leu Glu Lys
        115                 120                 125

Gln Leu Phe Tyr Tyr Ile Gly Thr Met Leu Pro Asn Thr Arg Pro His
    130                 135                 140

Ser Tyr Val Phe Tyr Gln Leu Arg Cys His Leu Ser Tyr Val Ala Leu
145                 150                 155                 160

Ser Ile Asn Gly Asp Lys Phe Gln Tyr Thr Gly Ala Met Thr Ser Lys
                165                 170                 175
```

-continued

```
Phe Leu Met Gly Thr Tyr Lys Arg Val Thr Glu Lys Gly Asp Glu His
            180                 185                 190

Val Leu Ser Leu Val Phe Gly Lys Thr Lys Asp Leu Pro Asp Leu Arg
        195                 200                 205

Gly Pro Phe Ser Tyr Pro Ser Leu Thr Ser Ala Gln Ser Gly Asp Tyr
    210                 215                 220

Ser Leu Val Ile Val Thr Thr Phe Val His Tyr Ala Asn Phe His Asn
225                 230                 235                 240

Tyr Phe Val Pro Asn Leu Lys Asp Met Phe Ser Arg Ala Val Thr Met
                245                 250                 255

Thr Ala Ala Ser Tyr Ala Arg Tyr Val Leu Gln Lys Leu Val Leu Leu
            260                 265                 270

Glu Met Lys Gly Gly Cys Arg Glu Pro Glu Leu Asp Thr Glu Thr Leu
        275                 280                 285

Thr Thr Met Phe Glu Val Ser Val Ala Phe Phe Lys Val Gly His Ala
    290                 295                 300

Val Gly Glu Thr Gly Asn Gly Cys Val Asp Leu Arg Trp Leu Ala Lys
305                 310                 315                 320

Ser Phe Phe Glu Leu Thr Val Leu Lys Asp Ile Ile Gly Ile Cys Tyr
                325                 330                 335

Gly Ala Thr Val Lys Gly Met Gln Ser Tyr Gly Leu Glu Arg Leu Ala
            340                 345                 350

Ala Met Leu Met Ala Thr Val Lys Met Glu Glu Leu Gly His Leu Thr
        355                 360                 365

Thr Glu Lys Gln Glu Tyr Ala Leu Arg Leu Ala Thr Val Gly Tyr Pro
    370                 375                 380

Lys Ala Gly Val Tyr Ser Gly Leu Ile Gly Gly Ala Thr Ser Val Leu
385                 390                 395                 400

Leu Ser Ala Tyr Asn Arg His Pro Leu Phe Gln Pro Leu His Thr Val
                405                 410                 415

Met Arg Glu Thr Leu Phe Ile Gly Ser His Val Val Leu Arg Glu Leu
            420                 425                 430

Arg Leu Asn Val Thr Thr Gln Gly Pro Asn Leu Ala Leu Tyr Gln Leu
        435                 440                 445

Leu Ser Thr Ala Leu Cys Ser Ala Leu Glu Ile Gly Glu Val Leu Arg
    450                 455                 460

Gly Leu Ala Leu Gly Thr Glu Ser Gly Leu Phe Ser Pro Cys Tyr Leu
465                 470                 475                 480

Ser Leu Arg Phe Asp Leu Thr Arg Asp Lys Leu Leu Ser Met Ala Pro
                485                 490                 495

Gln Glu Ala Thr Leu Asp Gln Ala Ala Val Ser Asn Ala Val Asp Gly
            500                 505                 510

Phe Leu Gly Arg Leu Ser Leu Glu Arg Glu Asp Arg Asp Ala Trp His
        515                 520                 525

Leu Pro Ala Tyr Lys Cys Val Asp Arg Leu Asp Lys Val Leu Met Ile
    530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
                565                 570                 575

Leu Phe Leu Ser Pro Val Ile Met Asn Lys Cys Ser Gln Gly Ala Val
            580                 585                 590

Ala Gly Glu Pro Arg Gln Ile Pro Lys Ile Gln Asn Phe Thr Arg Thr
```

-continued

```
        595                 600                 605

Gln Lys Ser Cys Ile Phe Cys Gly Phe Ala Leu Leu Ser Tyr Asp Glu
    610                 615                 620

Lys Glu Gly Leu Glu Thr Thr Thr Tyr Ile Thr Ser Gln Glu Val Gln
625                 630                 635                 640

Asn Ser Ile Leu Ser Ser Asn Tyr Phe Asp Phe Asp Asn Leu His Val
                645                 650                 655

His Tyr Leu Leu Leu Thr Thr Asn Gly Thr Val Met Glu Ile Ala Gly
            660                 665                 670

Leu Tyr Glu Glu Arg Ala His Ser Gly Gly Ser Gly Glu Ser Gln Val
        675                 680                 685

Arg Gln Gln Phe Ser Lys Asp Ile Glu Lys Leu Leu Asn Glu Gln Val
    690                 695                 700

Asn Lys Glu Met Gln Ser Ser Asn Leu Tyr Met Ser Met Ser Ser Trp
705                 710                 715                 720

Cys Tyr Thr His Ser Leu Asp Gly Ala Gly Leu Phe Leu Phe Asp His
                725                 730                 735

Ala Ala Glu Glu Tyr Glu His Ala Lys Lys Leu Ile Ile Phe Leu Asn
            740                 745                 750

Glu Asn Asn Val Pro Val Gln Leu Thr Ser Ile Ser Ala Pro Glu His
        755                 760                 765

Lys Phe Glu Gly Leu Thr Gln Ile Phe Gln Lys Ala Tyr Glu His Glu
    770                 775                 780

Gln His Ile Ser Glu Ser Ile Asn Asn Ile Val Asp His Ala Ile Lys
785                 790                 795                 800

Ser Lys Asp His Ala Thr Phe Asn Phe Leu Gln Trp Tyr Val Ala Glu
                805                 810                 815

Gln His Glu Glu Glu Val Leu Phe Lys Asp Ile Leu Asp Lys Ile Glu
            820                 825                 830

Leu Ile Gly Asn Glu Asn His Gly Leu Tyr Leu Ala Asp Gln Tyr Val
        835                 840                 845

Lys Gly Ile Ala Lys Ser Arg Lys Ser Gly Ser Arg Lys Arg Arg Ser
    850                 855                 860

Gly Ser Gly Ala Pro Val Lys Gln Thr Leu Asn Phe Asp Leu Leu Lys
865                 870                 875                 880

Leu Ala Gly Asp Val Glu Ser Asn Pro Gly Pro Met Arg Ala Val Gly
                885                 890                 895

Val Phe Leu Ala Ile Cys Leu Val Thr Ile Phe Val Leu Pro Thr Trp
            900                 905                 910

Gly Asn Trp Ala Tyr Pro Cys Cys His Val Thr Gln Leu Arg Ala Gln
        915                 920                 925

His Leu Leu Ala Leu Glu Asn Ile Ser Asp Ile Tyr Leu Val Ser Asn
    930                 935                 940

Gln Thr Cys Asp Gly Phe Ser Leu Ala Ser Leu Asn Ser Pro Lys Asn
945                 950                 955                 960

Gly Ser Asn Gln Leu Val Ile Ser Arg Cys Ala Asn Gly Leu Asn Val
                965                 970                 975

Val Ser Phe Phe Ile Ser Ile Leu Lys Arg Ser Ser Ser Ala Leu Thr
            980                 985                 990

Gly His Leu Arg Glu Leu Leu Thr  Thr Leu Glu Thr Leu  Tyr Gly Ser
        995                 1000                1005

Phe Ser  Val Glu Asp Leu Phe  Gly Ala Asn Leu Asn  Arg Tyr Ala
    1010                 1015                 1020
```

```
Trp His  Arg Gly Gly Arg Lys  Arg Arg Ser Gly Ser  Gly Ala Pro
    1025                 1030                 1035

Val Lys  Gln Thr Leu Asn Phe  Asp Leu Leu Lys Leu  Ala Gly Asp
    1040                 1045                 1050

Val Glu  Ser Asn Pro Gly Pro  Met Pro Met Gly Ser  Leu Gln Pro
    1055                 1060                 1065

Leu Ala  Thr Leu Tyr Leu Leu  Gly Met Leu Val Ala  Ser Val Leu
    1070                 1075                 1080

Ala Gly  Gly Arg Val Ala Ala  Ala Ala Ile Thr Trp  Val Pro Lys
    1085                 1090                 1095

Pro Asn  Val Glu Val Trp Pro  Val Asp Pro Pro Pro  Pro Val Asn
    1100                 1105                 1110

Phe Asn  Lys Thr Ala Glu Gln  Glu Tyr Gly Asp Lys  Glu Val Lys
    1115                 1120                 1125

Leu Pro  His Trp Thr Pro Thr  Leu His Thr Phe Gln  Val Pro Gln
    1130                 1135                 1140

Asn Tyr  Thr Lys Ala Asn Cys  Thr Tyr Cys Asn Thr  Arg Glu Tyr
    1145                 1150                 1155

Thr Phe  Ser Tyr Lys Gly Cys  Cys Phe Tyr Phe Thr  Lys Lys Lys
    1160                 1165                 1170

His Thr  Trp Asn Gly Cys Phe  Gln Ala Cys Ala Glu  Leu Tyr Pro
    1175                 1180                 1185

Cys Thr  Tyr Phe Tyr Gly Pro  Thr Pro Asp Ile Leu  Pro Val Val
    1190                 1195                 1200

Thr Arg  Asn Leu Asn Ala Ile  Glu Ser Leu Trp Val  Gly Val Tyr
    1205                 1210                 1215

Arg Val  Gly Glu Gly Asn Trp  Thr Ser Leu Asp Gly  Gly Thr Phe
    1220                 1225                 1230

Lys Val  Tyr Gln Ile Phe Gly  Ser His Cys Thr Tyr  Val Ser Lys
    1235                 1240                 1245

Phe Ser  Thr Val Pro Val Ser  His His Glu Cys Ser  Phe Leu Lys
    1250                 1255                 1260

Pro Cys  Leu Cys Val Ser Gln  Arg Ser Asn Ser
    1265                 1270
```

<210> SEQ ID NO 145
<211> LENGTH: 2595
<212> TYPE: DNA
<213> ORGANISM: Artificial Sequence
<220> FEATURE:
<223> OTHER INFORMATION: gH-(SGGG)2-ferritin sequence

<400> SEQUENCE: 145

```
atgcagctcc tgtgcgtgtt ctgtctggtg ctgctgtggg aagtgggagc cgcttctctg      60

agtgaggtga agctgcacct ggacattgaa ggccacgcct cccattacac tatcccttgg     120

accgagctga tggctaaagt gccaggactg tctcctgagg ctctgtggcg ggaagctaat     180

gtgaccgagg atctggcctc tatgctgaac agatacaagc tgatctataa aaccagtggc     240

acactgggga ttgctctggc tgagccagtg gacatccccg ccgtgtcaga aggaagcatg     300

caggtggatg ctagtaaggt gcatccaggg gtgattagcg gactgaacag cccagcttgc     360

atgctgagcg ctcctctgga gaaacagctc ttctactata tcggcaccat gctgcctaat     420

acacggccac acagctacgt gttttatcag ctcagatgtc atctgtccta cgtggccctg     480

tctattaacg gggacaagtt ccagtataca ggagctatga cttccaaatt tctgatggga     540
```

```
acttacaagc gggtgaccga gaaaggcgat gaacacgtgc tgtctctggt gttcgggaag    600

acaaaagacc tgcccgatct gagaggaccc ttttcctacc cttctctgac tagtgcccag    660

tcaggcgact atagcctggt gatcgtgacc acattcgtgc actacgctaa cttccataat    720

tattttgtgc ccaatctgaa ggatatgttt tcccgggccg tgaccatgac agccgcttct    780

tacgctagat atgtgctgca gaagctggtg ctgctggaga tgaaaggcgg gtgccgggag    840

cctgaactgg acactgaaac cctgactacc atgttcgagg tgtccgtggc cttctttaaa    900

gtgggacacg ctgtgggaga gacaggaaac ggatgcgtgg acctgagatg gctggccaag    960

agcttctttg aactgaccgt gctgaaagat atcattggaa tctgttacgg cgccacagtg   1020

aaaggaatgc agagctatgg cctggagagg ctggccgcta tgctgatggc caccgtgaag   1080

atggaggaac tgggccacct gacaactgag aaacaggaat acgctctgag gctggctacc   1140

gtgggatacc caaaggccgg ggtgtattcc ggactgattg gaggcgccac atctgtgctg   1200

ctgagtgctt ataataggca cccactgttc cagcccctgc atacagtgat gcgcgagact   1260

ctgtttatcg ggtctcatgt ggtgctgcgg gaactgagac tgaatgtgac cacacaggga   1320

cccaacctgg ccctgtacca gctcctgagt actgccctgt gctcagctct ggagattgga   1380

gaagtgctga ggggactggc cctggggacc gagtcaggac tgttcagccc ttgttatctg   1440

tcactgaggt ttgacctgac tcgcgataag ctgctgagca tggccccaca ggaagctacc   1500

ctggaccagg ccgctgtgag caatgccgtg gatggattcc tgggcaggct gtccctggag   1560

agggaagacc gcgatgcctg gcacctgcca gcttacaagt gcgtggaccg cctggataaa   1620

gtgctgatga tcattcccct gatcaacgtg accttcatca ttagctccga cagggaagtg   1680

agaggcagcg ctctgtacga agcttccact acctatctgt ctagttcact gtttctgtca   1740

cctgtgatta tgaataagtg tagccaggga gctgtggctg gagagcccag acagatccca   1800

aagattcaga acttcacacg cactcagaaa agttgcatct tctgtggctt tgccctgctg   1860

tcatacgatg agaaagaagg gctggagaca actacctata ttacatctca ggaagtgcag   1920

aacagtatcc tgagctccaa ttacttcgac tttgataacc tgcacgtgca ttatctgctg   1980

ctgacaacta acggcaccgt gatggagatc gctggactgt acgaggaaag ggctcactct   2040

ggcggcggta gcggcggtgg ctccggagag agccaggtga ggcagcagtt cagcaaggac   2100

atcgagaagc tgctgaacga gcaggtgaac aaggagatgc agagcagcaa cctgtacatg   2160

agcatgagca gctggtgcta cacccacagc ctggacggcg ccggcctgtt cctgttcgac   2220

cacgccgccg aggagtacga gcacgccaag aagctgatca tcttcctgaa cgagaacaac   2280

gtgcccgtgc agctgaccag catcagcgcc cccgagcaca agttcgaggg cctgacccag   2340

atcttccaga aggcctacga gcacgagcag cacatcagcg agagcatcaa caacatcgtg   2400

gaccacgcca tcaagagcaa ggaccacgcc accttcaact tcctgcagtg gtacgtggcc   2460

gagcagcacg aggaggaggt gctgttcaag gacatcctgg acaagatcga gctgatcggc   2520

aacgagaacc acggcctgta cctggccgac cagtacgtga agggcatcgc caagagcagg   2580

aagagcggat cctag                                                    2595
```

<210> SEQ ID NO 146
<211> LENGTH: 864
<212> TYPE: PRT
<213> ORGANISM: Artificial Sequence
<220> FEATURE:
<223> OTHER INFORMATION: Amino acid sequence encoded by SEQ ID NO:146
(gH-(SGGG)2-ferritin sequence)

-continued

<400> SEQUENCE: 146

```
Met Gln Leu Leu Cys Val Phe Cys Leu Val Leu Leu Trp Glu Val Gly
1               5                   10                  15

Ala Ala Ser Leu Ser Glu Val Lys Leu His Leu Asp Ile Glu Gly His
            20                  25                  30

Ala Ser His Tyr Thr Ile Pro Trp Thr Glu Leu Met Ala Lys Val Pro
        35                  40                  45

Gly Leu Ser Pro Glu Ala Leu Trp Arg Glu Ala Asn Val Thr Glu Asp
    50                  55                  60

Leu Ala Ser Met Leu Asn Arg Tyr Lys Leu Ile Tyr Lys Thr Ser Gly
65                  70                  75                  80

Thr Leu Gly Ile Ala Leu Ala Glu Pro Val Asp Ile Pro Ala Val Ser
                85                  90                  95

Glu Gly Ser Met Gln Val Asp Ala Ser Lys Val His Pro Gly Val Ile
            100                 105                 110

Ser Gly Leu Asn Ser Pro Ala Cys Met Leu Ser Ala Pro Leu Glu Lys
        115                 120                 125

Gln Leu Phe Tyr Tyr Ile Gly Thr Met Leu Pro Asn Thr Arg Pro His
    130                 135                 140

Ser Tyr Val Phe Tyr Gln Leu Arg Cys His Leu Ser Tyr Val Ala Leu
145                 150                 155                 160

Ser Ile Asn Gly Asp Lys Phe Gln Tyr Thr Gly Ala Met Thr Ser Lys
                165                 170                 175

Phe Leu Met Gly Thr Tyr Lys Arg Val Thr Glu Lys Gly Asp Glu His
            180                 185                 190

Val Leu Ser Leu Val Phe Gly Lys Thr Lys Asp Leu Pro Asp Leu Arg
        195                 200                 205

Gly Pro Phe Ser Tyr Pro Ser Leu Thr Ser Ala Gln Ser Gly Asp Tyr
    210                 215                 220

Ser Leu Val Ile Val Thr Thr Phe Val His Tyr Ala Asn Phe His Asn
225                 230                 235                 240

Tyr Phe Val Pro Asn Leu Lys Asp Met Phe Ser Arg Ala Val Thr Met
                245                 250                 255

Thr Ala Ala Ser Tyr Ala Arg Tyr Val Leu Gln Lys Leu Val Leu Leu
            260                 265                 270

Glu Met Lys Gly Gly Cys Arg Glu Pro Glu Leu Asp Thr Glu Thr Leu
        275                 280                 285

Thr Thr Met Phe Glu Val Ser Val Ala Phe Phe Lys Val Gly His Ala
    290                 295                 300

Val Gly Glu Thr Gly Asn Gly Cys Val Asp Leu Arg Trp Leu Ala Lys
305                 310                 315                 320

Ser Phe Phe Glu Leu Thr Val Leu Lys Asp Ile Ile Gly Ile Cys Tyr
                325                 330                 335

Gly Ala Thr Val Lys Gly Met Gln Ser Tyr Gly Leu Glu Arg Leu Ala
            340                 345                 350

Ala Met Leu Met Ala Thr Val Lys Met Glu Glu Leu Gly His Leu Thr
        355                 360                 365

Thr Glu Lys Gln Glu Tyr Ala Leu Arg Leu Ala Thr Val Gly Tyr Pro
    370                 375                 380

Lys Ala Gly Val Tyr Ser Gly Leu Ile Gly Gly Ala Thr Ser Val Leu
385                 390                 395                 400

Leu Ser Ala Tyr Asn Arg His Pro Leu Phe Gln Pro Leu His Thr Val
```

-continued

```
                405                 410                 415

Met Arg Glu Thr Leu Phe Ile Gly Ser His Val Val Leu Arg Glu Leu
            420                 425                 430

Arg Leu Asn Val Thr Thr Gln Gly Pro Asn Leu Ala Leu Tyr Gln Leu
        435                 440                 445

Leu Ser Thr Ala Leu Cys Ser Ala Leu Glu Ile Gly Glu Val Leu Arg
    450                 455                 460

Gly Leu Ala Leu Gly Thr Glu Ser Gly Leu Phe Ser Pro Cys Tyr Leu
465                 470                 475                 480

Ser Leu Arg Phe Asp Leu Thr Arg Asp Lys Leu Leu Ser Met Ala Pro
                485                 490                 495

Gln Glu Ala Thr Leu Asp Gln Ala Ala Val Ser Asn Ala Val Asp Gly
            500                 505                 510

Phe Leu Gly Arg Leu Ser Leu Glu Arg Glu Asp Arg Asp Ala Trp His
        515                 520                 525

Leu Pro Ala Tyr Lys Cys Val Asp Arg Leu Asp Lys Val Leu Met Ile
    530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
                565                 570                 575

Leu Phe Leu Ser Pro Val Ile Met Asn Lys Cys Ser Gln Gly Ala Val
            580                 585                 590

Ala Gly Glu Pro Arg Gln Ile Pro Lys Ile Gln Asn Phe Thr Arg Thr
        595                 600                 605

Gln Lys Ser Cys Ile Phe Cys Gly Phe Ala Leu Leu Ser Tyr Asp Glu
    610                 615                 620

Lys Glu Gly Leu Glu Thr Thr Thr Tyr Ile Thr Ser Gln Glu Val Gln
625                 630                 635                 640

Asn Ser Ile Leu Ser Ser Asn Tyr Phe Asp Phe Asp Asn Leu His Val
                645                 650                 655

His Tyr Leu Leu Leu Thr Thr Asn Gly Thr Val Met Glu Ile Ala Gly
            660                 665                 670

Leu Tyr Glu Glu Arg Ala His Ser Gly Gly Gly Ser Gly Gly Gly Ser
        675                 680                 685

Gly Glu Ser Gln Val Arg Gln Gln Phe Ser Lys Asp Ile Glu Lys Leu
    690                 695                 700

Leu Asn Glu Gln Val Asn Lys Glu Met Gln Ser Ser Asn Leu Tyr Met
705                 710                 715                 720

Ser Met Ser Ser Trp Cys Tyr Thr His Ser Leu Asp Gly Ala Gly Leu
                725                 730                 735

Phe Leu Phe Asp His Ala Ala Glu Glu Tyr Glu His Ala Lys Lys Leu
            740                 745                 750

Ile Ile Phe Leu Asn Glu Asn Asn Val Pro Val Gln Leu Thr Ser Ile
        755                 760                 765

Ser Ala Pro Glu His Lys Phe Glu Gly Leu Thr Gln Ile Phe Gln Lys
    770                 775                 780

Ala Tyr Glu His Glu Gln His Ile Ser Glu Ser Ile Asn Asn Ile Val
785                 790                 795                 800

Asp His Ala Ile Lys Ser Lys Asp His Ala Thr Phe Asn Phe Leu Gln
                805                 810                 815

Trp Tyr Val Ala Glu Gln His Glu Glu Glu Val Leu Phe Lys Asp Ile
            820                 825                 830
```

-continued

```
Leu Asp Lys Ile Glu Leu Ile Gly Asn Glu Asn His Gly Leu Tyr Leu
        835                 840                 845

Ala Asp Gln Tyr Val Lys Gly Ile Ala Lys Ser Arg Lys Ser Gly Ser
    850                 855                 860
```

EPSTEIN-BARR VIRUS VACCINES

CROSS REFERENCE TO RELATED APPLICATIONS

This application is a national stage application under 35 U.S.C. 371 and claims the benefit of PCT Application No. PCT/US2014/060142 having an international filing date of Oct. 10, 2014, which designated the United States, which PCT application claimed the benefit of U.S. Provisional Application No. 61/889,840 filed October 2013, and U.S. Provisional Application No. 61/921,284 filed Dec. 27, 2013, the disclosure of each of which are incorporated herein by reference.

REFERENCE TO SEQUENCE LISTING

This application contains a Sequence Listing submitted as an electronic text file named "6137NIAID-34-PROV_Sequence_Listing _ST25.txt", having a size in bytes of 412 KB, and created on Oct. 11, 2013. The information contained in this electronic file is hereby incorporated by reference in its entirety pursuant to 37 CFR § 1.52(e)(5).

SUMMARY OF THE INVENTION

The present invention provides novel, nanoparticle-based vaccines for Epstein-Barr virus that are easily manufactured, potent, and which elicit neutralizing antibodies to Epstein-Barr virus. In particular, the present invention provides novel Epstein-Barr virus protein-ferritin nanoparticle (np) vaccines. Such nanoparticles comprise fusion proteins, each of which comprises a monomeric subunit of a self-assembly protein, such as ferritin, joined to an immunogenic portion of an Epstein-Barr virus envelope protein. Because such nanoparticles display Epstein-Barr virus proteins on their surface, they can be used to vaccinate an individual against Epstein-Barr virus.

One embodiment of the present invention is a nanoparticle that includes a first fusion protein that is joined to at least one immunogenic portion from a first Epstein-Barr virus envelope protein that is selected from the group consisting of gp350, gH, gL, gp42, gB and BMRF2. The first fusion protein includes at least 25 contiguous amino acids from a monomeric subunit protein capable of self-assembling into a nanoparticle. Further, the nanoparticle expresses the at least one immunogenic portion on its surface.

The monomeric subunit of the self-assembly protein can be selected from a monomeric ferritin subunit protein, a monomeric encapsulin protein, a monomeric 03-33 protein, a monomeric SOR protein, a monomeric LS protein and a monomeric PDC protein. In the embodiment of a monomeric ferritin subunit protein, it can be selected from a bacterial, plant, algal, insect, fungal, and mammalian ferritin. More specifically, the monomeric subunit protein can be selected from a monomeric subunit of a *Helicobacter pylori* ferritin protein, a monomeric subunit of a *Escherichia coli* protein and a monomeric subunit of a bullfrog ferritin protein. Also, the monomeric ferritin subunit protein can be a hybrid protein that includes at least a portion of a bullfrog ferritin protein joined to at least a portion of a ferritin protein that is selected from a *Helicobacter pylori* ferritin protein and *Escherichia coli* ferritin protein.

The monomeric subunit self-assembling protein can include at least 25 contiguous amino acids of, be at least about 80% identical to or comprise an amino acid sequence selected from SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29.

The first Epstein-Barr virus envelope protein can be from Epstein-Barr virus type 1 or Epstein-Barr virus type 2. Also, the at least one immunogenic portion from the first Epstein-Barr virus envelope protein can include at least 100 amino acids from an amino acid sequence selected from SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132, SEQ ID NO:134 and SEQ ID NO:136. Further, the at least one immunogenic portion can include at least one domain selected from EBV gp350 Domain I, EBV gp350 Domain II and EBV gp350 Domain III. In addition, the at least one immunogenic portion can include the amino acid sequences of EBV gp350 Domain I and Domain II. Further, the at least one immunogenic portion can include the EBV gp350 CR2-binding site.

In this embodiment, the first EBV envelope protein can include an amino acid sequence that is at least about 80% identical to, is identical to or can elicit an immune response to an amino acid sequence selected from SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132, SEQ ID NO:134 and SEQ ID NO:136.

The first fusion protein can comprise a linker sequence.

The nanoparticle can elicit an immune response against an Epstein-Barr virus, including a strain of Epstein-Barr virus that is heterologous to the strain Epstein-Barr virus from which the Epstein-Barr virus envelope protein was obtained, as well as to an Epstein-Barr virus that is antigenically divergent from the Epstein-Barr virus from which the Epstein-Barr virus envelope protein was obtained.

The first fusion protein can include an amino acid sequence that is at least about 80% identical to or is identical to a sequence selected from SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:134, SEQ ID NO:142, SEQ ID NO:144 and SEQ ID NO:146, wherein the nanoparticle elicits an immune response against an Epstein-Barr virus.

The nanoparticle can further include a second fusion protein that includes at least one immunogenic portion from a second Epstein-Barr virus envelope protein that is selected from gp350, gH, gL, gp42, gB and BMRF2. In this embodiment, the first and second Epstein-Barr virus envelope proteins are not the same and the nanoparticle expresses the at least one immunogenic portion from a second fusion protein on its surface.

A further embodiment of the present invention is a vaccine composition that includes any one of the foregoing described nanoparticles. The vaccine composition can further include at least one additional nanoparticle that includes a second fusion protein with at least 25 contiguous amino acids from a monomeric subunit protein that can self-assemble into a nanoparticle and that is joined to at least one immunogenic portion from a second Epstein-Barr envelope protein that can be gp350, gH, gL, gp42, gB and BMRF2. In this embodiment, the at least one immunogenic portion of the second fusion protein is from an Epstein-Barr virus envelope protein from a different strain of Epstein-Barr virus than the first Epstein-Barr virus envelope protein and the nanoparticle expresses the at least one immunogenic portion of the second fusion portion on its surface.

A further embodiment of the present invention is a method to produce a vaccine against Epstein-Barr virus. The method includes expressing a fusion protein that includes at least 25 contiguous amino acids from a monomeric subunit protein that can self-assemble into a nanoparticle and that is joined to at least one immunogenic portion from a first Epstein-Barr virus envelope protein selected from gp350, gH, gL, gp42, gB and BMRF2. The step of expressing is conducted under conditions such that the fusion protein forms a nanoparticle displaying the at least one immunogenic portion of an Epstein-Barr virus envelope protein on its surface. The method further includes recovering the nanoparticle.

A further embodiment of the present invention is a method to vaccinate an individual against Epstein-Barr virus that includes administering a nanoparticle to an individual such that the nanoparticle elicits an immune response against Epstein-Barr virus. The nanoparticle includes a fusion protein that includes at least 25 contiguous amino acids from a monomeric subunit protein that can self-assemble into a nanoparticle and that is joined to at least one immunogenic portion of a first Epstein-Barr virus protein selected from gp350, gH, gL, gp42, gB and BMRF2. In this embodiment, the nanoparticle displays the at least one immunogenic portion from an Epstein-Barr virus envelope protein on its surface. In this method to vaccinate, the nanoparticle can elicit an immune response to an Epstein-Barr virus strain that is heterologous to the strain of Epstein-Barr virus from which the envelope protein was obtained, or to an Epstein-Barr virus that is antigenically divergent from the Epstein-Barr virus from which the envelope protein was obtained.

The method to vaccinate can include administering to the individual a first vaccine composition and then at a later time administering a second vaccine composition that includes a nanoparticle that comprises a fusion protein comprising at least 25 contiguous amino acids from a monomeric subunit protein that can self-assemble into a nanoparticle and that is joined to at least one immunogenic portion of the first Epstein-Barr virus envelope protein selected from gp350, gH, gL, gp42, gB and BMRF2. In this embodiment, the nanoparticle displays the at least one immunogenic portion of an Epstein-Barr virus envelope protein on its surface. In this embodiment, the fusion protein can include an amino acid sequence that is at least about 80% identical to or is identical to a sequence that is selected from SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101 SEQ ID NO:104, SEQ ID NO:128, SEQ ID NO:134, SEQ ID NO:142, SEQ ID NO:144 and SEQ ID NO:146.

In this embodiment, the second vaccine composition may be administered between ten days and four weeks following administration of the first vaccine composition. In this embodiment, the second vaccine composition may be administered between ten days and two months following administration of the first vaccine composition. In one embodiment, a third vaccine composition may be administered six months after administration of the first vaccine composition.

A further embodiment of the present invention is a fusion protein that includes at least 25 contiguous amino acids from a monomeric subunit protein that can self-assemble into a nanoparticle and that is joined to at least one immunogenic portion from an Epstein-Barr virus envelope protein selected from gp350, gH, gL, gp42, gB and BMRF2. In this embodiment, the monomeric subunit can be selected from a monomeric ferritin subunit protein, a monomeric encapsulin protein, a monomeric 03-33 protein, a monomeric SOR protein, a monomeric LS protein and a monomeric PDC protein. The monomeric ferritin subunit protein can be selected from a bacterial, plant, algal, insect, fungal and mammalian ferritin. Further, the monomeric ferritin subunit protein can be selected from a monomeric subunit of a *Helicobacter pylori* ferritin protein, a monomeric subunit of an *Escherichia coli* ferritin protein and a monomeric subunit of a bullfrog ferritin protein. Further, the monomeric ferritin subunit protein can be a hybrid protein that includes at least a portion of a bullfrog ferritin protein joined to at least a portion of a *Helicobacter pylori* ferritin protein or an *Escherichia coli* ferritin protein. Still further, the monomeric ferritin subunit protein can comprise an amino acid sequence that is at least about 80% identical to or is identical to or comprises at least 25 contiguous amino acids selected from SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29, wherein the fusion protein can self-assemble into nanoparticles. The fusion protein can be an Epstein-Barr virus envelope protein type 1 or type 2.

The at least one immunogenic portion of the fusion protein can comprise at least 100 amino acids from an amino acid sequence selected from SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136. The at least one immunogenic portion can include at least one domain selected from EBV gp350 Domain I, EBV gp350 Domain II and EBV gp350 Domain III. Further, the at least one immunogenic portion can include the amino acid sequences of EBV gp350 Domain I and Domain II. Still further, the at least one immunogenic portion can include the EBV gp350 CR2-binding site.

The EBV envelope protein can include an amino acid sequence at least about 80% identical to or is identical to an amino acid sequence selected from SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136. The EBV envelope protein of the fusion protein can be capable of eliciting an immune response to the protein that includes an amino acid sequence selected from SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136.

The fusion protein can also include a linker sequence.

Further embodiments of the present invention include nucleic acid molecules that encode the foregoing described fusion proteins. The nucleic acid molecule can be functionally linked to a promoter.

A still further embodiment of the present invention is a recombinant cell that includes the foregoing nucleic acid molecule.

A further embodiment of the present invention is a recombinant virus that includes the foregoing described nucleic acid molecule.

BACKGROUND

Epstein-Barr virus (EBV), also referred to as human herpesvirus 4 (HHV-4), is the principle etiological agent of infectious mononucleosis (IM) and is also associated with several human cancers, with more than 300,000 people being affected each year worldwide. The World Health Organization estimates that 95% of adults worldwide have been infected with EBV and are carriers of the virus. For the majority of individuals, EBV does not cause any symptoms and is indistinguishable from common, mild childhood illnesses. Currently, there is no vaccine for EBV. However, prevention of IM and EBV-associated malignancies through vaccination would have a substantial public health and economic benefit.

EBV has a linear, double-stranded DNA genome comprising approximately 192 kilobases (KB) of DNA, surrounded by a protein capsid. The capsid is surrounded by a protein tegument, which in turn is surrounded by an envelope. The EBV envelope contains several proteins, including glycoprotein gp350, gH, gB, gM, gp42, gL, gp78, gp150 and gN. The most abundant envelope glycoprotein is 350/220 (gp350), which binds complement receptor 2 (CR2 or CD21) enabling EBV infection of B cells, while glycoproteins gH and gp42 bind integrins and human leukocyte antigen class II molecules, respectively. Antibodies directed toward the putative CR2-binding site (CR2BS) on gp350 have been shown to potently inhibit EBV infections of B cells, and thus vaccine efforts against EBV have been largely focused on gp350.

In addition to infecting B cells, EBV also infects epithelial cells in the oropharynx where it is thought to spread to B cells. Current data suggests that infection of epithelial cells by EBV is initiated by attachment of EBV BMRF2 protein to epithelial cells followed by binding of EBV gH/gL to integrins, which serve as receptors for the virus on epithelial cells. Antibodies to gH/gL in human plasma blocks EBV infection of epithelial cells (Bu and Cohen, unpublished data) suggesting that a vaccine capable of inducing antibodies to EBV gH/gL may help to prevent infection or human disease due to EBV.

While work on EBV vaccines has continued, to date there is no efficacious EBV vaccine. For example, a recently completed phase 2 clinical trial of an adjuvanted recombinant gp350 protein vaccine showed that the vaccine did not protect against EBV infection but did reduce the incidence of IM by 78% (Sokal, E. M., et al. J Infect Dis. 196:1749-53, 2007). Thus, there remains a need for an efficacious Epstein-Barr virus vaccine that provides robust protection against EBV. The present invention meets this need by providing a novel ENV-SA protein-based nanoparticle (ENV-SA np) vaccine that is easily manufactured, potent, and elicits neutralizing antibodies against EBV.

and gp42 (B) in immune sera at week 5 were measured by a luciferase immunoprecipitation system (LIPS) assay. LIPS assay was preformed as previously described (Sashihara J., et al., Virology. 391, 249-256, 2009). Bar indicates the median with range. *, $p<0.05$; , $p<0.01$; *, $p<0.001$; ns, no significant difference.

Figure 16:
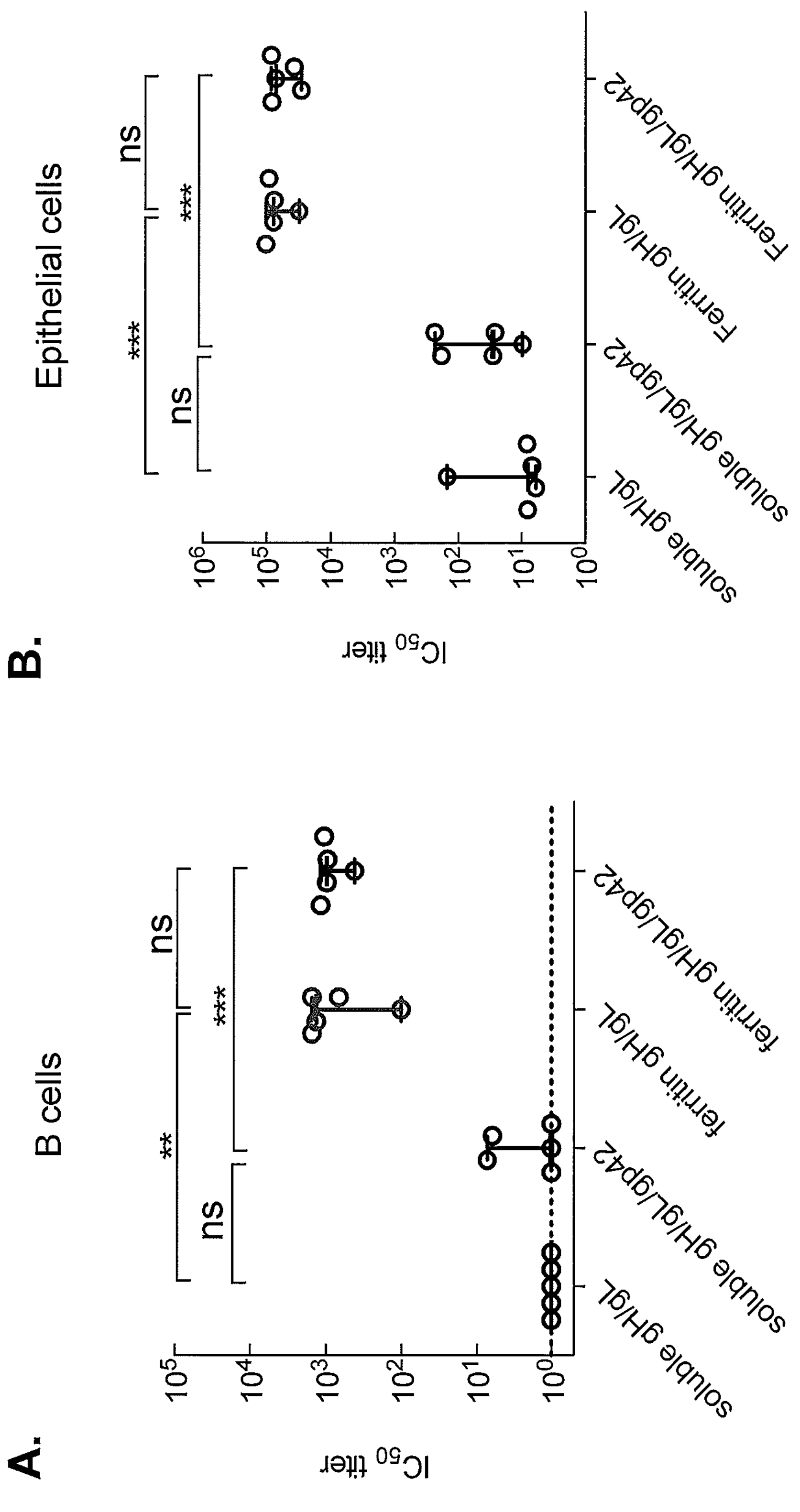

FIG. 16. Comparison of neutralization of soluble gH/gL, soluble gH/gL/gp42, ferritin-based gH/gL nanoparticle and ferritin-based gH/gL/gp42 nanoparticles in B cells (A) and epithelial cells (B). Groups of BALB/c mice (n=5) were immunized with 0.5 μg indicated proteins with a Ribi adjuvant at week 0 and 3. (A) The neutralization assay was based on infection of B cells with GFP reporter virus (Sashihara J., et al., Virology. 391, 249-256, 2009) and the titer is shown as the dilution of serum capable to inhibit virus infection by 50% ($IC_{50}$). (B) The neutralization of EBV infection of epithelial cells was performed by incubation of mouse sera serially diluted in a 2-fold steps with GFP reporter virus for 2 hours. The mixture was added to SVK-CR2 cells (an epithelial cell line that expresses CR2, a receptor for EBV) in a 96-well plate and incubated for 3 days at 37° C. Cells were washed with 1×PBS, trypsinized, and fixed in 2% paraformaldehyde in PBS.GFP positive cells were quantified and the titer is shown as the dilution of serum able to inhibit virus infection by 50% ($IC_{50}$). Each dot represents an individual mouse. Bar indicates the median with range. *, $p<0.05$; , $p<0.01$; *, $p<0.001$, ns, no significant difference.

Figure 17:
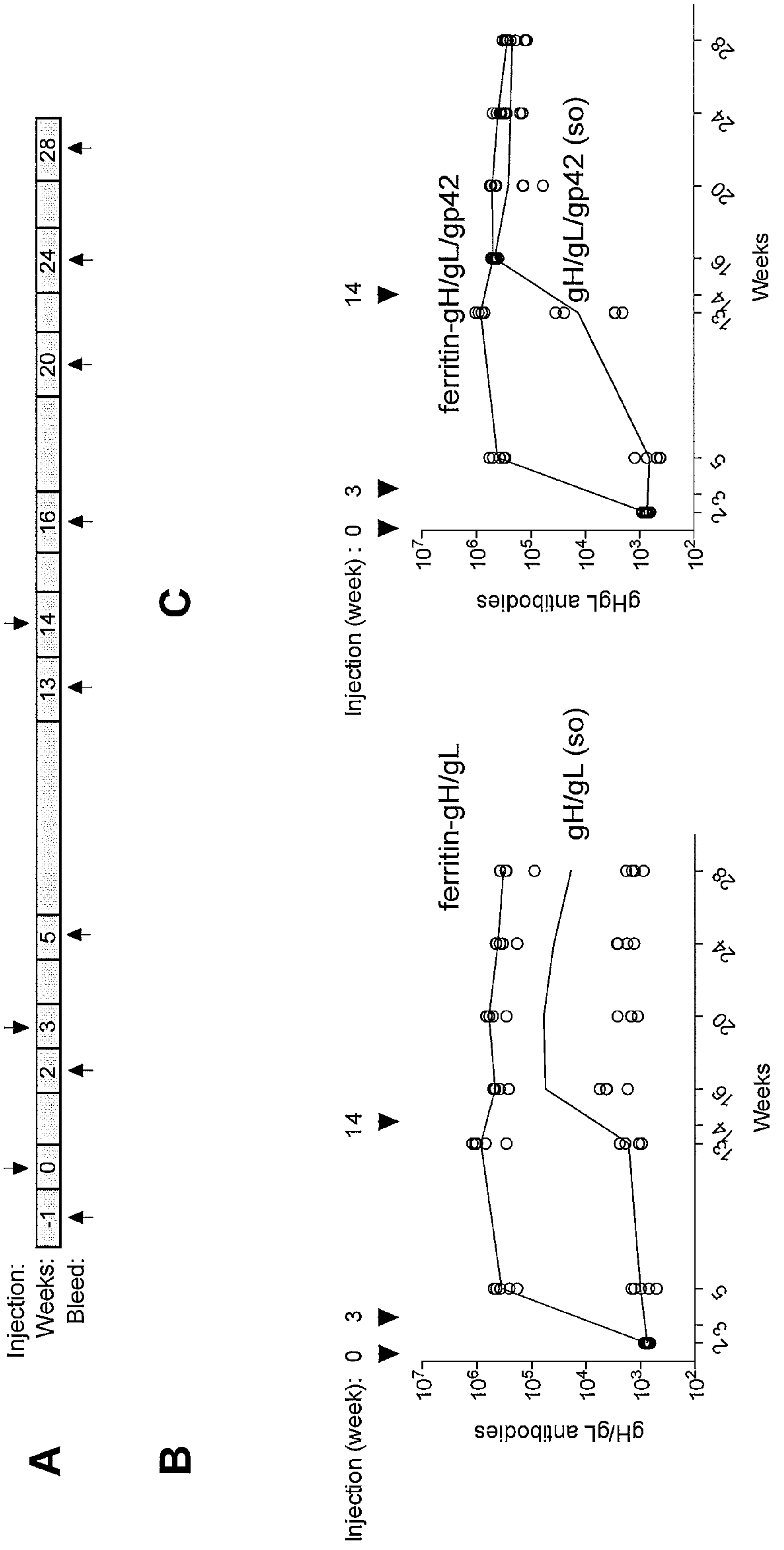

FIG. 17. (A) Immunization and sampling schedule. Comparison of kinetics of gH/gL antibody titers in sera from mice immunized with soluble gH/gL or gH/gL ferritin-based-nanoparticles (B) and soluble gH/gL/gp42 or gH/gL/gp42 ferritin-based-nanoparticles (C).

Figure 18:
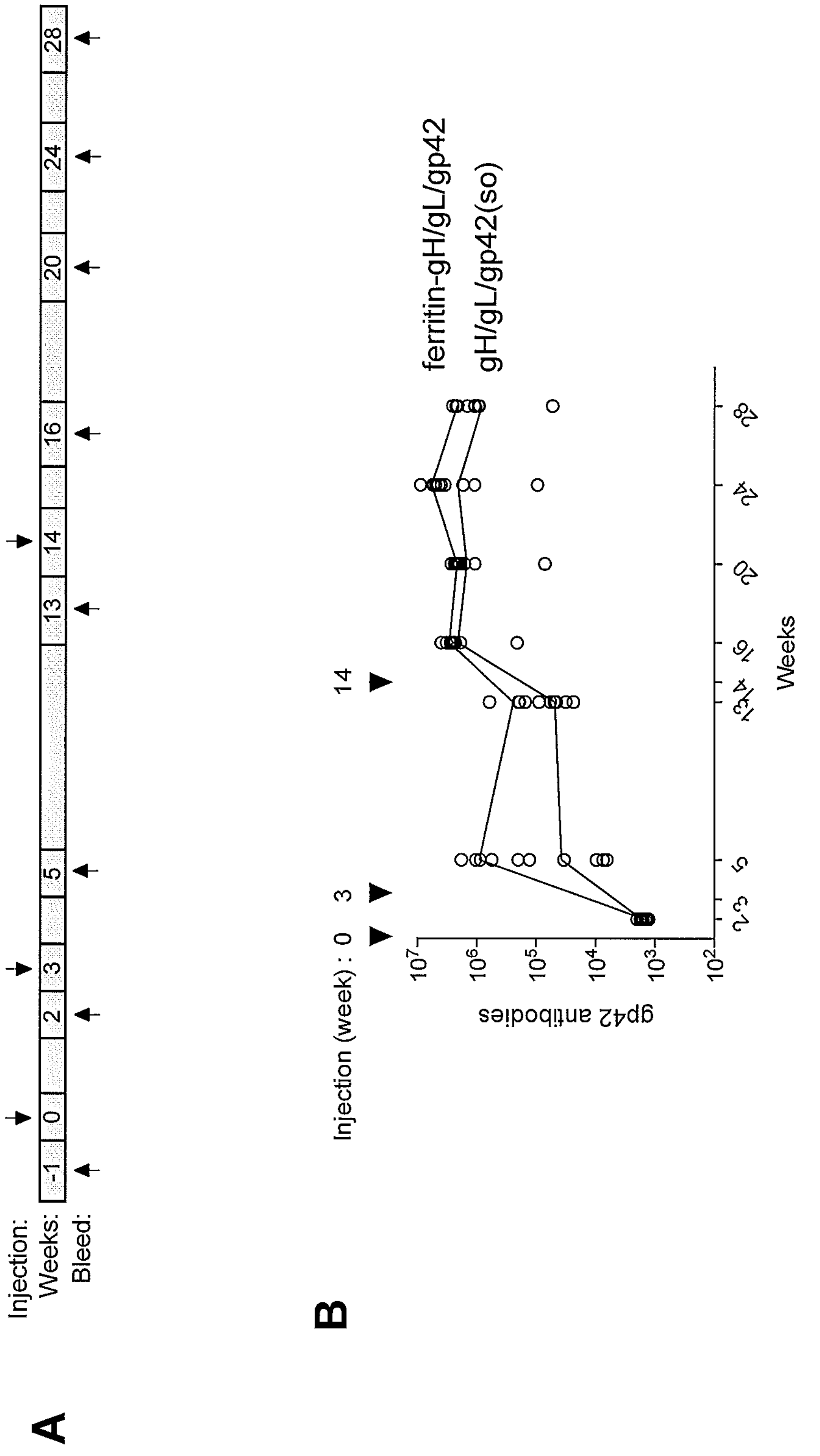

FIG. 18. (A) Immunization and sampling schedule. (B) Comparison of kinetics of gp42 antibody titers in sera from mice immunized with either soluble gH/gL/gp42 or gH/gL/gp42 ferritin-based-nanoparticles.

Figure 19:
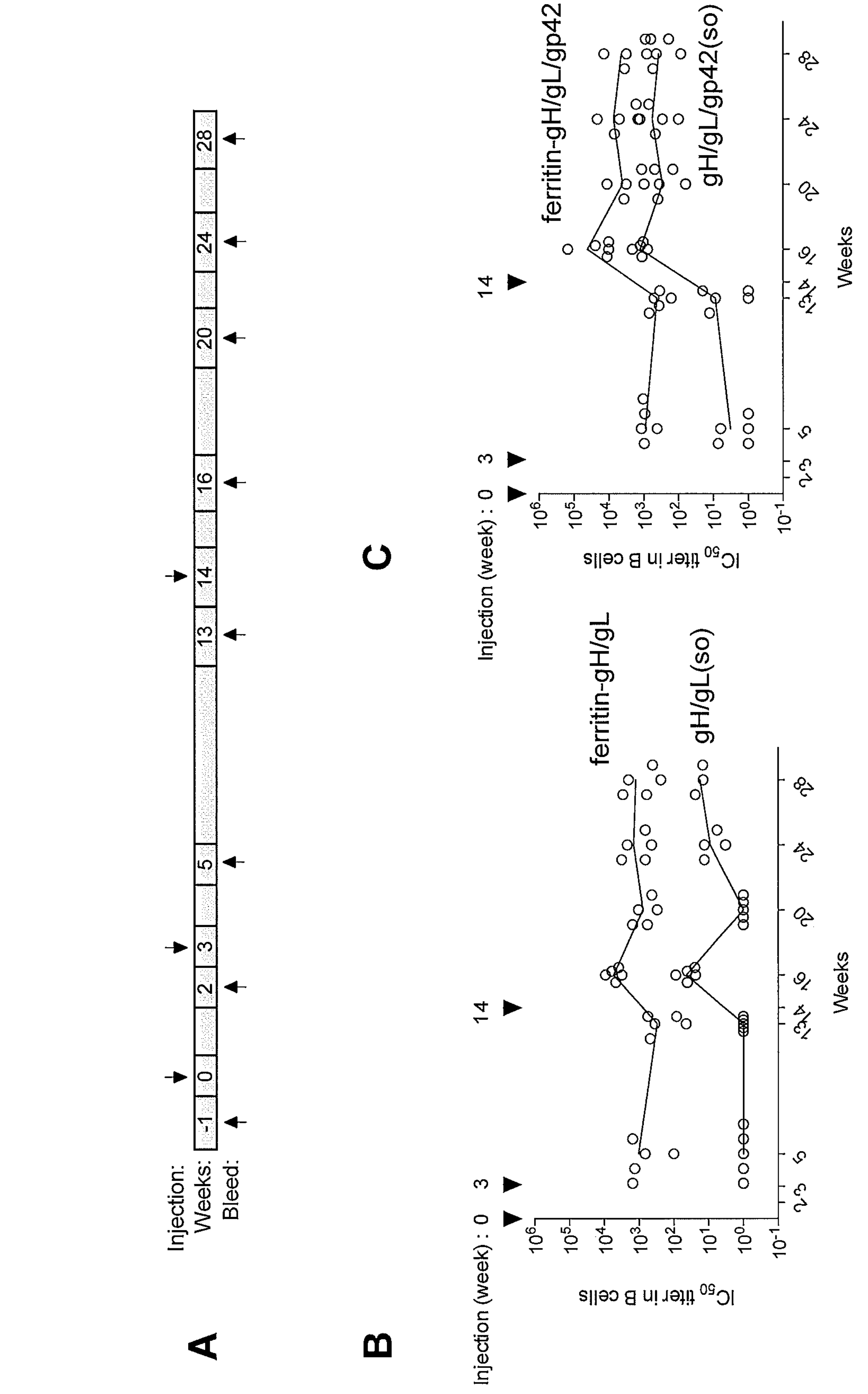

FIG. 19. (A) Immunization and sampling schedule. Comparison of kinetics of B cell neutralizing antibody titers in mice immunized with soluble gH/gL or gH/gL ferritin-based-nanoparticles (B) and soluble gH/gL/gp42 or gH/gL/gp42 ferritin-based-nanoparticles (C).

Figure 20:
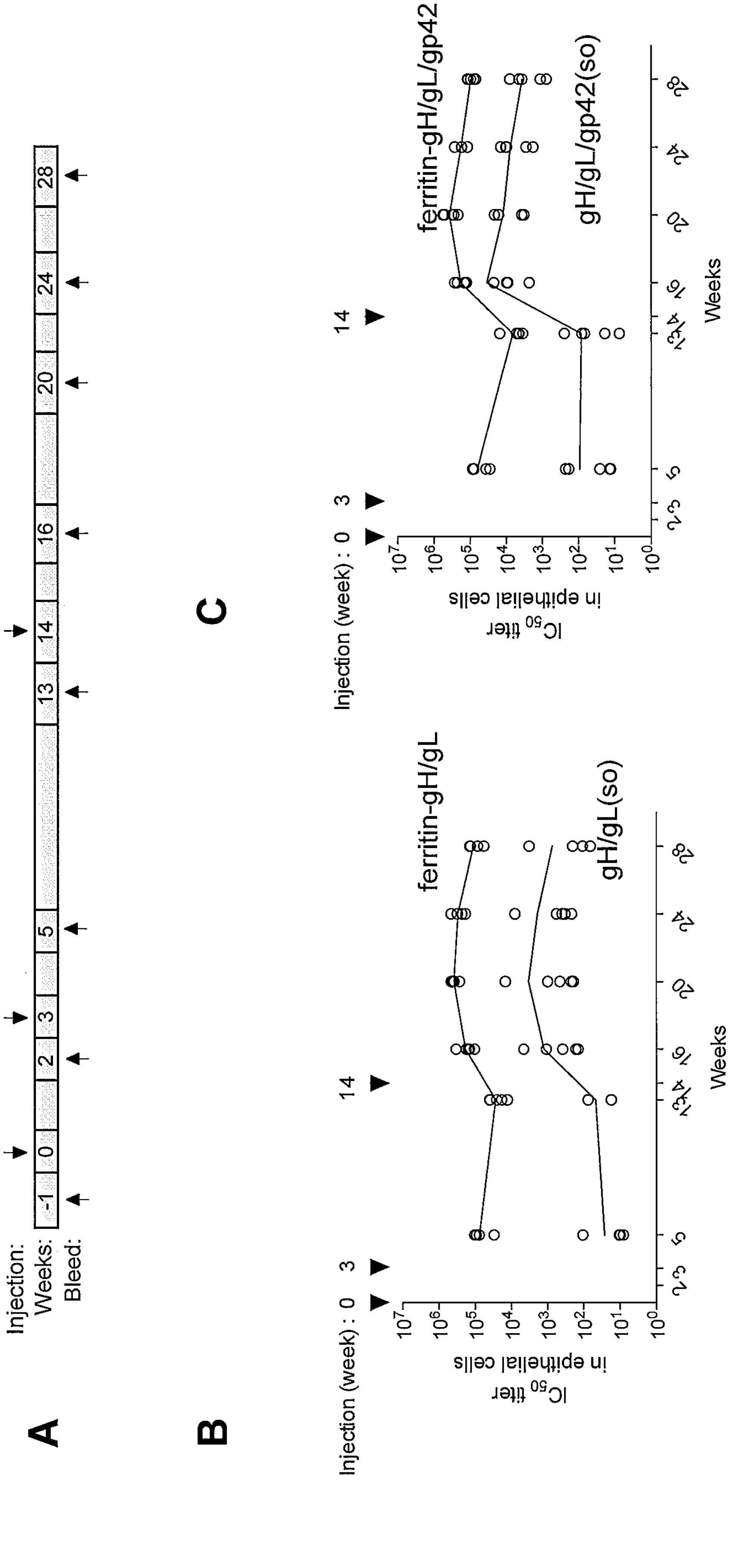

FIG. 20. (A) Immunization and sampling schedule. Comparison of kinetics of epithelial cell neutralizing antibody titers in mice immunized with soluble gH/gL or gH/gL ferritin-based-nanoparticles (B) and soluble gH/gL/gp42 or gH/gL/gp42 ferritin-based-nanoparticles (C).

Figure 21:
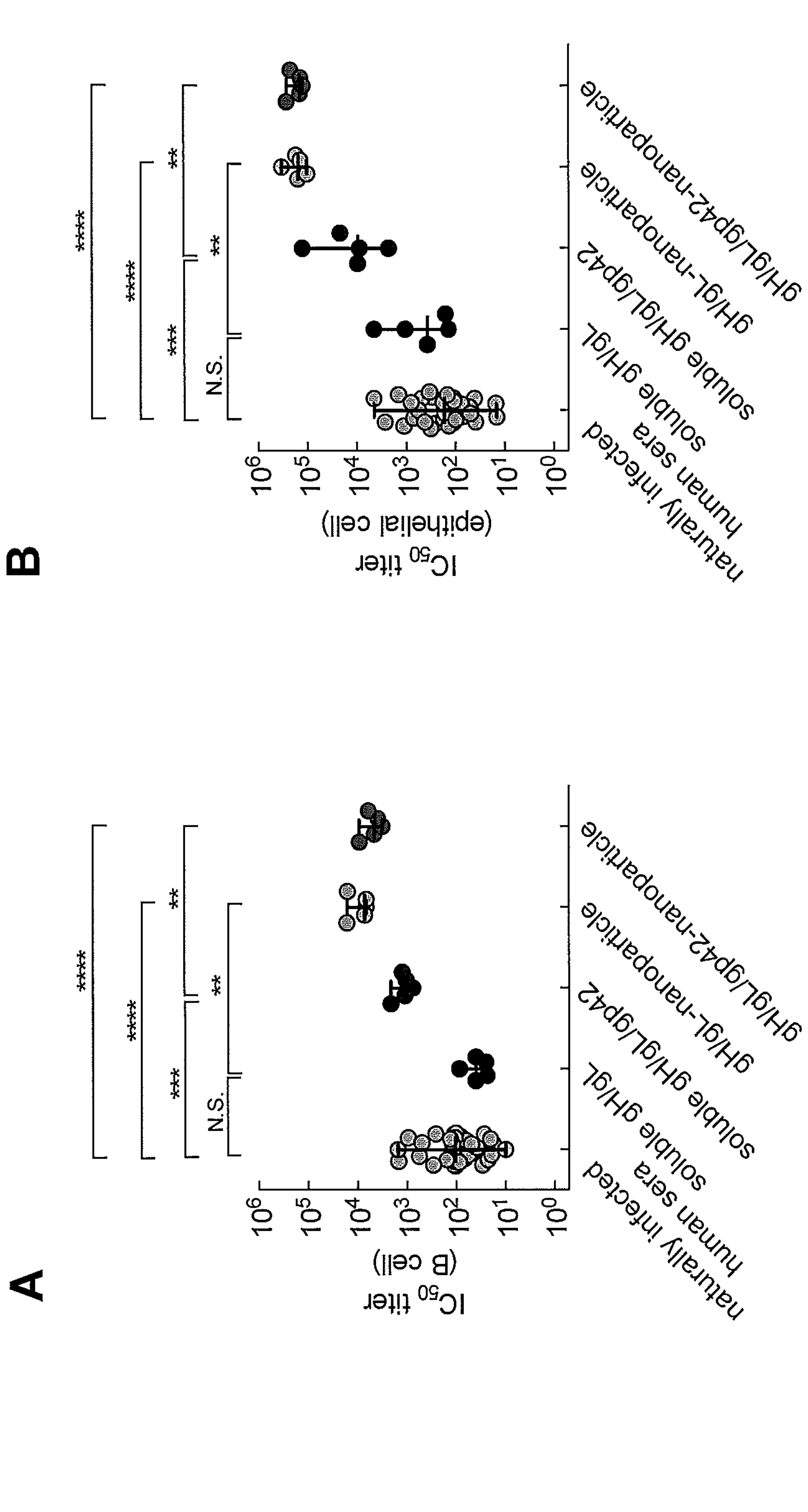

FIG. 21. (A) B cell neutralizing antibody and (B) epithelial cell neutralizing antibody titers after the 3rd dose in sera of mice immunized with soluble proteins or ferritin-based-nanoparticles compared to sera from naturally infected humans. Each dot represents one individual. The median titers with the range are plotted. N. S. indicates that the difference was not statistically significant. , $p<0.01$, *, $p<0.001$, and ****, $p<0.0001$.

Figure 22:
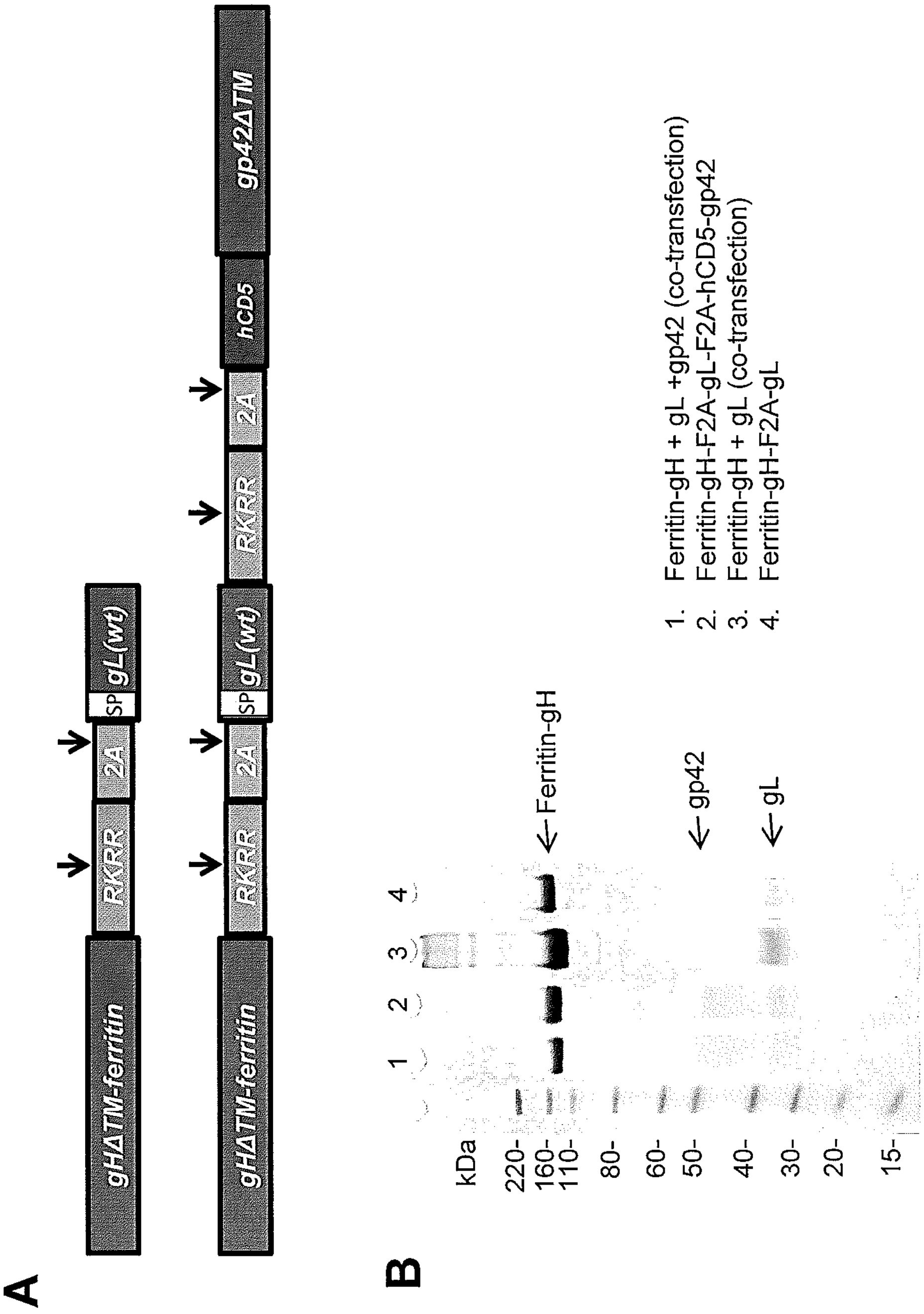

FIG. 22. (A) Design of single polypeptides expressing either gH/gL-nanoparticles or gH/gL/gp42-nanoparticles. (B) SDS-PAGE analysis of purified gH/gL nanoparticles and gH/gL/gp42 nanoparticles by size exclusion chromatography (B). Lanes show proteins purified from cells co-transfected with plasmids expressing individual proteins (cotransfection) or one plasmid expressing a single polypeptide that is spontaneously cleaved inside the cell.

Figure 23:
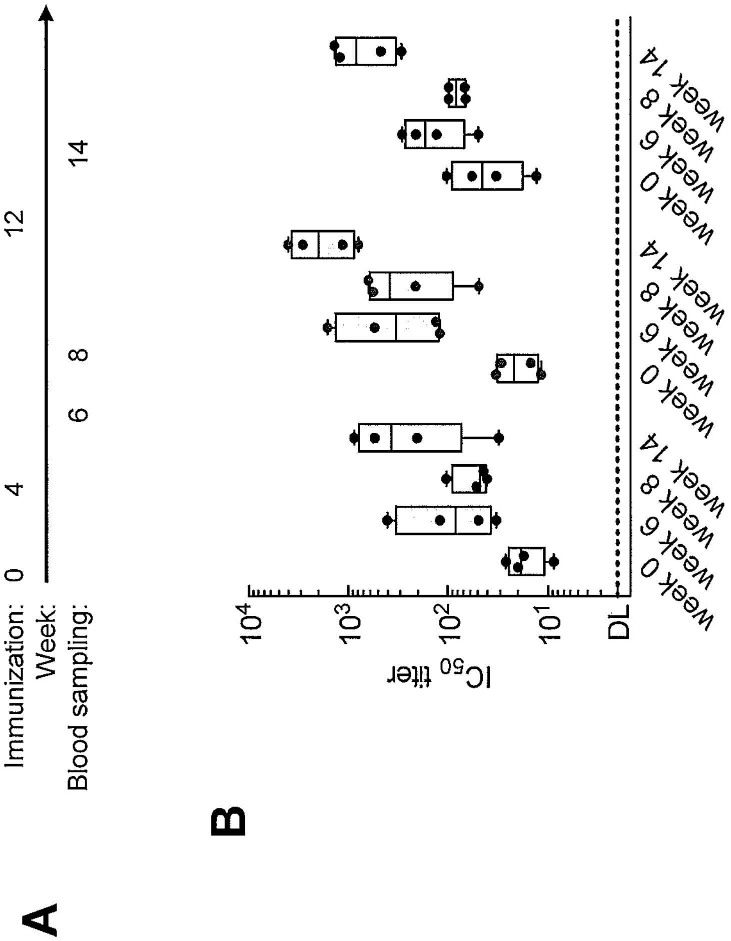

FIG. 23. Immunogenicity of EBV gp350-nanoparticles in cynomolgus monkeys. (A) Immunization schedule. (B) Titer of neutralizing virus in plasma from monkeys immunized with 50 μg of soluble gp350 ectodomain protein (left four bars), 25 μg of gp350 D123-ferritin (center four bars) or 25 μg of gp350 D123-encapsulin (right four bars) using the Sigma Adjuvant System.

Figure 24:
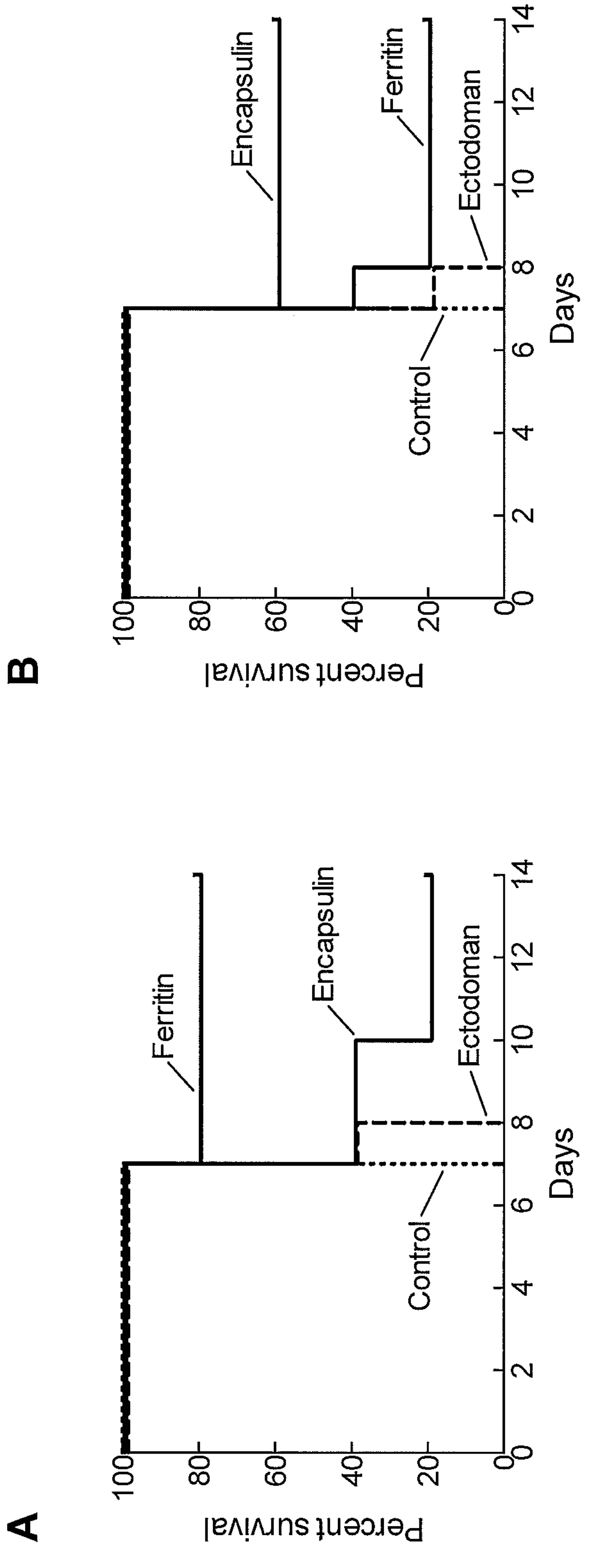

FIG. 24. Survival curve for EBV gp350 immunized mice after challenge with recombinant vaccinia virus expressing EBV gp350. Mice were either not immunized (control) or immunized 3 times with 0.5 ug (left) or 5.0 μg (right) of gp350 ectodomain, gp350 D123-ferritin, or gp350 D123-encapsulin. Five mice were immunized in each group.

Figure 25:
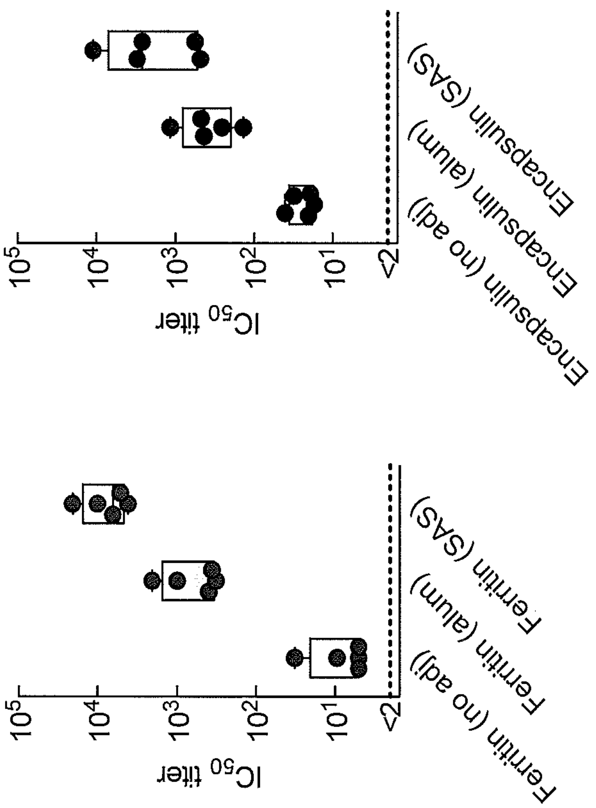

FIG. 25. Immunogenicity of EBV gp350-nanoparticles with no adjuvant, aluminum phosphate gel (alum), or Sigma Adjuvant System (SAS) adjuvant. Mice were immunized with 5 μg of gp350 D123-ferritin (left) or gp350 D123-encapsulin (right) at weeks 0, 4 and 16. Blood samples were collected 2 weeks after the final immunization and virus neutralization titers were measured.

DETAILED DESCRIPTION OF THE INVENTION

The present invention relates to a novel vaccine for Epstein-Barr virus (EBV). More specifically, the present invention relates to novel fusion proteins comprising EBV envelope proteins, wherein the fusion proteins self-assemble into nanoparticles that display immunogenic portions of the EBV envelope proteins on their surface. Such nanoparticles are useful for vaccinating individuals against EBV. Accordingly, the present invention also relates to fusion proteins for producing such nanoparticles and nucleic acid molecules encoding such proteins. Additionally, the present invention relates to, methods of producing nanoparticles of the present invention, and methods of using such nanoparticles to vaccinate individuals against EBV.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly the terms "comprising", "including" and "having" can be used interchangeably. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In addition to the above, unless specifically defined otherwise, the following terms and phrases, which are common to the various embodiments disclosed herein, are defined as follows:

As used herein, the term immunogenic refers to the ability of a specific protein, or a specific region thereof, to elicit an immune response to the specific protein, or to proteins comprising an amino acid sequence having a high degree of identity with the specific protein. According to the present invention, two proteins having a high degree of identity have amino acid sequences at least 80% identical, at least 85% identical, at least 87% identical, at least 90% identical, at least 92% identical, at least 94% identical, at least 96% identical, at least 98% identical or at least 99% identical.

As used herein, an immune response to a vaccine, or nanoparticle, of the present invention is the development in a subject of a humoral and/or a cellular immune response to an EBV envelope protein present in the vaccine. For purposes of the present invention, a "humoral immune response" refers to an immune response mediated by antibody molecules, including secretory (IgA) or IgG molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A cellular immune response also refers to the production of cytokines, chemokines and other such molecules produced by activated T-cells and/or other white blood cells, including those derived from CD4+ and CD8+T-cells.

Thus, an immunological response may be one that stimulates CTLs, and/or the production or activation of helper T-cells. The production of chemokines and/or cytokines may also be stimulated. The vaccine may also elicit an antibody-mediated immune response. Hence, an immunological response may include one or more of the following effects: the production of antibodies (e.g., IgA or IgG) by B-cells; and/or the activation of suppressor, cytotoxic, or helper T-cells and/or T-cells directed specifically to a protein present in the vaccine. These responses may serve to neutralize infectivity, and/or mediate antibody-complement, or antibody dependent cell cytotoxicity (ADCC) to provide protection to an immunized individual. Such responses can be determined using standard immunoassays and neutralization assays, well known in the art.

According to the present invention all nomenclature used to describe EBV, and components thereof, is that commonly used by those skilled in the art. Thus, EBV (or HHV-4) refers to all Epstein-Barr viruses including, but not limited to, EBV Type I, EBV Type II, EBV strain B95-8, EBV strain Cao and EBV strain RAJI. A TYPE of EBV refers to either a TYPE I EBV or a TYPE II EBV. Methods of classifying Epstein-Barr viruses are known to those skilled in the art.

As used herein, neutralizing antibodies are antibodies that prevent EBV from infecting a cell, completing one round of replication or establishing latency. As defined herein, one round of replication refers the life cycle of the virus, starting with attachment of the virus to a host cell and ending with budding of newly formed virus from the host cell. This life cycle includes, but is not limited to, the steps of attaching to a cell, entering a cell, production of viral proteins, formation of new viral particles and budding of viral particles from the host cell membrane.

As used herein, broadly neutralizing antibodies are antibodies that neutralize more than one type and/or strain of EBV. For example, broadly neutralizing antibodies elicited against an envelope protein from a Type I EBV may neutralize a Type II virus.

As used herein, an EBV envelope protein refers to a full-length EBV envelope protein or any portion thereof, which is capable of eliciting an immune response. An epitope of a full-length EBV envelope protein refers to a portion of such protein that can elicit a neutralizing antibody response against the homologous EBV strain, i.e., a strain from which the EBV envelope protein is derived. In some embodiments, such an epitope can also elicit a neutralizing antibody response against a heterologous strain of EBV, i.e., a strain having an envelope protein that is not identical to the envelope protein of the immunogen.

As used herein, a variant refers to a protein, or nucleic acid molecule, the sequence of which is similar, but not identical to, a reference sequence, wherein the activity of the variant protein (or the protein encoded by the variant nucleic acid molecule) is not significantly altered. These variations in sequence can be naturally occurring variations or they can be engineered through the use of genetic engineering technique know to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp. 9.31-9.57), or in Current Protocols in Molecular Biology, John Wiley & Sons, N.Y. (1989), 6.3.1-6.3.6, both of which are incorporated herein by reference in their entirety.

With regard to variants, any type of alteration in the amino acid, or nucleic acid, sequence is permissible so long as the resulting variant protein retains the ability to elicit neutralizing antibodies against an Epstein-Barr virus. Examples of such variations include, but are not limited to, deletions, insertions, substitutions and combinations thereof. For example, with regard to proteins, it is well understood by those skilled in the art that one or more (e.g., 2, 3, 4, 5, 6, 7, 8, 9 or 10), amino acids can often be removed from the amino and/or carboxy terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein.

As noted, variant proteins of the present invention can contain amino acid substitutions relative to the proteins disclosed herein. Any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

Naturally occurring residues may be divided into classes based on common side chain properties:

1) hydrophobic: Met, Ala, Val, Leu, Ile;
2) neutral hydrophilic: Asn, Gln, Cys, Ser, Thr;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class.

In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6);

histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological invention, as in the present case. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Desired amino acid substitutions (whether conservative or non-conservative) can be determined by those skilled in the art at the time such substitutions are desired. For example, amino acid substitutions can be used to identify important residues of the EBV envelope protein or the monomeric subunit protein, or to increase or decrease the immunogenicity, solubility or stability of the proteins described herein. Exemplary amino acid substitutions are shown below in Table 1.

TABLE 1

Amino Acid Substitutions

| Original Amino Acid | Exemplary Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |

TABLE 1-continued

Amino Acid Substitutions

| Original Amino Acid | Exemplary Substitutions |
|---|---|
| Tyr | Trp, Phe, Thr, Ser |
| Val | Ile, Met, Leu, Phe, Ala |

As used herein, the phrase significantly affect a proteins activity refers to a decrease in the activity of a protein by at least 10%, at least 20%, at least 30%, at least 40% or at least 50%. With regard to the present invention, such an activity may be measured, for example, as the ability of a protein to elicit neutralizing antibodies against an EBV virus or to self-assemble into a nanoparticle. Such activity may be measured by measuring the titer of such antibodies against EBV, or by measuring the types or strains of virus neutralized by the elicited antibodies. Methods of determining antibody titers and methods of performing virus neutralization assays are known to those skilled in the art. In addition to the activities described above, variant EBV proteins may also be analyzed for their ability to bind receptors (e.g., complement receptor 2) or other proteins. For example, it is understood that EBV gH binds EBV gL to form dimers. Likewise, it is understood that EBV gH binds EBV gL and gp42 to form trimers. Thus, variant EBV proteins may be analyzed for their ability to bind to one another. Methods of measuring such activities are known to those skilled in the art.

As used herein, a fusion protein is a recombinant protein containing amino acid sequence from at least two unrelated proteins that have been joined together, via a peptide bond, to make a single protein. The unrelated amino acid sequences can be joined directly to each other or they can be joined using a linker sequence. As used herein, proteins are unrelated, if their amino acid sequences are not normally found joined together via a peptide bond in their natural environment(s) (e.g., inside a cell). For example, the amino acid sequences of monomeric subunits that make up ferritin, and the amino acid sequences of ENV envelope proteins are not normally found joined together via a peptide bond.

The terms individual, subject, and patient are well-recognized in the art, and are herein used interchangeably to refer to any human or non-human primate susceptible to infection with EBV. Examples include, but are not limited to, humans and other primates, including non-human primates such as chimpanzees and other apes and monkey species. The terms individual, subject, and patient by themselves, do not denote a particular age, sex, race, and the like. Thus, individuals of any age, whether male or female, are intended to be covered by the present disclosure and include, but are not limited to the elderly, adults, children, babies, infants, and toddlers. Likewise, the methods of the present invention can be applied to any race, including, for example, Caucasian (white), African-American (black), Native American, Native Hawaiian, Hispanic, Latino, Asian, and European. An infected subject is a subject that is known to have EBV in their body.

As used herein, the terms exposed, exposure, and the like, indicate the subject has come in contact with a person of animal that is known to be infected with EBV.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

According to the present invention, vaccines are provided that elicit a neutralizing immune response against Epstein-Barr virus envelope proteins. Some vaccines disclosed herein may elicit an immune response against the entire envelope protein, while others may elicit an immune response against a specific region or portion of an envelope protein. Moreover, the inventors have discovered that specific fusion proteins comprising portions of envelope protein are useful for eliciting an immune response against Epstein-Barr viruses. Each of these embodiments will now be disclosed in detail below.

The inventors have discovered that fusion of an EBV envelope (ENV) protein with a self-assembly (SA) protein, to produce an ENV-SA fusion protein, results in a vaccine that elicits a robust immune response to EBV virus. Such ENV-SA fusion proteins self-assemble into nanoparticles that display immunogenic portions of the EBV protein on their surface. These nanoparticles are useful for vaccinating individuals against EBV. Thus, one embodiment of the present invention is an ENV-SA fusion protein comprising a self-assembling subunit protein disclosed herein joined to an EBV envelope (ENV) protein disclosed herein, wherein the ENV-SA fusion protein is capable of self-assembling into nanoparticles.

According to the present invention, a self-assembling (SA) subunit protein of the present invention is a full length, monomeric polypeptide, or any portion thereof, which is capable of directing self-assembly of monomeric self-assembling subunit proteins into a nanoparticle. Examples of self-assembly proteins of the present invention include ferritin, encapsulin, sulfur oxygenase reductase (SOR), lumazine synthase (LS) and pyruvate dehydrogenase complex (PDC) dihydrolipoamide acetyltransferase (E2). Representative examples of such proteins are listed below in Table 2.

TABLE 2

| SEQ ID NO | Organism | Comments |
|---|---|---|
| | | FERRITIN |
| 1 | *Helicobacter pylori* | Coding sequence for ferritin monomeric subunit protein from *H. pylori* |
| 2 | *Helicobacter pylori* | Amino acid sequence encoded by SEQ ID NO: 1 |
| 3 | *Helicobacter pylori* | Complement of SEQ ID NO 1 |
| 4 | *Escherichia coli* | Coding sequence for ferritin monomeric subunit protein from *E. coli* (gi 446839951_WP_000917207.1) |
| 5 | *Escherichia coli* | Amino acid sequence encoded by SEQ ID NO: 4 |
| 6 | *Escherichia coli* | Complement of SEQ ID NO 4 |
| 7 | *Rana catesbeiana* | Coding sequence for bullfrog ferritin monomeric subunit protein (gi 13675 gb AAA49524.1) |
| 8 | *Rana catesbeiana* | Amino acid sequence encoded by SEQ ID NO: 7 |
| 9 | *Rana catesbeiana* | Complement of SEQ ID NO: 7 |
| | | FERRITIN PROTEINS |
| 10 | Artificial Sequence | Coding sequence for *H. pylori*-ferritin/bullfrog-ferritin fusion protein |
| 11 | Artificial Sequence | Amino acid sequence encoded by SEQ ID NO: 10 |
| 12 | Artificial Sequence | Complement of SEQ ID NO 10 |
| 13 | Artificial Sequence | Coding sequence for *E. coli*-ferritin/bullfrog-ferritin fusion protein |
| 14 | Artificial Sequence | Amino acid sequence encoded by SEQ ID NO: 13 |
| 15 | Artificial Sequence | Complement of SEQ ID NO: 13 |
| | | OTHER SELF-ASSEMBING MONOMERIC SUBUNITS |
| 16 | *Thermotoga maritime* | Coding sequence for encapsulin protein |
| 17 | *Thermotoga maritime* | Amino acid sequence encoded by SEQ ID NO: 16 |

TABLE 2-continued

| SEQ ID NO | Organism | Comments |
|---|---|---|
| 18 | *Thermotoga maritime* | Complement of SEQ ID NO: 16 |
| 19 | Artificial Sequence | Coding sequence for *Salmonella enteritis* 03-33 protein (gi 390136278 pdb 3VCD) |
| 20 | Artificial Sequence | Amino acid sequence encoded by SEQ ID NO: 19 |
| 21 | Artificial Sequence | Complement of SEQ ID NO: 19 |
| 22 | *Acidianus ambivalens* | Coding sequence for sulfur oxygenase reductase protein from *Acidianus ambivalens* (gi 93279016 pdb 2CB2) |
| 23 | *Acidianus ambivalens* | Amino acid sequence encoded by SEQ ID NO: 22 |
| 24 | *Acidianus ambivalens* | Complement of SEQ ID NO: 22 |
| 25 | *Aquifex aeolicus* | Coding sequence for lumazine synthase protein from *Aquifex aeolicus* (gi 18159011 pdb1HQK) |
| 26 | *Aquifex aeolicus* | Amino acid sequence encoded by SEQ ID NO: 25 |
| 27 | *Aquifex aeolicus* | Complement of SEQ ID NO: 25 |
| 28 | *Bacillus stearothermophilus* | Coding sequence for dihydrolipoamide acetyltransferase (E2p) protein from *Bacillus stearothermophilus* (gi 4558102 pdb1B5S |
| 29 | *Bacillus stearothermophilus* | Amino acid sequence encoded by SEQ ID NO: 28 |
| 30 | *Bacillus stearothermophilus* | Complement of SEQ ID NO: 28 |
| | | EBV PROTEINS |
| 31 | Epstein Barr Virus | Coding sequence for EBV gp350 protein |
| 32 | Epstein Barr Virus | Amino acid sequence encoded by SEQ ID NO: 31 |
| 33 | Epstein Barr Virus | Complement of SEQ ID NO: 31 |
| 34 | Epstein Barr Virus | Coding sequence for EBV gp350 protein (2-860) ecto domain |
| 35 | Epstein Barr Virus | Amino acid sequence encoded by SEQ ID NO: 34 |
| 36 | Epstein Barr Virus | Complement of SEQ ID NO: 34 |
| 37 | Epstein Barr Virus | Coding sequence for EBV gp350 protein (2-470) RBD domain |
| 38 | Epstein Barr Virus | Amino acid sequence encoded by SEQ ID NO: 37 |
| 39 | Epstein Barr Virus | Complement of SEQ ID NO: 37 |
| 40 | Epstein Barr Virus | Coding sequence for EBV gp350 protein (4-153) Domain I |
| 41 | Epstein Barr Virus | Amino acid sequence encoded by SEQ ID NO: 40 |
| 42 | Epstein Barr Virus | Complement of SEQ ID NO: 40 |
| 43 | Epstein Barr Virus | Coding sequence for EBV gp350 protein (165-305) Domain II |
| 44 | Epstein Barr Virus | Amino acid sequence encoded by SEQ ID NO: 43 |
| 45 | Epstein Barr Virus | Complement of SEQ ID NO: 43 |
| 46 | Epstein Barr Virus | Coding sequence for EBV gp350 protein (317-426) Domain III |
| 47 | Epstein Barr Virus | Amino acid sequence encoded by SEQ ID NO: 46 |
| 48 | Epstein Barr Virus | Complement of SEQ ID NO: 46 |
| 49 | Epstein Barr Virus | Coding sequence for EBV gp350 protein (2-317) Domains I/II |
| 50 | Epstein Barr Virus | Amino acid sequence encoded by SEQ ID NO: 49 |
| 51 | Epstein Barr Virus | Complement of SEQ ID NO: 49 |
| 52 | Epstein Barr Virus | Coding sequence for EBV gp350 protein (2-425) Domains I/II/III |
| 53 | Epstein Barr Virus | Amino acid sequence encoded by SEQ ID NO: 52 |
| 54 | Epstein Barr Virus | Complement of SEQ ID NO: 52 |
| 55 | Epstein Barr Virus | Coding sequence for soluble EBV gp350 ectodomain protein |
| 56 | Epstein Barr Virus | Amino acid sequence encoded by SEQ ID NO: 55 |
| 57 | Epstein Barr Virus | Compliment of SEQ ID NO: 55 |
| 58 | Epstein Barr Virus | Coding sequence for soluble EBV gp350 Domains I/II/III |
| 59 | Epstein Barr Virus | Amino acid sequence encoded by SEQ ID NO: 58 |
| 60 | Epstein Barr Virus | Complement of SEQ ID NO: 58 |
| 61 | Epstein Barr Virus | Coding sequence for EBV gH protein |
| 62 | Epstein Barr Virus | Amino acid sequence encoded by SEQ ID NO: 61 |
| 63 | Epstein Barr Virus | Complement of SEQ ID NO: 61 |
| 64 | Epstein Barr Virus | Coding sequence for EBV gL protein |
| 65 | Epstein Barr Virus | Amino acid sequence encoded by SEQ ID NO: 64 |
| 66 | Epstein Barr Virus | Complement of SEQ ID NO: 64 |
| 67 | Epstein Barr Virus | Coding sequence for EBV gp42 protein |
| 68 | Epstein Barr Virus | Amino acid sequence encoded by SEQ ID NO: 67 |
| 69 | Epstein Barr Virus | Complement of SEQ ID NO: 67 |
| | | EBV FUSION PROTEINS |
| 70 | Artificial Sequence | Nucleic acid sequence encoding EBV gp350(2-860) ecto-ferritin (*E. coli* ferritin/bullfrog ferritin) fusion protein |
| 71 | Artificial Sequence | Amino acid sequence encoded by SEQ ID NO: 70 |
| 72 | Artificial Sequence | Complement of SEQ ID NO: 70 |

TABLE 2-continued

| SEQ ID NO | Organism | Comments |
|---|---|---|
| 73 | Artificial Sequence | Nucleic acid sequence encoding EBV gp350 (2-470) RBD-ferritin (*E. coli* ferritin/bullfrog ferritin)fusion protein |
| 74 | Artificial Sequence | Amino acid sequence encoded by SEQ ID NO: 73 |
| 75 | Artificial Sequence | Complement of SEQ ID NO: 73 |
| 76 | Artificial Sequence | Nucleic acid sequence encoding EBV gp350 (2-317) Domain I/II-ferritin (*E. coli* ferritin/bullfrog ferritin)fusion protein |
| 77 | Artificial Sequence | Amino acid sequence encoded by SEQ ID NO: 76 |
| 78 | Artificial Sequence | Complement of SEQ ID NO: 76 |
| 79 | Artificial Sequence | Nucleic acid sequence encoding EBV gp350 (2-425) Domain I/II/III-ferritin (*E. coli* ferritin/bullfrog ferritin)fusion protein |
| 80 | Artificial Sequence | Amino acid sequence encoded by SEQ ID NO: 79 |
| 81 | Artificial Sequence | Complement of SEQ ID NO: 79 |
| 82 | Artificial Sequence | Nucleic acid sequence encoding EBV gp350 (2-860) ecto-ferritin (*H. pylori* ferritin/bullfrog ferritin) fusion protein |
| 83 | Artificial Sequence | Amino acid sequence encoded by SEQ ID NO: 82 |
| 84 | Artificial Sequence | Complement of SEQ ID NO: 82 |
| 85 | Artificial Sequence | Nucleic acid sequence encoding EBV gp350(2-317) Domain VII-ferritin (*H. pylori* ferritin/bullfrog ferritin)fusion protein |
| 86 | Artificial Sequence | Amino acid sequence encoded by SEQ ID NO: 85 |
| 87 | Artificial Sequence | Complement of SEQ ID NO: 85 |
| 88 | Artificial Sequence | Nucleic acid sequence encoding EBV gp350 (2-425) Domain I/II/III-ferritin (*H. pylori* ferritin/bullfrog ferritin)fusion protein |
| 89 | Artificial Sequence | Amino acid sequence encoded by SEQ ID NO: 88 |
| 90 | Artificial Sequence | Complement of SEQ ID NO: 88 |
| 91 | Artificial Sequence | Nucleic acid sequence encoding EBV gp350 (2-470) RBD-ferritin (*H. pylori* ferritin/bullfrog ferritin)fusion protein |
| 92 | Artificial Sequence | Amino acid sequence encoded by SEQ ID NO: 91 |
| 93 | Artificial Sequence | Complement of SEQ ID NO: 91 |
| 94 | Artificial Sequence | Nucleic acid sequence encoding EBV gp350 (2-860) ecto-encapsulin fusion protein |
| 95 | Artificial Sequence | Amino acid sequence encoded by SEQ ID NO: 94 |
| 96 | Artificial Sequence | Complement of SEQ ID NO: 94 |
| 97 | Artificial Sequence | Nucleic acid sequence encoding EBV gp350 (2-470) RBD-encapsulin fusion protein |
| 98 | Artificial Sequence | Amino acid sequence encoded by SEQ ID NO: 97 |
| 99 | Artificial Sequence | Complement of SEQ ID NO: 97 |
| 100 | Artificial Sequence | Nucleic acid sequence encoding EBV gp350 (317) Domain I/II-encapsulin fusion protein |
| 101 | Artificial Sequence | Amino acid sequence encoded by SEQ ID NO: 100 |
| 102 | Artificial Sequence | Complement of SEQ ID NO: 100 |
| 103 | Artificial Sequence | Nucleic acid sequence encoding EBV gp350 (2-425) Domain I/II/III-encapsulin fusion protein |
| 104 | Artificial Sequence | Amino acid sequence encoded by SEQ ID NO: 103 |
| 105 | Artificial Sequence | Complement of SEQ ID NO: 103 |
| 106 | Artificial Sequence | Nucleic acid sequence of VRC 3421 |
| 107 | Artificial Sequence | Nucleic acid sequence of VRC 3422 |
| 108 | Artificial Sequence | Nucleic acid sequence of VRC 3423 |
| 109 | Artificial Sequence | Nucleic acid sequence of VRC 3424 |
| 110 | Artificial Sequence | Nucleic acid sequence of VRC 3425 |

TABLE 2-continued

| SEQ ID NO | Organism | Comments |
|---|---|---|
| 111 | Artificial Sequence | Nucleic acid sequence of VRC 3426 |
| 112 | Artificial Sequence | Nucleic acid sequence of VRC 3427 |
| 113 | Artificial Sequence | Nucleic acid sequence of VRC 3428 |
| 114 | Artificial Sequence | Nucleic acid sequence of VRC 3429 |
| 115 | Artificial Sequence | Nucleic acid sequence of VRC 3430 |
| 116 | Artificial Sequence | Nucleic acid sequence of VRC 3431 |
| 117 | Artificial Sequence | Nucleic acid sequence of VRC 3432 |
| 118 | Artificial Sequence | Nucleic acid sequence of VRC 3384 |
| 119 | Artificial Sequence | Nucleic acid sequence of VRC 3419 |
| 120 | Artificial Sequence | Nucleic acid sequence of VRC 3420 |
| 121 | Artificial Sequence | Nucleic acid sequence of VRC 3361 |
| 122 | Artificial Sequence | Nucleic acid sequence of VRC 3796 |
| 123 | Artificial Sequence | Nucleic acid sequence of VRC 3797 |
| 124 | Artificial Sequence | Nucleic acid sequence of VRC 2194 |
| 125 | Artificial Sequence | Nucleic acid sequence of VRC 2195 |
| 126 | Artificial Sequence | Nucleic acid sequence of VRC 2196 |
| 127 | Artificial Sequence | Nucleic acid sequence encoding gH-ferritin protein |
| 128 | Artificial Sequence | Protein encoded by SEQ ID NO: 127 |
| 129 | Artificial Sequence | Nucleic acid sequence encoding soluble gp42 protein |
| 130 | Artificial Sequence | Protein encoded by SEQ ID NO: 129 |
| 131 | Epstein Barr Virus | Nucleic acid sequence encoding gL protein |
| 132 | Epstein Barr Virus | Protein encoded by SEQ ID NO: 131 |
| 133 | Artificial Sequence | Nucleic acid sequence encoding encapsulin-gp42 |
| 134 | Artificial Sequence | Protein encoded by SEQ ID NO: 133 |
| 135 | Artificial Sequence | Nucleic acid sequence encoding soluble gH |
| 136 | Artificial Sequence | Protein encoded by SEQ ID NO: 135 |
| 137 | Picornavirus | Nucleic acid molecule encoding picornavirus 2A protease cleavage site |
| 138 | Picornavirus | Peptide encoded by SEQ ID NO: 137 (picornavirus 2A protease cleavage site) |
| 139 | Human | Nucleic acid sequence encoding human CD5 leader peptide sequence |
| 140 | Human | Amino acid sequence encoded by SEQ ID NO: 139 (human CD5 leader peptide sequence) |
| 141 | Artificial Sequence | Nucleic acid sequence encoding ferritin-gH-F2A-gL polyprotein |
| 142 | Artificial Sequence | Amino acid sequence encoded by SEQ ID NO: 141 (ferritin-gH-F2A-gL polyprotein) |
| 143 | Artificial Sequence | Nucleic acid sequence encoding ferritin-gH-F2A-gL-F2A-gp42 polyprotein |
| 144 | Artificial Sequence | Amino acid sequence encoded by SEQ ID NO: 143 (ferritin-gH-F2A-gL-F2A-gp42 polyprotein) |
| 145 | Artificial Sequence | Nucleic acid sequence encoding ferritin-gH fusion protein having SGGG linker |
| 146 | Artificial Sequence | Amino acid sequence encoded by SEQ ID NO: 145 (ferritin-gH fusion protein having SGGG linker) |

Thus one embodiment of the present invention is an ENV-SA fusion protein comprising a self-assembling subunit protein selected from the group consisting of ferritin, encapsulin, sulfur oxygenase reductase, lumazine synthase and dihydrolipoamide acetyltransferase (E2), joined to an EBV envelope (ENV) protein disclosed herein, wherein the ENV-SA fusion protein is capable of self-assembling into nanoparticles.

In one embodiment, the self-assembly protein is ferritin. Ferritin forms a spherical protein found in all animals, bacteria, and plants, that acts primarily to control the rate and location of polynuclear $Fe(III)_2O_3$ formation through the transportation of hydrated iron ions and protons to and from a mineralized core. The spherical form of ferritin is made up of monomeric subunit proteins (also referred to as monomeric ferritin subunits), which are polypeptides having a molecule weight of approximately 17-20 kDa. An example of the sequence of one such monomeric ferritin subunit is represented by SEQ ID NO:2. Each monomeric ferritin subunit has the topology of a helix bundle which includes a four antiparallel helix motif, with a fifth shorter helix (the c-terminal helix) lying roughly perpendicular to the long axis of the 4 helix bundle. According to convention, the helices are labeled 'A, B, C, and D & E' from the N-terminus respectively. The N-terminal sequence lies adjacent to the capsid three-fold axis and extends to the surface, while the E helices pack together at the four-fold axis with the C-terminus extending into the particle core. The consequence of this packing creates two pores on the capsid surface. It is expected that one or both of these pores represent the point by which the hydrated iron diffuses into and out of the capsid. Following production, these monomeric ferritin subunit proteins self-assemble into the spherical ferritin protein. Thus, the spherical form of ferritin comprises 24 monomeric, ferritin subunit proteins, and has a capsid-like structure having 432 symmetry.

According to the present invention, a monomeric ferritin subunit of the present invention is a full length, single polypeptide of a ferritin protein, or any portion thereof, which is capable of directing self-assembly of monomeric ferritin subunits into the spherical form of the protein. Amino acid sequences from monomeric ferritin subunits of any known ferritin protein can be used to produce fusion proteins of the present invention, so long as the monomeric ferritin subunit is capable of directing self-assembly of the fusion protein into a nanoparticle displaying an EBV ENV protein on its surface. In one embodiment, the monomeric subunit is from a ferritin protein selected from the group consisting of a bacterial ferritin protein, a plant ferritin protein, an algal ferritin protein, an insect ferritin protein, a fungal ferritin protein and a mammalian ferritin protein. In one embodiment, the ferritin protein is from *Helicobacter pylori*. In one embodiment, the ferritin protein is from *E. coli*. In one embodiment, the ferritin protein is bullfrog ferritin. In one embodiment, the ferritin protein comprises amino acid sequences from one or more ferritin proteins selected from the group consisting of *H. pylori* ferritin, *E. coli* ferritin and bullfrog ferritin. Amino acid sequences from representative ferritin proteins of the present invention are disclosed herein as SEQ ID NO:2 (*H. pylori* ferritin), SEQ ID NO:5 (*E. coli* ferritin), SEQ ID NO:8 (bullfrog ferritin), SEQ ID NO:11 (*H. pylori* ferritin-bullfrog ferritin fusion) and SEQ ID NO:14 (*E. coli* ferritin-bullfrog ferritin fusion).

In one embodiment, the self-assembly protein is encapsulin. According to the present invention, a monomeric encapsulin subunit of the present invention is a full length, single polypeptide of an encapsulin protein, or any portion thereof, which is capable of directing self-assembly of monomeric encapsulin subunits into a nanoparticle. Amino acid sequences from monomeric encapsulin subunits of any known encapsulin protein can be used to produce fusion proteins of the present invention, so long as the monomeric encapsulin subunit is capable of directing self-assembly of the fusion protein into a nanoparticle displaying an EBV ENV protein on its surface. The amino acid sequence of a representative encapsulin protein is disclosed herein as SEQ ID NO:17.

In one embodiment, the self-assembly protein is artificially designed *Salmonella enteritis* 03-33 subunit protein. According to the present invention, a monomeric 03-33 subunit of the present invention is a full length, single polypeptide of an 03-33 protein, or any portion thereof, which is capable of directing self-assembly of monomeric 03-33 subunits into a nanoparticle. Amino acid sequences from monomeric 03-33 subunits of any known 03-33 protein can be used to produce fusion proteins of the present invention, so long as the monomeric 03-33 subunit is capable of directing self-assembly of the fusion protein into a nanoparticle displaying an EBV ENV protein on its surface. The amino acid sequence of a representative 03-33 protein is disclosed herein as SEQ ID NO:20.

In one embodiment, the self-assembly protein is sulfur oxygenase reductase (SOR). According to the present invention, a monomeric SOR subunit of the present invention is a full length, single polypeptide of an SOR protein, or any portion thereof, which is capable of directing self-assembly of monomeric SOR subunits into a nanoparticle. Amino acid sequences from monomeric SOR subunits of any known SOR protein can be used to produce fusion proteins of the present invention, so long as the monomeric SOR subunit is capable of directing self-assembly of the fusion protein into a nanoparticle displaying an EBV ENV protein on its surface. The amino acid sequence of a representative SOR protein is disclosed herein as SEQ ID NO:23.

In one embodiment, the self-assembly protein is lumazine synthase (LS). According to the present invention, a monomeric LS subunit of the present invention is a full length, single polypeptide of an LS protein, or any portion thereof, which is capable of directing self-assembly of monomeric LS subunits into a nanoparticle. Amino acid sequences from monomeric LS subunits of any known LS protein can be used to produce fusion proteins of the present invention, so long as the monomeric LS subunit is capable of directing self-assembly of the fusion protein into a nanoparticle displaying an EBV ENV protein on its surface. The amino acid sequence of a representative LS protein is disclosed herein as SEQ ID NO:26.

In one embodiment, the self-assembly protein is pyruvate dehydrogenase complex (PDC) dihydrolipoamide acetyltransferase (E2p). According to the present invention, a monomeric E2p subunit of the present invention is a full length, single polypeptide of an E2p protein, or any portion thereof, which is capable of directing self-assembly of monomeric E2p subunits into a nanoparticle. Amino acid sequences from monomeric E2p subunits of any known E2p protein can be used to produce fusion proteins of the present invention, so long as the monomeric E2p subunit is capable of directing self-assembly of the fusion protein into a nanoparticle displaying an EBV ENV protein on its surface. The amino acid sequence of a representative E2p protein is disclosed herein as SEQ ID NO:29.

ENV-SA fusion proteins of the present invention need not comprise the full-length sequence of a monomeric subunit polypeptide of a self-assembly (SA) protein. Portions, or regions, of the monomeric SA subunit protein can be utilized so long as the portion comprises an amino acid sequence that directs self-assembly of the EBV-SA fusion protein into a nanoparticle. One example of such a portion is located between amino acids 5 and 167 of the *Helicobacter pylori* ferritin protein. More specific regions of the ferritin protein are described in Zhang, Y. Self-Assembly in the Ferritin Nano-Cage Protein Super Family. 2011, Int. J. Mol. Sci., 12, 5406-5421, which is incorporated herein by reference in its entirety.

One embodiment of the present invention is an ENV-SA fusion protein comprising an Epstein-Barr virus ENV protein of the present invention joined to at least 25 contiguous amino acids, at least 50 contiguous amino acids, at least 75 contiguous amino acids, at least 100 contiguous amino acids, or at least 150 contiguous amino acids from a protein selected from the group consisting of ferritin, encapsulin, sulfur oxygenase reductase, lumazine synthase and pyruvate dehydrogenase complex (PDC) dihydrolipoamide acetyltransferase (E2), wherein the ENV-SA fusion protein is capable of self-assembling into nanoparticles. One embodiment of the present invention is an ENV-SA fusion protein comprising an ENV protein of the present invention joined to at least 25 contiguous amino acids, at least 50 contiguous amino acids, at least 75 contiguous amino acids, at least 100 contiguous amino acids, or at least 150 contiguous amino acids from an amino acid sequence selected from the group consisting of SEQ ID NO:2, SEQ ID NO:5 SEQ ID NO:8, SEQ ID NO:11, SEQ ID NO:14, SEQ ID NO:17, SEQ ID NO:20, SEQ ID NO:23, SEQ ID NO:26 and SEQ ID NO:29, wherein the ENV-SA fusion protein is capable of self-assembling into nanoparticles. In one embodiment of the present, the ENV-SA fusion protein comprises an ENV-protein of the present invention joined to at least 25 contiguous amino acids, at least 50 contiguous amino acids, at least 75 contiguous amino acids, at least 100 contiguous amino acids, or at least 150 contiguous amino acids from amino acid residues 5-167 of SEQ ID NO:2, SEQ ID NO:5 or SEQ ID NO:8, wherein the ENV-SA fusion protein is capable of self-assembling into nanoparticles.

As has been previously discussed, it is well-known in the art that some variations can be made in the amino acid sequence of a protein without affecting the activity of that protein. Such variations include insertion of amino acid residues, deletions of amino acid residues, and substitutions of amino acid residues. Thus, in one embodiment, the sequence of a SA protein subunit is divergent enough from the sequence of a SA protein subunit found in nature, such that when the variant SA protein subunit is introduced into an animal, such as a mouse, it does not result in the production of antibodies that react with the natural SA protein. According to the present invention, such a monomeric subunit is referred to as immunogenically neutral. One embodiment of the present invention is an ENV-SA fusion protein comprising an ENV protein of the present invention joined to an amino acid sequence at least 80%, at least 85%, at least 90%, at least 95%, and at least 97% identical to the amino acid sequence of a monomeric SA protein subunit that is responsible for directing self-assembly of the monomeric ferritin subunits into a nanoparticle, wherein the ENV-SA fusion protein is capable of self-assembling into nanoparticles. In one embodiment, the ENV-SA fusion protein comprises a polypeptide sequence identical in sequence to a monomeric SA protein subunit selected from the group consisting of ferritin, encapsulin, sulfur oxygenase reductase, lumazine synthase and pyruvate dehydrogenase complex (PDC) dihydrolipoamide acetyltransferase (E2). One embodiment of the present invention is an ENV-SA fusion protein comprising an ENV protein of the present invention joined to an amino acid sequence at least 80%, at least 85%, at least 90%, at least 95%, and at least 97% identical to the amino acid sequence of a monomeric SA protein subunit selected from the group consisting of ferritin, encapsulin, sulfur oxygenase reductase, lumazine synthase and pyruvate dehydrogenase complex (PDC) dihydrolipoamide acetyltransferase (E2), wherein the ENV-SA fusion protein is capable of self-assembling into nanoparticles. One embodiment of the present invention is an ENV-SA fusion protein comprising an ENV protein of the present invention joined to an amino acid sequence at least 80%, at least 85%, at least 90%, at least 95%, and at least 97% identical to a sequence selected from the group consisting of SEQ ID NO:2, SEQ ID NO:5 SEQ ID NO:8, SEQ ID NO:11, SEQ ID NO:14, SEQ ID NO:17, SEQ ID NO:20, SEQ ID NO:23, SEQ ID NO:26 and SEQ ID NO:29, wherein the ENV-SA fusion protein is capable of self-assembling into nanoparticles. One embodiment of the present invention is an ENV-SA fusion protein comprising an ENV protein of the present invention joined to an amino acid sequence at least 80%, at least 85%, at least 90%, at least 95%, and at least 97% identical to amino acid 5-167 from SEQ ID NO:2, SEQ ID NO:5 or SEQ ID NO:8, wherein the ENV-SA fusion protein is capable of self-assembling into nanoparticles.

In some embodiments, it may be useful to engineer mutations into the amino acid sequences of proteins of the present invention. For example, it may be useful to alter sites such as enzyme recognition sites or glycosylation sites in the monomeric ferritin subunit, the trimerization domain, or linker sequences, in order to give the fusion protein beneficial properties (e.g., stability, solubility, half-life, mask portions of the protein from immune surveillance). For example, it is known that the monomeric subunit of ferritin is not glycosylated naturally. However, it can be glycosylated if it is expressed as a secreted protein in mammalian or yeast cells. Thus, in one embodiment, potential N-linked glycosylation sites in the amino acid sequences from the monomeric ferritin subunit are mutated so that the mutated ferritin subunit sequences are no longer glycosylated at the mutated site.

According to the present invention, the EBV envelope protein portion of ENV-SA fusion proteins of the present invention can be from any EBV virus, so long as the ENV-SA fusion protein elicits an immune response against Epstein-Barr virus. Thus, one embodiment of the preset invention is an ENV-SA fusion protein comprising a self-assembly (SA) protein of the present invention joined to an amino acid sequence from an EBV envelope protein, wherein the ENV-SA fusion protein is capable of self-assembling into nanoparticles. One embodiment of the preset invention is an ENV-SA fusion protein comprising a self-assembly (SA) protein of the present invention joined to an amino acid sequence from a Type I EBV envelope protein, wherein the ENV-SA fusion protein is capable of self-assembling into nanoparticles. One embodiment of the preset invention is an ENV-SA fusion protein comprising a self-assembly (SA) protein of the present invention joined to an amino acid sequence from a Type II EBV envelope protein, wherein the ENV-SA fusion protein is capable of self-assembling into nanoparticles. One embodiment of the preset invention is an ENV-SA fusion protein comprising a SA protein of the present invention joined to an amino acid sequence from an EBV ENV protein listed in Table 2. One embodiment of the preset invention is an ENV-SA fusion protein comprising a SA protein of the present invention joined to an amino acid sequence from a protein selected from the group consisting of EBV gp350 protein, EBV gH protein, EBV gL protein and EBV gp42 protein. One embodiment of the present invention is an ENV-SA fusion protein comprising a SA protein of the present invention joined to an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132.

Preferred ENV envelope proteins to use in constructing ENV-SA fusion proteins of the present invention are those that elicit an immune response against Epstein-Barr virus. Even more preferred EBV ENV proteins are those that are capable of eliciting antibodies to EBV. One embodiment of the present invention is an ENV-SA fusion protein that elicits antibodies to a Type I or Type II Epstein-Barr virus. One embodiment of the present invention is an ENV-SA fusion protein that elicits antibodies to an EBV ENV protein listed in Table 2. Preferred antibodies elicited by ENV-SA fusion proteins of the present invention are those that neutralize an Epstein-Barr virus. Thus, one embodiment of the present invention is an ENV-SA fusion protein that elicits neutralizing antibodies to a Type I or Type II EBV.

Neutralizing antibodies elicited by an ENV-SA fusion protein of the present invention can neutralize viral infections by affecting any step in the life cycle of the virus. Thus, in one embodiment of the present invention, an ENV-SA fusion protein elicits neutralizing antibodies that prevent EBV from attaching to the host cell. In one embodiment of the present invention, an ENV-SA fusion protein elicits neutralizing antibodies that prevent fusion of the viral envelope with the host cell membrane.

It will be understood by those skilled in the art that particularly useful ENV-SA proteins of the present invention are those comprising an immunogenic portion of an EBV envelope protein. Thus, one embodiment of the present invention is an ENV-SA fusion protein comprising a SA protein of the present invention joined to at least one immunogenic portion of an EBV ENV protein. One embodiment of the present invention is an ENV-SA protein comprising a SA protein of the present invention joined to at least one immunogenic portion of an ENV protein selected from the group consisting of EBV gp350 protein, EBV gH protein, EBV gL protein and EBV gp42 protein. One embodiment of the present invention is an ENV-SA protein comprising a SA protein of the present invention joined to at least one immunogenic portion of an ENV protein from the ENV proteins listed in Table 2. In one embodiment, an ENV-SA fusion protein comprising an immunogenic portion of an ENV protein elicits the production of neutralizing antibodies against EBV.

Immunogenic portions of proteins comprise epitopes, which are clusters of amino acid residues that are recognized by the immune system, thus eliciting an immune response. Such epitopes may consist of contiguous amino acids residues (i.e., amino acid residues that are adjacent to one another in the protein), or they may consist of non-contiguous amino acid residues (i.e., amino acid residues that are not adjacent one another in the protein) but which are in close special proximity in the finally folded protein. It is well understood by those skilled in the art that such epitopes require a minimum of six amino acid residues in order to be recognized by the immune system. Thus, one embodiment of the present invention is an ENV-SA fusion protein comprising an immunogenic portion from the ENV protein, wherein the immunogenic portion comprises at least one epitope.

It is known in the art that some variation in a protein sequence can be tolerated without significantly affecting the activity of the protein. Thus, one embodiment of the present invention is an ENV-SA fusion protein comprising a SA protein of the present invention joined to an amino acid sequence that is a variant of an ENV protein from a Type I or Type II Epstein-Barr virus. One embodiment of the present invention is an ENV-SA fusion protein comprising a ferritin protein of the present invention joined to an amino acid sequence at least about 80%, at least about 85%, at least about 90%, at least about 95%, at least about 97% or at least about 99% identical to the sequence of an ENV protein from a Type I or Type II Epstein-Barr virus, wherein the ENV-SA fusion protein elicits the production of neutralizing antibodies against EBV. One embodiment of the present invention is an ENV-SA fusion protein comprising an SA protein of the present invention joined to an amino acid sequence at least about 80%, at least about 85%, at least about 90%, at least about 95%, at least about 97% or at least about 99% identical to the sequence of an ENV protein from those listed in Table 2, wherein the ENV-SA fusion protein elicits the production of neutralizing antibodies against EBV. One embodiment of the present invention is an ENV-SA fusion protein comprising an SA protein of the present invention joined to an amino acid sequence at least about 80%, at least about 85%, at least about 90%, at least about 95%, at least about 97% or at least about 99% identical to the sequence of an ENV protein selected from the group consisting of consisting of EBV gp350 protein, EBV gH protein, EBV gL protein and EBV gp42 protein, wherein the ENV-SA fusion protein elicits the production of neutralizing antibodies against EBV. One embodiment of the present invention is an ENV-SA fusion protein comprising an SA protein of the present invention joined to amino acid sequence at least about 80%, at least about 85%, at least about 90%, at least about 95%, at least about 97% or at least about 99% identical to a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136, wherein the ENV-SA fusion protein elicits the production of neutralizing antibodies against EBV. One embodiment of the present invention is an ENV-SA fusion protein comprising a SA protein of the present invention joined to amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136.

One embodiment of the present invention is an ENV-SA fusion protein comprising an amino acid sequence at least 80%, at least about 85%, at least about 90%, at least about 95%, at least about 97% or at least about 99% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:130, SEQ ID NO:134 and SEQ ID NO:146. One embodiment of the present invention is an ENV-SA fusion protein comprising an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:130, SEQ ID NO:134 and SEQ ID NO:146.

It is known in the art that the EBV ENV proteins have various regions, or domains, each possessing specific activities. For example, EBV gp350 has an ectodomain that extends out from the viral membrane and comprises the receptor binding domain (RBD). Thus, it will be understood by those skilled in the art that ENV-SA fusion proteins of the present invention need not comprise the entire sequence of the EBV ENV protein. Instead, an ENV-SA fusion protein can comprise only those portions, regions, domains, and the like, that contain the necessary activities for practicing the present invention. For example, an ENV-SA fusion protein may contain only those amino acid sequences from the ENV protein that contain antigenic sites, epitopes, immunodominant epitopes, and the like.

One embodiment of the present invention is an ENV-SA fusion protein comprising a SA protein of the present invention joined to at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein from a Type I or Type II EBV, wherein the ENV-SA fusion protein elicits the production of neutralizing antibodies against EBV. One embodiment of the present invention is an ENV-SA fusion protein comprising a SA protein of the present invention joined to at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an ENV protein from those listed in Table 2, wherein the ENV-SA fusion protein elicits the production of neutralizing antibodies against EBV. One embodiment of the present invention is an ENV-SA fusion protein comprising a SA protein of the present invention joined to at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an ENV protein selected from the group consisting of consisting of EBV gp350 protein, EBV gH protein, EBV gL protein and EBV gp42 protein, wherein the ENV-SA fusion protein elicits the production of neutralizing antibodies against EBV. One embodiment of the present invention is an ENV-SA fusion protein comprising a SA protein of the present invention joined to at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein consisting of a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136.

One embodiment of the present invention is an ENV-SA fusion protein comprising a SA protein of the present invention joined to at least one domain from an EBV gp350 protein, wherein the domain is selected from the group consisting of an ectodomain, an RDB domain, Domain I, Domain II and Domain III. According to the present invention, an ectodomain of an EBV gp350 protein refers to the portion of the gp350 protein that lies outside its transmembrane domain. One embodiment of the present invention is an ENV-SA fusion protein comprising a SA protein of the present invention joined a sequence selected from the group consisting of SEQ ID NO:35, SEQ ID NO:38, SEQ ID NO:41, SEQ ID NO:44, SEQ ID NO:47, SEQ ID NO:50, SEQ ID NO:53, SEQ ID NO:55 and SEQ ID NO:58.

ENV-SA proteins of the present invention are constructed by joining a SA protein of the present invention with an ENV protein of the present invention. In some embodiments, joining of the various proteins and/or domains can be done such that the sequences are directly linked. In other embodiments, it may be necessary to employ linkers (also referred to as a spacer sequences) between the various proteins and/or domains so that the so that they are in the proper orientation. More specifically, linker sequence can be inserted so that the ENV protein is positioned in such a way to maintain the ability to elicit an immune response against EBV. Linker sequences of the present invention comprise amino acids. Preferable amino acids to use are those having small side chains and/or those which are not charged. Such amino acids are less likely to interfere with proper folding and activity of the fusion protein. Accordingly, preferred amino acids to use in linker sequences, either alone or in combination are serine, glycine and alanine. Examples of such linker sequences include, but are not limited to, SGG, SGGG, GSG, GG, NGTGGSG and iterations thereof. Amino acids can be added or subtracted as needed. Those skilled in the art are capable of determining appropriate linker sequences for proteins of the present invention.

In accordance with the invention, suitable portions of the ENV protein can be joined to the SA protein by fusion with the N-terminal sequence, as an endocapsid product by fusion with the C-terminus, or a combination thereof. In one embodiment, the ENV portion of the fusion protein is joined to the N-terminal sequence of the SA portion of the fusion protein. In one embodiment, the ENV portion of the fusion protein is joined to the C-terminal sequence of the SA portion of the fusion protein.

The present inventors have also discovered that the production of nanoparticles of the present invention can be facilitated by using constructs expressing a fusion protein comprising multiple EBV proteins. Thus, one embodiment of the present invention is an ENV-SA fusion protein comprising a self-assembly (SA) protein of the present invention joined to amino acid sequences from two or more EBV envelope (ENV) proteins, wherein the ENV-SA fusion protein is capable of self-assembling into nanoparticles. In one embodiment, the two or more EBV envelope proteins are from Type I and/or Type II EBV. In one embodiment, the amino acid sequences are from two or more ENV envelope proteins listed in Table 2. In one embodiment, the ENV-SA fusion protein comprises a self-assembly protein joined to immunogenic portions from two or more EBV envelope proteins. In one embodiment, the two or more EBV envelope proteins are selected from the group consisting of EBV gp350 protein, EBV gH protein, EBV gL protein and EBV gp42 protein. In one embodiment, the two or more EBV envelope proteins comprise amino acid sequences selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132.

One embodiment of the present invention is an ENV-SA fusion protein comprising a self-assembly (SA) protein of the present invention joined to amino acid sequences from two or more an EBV envelope (ENV) proteins, wherein the ENV-SA fusion protein is capable of self-assembling into nanoparticles and wherein the two or more EBV envelope proteins are capable of eliciting antibodies to a Type I and/or Type II EBV. In one embodiment, the two or more EBV envelope proteins are capable of eliciting antibodies to at least one EBV envelope protein listed in Table 2. In a preferred embodiment the ENV-SA fusion protein elicits neutralizing antibodies to a Type I and/or a Type II EBV.

One embodiment of the present invention is an ENV-SA fusion protein comprising a self-assembly (SA) protein of the present invention joined to amino acid sequences from two or more an EBV envelope (ENV) proteins, wherein the ENV-SA fusion protein is capable of self-assembling into nanoparticles, and wherein the amino acid sequence from each of the two or more EBV envelope proteins comprises an immunogenic portion of an EBV envelope protein. In one embodiment, at least one of the immunogenic portions is capable of eliciting antibodies to a Type I and/or Type II EBV. In a preferred embodiment, the antibodies are neutralizing antibodies. In one embodiment, the immunogenic portions are from an EBV envelope protein listed in Table 2. In one embodiment, the immunogenic portions are from an EBV envelope protein comprising an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132.

One embodiment of the present invention is an ENV-SA fusion protein comprising a self-assembly (SA) protein of the present invention joined to amino acid sequences from two or more an EBV envelope (ENV) proteins, wherein the two or more EBV envelope proteins are variants of EBV envelope proteins from a Type I and/or Type II EBV, and wherein the ENV-SA fusion protein is capable of self-assembling into nanoparticles. In one embodiment, the two or more EBV envelope proteins comprise amino acid sequences at least about 80%, at least about 85%, at least about 90%, at least about 95%, at least about 97% or at least about 99% identical to the sequence of an EBV envelope protein from a Type I and/or a Type II EBV. In one embodiment, the two or more EBV envelope proteins comprise amino acid sequences at least about 80%, at least about 85%, at least about 90%, at least about 95%, at least about 97% or at least about 99% identical to the sequence of an EBV envelope protein selected from the group consisting of EBV gp350 protein, EBV gH protein, EBV gL protein and EBV gp42 protein. In one embodiment, the two or more EBV envelope proteins comprise amino acid sequences at least about 80%, at least about 85%, at least about 90%, at least about 95%, at least about 97% or at least about 99% identical to the sequence of an EBV envelope protein listed in Table 2. In one embodiment, the two or more EBV envelope proteins comprise amino acid sequences at least about 80%, at least about 85%, at least about 90%, at least about 95%, at least about 97% or at least about 99% identical to a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132.

One embodiment of the present invention is an ENV-SA fusion protein comprising a self-assembly (SA) protein of the present invention joined to amino acid sequences from two or more EBV envelope (ENV) proteins, wherein each amino acid sequence from the two or more EBV envelope proteins is at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids in length, and wherein the ENV-SA fusion protein is capable of self-assembling into nanoparticles. In one embodiment, at least one of the amino acid sequences is capable of eliciting antibodies to a Type I and/or Type II EBV. In a preferred embodiment, the antibodies are neutralizing antibodies. In one embodiment, each amino acid sequence from the two or more EBV envelope proteins comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an EBV envelope protein selected from the group consisting of EBV gH protein, EBV gL protein, EBV gp42 protein and EBV gp350 protein. In one embodiment, each amino acid sequence from the two or more EBV envelope proteins comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an EBV envelope protein listed in Table 2. In one embodiment, each amino acid sequence from the two or more EBV envelope proteins comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein having an amino acid sequence at least about 80%, at least about 85%, at least about 90%, at least about 95%, at least about 97% or at least about 99% identical to a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132. In one embodiment, each amino acid sequence from the two or more EBV envelope proteins comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein having an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132.

In certain embodiments, sequences within the fusion protein are directly joined. In alternative embodiments, it is useful to employ linkers, spacers or other types of sequences in order to obtain desired results. Such sequences can be inserted between specific fusion elements in order to, for example, maintain stoichiometry (or molecular ratio) of the final proteins, maintain proper orientation of domains in the final fusion protein, to facilitate transport of the final protein within or out of a cell, or to allow cleavage of the final protein. Thus, examples of useful sequences to utilize include, but are not limited to, linker sequences, spacer sequences, binding sequences, cleavage sequences, leader sequences and secretion signal sequences. Examples of constructs utilizing such sequences are shown in FIG. 22. Thus, one embodiment of the present invention is a ENV-SA fusion protein comprising one or more sequences selected from the group consisting of spacer sequences, binding sequences, cleavage sequences, leader sequences and secretion signal sequences. In one embodiment, the ENV-SA fusion protein comprises one or more protease cleavage sequence. In one embodiment, the cleavage site is a self-cleavage site. In one embodiment, the cleavage sequence is a picornavirus protease cleavage sequence. In one embodiment, the cleavage sequence is a furin cleavage sequence (Arg-Lys-Arg-Arg). In one embodiment, the ENV-SA fusion protein comprises a sequence that directs secretion of the protein. In one embodiment, the fusion protein comprises a leader sequence from human CD5. In one embodiment, the fusion protein comprises one or more sequences selected from the group consisting of SEQ ID NO:138, SEQ ID NO:140, RKRR and functional variants thereof.

One embodiment of the present invention is a ENV-SA fusion protein comprising a self-assembly (SA) protein of the present invention joined to amino acid sequences from two or more EBV envelope (ENV) proteins, wherein the fusion protein comprises at least one cleavage site positioned such that cleavage, including self-cleavage, at the cleavage site results in a SA-gH fusion protein. In one embodiment, the SA-gH fusion protein is capable of forming a dimer with EBVgL. In one embodiment, the SA-gH fusion protein is capable of forming a trimer with EBV gL and EBV gp42. In one embodiment, the ENV-SA fusion protein comprises an EBV gH protein and one or more of EBV gL and EBV gp42 protein. In one embodiment, the fusion protein comprises additional cleavage sites such that cleavage, including self-cleavage, of the fusion protein results in a SA-gH fusion protein and one or more of an EBV gL protein and EBV gp42 protein. One embodiment of the present invention is a fusion protein comprising an amino acid sequence at least about 80%, at least about 85%, at least about 90%, at least about 95%, at least about 97% or at least about 99% identical to a sequence selected from the group consisting of SEQ ID NO:142 and SEQ ID NO:144. One embodiment of the present invention is a fusion protein comprising SEQ ID NO:142 or SEQ ID NO:144.

Proteins of the present invention are encoded by nucleic acid molecules of the present invention. In addition, they are expressed by nucleic acid constructs of the present invention. As used herein a nucleic acid construct is a recombinant expression vector, i.e., a vector linked to a nucleic acid molecule encoding a protein such that the nucleic acid molecule can effect expression of the protein when the nucleic acid construct is administered to, for example, a subject or an organ, tissue or cell. The vector also enables transport of the nucleic acid molecule to a cell within an environment, such as, but not limited to, an organism, tissue, or cell culture. A nucleic acid construct of the present disclosure is produced by human intervention. The nucleic acid construct can be DNA, RNA or variants thereof. The vector can be a DNA plasmid, a viral vector, or other vector. In one embodiment, a vector can be a cytomegalovirus (CMV), retrovirus, adenovirus, adeno-associated virus, herpes virus, vaccinia virus, poliovirus, sindbis virus, or any other DNA or RNA virus vector. In one embodiment, a vector can be a pseudotyped lentiviral or retroviral vector. In one embodiment, a vector can be a DNA plasmid. In one embodiment, a vector can be a DNA plasmid comprising viral components and plasmid components to enable nucleic acid molecule delivery and expression. Methods for the construction of nucleic acid constructs of the present disclosure are well known. See, for example, *Molecular Cloning: a Laboratory Manual,* 3$^{rd}$ edition, Sambrook et al. 2001 Cold Spring Harbor Laboratory Press, and *Current Protocols in Molecular Biology*, Ausubel et al. eds., John Wiley & Sons, 1994. In one embodiment, the vector is a DNA plasmid, such as a CMV/R plasmid such as CMV/R or CMV/R 8 KB (also referred to herein as CMV/R 8 kb). Examples of CMV/R and CMV/R 8 kb are provided herein. CMV/R is also described in U.S. Pat. No. 7,094,598 B2, issued Aug. 22, 2006.

As used herein, a nucleic acid molecule comprises a nucleic acid sequence that encodes a SA monomeric subunit, an ENV protein, and/or an ENV-ferritin SA protein of the present invention. A nucleic acid molecule can be produced recombinantly, synthetically, or by a combination of recombinant and synthetic procedures. A nucleic acid molecule of the disclosure can have a wild-type nucleic acid sequence or a codon-modified nucleic acid sequence to, for example, incorporate codons better recognized by the human translation system. In one embodiment, a nucleic acid molecule can be genetically-engineered to introduce, or eliminate, codons encoding different amino acids, such as to introduce codons that encode an N-linked glycosylation site. Methods to produce nucleic acid molecules of the disclosure are known in the art, particularly once the nucleic acid sequence is know. It is to be appreciated that a nucleic acid construct can comprise one nucleic acid molecule or more than one nucleic acid molecule. It is also to be appreciated that a nucleic acid molecule can encode one protein or more than one protein.

Preferred nucleic acid molecules are those that encode a SA monomeric subunit, an ENV protein, and/or an ENV-SA fusion protein comprising a monomeric subunit of a SA protein joined to an EBV ENV protein. Thus, one embodiment of the present invention is a nucleic acid molecule comprising a nucleic acid sequence encoding a protein that comprises a monomeric subunit of a SA protein joined to an EBV ENV protein. In one embodiment, the monomeric subunit of an SA protein comprises an amino acid sequence at least 80%, at least 85%, at least 90%, at least 92%, at least 94%, at least 96%, at least 98% or at least 99% identical to a sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29. In one embodiment, the monomeric subunit comprises an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29. In one embodiment the EBV ENV protein comprises an amino acid sequence at least 80%, at least 85%, at least 90%, at least 92%, at least 94%, at least 96%, at least 98% or at least 99% identical to a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136. In one embodiment the EBV ENV protein comprises a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136. In one embodiment the EBV ENV protein comprises at least 25 amino acids, at least 50 amino acids, at least 75 amino acids, at least 100 amino acids, at least 150 amino acids, or at least 200 amino acids from a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136.

One embodiment of the present invention is a nucleic acid molecule comprising a nucleic sequence encoding a protein comprising an amino acid sequence at least 80%, at least 85%, at least 90%, at least 92%, at least 94%, at least 96%, at least 98% or at least 99% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:130, SEQ ID NO:134 and SEQ ID NO:146. One embodiment of the present invention is a nucleic acid molecule comprising a nucleic sequence encoding an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:130, SEQ ID NO:134 and SEQ ID NO:146.

Also embodied in the present invention are nucleic acid sequences that are variants of nucleic acid sequence encoding protein of the present invention. Such variants include nucleotide insertions, deletions, and substitutions, so long as they do not affect the ability of fusion proteins of the present invention to self-assemble into nanoparticles, or significantly affect the ability of the EBV envelope portion of fusion proteins to elicit an immune response to an Epstein-Barr virus. Thus, one embodiment of the present invention is a nucleic acid molecule encoding a fusion protein of the present invention, wherein the monomeric subunit of the SA protein is encoded by a nucleotide sequence at least 85%, at least 90%, at least 95%, or at least 97% identical to a nucleotide sequence selected from the group consisting of SEQ ID NO:1, SEQ ID NO:4, SEQ ID NO:7, SEQ ID NO:10, SEQ ID NO:13, SEQ ID NO:16, SEQ ID NO:19, SEQ ID NO:22, SEQ ID NO:2 and SEQ ID NO:28. One embodiment of the present invention is a nucleic acid molecule encoding an ENV-SA fusion protein of the present invention, wherein the ENV protein is encoded by a nucleotide sequence at least 85%, at least 90%, at least 95%, at least 97% identical or at least 99% identical to a nucleic acid sequence encoding an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136.

One embodiment of the present invention is a nucleic acid molecule comprising a nucleic acid sequence at least about 80%, at least about 85%, at least about 90%, at least about 95%, at least about 97% or at least about 99% identical to a nucleic acid sequence selected from the group consisting of SEQ ID NO:10, SEQ ID NO:13 and SEQ ID NO:16. One embodiment of the present invention is a nucleic acid molecule comprising a nucleic acid sequence selected from the group consisting of SEQ ID NO:10, SEQ ID NO:13 and SEQ ID NO:16.

One embodiment of the present invention is a nucleic acid molecule comprising a nucleic acid sequence at least about 80%, at least about 85%, at least about 90%, at least about 95%, at least about 97% or at least about 99% identical to a nucleic acid sequence selected from the group consisting of SEQ ID NO:70, SEQ ID NO:73, SEQ ID NO:76, SEQ ID NO:79, SEQ ID NO:82, SEQ ID NO:85, SEQ ID NO:88 and SEQ ID NO:92. One embodiment of the present invention is a nucleic acid molecule comprising a nucleic acid sequence selected from the group consisting of SEQ ID NO:70, SEQ ID NO:73, SEQ ID NO:76, SEQ ID NO:79, SEQ ID NO:82, SEQ ID NO:85, SEQ ID NO:88, SEQ ID NO:91, SEQ ID NO:94, SEQ ID NO:97, SEQ ID NO:100, SEQ ID NO:103, SEQ ID NO:127, SEQ ID NO:129, SEQ ID NO:133 and SEQ ID NO:145.

One embodiment of the present invention is a nucleic acid molecule encoding an ENV-SA fusion protein comprising a self-assembly (SA) protein of the present invention joined to amino acid sequences from two or more an EBV envelope (ENV) proteins, wherein the ENV-SA fusion protein is capable of self-assembling into nanoparticles. In one embodiment, the two or more EBV envelope proteins are from Type I and/or Type II EBV. In one embodiment, the amino acid sequences are from two or more ENV envelope proteins listed in Table 2. In one embodiment, the ENV-SA fusion protein comprises a self-assembly protein joined to immunogenic portions from two or more EBV envelope proteins. In one embodiment, the two or more EBV envelope proteins are selected from the group consisting of EBV gp350 protein, EBV gH protein, EBV gL protein and EBV gp42 protein. In one embodiment, the two or more EBV envelope proteins comprise amino acid sequences selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132.

One embodiment of the present invention is nucleic acid molecule encoding a ENV-SA fusion protein comprising a self-assembly (SA) protein of the present invention joined to amino acid sequences from two or more an EBV envelope (ENV) proteins, wherein the ENV-SA fusion protein is capable of self-assembling into nanoparticles and wherein the two or more EBV envelope proteins are capable of eliciting antibodies to a Type I and/or Type II EBV. In one embodiment, the two or more EBV envelope proteins are capable of eliciting antibodies to at least one EBV envelope protein listed in Table 2. In a preferred embodiment the ENV-SA fusion protein elicits neutralizing antibodies to a Type I and/or a Type II EBV.

One embodiment of the present invention is a nucleic acid molecule encoding a ENV-SA fusion protein comprising a self-assembly (SA) protein of the present invention joined to amino acid sequences from two or more an EBV envelope (ENV) proteins, wherein the ENV-SA fusion protein is capable of self-assembling into nanoparticles, and wherein the amino acid sequence from each of the two or more EBV envelope proteins comprises an immunogenic portion of an EBV envelope protein. In one embodiment, at least one of the immunogenic portions is capable of eliciting antibodies to a Type I and/or Type II EBV. In a preferred embodiment, the antibodies are neutralizing antibodies. In one embodiment, the immunogenic portions are from an EBV envelope protein listed in Table 2. In one embodiment, the immunogenic portions are from an EBV envelope protein comprising an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132.

One embodiment of the present invention is a nucleic acid molecule encoding a ENV-SA fusion protein comprising a self-assembly (SA) protein of the present invention joined to amino acid sequences from two or more EBV envelope (ENV) proteins, wherein the two or more EBV envelope proteins are variants of EBV envelope proteins from a Type I and/or Type II EBV, and wherein the ENV-SA fusion protein is capable of self-assembling into nanoparticles. In one embodiment, the two or more EBV envelope proteins comprise amino acid sequences at least about 80%, at least about 85%, at least about 90%, at least about 95%, at least about 97% or at least about 99% identical to the sequence of an EBV envelope protein from a Type I and/or a Type II EBV. In one embodiment, the two or more EBV envelope proteins comprise amino acid sequences at least about 80%, at least about 85%, at least about 90%, at least about 95%, at least about 97% or at least about 99% identical to the sequence of an EBV envelope protein selected from the group consisting of EBV gp350 protein, EBV gH protein, EBV gL protein and EBV gp42 protein. In one embodiment, the two or more EBV envelope proteins comprise amino acid sequences at least about 80%, at least about 85%, at least about 90%, at least about 95%, at least about 97% or at least about 99% identical to the sequence of an EBV envelope protein listed in Table 2. In one embodiment, the two or more EBV envelope proteins comprise amino acid sequences at least about 80%, at least about 85%, at least about 90%, at least about 95%, at least about 97% or at least about 99% identical to a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132.

One embodiment of the present invention is a nucleic acid molecule encoding a ENV-SA fusion protein comprising a self-assembly (SA) protein of the present invention joined to amino acid sequences from two or more EBV envelope (ENV) proteins, wherein each amino acid sequence from the two or more EBV envelope proteins is at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids in length, and wherein the ENV-SA fusion protein is capable of self-assembling into nanoparticles. In one embodiment, at least one of the amino acid sequences is capable of eliciting antibodies to a Type I and/or Type II EBV. In a preferred embodiment, the antibodies are neutralizing antibodies. In one embodiment, each amino acid sequence from the two or more EBV envelope proteins comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an EBV envelope protein selected from the group consisting of EBV gH protein, EBV gL protein, EBV gp42 protein and EBV gp350 protein. In one embodiment, each amino acid sequence from the two or more EBV envelope proteins comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an EBV envelope protein listed in Table 2. In one embodiment, each amino acid sequence from the two or more EBV envelope proteins comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein having an amino acid sequence at least about 80%, at least about 85%, at least about 90%, at least about 95%, at least about 97% or at least about 99% identical to a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132. In one embodiment, each amino acid sequence from the two or more EBV envelope proteins comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein having an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132.

One embodiment of the present invention is a nucleic acid molecule comprising a nucleotide sequence at least about 80%, at least about 85%, at least about 90%, at least about 95%, at least about 97% or at least about 99% identical to a sequence selected from the group consisting of SEQ ID NO:141 and SEQ ID NO:143. One embodiment of the present invention is a nucleic acid molecule comprising SEQ ID NO:141 or SEQ ID NO:143.

Also encompassed by the present invention are expression systems for producing fusion proteins of the present invention. In one embodiment, nucleic acid molecules of the present invention are operationally linked to a promoter. As used herein, operationally linked means that proteins encoded by the linked nucleic acid molecules can be expressed when the linked promoter is activated. Promoters useful for practicing the present invention are known to those skilled in the art. One embodiment of the present invention is a recombinant cell comprising a nucleic acid molecule of the present invention. One embodiment of the present invention is a recombinant virus comprising a nucleic acid molecule of the present invention.

As indicated above, the recombinant production of the ENV-SA fusion proteins of the present invention can take place using any suitable conventional recombinant technology currently known in the field. For example, molecular cloning of a construct expressing a fusion protein, such as a SA protein of the present invention with a suitable protein such as a recombinant EBV ENV protein, can be carried out via expression in *E. coli*. The construct may then be transformed into protein expression cells, grown to suitable size, and induced to produce the fusion protein.

As has been described, because ENV-SA fusion proteins of the present invention comprise a monomeric self-assembly (SA) protein, they can self-assemble. According to the present invention, the supramolecule resulting from such self-assembly is referred to as an ENV-expressing, SA protein-based nanoparticle. For ease of discussion, the ENV-expressing, SA protein-based nanoparticle will simply be referred to as a, or the, nanoparticle (np). Nanoparticles of the present invention comprise fusion proteins comprising a SA monomeric subunit joined to an EBV ENV protein. Such nanoparticles display at least a portion of the ENV protein on their surface. In such a construction, the ENV protein is accessible to the immune system and thus can elicit an immune response. Thus, one embodiment of the present invention is a nanoparticle comprising an ENV-SA fusion protein, wherein the fusion protein comprises a monomeric SA subunit joined to an EBV ENV protein. In one embodiment, the nanoparticle is an octahedron. In one embodiment, the ENV protein is capable of eliciting neutralizing antibodies to EBV. In one embodiment, the monomeric SA subunit comprises at least 50 amino acids, at least 100 amino acids, or at least 150 amino acids from an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29. In one embodiment, the monomeric SA subunit comprises an amino acid sequence at least 85%, at least 90%, at least 95%, at least 97% at least 99% identical to an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29. In one embodiment, the monomeric SA subunit comprises an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29.

In one embodiment, the ENV protein comprises at least one epitope from an EBV ENV protein listed in Table 2. In one embodiment, the ENV protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an ENV protein listed in Table 2. In one embodiment, the ENV protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein consisting of a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136. In one embodiment, the ENV protein comprises a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68.

In one embodiment, the ENV protein comprises an amino acid sequence at least 80%, at least 85%, at least 90%, at least 95%, at least 97%, at least 99% identical to the sequence of an ENV protein listed in Table 2. In one embodiment, the ENV protein comprises an amino acid sequence at least 80%, at least 85%, at least 90%, at least 95%, at least 97%, at least 99% identical to a protein sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136.

In one embodiment, the ENV-SA fusion protein comprises an amino acid sequence at least 80%, at least 85%, at least 90%, at least 95%, at least 97%, at least 99% identical to a protein sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:130, SEQ ID NO:134 and SEQ ID NO:146. In one embodiment, the ENV-SA fusion protein comprises an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:130, SEQ ID NO:134 and SEQ ID NO:146.

Nanoparticles of the present invention may comprise more than one type of fusion protein. That is, a nanoparticle of the present invention may comprise at least two types of fusion proteins, each of which comprises amino acid sequences from different EBV ENV proteins (e.g., gp350 and gH). Moreover, the different types of fusion proteins may comprise amino acid sequences from the same or different SA protein (i.e., ferritin and/or encapsulin). Furthermore, in addition to at least one ENV-SA fusion protein, nanoparticles of the present invention may comprise proteins that are not fused to a SA protein. For example, in addition to comprising an ENV-SA fusion protein (e.g., EBV gH-ferritin protein) a nanoparticle of the present invention may also comprise one or more proteins comprising an amino acid sequence from other EBV ENV proteins, or portions or variants thereof. Examples of such proteins include, but are not limited to gp350, gH, gL and gp42. Such additional one or more proteins may, but need not, form a complex with each other or with the ENV-SA fusion protein.

Because ENV-SA fusion proteins and nanoparticles of the present invention can elicit an immune response to an Epstein-Barr virus, they can be used as vaccines to protect individuals against infection by EBV. According to the present invention a vaccine can be an ENV-SA fusion protein, or a nanoparticle of the present invention. Thus, one embodiment of the present invention is a vaccine comprising an ENV-SA fusion protein or a nanoparticle of the present invention. Vaccines of the present invention can also contain other components such as adjuvants, buffers and the like. Although any adjuvant can be used, preferred embodiments can contain: chemical adjuvants such as aluminum phosphate, benzyalkonium chloride, ubenimex, and QS21; genetic adjuvants such as the IL-2 gene or fragments thereof, the granulocyte macrophage colony-stimulating factor (GM-CSF) gene or fragments thereof, the IL-18 gene or fragments thereof, the chemokine (C-C motif) ligand 21 (CCL21) gene or fragments thereof, the IL-6 gene or fragments thereof, CpG, LPS, TLR agonists, and other immune stimulatory genes; protein adjuvants such IL-2 or fragments thereof, the granulocyte macrophage colony-stimulating factor (GM-CSF) or fragments thereof, IL-18 or fragments thereof, the chemokine (C-C motif) ligand 21 (CCL21) or fragments thereof, IL-6 or fragments thereof, CpG, LPS, TLR agonists and other immune stimulatory cytokines or fragments thereof; lipid adjuvants such as cationic liposomes, N3 (cationic lipid), monophosphoryl lipid A (MPL1); other adjuvants including cholera toxin, enterotoxin, Fms-like tyrosine kinase-3 ligand (Flt-3L), bupivacaine, marcaine, and levamisole.

One embodiment of the disclosure is a SA protein-based nanoparticle vaccine that includes more than one EBV ENV protein. Such a vaccine can include a combination of different EBV envelope proteins, either in a single nanoparticle or as a mixture of nanoparticles, at least two of which have unique EBV ENV proteins. A multivalent vaccine can comprise as many EBV envelope proteins as necessary in order to result in production of the desired immune response. In one embodiment, the vaccine comprises ENV proteins from at least two different Types of EBV (bi-valent). In one embodiment, the vaccine comprises a ENV protein from at least three different Epstein-Barr viruses (tri-valent).

One embodiment of the present invention is a method to vaccinate an individual against EBV, the method comprising administering a nanoparticle to an individual such that an immune response against EBV is produced in the individual, wherein the nanoparticle comprises a monomeric subunit from an SA protein of the present invention joined to an EBV envelope protein of the present invention protein, and wherein the nanoparticle displays the EBV envelope on its surface. In one embodiment, the nanoparticle is a monovalent nanoparticle. In one embodiment, the nanoparticle is multivalent nanoparticle. Another embodiment of the present invention is a method to vaccinate an individual against infection with EBV, the method comprising:

a) obtaining a nanoparticle comprising monomeric subunits, wherein the monomeric subunits comprise an SA protein joined to an EBV ENV protein, and wherein the nanoparticle displays the EBV ENV protein on its surface; and, b) administering the nanoparticle to an individual such that an immune response against EBV is produced.

One embodiment of the present invention is a method to vaccinate an individual against EBV, the method comprising administering a vaccine of the embodiments to an individual such that an immune response against EBV is produced in the individual, wherein the vaccine comprises at least one nanoparticle comprising a monomeric subunit of an SA protein of the present invention joined to an EBV envelope protein of the present invention protein, and wherein the nanoparticle displays the EBV ENV protein on its surface. In one embodiment, the vaccine is a nanoparticle. In one embodiment, the vaccine is a monovalent vaccine. In one embodiment, the vaccine is multivalent vaccine. Another embodiment of the present invention is a method to vaccinate an individual against infection with EBV, the method comprising:

a) obtaining a vaccine comprising at least one nanoparticle comprising an ENV-SA fusion protein, wherein the fusion protein comprises an SA protein joined to an EBV ENV protein, and wherein the nanoparticle displays the EBV ENV on its surface; and, b) administering the vaccine to an individual such that an immune response against EBV is produced.

In one embodiment, the nanoparticle is a monovalent nanoparticle. In one embodiment, the nanoparticle is multivalent nanoparticle. In one embodiment, the nanoparticle is an octahedron. In one embodiment, the EBV ENV protein is capable of eliciting neutralizing antibodies to EBV. In one embodiment, the SA portion of the fusion protein comprise at least 50 amino acids, at least 100 amino acids, or at least 150 amino acids from an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29. In one embodiment, the SA portion of the fusion protein comprises an amino acid sequence at least 85%, at least 90%, at least 95%, at least 97% at least 99% identical to an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29. In one embodiment, the ENV portion of the fusion protein comprises at least one epitope from an ENV protein listed in Table 2. In one embodiment, the ENV portion of the fusion protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an ENV listed in Table 2. In one embodiment, the ENV portion of the fusion protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein consisting of a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136. In one embodiment, the ENV portion of the fusion protein comprises an amino acid sequence at least 80%, at least 85%, at least 90%, at least 95%, at least 97%, at least 99% identical to the sequence of an ENV protein listed in Table 2. In one embodiment, the ENV portion of the fusion protein comprises an amino acid sequence at least 80%, at least 85%, at least 90%, at least 95%, at least 97%, at least 99% identical to a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136. In one embodiment, the ENV-SA fusion protein comprises an amino acid sequence at least 80%, at least 85%, at least 90%, at least 95%, at least 97%, at least 99% identical to a protein sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:130 and SEQ ID NO:134. In one embodiment, the ENV-SA fusion protein comprises an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:130 and SEQ ID NO:134.

Vaccines of the present invention can be used to vaccinate individuals using a prime/boost protocol. Such a protocol is described in U.S. Patent Publication No. 20110177122, which is incorporated herein by reference in its entirety. In such a protocol, a first vaccine composition may be administered to the individual (prime) and then after a period of time, a second vaccine composition may be administered to the individual (boost). Administration of the boosting composition may be performed days, weeks or months after administration of the priming composition, preferably about 10 days, about two weeks, about three weeks, about 4 weeks, about 8 weeks, about 16 weeks, about 20 weeks, about 24 weeks, about 28 weeks, or about 32 weeks. In one embodiment, the boosting composition is formulated for administration about 1 week, about 2 weeks, about 3 weeks, about 4 weeks, about 5 weeks, about 6 weeks, about 7 weeks, about 8 weeks, about 9 weeks, about 16 weeks, about 20 weeks, about 24 weeks, about 28 weeks, or about 32 weeks after administration of the priming composition. In one embodiment, a second boosting composition (i.e., third vaccine composition) is administered at some period of time following administration of the first boosting composition. For example, a second boosting composition may be administered at a time about 8 weeks, about 9 weeks, about 10 weeks, about 12 weeks, about 16 weeks, about 20 weeks, about 24 weeks, about or 32 weeks after administration of the priming composition. In one embodiment, a second boosting composition is administered 6 months after administration of the priming composition. As used herein, and with specific regard to the timing of administration of a vaccine composition, the term about refers to a variation of no more than 10%. Thus for example, about 10 days specifies a time period of 9-11 days. Likewise, for example, about 6 months specifies a time period of 162-196 days.

The first and second vaccine compositions can be, but need not be, the same composition. Thus, in one embodiment of the present invention, the step of administering the vaccine comprises administering a first vaccine composition, and then at a later time, administering a second vaccine composition. In one embodiment, the first vaccine composition comprises a nanoparticle comprising an ENV-SA fusion protein of the present invention. In one embodiment, the first vaccine composition comprises a nanoparticle comprising EBV ENV protein. In one embodiment, the ENV of the first vaccine composition comprises an amino acid sequence at least about 80% identical, at least 85% identical, at least 90% identical, at least 95% identical, at least 97% identical or at least 99% identical to an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132, SEQ ID NO:136 and SEQ ID NO:146. In one embodiment, the first vaccine composition comprises an ENV-SA fusion protein comprising an amino acid sequence at least 80% identical, at least 85% identical, at least 90% identical, at least 95% identical, at least 97% identical or at least 99% identical to a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132, SEQ ID NO:136 and SEQ ID NO:146, wherein the nanoparticle elicits an immune response against EBV. In one embodiment, the first vaccine composition comprises an ENV-SA fusion protein comprising an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68. In one embodiment, second vaccine composition comprises a nanoparticle comprising an ENV-SA fusion protein of the present invention. In one embodiment, the individual has been exposed to EBV. As used herein, the terms exposed, exposure, and the like, indicate the subject has come in contact with a person of animal that is known to be infected with an EBV. Vaccines of the present invention may be administered using techniques well known to those in the art. Techniques for formulation and administration may be found, for example, in "Remington's Pharmaceutical Sciences", $18^{th}$ ed., 1990, Mack Publishing Co., Easton, Pa. Vaccines may be administered by means including, but not limited to, traditional syringes, needleless injection devices, or microprojectile bombardment gene guns. Suitable routes of administration include, but are not limited to, parenteral delivery, such as intramuscular, intradermal, subcutaneous, intramedullary injections, as well as, intrathecal, direct intraventricular, intravenous, intraperitoneal, intranasal, or intraocular injections, just to name a few. For injection, the compounds of one embodiment of the invention may be formulated in aqueous solutions, preferably in physiologically compatible buffers such as Hanks' solution, Ringer's solution, or physiological saline buffer.

In one embodiment, vaccines, or nanoparticles, of the present invention can be used to protect an individual against infection by heterologous EBV. That is, a vaccine made using an ENV protein from one Type of EBV is capable of protecting an individual against infection by a different Type of EBV. For example, a vaccine made using one or more ENV protein from Type I EBV, may be used to protect an individual against infection by a Type II EBV.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention.

EXAMPLES

Example 1

Design of EBV Surface Protein-Based Nanoparticles

This Example describes the construction of nanoparticles comprising EBV surface proteins and ferritin or encapsulin.

Two potential platforms were considered for construction of self-assembling nanoparticles capable of displaying antigens on their surface: ferritin (Cho, et al. J Mol Biol, 2009; Stillman, et al. J Mol Biol, 2001) and encapsulin (Sutter, et al. Nat Struct Mol Biol, 2008). Ferritin forms a 4-3-2 point octahedron consisting of 24 subunits while encapsulin forms a 5-3-2 point icosahedron (T=1) consisting of 60 identical subunits. Comparison of ferritin structures revealed that several ferritins including human light chain (Z. Wang, C. Li, M. Ellenburg, E. Soistman, J. Ruble, B. Wright, J. X. Ho, D. C. Carter, Structure of human ferritin L chain. *Acta Crystallogr D Biol Crystallogr* 62, 800-806 (2006)) (PDB: 2ffx) and bullfrog lower subunit (J. Trikha, E. C. Theil, N. M. Allewell, High resolution crystal structures of amphibian red-cell L ferritin: potential roles for structural plasticity and solvation in function. *J Mol Biol* 248, 949-967 (1995)) (PDB: 1rcc) contain an N-terminal extension, which is not present in nonheme-type ferritins from *Helicobacter pylori* (K. J. Cho, H. J. Shin, J. H. Lee, K. J. Kim, S. S. Park, Y. Lee, C. Lee, S. S. Park, K. H. Kim, The crystal structure of ferritin from *Helicobacter pylori* reveals unusual conformational changes for iron uptake. *J Mol Biol* 390, 83-98 (2009)) (PDB: 3egm) or *Escherichia coli* (T. J. Stillman, P. D. Hempstead, P. J. Artymiuk, S. C. Andrews, A. J. Hudson, A. Treffry, J. R. Guest, P. M. Harrison, The high-resolution X-ray crystallographic structure of the ferritin (EcFtnA) of *Escherichia coli*; comparison with human H ferritin (HuHF) and the structures of the Fe(3+) and Zn(2+) derivatives. *J Mol Biol* 307, 587-603 (2001)) (PDB: 1eum). This N-terminal extension causes the most N-terminal residue to project radially from the assembled nanoparticle's center, and the termini to be evenly distributed on the surface of the ferritin particle. Thus, to test the idea that the N-terminal extension of bullfrog ferritin could be added to the bacterial counterpart to make its N-temini exposed and evenly distributed on the surface of the nanoparticle, a hybrid ferritin protein was constructed that combined sequence from *H. pylori* ferritin or *E. coli* ferritin with the N-terminal extension from bullfrog ferritin. The details of this construction are listed below.

Encapsulin has not been studied as a scaffold to present heterologous proteins on its surface. In contrast to ferritins, encapsulin has its C-termini exposed on the surface, thus providing a potential site at which to fuse exogeneous sequences. The C-termini of encapsulin are projected radially and are also located dispersedly around the 5-fold symmetry axes.

Figure 1:
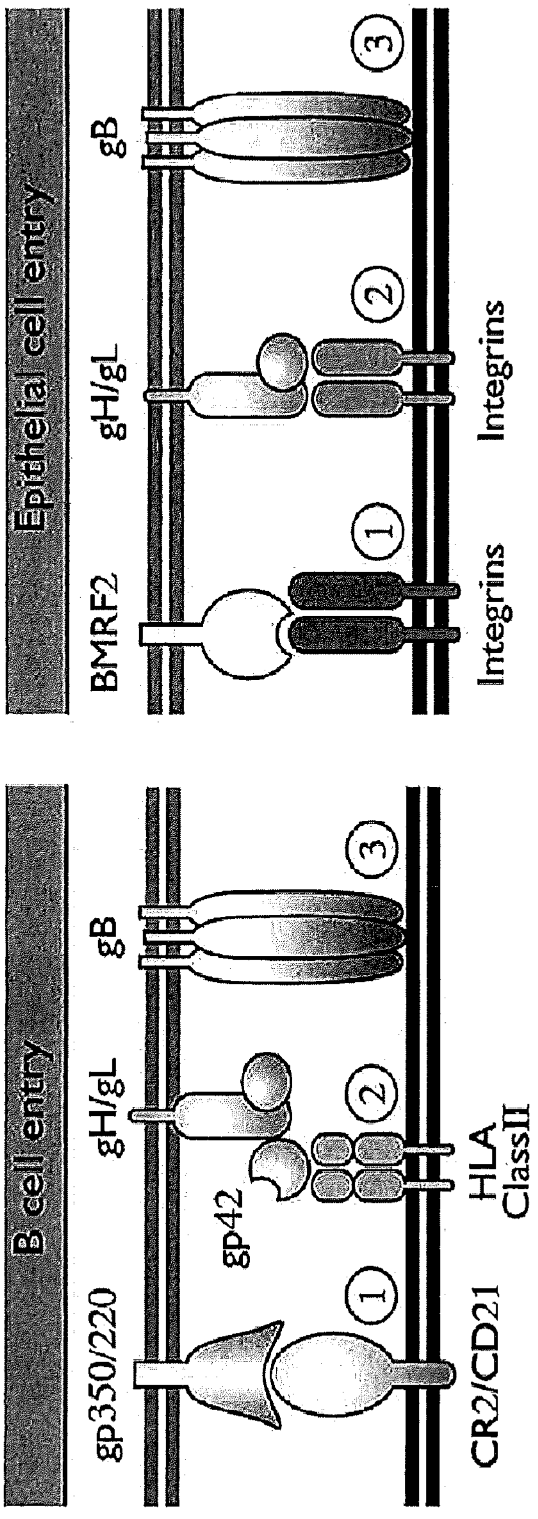
FIG. 1. Molecules essential for EBV infection of B cells and epithelial cells. Entry of EBV in B cells is initiated by attachment of EBV glycoprotein gp350 to its' cellular receptor CR2/CD21, followed by binding of viral glycoprotein gp42 (which also interacts with EBV gH/gL forming a trimer) to HLA class II. This triggers membrane fusion which is completed by glycoprotein gB. Entry of EBV into epithelial cells is thought to be initiated by binding of EBV BMRF2 to its cellular receptor integrins, followed by binding of gH/gL heterodimer to their cellular receptor integrins, and membrane fusion is subsequently triggered and completed by gB. (Figure from Longnecker R, Kieff E, and Cohen J I. Epstein-Barr virus. In: *Fields Virology* 2013).
Figure 2:
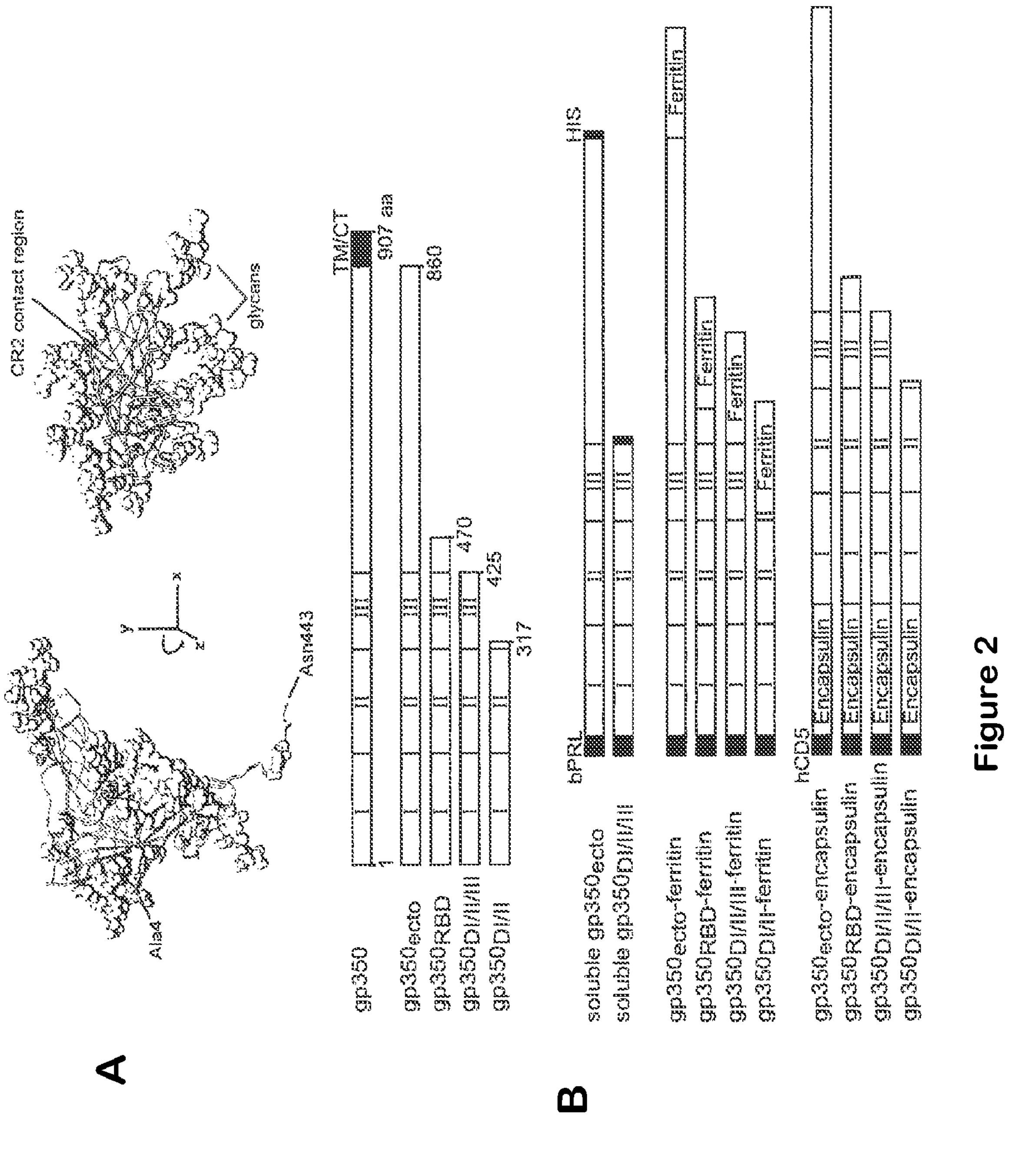
FIG. 2. Molecular design of truncated gp350 variants and gp350-based nanoparticles. (A) Molecular design of truncated gp350 containing CR2-binding site (CR2BS). Crystal structure of EBV gp350 receptor-binding domain (RBD) (PDB: 2h6o) is shown in surface representation (top). The N- and C-terminal residues in the crystal structures are indicated with amino acid number (B95-8 numbering) (left). Schematic representation of full length gp350 and its truncated variants (bottom). $Gp350_{ecto}$ is truncated by removing the transmembrane (TM) and cytoplasmic tail (CT). $Gp350_{RBD}$ is identical to the construct used for the crystallography study (Szakonyi, G., et al., *Nat Struct Mol Biol.* 13, 996-1001, 2006) and it contains intact domains I-III and an extended tail. $Gp350_{DI/II/III}$ and $gp350_{DI/II}$ are truncated further while retaining intact domains I-III and I-II, respectively. (B) Design of soluble monomeric gp350 and gp350-based nanoparticles. The soluble gp350 monomer constructs are made by genetically adding a modified bovine prolactin leader sequence (bPRL) and a poly histidine tag (HIS) at the N- and the C-terminus of gp350, respectively. The gp350-based ferritins are constructed by genetically fusing a bPRL sequence followed by gp350 variants to the N-terminus of ferritin (*Helicobacter pylori*-bullfrog hybrid (Hp) or *Escherichia coli*-bullfrog hybrid (Ec)) with a Ser-Gly linker between gp350 variants and ferritin. The gp350-based encapsulins are constructed by genetically fusing a human CD5 leader (hCD5) sequence and gp350 variants to the N- and the C-termini of encapsulin (*Thermotoga maritima*), respectively with a $(Ser-Gly_3)_2$ linker between gp350 variants and encapsulin. These fusion genes are then cloned into the mammalian expression vector (CMV8x/R). Soluble $gp350_{ecto}$ and $gp350_{DI/II/III}$ are designated as VRC 3796 and 3797, respectively. Gp350 variants fused with Ec ferritin, Hp ferritin and encapsulin are designated as VRC 3421-3424, 3425-3428 and 3429-3432, respectively.

Glycoprotein 350 (gp350) of Epstein-Barr virus (EBV) is the most abundant viral surface protein and is a major target of neutralizing antibodies in naturally infected individuals (Thorley-Lawson D A, Poodry C A. Identification and isolation of the main component (gp350-gp220) of Epstein-Barr virus responsible for generating neutralizing antibodies in vivo. J Virol. 1982; 43:730-736.). Gp350 is a type I transmembrane protein comprising of 907 amino acids containing an ectodomain of 860 amino acids, a transmembrane domain and a cytoplasmic tail. To test the ability of gp350 to induce an immune response, truncation variants of gp350 were fused to ferritin or encapsulin without disturbing the self-assembly capability of the self-assembling protein (see FIG. 2). These fusion proteins were constructed by creating expression vectors encoding the fusion genes encoding the gp350 variants and either *H. pylori*-bullfrog (HpBf), *E. coli*-bullfrog (EcBf) or encapsulin. The details of this construction are given below.

A. Gene Synthesis and Vector Construction

All genes used in the study were optimized for mammalian codon usage. The gene encoding *Helicobacter pylori*-bullfrog hybrid ferritin was constructed by genetically fusing the N-terminus extension region (residues 2-9) of bullfrog (*Rana catesbeiana*) ferritin lower subunit (UniProtKB: P07797) to residues 3-167 of *H. pylori* nonheme ferritin (UniProtKB: Q9ZLI1. A point mutation was created at residue 8 (N8Q) of the bullfrog portion in order to abolish a potential N-linked glycosylation site. Similarly, point mutations were created at residue 7 (I7E) and 19 (N19Q) of the *H. pylori* ferritin in order to make a salt bridge with 6R of bullfrog N-terminus part and abolish a potential N-linked glycosylation site, respectively.

The gene encoding *Escherichia coli*-bullfrog hybrid ferritin was constructed similarly but without the N8Q mutation in the bullfrog N-terminus extension region and with *E. coli* ferritin-1 (UniProtKB: P0A998, residues 3-162 having a point mutation at residue 7 (I7E) to make a salt bridge with 6R of bullfrog N-terminus part). These constructs also contained extra SG residues at the end of *H. pylori* or *E. coli* ferritin for cloning purpose.

The gene encoding encapsulin was constructed by genetically fusing the human CD5 signal sequence to *Termotoga maritima* bacteriocin (also known as maritimacin or encapsulin, UniProtKB: Q9WZP2, residues 1-264).

The gene encoding Epstein-Barr virus strain B95-8 full-length gp350 (UniProtKB: P03200, residues 1-907) was synthesized and the gene fragments corresponding to ectodomain (residues 2-860), receptor-binding domain (RBD, residues 2-470), domains I, II and III ($D_{I/II/III}$ or $D_{123}$, residues 2-425) and domains I and II (residues 2-317) were amplified by polymerase chain reactions with appropriate primers. Amplified gene fragments were genetically fused to a modified bovine prolactin (bPRL) secretion signal sequence and the hybrid ferritin with a SG linker to give rise to the gp350-ferritin fusion genes.

Figure 3:
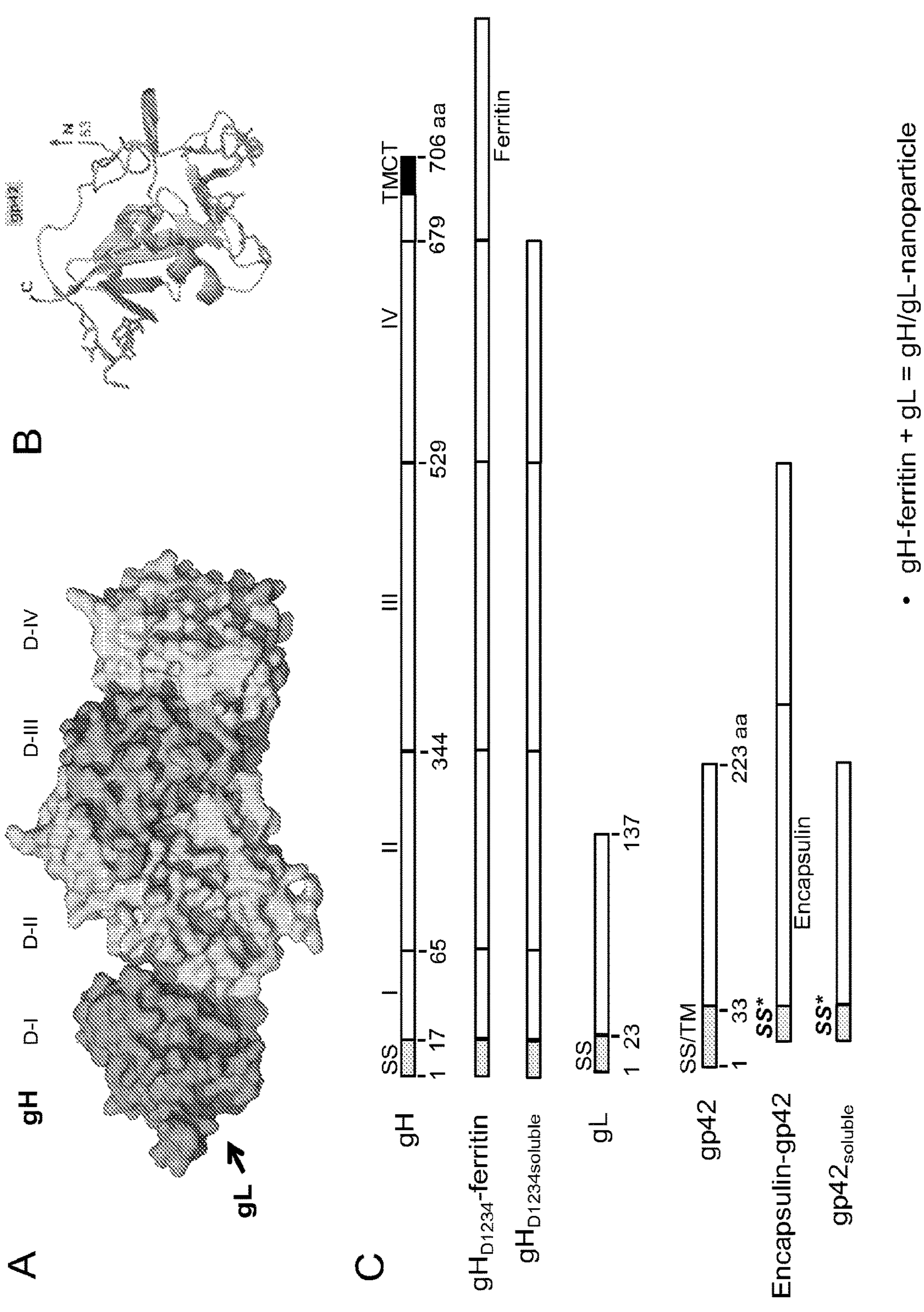
FIG. 3. Molecular structure and design of gH/gL ferritin-based, gH/gL/gp42 ferritin-based and gH/gL/gp42 encapsulin-based nanoparticles. (A) Crystal structure of EBV gH/gL heterodimer (PDB: 3PHF). (B) Ribbon diagram of EBV gp42 (PDB: 3FD4). (C) Schematic representation of full-length gH, $gH_{D1234}$-ferritin fusion protein, $gH_{D1234}$ soluble, full-length gL, full-length gp42, encapsulin-gp42 and gp42 soluble proteins. gH-ferritin fusion protein is generated by fusion of gH ectodomain ($D_{1234}$) to the N-terminus of ferritin (*Helicobacter pylori*-bullfrog hybrid (Hp)). Soluble gH is constructed by deletion of transmembrane domain and cytoplasmic tail. $gH_{D1234}$ is identical to the construct used for the crystallography study (Matsuura, H., et al. *Proc. Natl. Acad. Sci. U.S.A.* 107:22641-22646, 2010). EBV gL is the full-length wild type gL. The encapsulin-gp42 is constructed by fusing a human CD5 leader (hCD5) sequence to the N-termini of encapsulin (*Thermotoga maritima*), followed by $(Ser-Gly_3)_2$ linker, and followed by gp42 (with deletion of N-terminal amino acids 1-33). Soluble gp42 is constructed by fusing a human CD5 leader (hCD5)_sequence to the N-terminus truncated gp42 in place of gp42 amino acids 1-33 which are deleted.

To construct the gp350-encapsulins fusion genes, amplified gene fragments were fused at the end of encapsulin gene with a $(SG_3)_2$ linker. To produce soluble gp350 ectodomain and $D_{123}$, the amplified gene fragments were fused with bPRL signal sequence and tagged with hexa-histidine at the end of the gp350 gene for purification purpose.

gH-ferritin was constructed by fusing the extracellular domain of gH (domains I, II, III, and IV) to the amino terminus of ferritin (FIG. 3).

Soluble gH was constructed by expressing the extracellular domain of gH (domains I, II, III, and IV) (FIG. 3).

Soluble gp42 was constructed by fusing a human CD5 leader (hCD5) sequence to the N-terminus truncated gp42 in place of gp42 amino acids 1-33.

The EBV gL protein used in this study is the fill-length, wild-type gL protein.

All gene constructs described above were cloned into CMV/R 8κb (VRC 8405) mammalian expression vectors for efficient expression.

B. Production and Purification of Recombinant Nanoparticles

FreeStyle 293-F or Expi293F cells (Life Technologies) were transiently transfected with the expression plasmids described in (A), either alone in or combination, using 293fectin or ExpiFectamine 293 transfection reagents, respectively (Life Technologies). For example, gp350 nanoparticles were made by transfecting individual gp350-ferritin or gp350-encapsulin constructs into recipient cells. gH/gL nanoparticles were made by co-transfecting plasmids expressing gH-ferritin and full length gL into cells, while gH/gL/gp42 nanoparticles were made by co-transfecting plasmids expressing gH-ferritin, full length gL, and soluble gp42 into cells. The cells were grown for 4 days after transfection, the culture supernatants harvested and the proteins or nanoparticles purified as described below.

Figure 4:
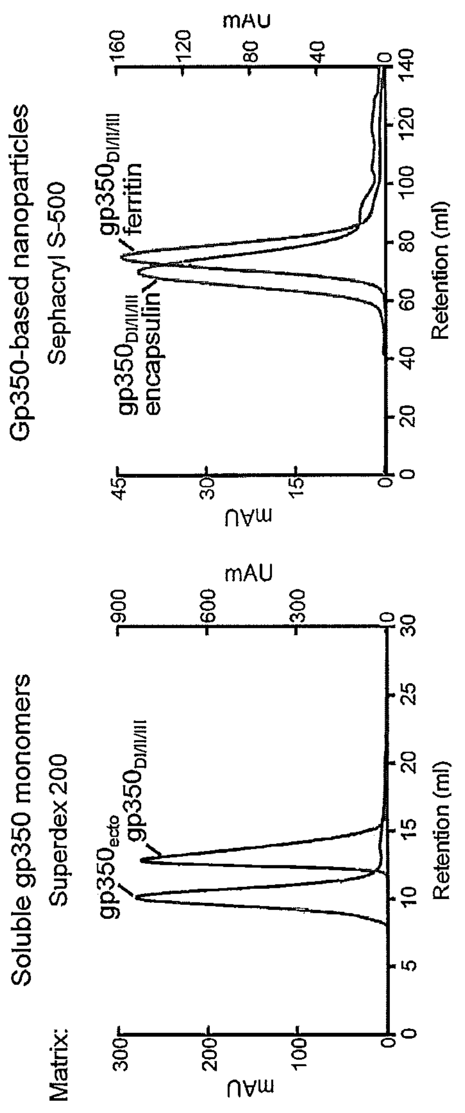
FIG. 4. Purification of truncated gp350 variants and gp350-based nanoparticles. (Left) Chromatograph resulting from size-exclusion chromatography (Superdex 200 10/300 GL) of immobilized metal ion ($Ni^{++}$) affinity chromatography purified, ferritin-based gp350 nanoparticles (gp350 ecto and gp350 DI/II/III) obtained from the supernatants of cells transfected with VRC 3796 and 3797 (Right) Chromatograph resulting from size-exclusion chromatography (Sephacryl S-500 16/60) of snowdrop lectin (*Galanthus nivalis*) affinity chromatography purified, encapsulin-based gp350 and ferritin-based gp350 nanoparticles obtained from the supernatants of cells transfected with VRC 3426 and 3430.
Figure 5:
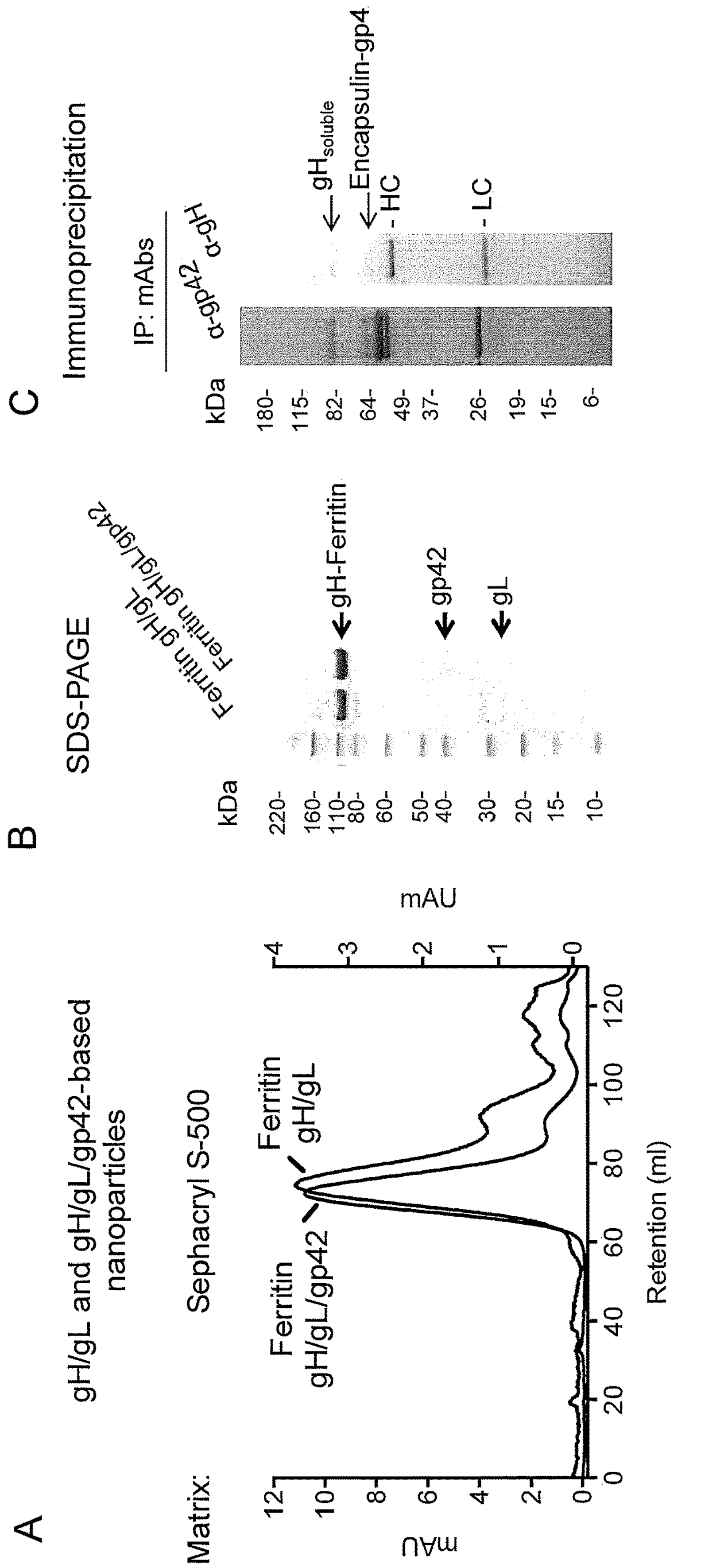
FIG. 5. Purification of gH/gL ferritin-based and gH/gL/gp42 ferritin-based nanoparticles. (A) Chromatograph resulting from size-exclusion chromatography (Sephacryl S-500 16/60 column) of snowdrop lectin (*Galanthus nivalis*) affinity chromatography purified, gH/gL and gH/gL/gp42 ferritin-based nanoparticles obtained from the supernatants of cells transfected with gH $_{D1234}$-ferritin and gL plasmids or gH $_{D1234}$-ferritin, gL, and soluble gp42 plasmids, respectively (B) Characterization of nanoparticles by SDS-PAGE. The bands corresponding to gH-ferritin, gp42, and gL are indicated. (C) Immunoprecipitation of gH/gL/gp42 encapsulin-based nanoparticle by mAbs. An anti-gp42 mAb (F2-1) and anti-gH/gL mAb (E1D1) were used to detect gH/gL/gp42 encapsulin-based nanoparticles. HC and LC denote antibody heavy and light chains, respectively.

Nanoparticles were purified using affinity and size-exclusion chromatography. Briefly, the cleared cell culture supernatants were concentrated using a 30 kDa molecular weight cut-off ultrafiltration unit (Pall) after which the buffer was replaced with PBS. The nanoparticles were then applied to a *Galanthus nivalis* agglutinin (GNA, snowdrop lectin) affinity column (EY Laboratories) and eluted using a solution of 1.0 M methyl α-D-mannopyranoside in PBS. The nanoparticles were further purified by size exclusion column chromatography using a HiPrep 16/60 Sephacryl S-500 HR column (GE Healthcare Life Sciences) in PBS and the peak fraction collected and used for further studies. The SEC chromatogram for the gp350-based nanoparticles is shown in FIG. 4 (right) while a SEC chromatogram for gH/gL-ferritin and gH/gL/gp42-ferritin nanoparticles is shown in FIG. 5A.

Soluble proteins were purified using ion affinity and SEC chromatography. Briefly, cleared cell culture supernatants were adjusted to 50 mM Tris, pH 8 and 500 mM NaCl, and applied to a metal ion affinity chromatography column containing Ni sepharose excel resin (GE Healthcare Life Sciences). After washing the column with buffer (50 mM Tris, 500 mM NaCl, 30 mM imidazole, pH 8.0), the proteins were eluted using elution buffer (50 mM Tris, 500 mM NaCl, 300 mM imidazole, pH 8.0). The proteins were then further purified by size exclusion column chromatography using a Superdex 200 10/300 GL or a Superose 6 10/300 GL column (GE Healthcare Life Sciences) in PBS and the peak fraction collected and used for further studies. A SEC chromatogram for soluble gp350 monomers is shown in FIG. 4 (left).

Figure 6:
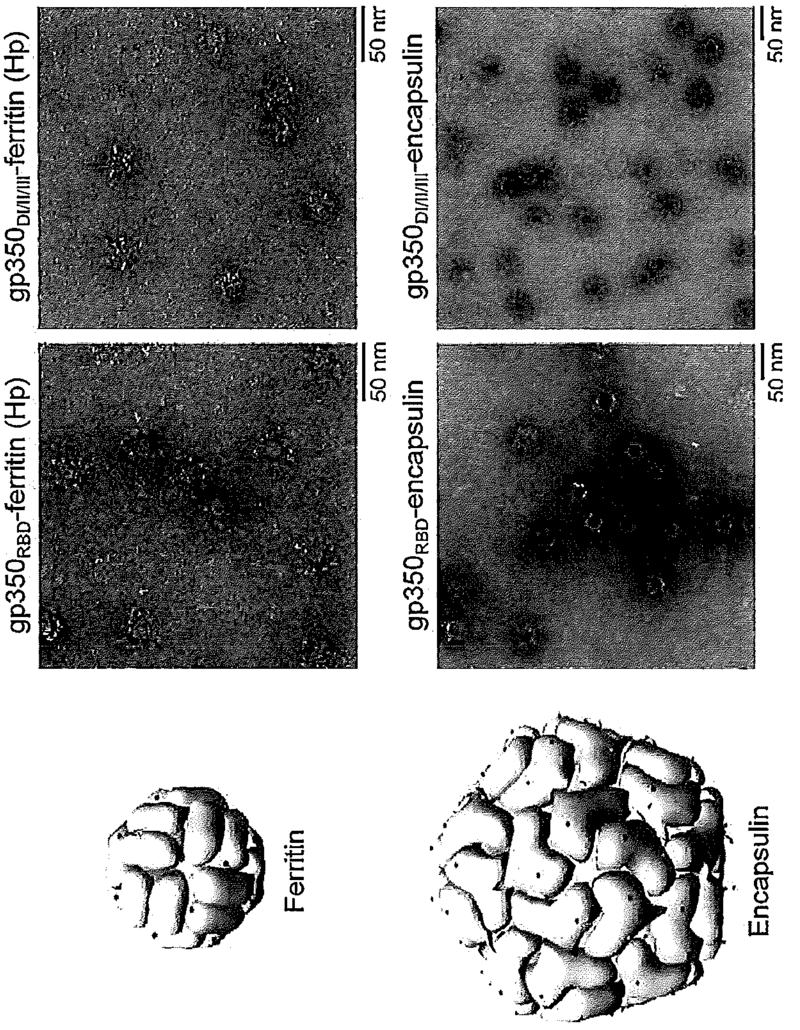
FIG. 6. Electron microscopic (EM) analyses of gp350-based nanoparticles. Assembled ferritin and encapsulin nanoparticles are shown (left). The sites of fusion (N-termini on ferritin and C-termini on encapsulin) are shown as black dots (24 sites on a ferritin and 60 sites on a encapsulin). Negative stain transmission EM pictures of gp350-based nanoparticles (middle and right), using Hp ferritin (top) and encapsulin (bottom) platforms. Gp350-based nanoparticles are derived from VRC 3426, 3427, 3430 and 3431.
Figure 7:
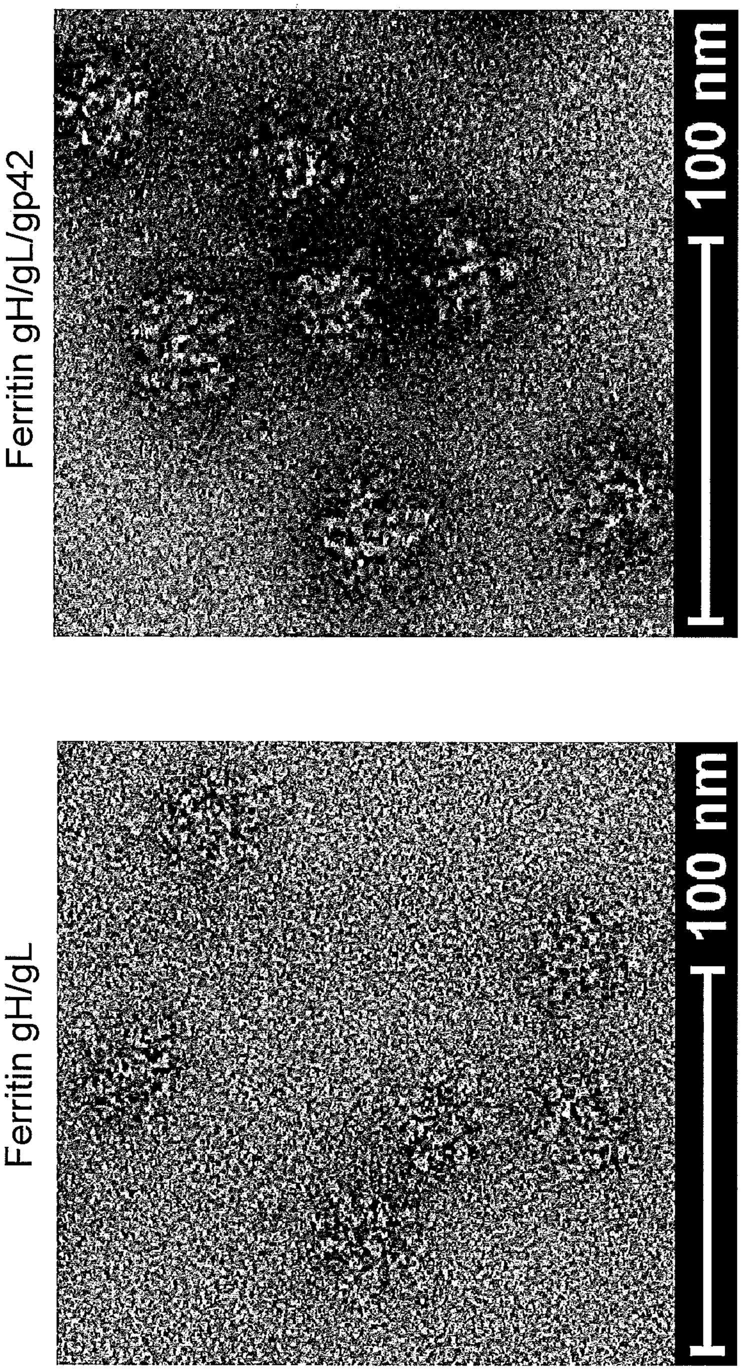
FIG. 7. Electron microscopic (EM) analysis of gH/gL ferritin and gH/gL/gp42 ferritin-based nanoparticles. Negative stain transmission EM images of gH/gL ferritin-based nanoparticles (left) and gH/gL/gp42 ferritin-based nanoparticles (right) are shown.

C. Characterization of EBV gp350-Based, gH/gL-Based, and gH/gL/gp42-Based Nanoparticles The purified nanoparticles were further examined by electron microscopic (EM) analysis. Briefly, for negative staining EM analysis, samples of about 50 μg $ml^{-1}$ were adsorbed to freshly glow-discharged carbon-coated grids, rinsed with PBS, and stained with 2% ammonium molybdate or 0.75% uranyl formate. Images were recorded on an FEI T20 microscope with a Eagle CCD camera. EM images of gp350-ferritin and gp350-encapsulin nanoparticles are shown in FIG. 6 while gH/gL ferritin-based nanoparticles and gH/gLgp42 ferritin-based nanoparticles are shown in FIG. 7, left and right, respectively. This analysis confirmed that the expressed proteins formed nanoparticles having globular protrusions from the spherical nanoparticle core.

Example 2

Antigenicity of gp350-Based Nanoparticles

To verify the antigenicity of the gp350-based nanoparticle, the reactivity of the nanoparticles was tested using the anti-gp350 monoclonal antibodies (mAbs) MAb 72A1 and MAb 2L10. MAb 72A1 recognizes the receptor-binding site of gp350, which mediates viral attachment to the host cell receptor, complement receptor 2 (CR2 or CD21). MAb 72A1 also potently neutralizes EBV (G. J. Hoffman, S. G. Lazarowitz, S. D. Hayward, Monoclonal antibody against a 250,000-dalton glycoprotein of Epstein-Barr virus identifies a membrane antigen and a neutralizing antigen. *Proc Natl Acad Sci USA* 77, 2979-2983 (1980), Sairenji T, Bertoni G, Medveczky M M, Medveczky P G, Nguyen Q V, Humphreys R E., Inhibition of Epstein-Barr virus (EBV) release from P3HR-1 and B95-8 cell lines by monoclonal antibodies to EBV membrane antigen gp350/220. J Virol. 1988 August; 62(8):2614-21.). The CR2-binding site (CR2BS) is one of the sites of vulnerability on the virus and therefore an attractive target for vaccine development. MAb 2L10 is a non-neutralizing antibody and does not compete with 72A1 (J. Luka, R. C. Chase, G. R. Pearson, A sensitive enzyme-linked immunosorbent assay (ELISA) against the major EBV-associated antigens. I. Correlation between ELISA and immunofluorescence titers using purified antigens. *J Immunol Methods* 67, 145-156 (1984)). To test the reactivity of the expressed proteins and nanoparticles with these antibodies, 100 ul of purified nanoparticles or soluble gp350 protein (at 25 nM) were coated onto MaxiSorp plates (Nunc). To each well was then added anti-gp350 antibody (MAb 72A1 or MAb 2L10) or anti-influenza hemagglutinin (MAb C179). Following appropriate incubation and removal of the antibody, bound MAbs were detected using a peroxidase-conjugated, secondary antibody (anti-mouse IgG) (Southern Biotech).

Figure 8:
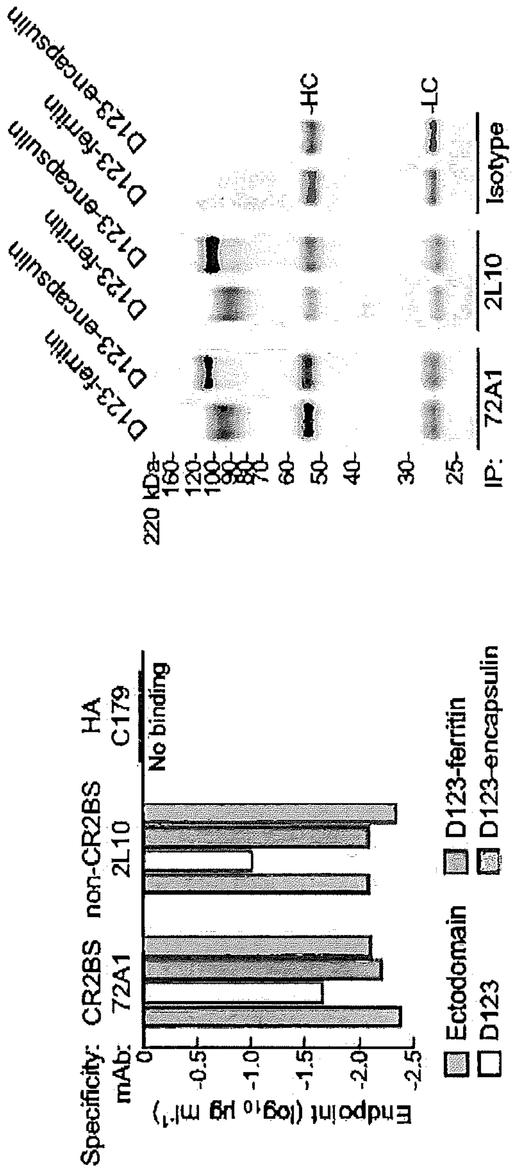
FIG. 8. Antigenic characterization of truncated gp350 variants and gp350-based nanoparticles. Binding properties of purified gp350 variants and gp350-based nanoparticles to anti-gp350 monoclonal antibodies (mAbs). Endpoint concentrations of binding mAbs were measured by ELISA (left). Immunoprecipitation of gp350-based nanoparticles by mAbs (right). A neutralizing anti-CR2BS mAb (72A1) and a non-neutralizing anti-gp350 (not specified, not anti-CR2BS) mAb (2L10) were used to detect gp350 variants and gp350-based nanoparticles. An anti-Influenza HA mAb (C179) was used as an isotype control. HC and LC denote antibody heavy and light chains, respectively. Soluble gp350 variants and gp350-based nanoparticles are derived from VRC 3796, 3797, 3426 and 3430.

The results of this study, which are shown in FIG. 8 (left), showed that both 72A1 and 2L10 mAbs recognized gp350-based nanoparticles as well as soluble gp350 ectodomain. In addition, both antibodies bound the soluble $D_{123}$ monomer to a lesser extent. Neither of the purified proteins bound the isotype control, MAb C179.

The antigenicity of the gp350-based nanoparticles was further confirmed by immunoprecipitation. Briefly, five micrograms of mAbs directed to gp350 CR2-binding site (72A1), gp350 non-CR2-binding site (2L10) or influenza hemagglutinin (C179) were incubated with purified nanoparticles (5 μg) at room temperature for 30 minutes. After incubation, pre-washed protein G Dynabeads (Life Technologies) were added to the reactions and incubated for another 30 minutes. PBS containing 0.01% Tween 20 was used as washing buffer. Immune complexes were then magnetically separated, washed and eluted in Lamini buffer containing reducing agent. A half volume of the reactions were then analyzed by SDS-PAGE. The results of this analysis are shown in FIG. 8 (right).

Example 3

Immune Response Induced by gp350-Based Nanoparticles

To evaluate the immunogenicity of the gp350-based nanoparticles, ten-week old mice were immunized at weeks 0 and 3 with 5.0 μg of both HpBf and EcBf ferritins and encapsulin nanoparticles expressing either gp350 RBD or $D_{123}$ on the surface in the presence of Sigma Adjuvant System (SAS, also known as Ribi). Immune sera were collected at 2 weeks after each immunization to analyze antibody response to gp350. Briefly, soluble gp350 ectodomain protein (2 μg $ml^{-1}$, 100 μl $well^{-1}$) were coated onto wells of a MaxiSorp plate (Nunc), after which to each well was added an aliquot of serially diluted immune sera. Following incubation and removal of the immune sera, to each well was added peroxidase-conjugated secondary antibody (anti-mouse IgG). Following incubation and removal of unbound secondary antibody, the wells were developed using a SureBlue chromogen (KPL) and the reaction was stopped by adding 0.5 M sulfuric acid. Absorbance at 450 nm was then measured by SpectraMax M2e (Molecular Devices). Endpoint titers were determined by calculating concentrations at the absorbance threshold (four times background) from the binding curve.

Figure 9:
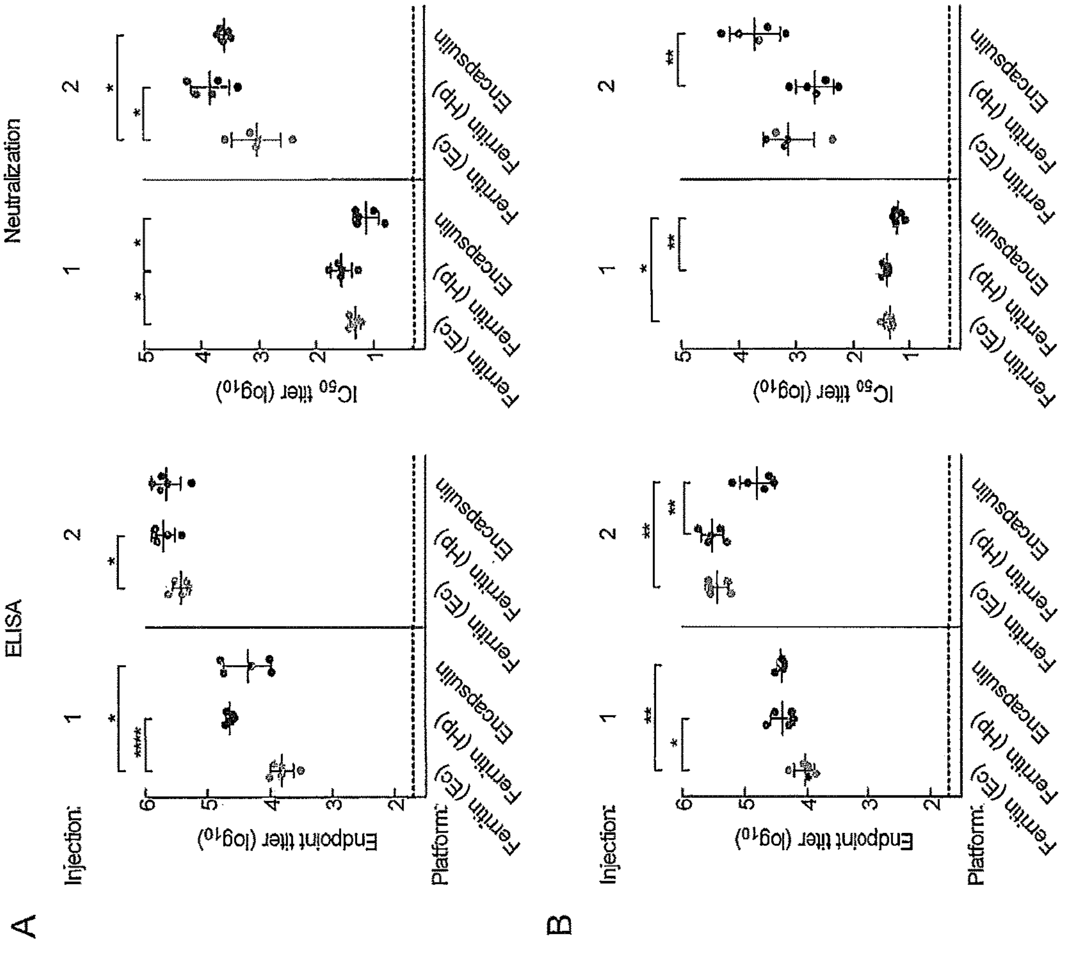
FIG. 9. Comparison of immunogenicity of different gp350-variants and nanoparticle platforms. Immunogenicity of gp350 $D_{123}$-based nanoparticles (A) and gp350 RBD-based nanoparticles (B). BALB/c mice (n=5) were immunized intramuscularly with 5 μg of indicated gp350-based nanoparticles mixed with a Ribi adjuvant at weeks 0 and 3. Immune sera were collected 2 weeks after the first (1) and the second (2) immunization. Immune sera were analyzed by measuring antibody binding titer against soluble $gp350_{ecto}$ by ELISA (left) and neutralizing titer (right). The endpoint titers of anti-$gp350_{ecto}$ are shown (left). The neutralization assay was based on the Raji B cell line and a GFP reporter virus (Sashihara J., et al., *Virology.* 391, 249-256, 2009) and the titer is shown as a dilution of serum needed to inhibit viral entry by 50% ($IC_{50}$). Each dot represents individual mouse. Bar indicates mean and s.d. *, $p<0.05$; , $p<0.01$; *, $p<0.001$; ****, $p<0.0001$. Gp350-based nanoparticles used for immunization are derived from VRC 3422, 3423, 3426, 3427, 3430 and 3431.

The results of this study, which are shown in FIG. 9, demonstrate that an antibody response to gp350 was detected in all gp350-based nanoparticle-immunized mice after a single dose at titers of $\sim 10^{3.9}$-$10^{4.9}$ and the titers were boosted about 10-fold by a second dose. Neutralizing antibody titers were also detected in all mice after a single dose although the titers were not high ($IC_{50}<50$). These titers were markedly boosted at ~100-fold by a second dose.

Example 4

Comparison of gp350-Based Nanoparticles and Soluble gp350 Protein

To compare immune responses elicited by the gp350-based nanoparticles to that of soluble gp350 proteins, ten-week old mice were immunized at weeks 0 and 3 with either soluble gp350 ectodomain or $D_{123}$ or $D_{123}$-nanoparticles at 5.0 and 0.5 μg in the presence of SAS as adjuvant. Immune sera were collected 2 weeks after the first (1) and the second (2) immunization and analyzed as described in Example 2 and 3.

Figure 10:
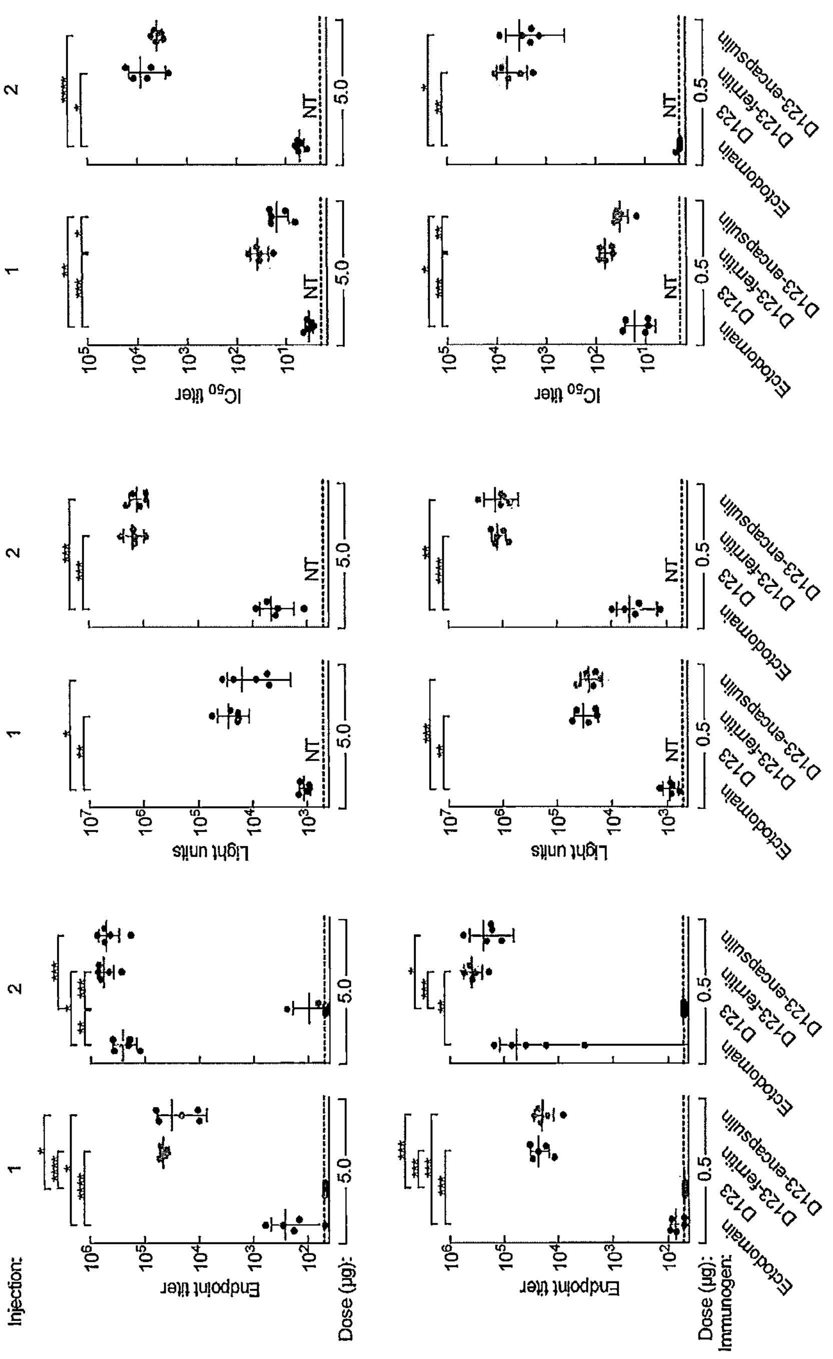
FIG. 10. Comparison of immunogenicity of soluble gp350 variants and gp350-based nanoparticle. Immune sera were analyzed by measuring anti-gp350 antibody binding titer by ELISA (left) and LIPS (center) assay and neutralization $IC_{50}$ titer (right). LIPS assay was performed as previously described (Sashihara J., et al., *Virology.* 391, 249-256, 2009). Each dot represents individual mouse. Bar indicates mean and s.d. *, $p<0.05$; , $p<0.01$; *, $p<0.001$; ****, $p<0.0001$. Gp350 variants and gp350-based nanoparticles used for immunization are derived from VRC 3796, 3797, 3426 and 3430.

The results of this study, which are shown in FIG. 10, show that at 2 weeks following the first immunization the $D_{123}$ nanoparticles elicited a higher antibody response than did either the soluble gp350 ectodomain or soluble $D_{123}$ protein (titers of 47,654±16,482 and 32,042±24907 for $D_{123}$-ferritin and $D_{123}$-encapsulin, respectively vs. 261±219 and <50 for gp350 ectodomain and $D_{123}$, respectively). However, following a second immunization, soluble gp350 ectodomain boosted ELISA titers dramatically to the titers at only ~2-3-fold lower than that of either $D_{123}$-ferritin- or $D_{123}$-encapsulin-immunized groups (261,116±116,301 vs. 567,764±188,536 or 499,128±211,748, respectively). Surprisingly, soluble gp350 $D_{123}$ failed to elicit antibody responses even after the second immunization (titers of 96±92) although the same $D_{123}$ displayed on ferritin and encapsulin was highly immunogenic. Because an earlier study (Sashihara, et al. Virology, 2009) demonstrated a strong correlation between titers measured in neutralization assay and immunoprecipitation-based assay (luciferase immunoprecipitation system, LIPS), the mouse immune sera was tested in an LIPS assay in addition to ELISA. For the LIPS assay, the fusion protein composed of gp350 and Remilla luciferase was incubated with sera and immunoprecipitated using protein A/G beads (Thermo Scientific) in 96-well filter bottom plates (Millipore). Luciferase activity of antibody-bound fusion proteins was then measured by adding coelenterazine substrate (Promega) and detecting by Centro LB 960 luminometer (Berthold Technologies).

These studies demonstrate that LIPS antibody titers in the sera of gp350 ectodomain-immunized mice were more than two logs lower than that of either $D_{123}$-ferritin- or $D_{123}$-encapsulin-nanoparticle-immunized mice ($10^{3.6\pm0.3}$ vs. $10^{6.2\pm0.2}$ or $10^{6.1\pm0.2}$, respectively) at 2 weeks after a second dose. To verify if the LIPS titers reflected neutralizing antibody titers, serum neutralizing antibody titers were determined by GFP-reporter assay (Sashihara, et al. Virology, 2009). Neutralization of EBV to B cells has been described previously (Sashihara, J., Burbelo, P. D., Savoldo, B., Pierson, T. C., Cohen, J. I., Human antibody titers to Epstein-Barr virus (EBV) gp350 correlate with neutralization of infectivity better than antibody titers to EBV gp42 using a rapid flow cytometry-based EBV neutralization assay. Virology 391, 249-256 (2009).) Briefly, immune sera were serially diluter in a 2-fold step and 25 ul of the diluted samples was incubated with B95-8/F virus for 2 hours. The mixture was added to Raji cells in the 96-well plate and incubated for 3 days at 37° C. (Raji cells were propagated in RPMI 1640 with complete supplements: 10% fetal bovine serum, 100 U/ml penicillin, 100 ug/ml streptomycin and 2 mM L-glutamine) Following incubation, cells were fixed in 2% paraformaldehyde in PBS and analyzed by Accuri C6 flow cytometer and BD CSampler software (BD Biosciences, San Jose, Calif., USA) to quantify the percentage of infected ells based on GFP expression. Neutralization antibody titers were expressed as the concentration of serum antibody needed to inhibit viral entry by 50% (IC50) calculating with controls in the absence of virus (0% infection) or serum (100% infection).

Surprisingly, the differences in neutralizing antibody titers between the sera from soluble gp350 ectodomain-immunized mice and that from either $D_{123}$-ferritin- or $D_{123}$-encapsulin-immunized mice were ~1000-fold after a second dose (5±1 vs. 8,594±5944 or 3,939±874, respectively) and the titers in soluble gp350 ectodomain-immunized group were barely above the threshold of the assay ($IC_{50}$<10). Together, the results revealed that immunization using soluble gp350 ectodomain induced mostly non-neutralizing antibodies which were only detectable in ELISA. ELISA, LIPS and neutralizing antibody titers in mice immunized with 5.0 and 0.5 μg of $D_{123}$-ferritin and $D_{123}$-encapsulin were virtually the same (<2-fold differences), while there was a slight reduction in ELISA and neutralizing antibody titers in mice immunized with both soluble gp350 ectodomain (4.4-fold decrease in ELISA titers and no neutralizing antibody titers in group immunized with lower dose).

Example 5

Durability of Neutralizing Antibody Response in gp350-Based Nanoparticle-Immunized Animals To assess the kinetics of virus neutralizing antibody responses in the mice immunized in Example 4, the titers of neutralizing antibody were determined longitudinally for >6 months. At 2 months following the second immunization, the neutralizing titers in $D_{123}$-ferritin- and $D_{123}$-encapsulin-immunized animals at both 5.0 and 0.5 μg doses declined about one log to $10^{2.4}$-$10^{3.1}$, however, the titers remained at the same level for another month without further immunization. All mice then received a third dose at week 16 and their serum neutralizing antibody titers monitored.

Figure 12:
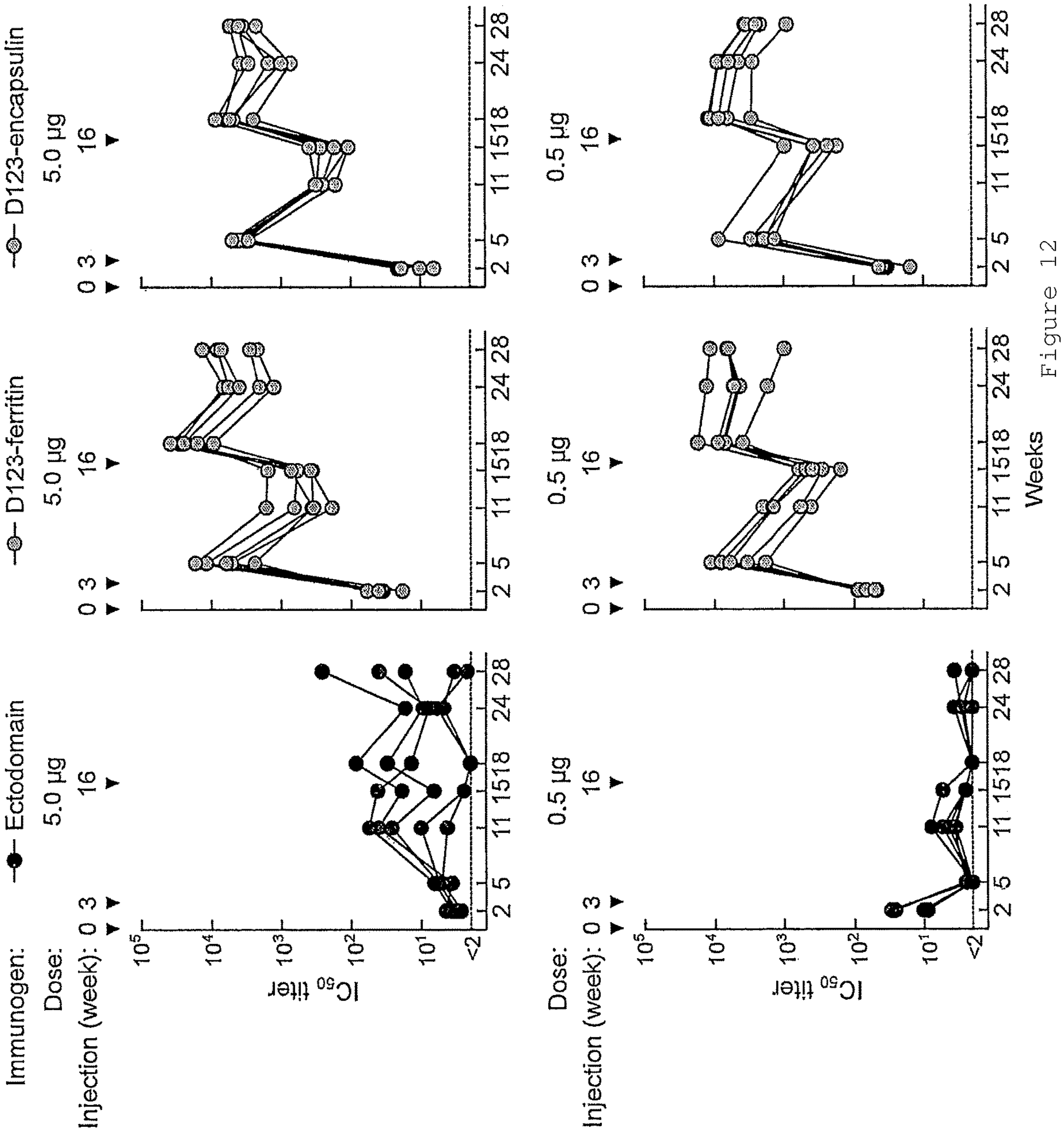
FIG. 12. Kinetics of serum neutralization titers after immunization with soluble gp350 and gp350 based nanoparticles. Groups of BALB/c mice (n=5) were immunized intramuscularly with 5 ug (upper panels) or 0.5 ug (lower panels) of soluble gp350 ectodomain (left), $D_{123}$-ferritin (center) or $D_{123}$-encapsulin (right) mixed with a Ribi adjuvant at weeks 0, 3, and 16. Immune sera were collected periodically after immunization and serum neutralization $IC_{50}$ titers were determined. gp350 ectodomain and gp350-based nanoparticles used for immunization are derived from VRC 3796, 3426 and 3430.

The results of this study are shown in FIG. 12. Expectedly, the titers were boosted by 33- and 26-fold in $D_{123}$-ferritin and $D_{123}$-encapsulin, respectively ($10^{4.3\pm0.2}$ and $10^{3.7\pm0.2}$, respectively), whereas the effect was not obvious in groups immunized with soluble gp350 ectodomain as measured at 2 weeks after the boost ($10^{1.0\pm0.7}$). The peak neutralizing antibody titers in $D_{123}$-ferritin were higher than that after the second immunization ($10^{3.8\pm0.3}$) and the titers did not wane as quickly as after the second immunization. The titers at 2 and 3 months after the third immunization were stable at $10^{3.3}$-$10^{3.8}$ in groups immunized with $D_{123}$-ferritin and $D_{123}$-encapsulin and that were 1.5-5.9 times lower than the peak and one log higher than the titers at the same time point after the second immunization. Similar kinetics and magnitudes of neutralizing antibody titers were observed when animals were immunized with a 10× smaller dosage (0.5 μg) of either gp350-based nanoparticles. However, at this dose the soluble gp350 ectodomain was unable to elicit any neutralizing antibody response.

Example 6

Characterization of Antibodies Elicited by gp350-Based Nanoparticles

To determine the fine specificity of the antibodies elicited by either soluble gp350 ectodomain or gp350-based nanoparticles, a surface plasmon resonance (SPR)-based antibody competition assay was performed. This assay detects specific populations of antibodies in immune sera, the specificity of which is similar to that of a competing mAb. Briefly, the soluble gp350 ectodomain was immobilized on a sensor chip via amine coupling reaction. Before measuring the binding of the immune sera, 72A1, 2L10 or C179 was injected to the flow cell to saturate the sites where the mAb recognizes on the chip. Immune sera (taken 2 weeks after the second immunization with Ribi-adjuvanted 5 μg of immunogen) was then injected to the antibody-saturated flow cells and the binding kinetics of the serum antibodies were measured. The serum antibodies directed to the same epitope as 72A1 were not able to bind to the 72A1-saturated gp350 and therefore resulted in lower overall binding compared to that of C179-saturated gp350. All data were normalized with an isotype control (C179-saturated) and shown as fraction response. Inhibition of serum antibody to bind to gp350 by 72A1 or 2L10 (X) was calculated by an equation: X=100−{(maximum response unit of 72A1- or 2L10-saturated flow cell/maximum response unit of isotype antibody-saturated flow cell)×100}. Surprisingly, when the competitor antibody was CR2BS-directed mAb 72A1, 52±11 and 60±12% of total anti-gp350 antibodies in the immune sera elicited by $D_{123}$-ferritin and $D_{123}$-encapsulin, respectively, was competed, whereas only 5±4% of anti-gp350 antibodies in immune sera elicited by soluble gp350 ectodomain was blocked.

Figure 11:
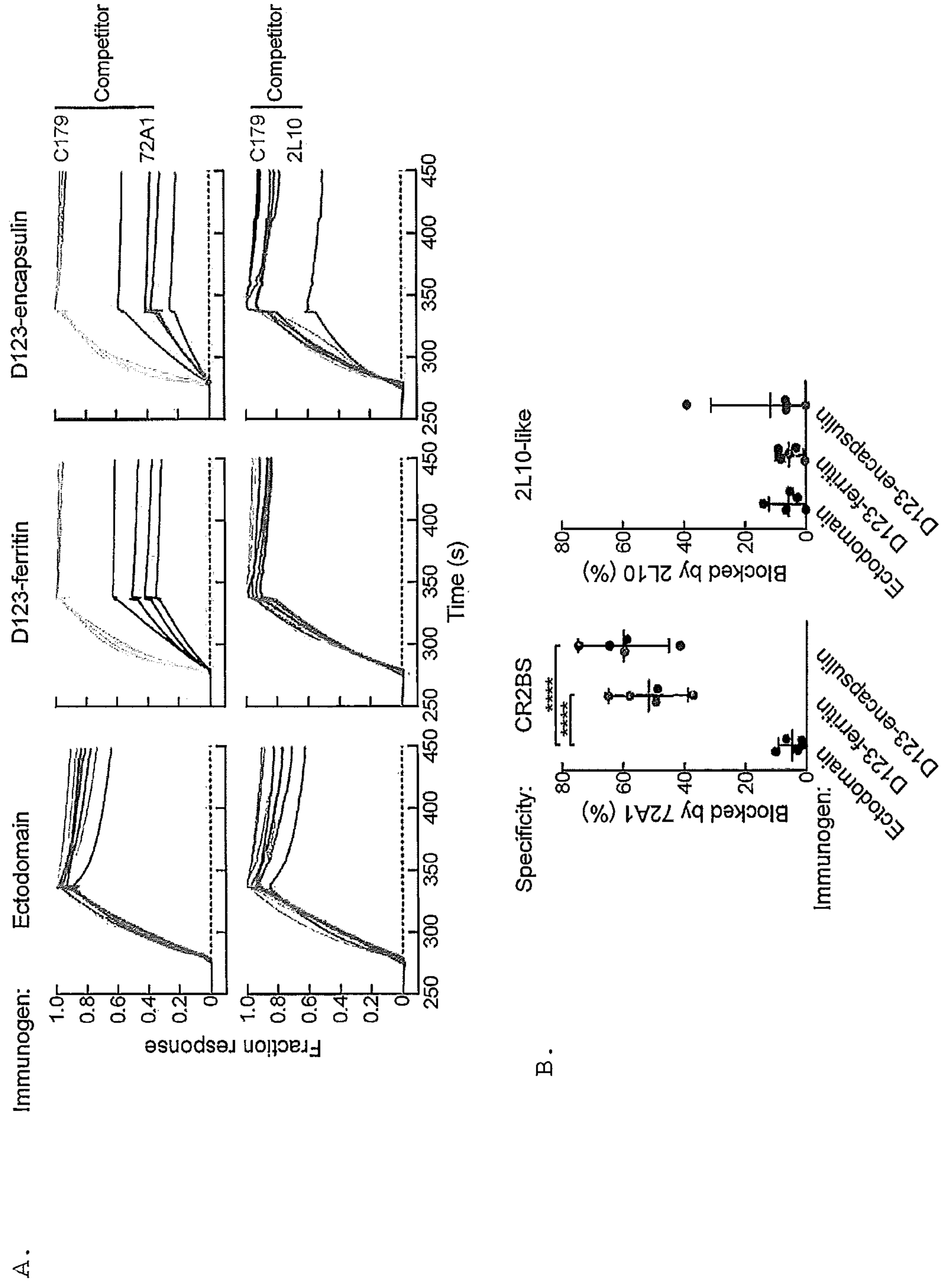
FIG. 11. Detection of CR2BS-directed antibodies in gp350-based nanoparticle-immune sera. (A) Surface plasmon resonance-based cross-competition assay of immune sera with an anti-CR2BS (72A1), an anti-gp350 (2L10, non-CR2BS directed) and an isotype control (C179, anti-influenza) mAbs. Each curve represents individual mouse. Cross-competition of immune sera by 72A1 (top) and 2L10 (bottom) were shown by different immunization groups. (B) Relative percentages of CR2BS-directed and 2L10-like antibodies in the immune sera. Each dot represents individual mouse and bar indicates mean and s.d. *, $p<0.05$; , $p<0.01$; *, $p<0.001$; ****, $p<0.0001$. Gp350 ectodomain and gp350-based nanoparticles used for immunization are derived from VRC 3796, 3426 and 3430.

The results of this analysis, which are shown in FIG. 11, demonstrate that the CR2BS on the gp350-based nanoparticles were indeed predominantly targeted by the antibody response and the same site on soluble gp350 ectodomain was not. Importantly, there was negligible fraction of anti-gp350 antibodies in these immune sera that was competed by a non-neutralizing, non-CR2BS-directed mAb 2L10 (6±5, 5±4 and 12±16% in soluble gp350 ectodomain, $D_{123}$-ferritin and $D_{123}$-encapsulin, respectively), suggesting the epitope recognized by 2L10 was not immunodominant in both soluble gp350 ectodomain and gp350-based nanoparticles.

Example 7

Figure 13:
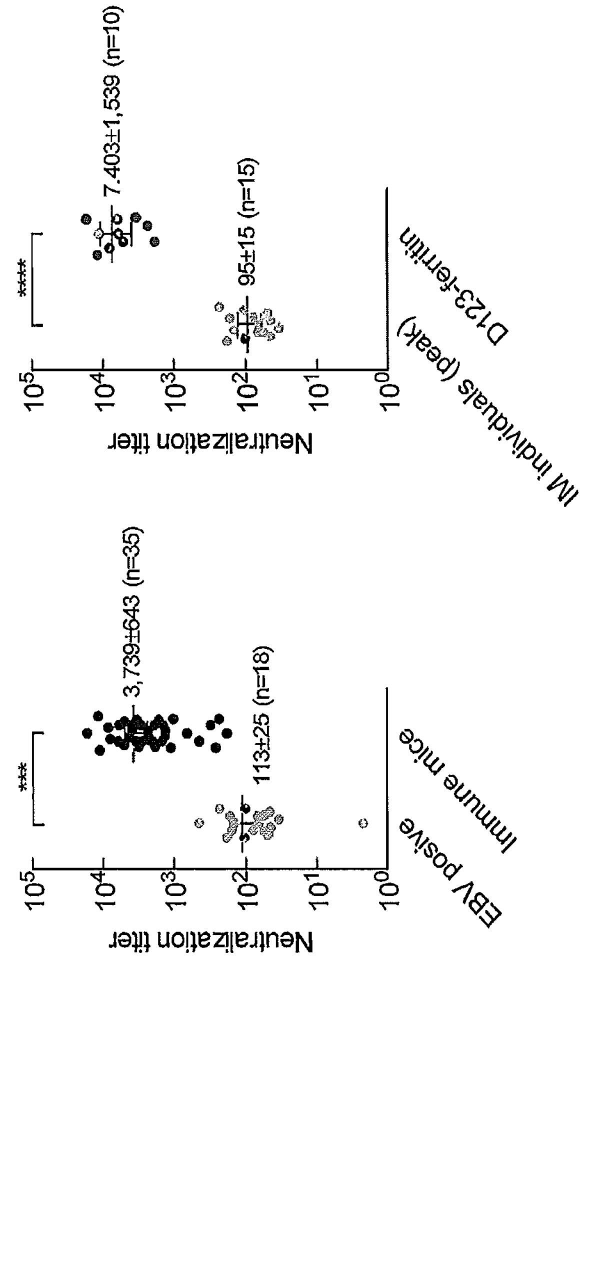
FIG. 13. Comparison of serum neutralization titers in EBV-positive human individuals and gp350-based nanoparticle-immunized mice. (left panel) Comparison of serum neutralization titer ($IC_{50}$) between a combination of EBV-seropositive individuals and persons with EBV-positive mononucleosis (n=18) and gp350-based nanoparticle-immunized mice (titers at 2 weeks after the second immunization, combined groups shown in FIGS. 9 and 10, n=35). (right panel) Comparison of serum neutralization titer ($IC_{50}$) between EBV-seropositive infectious mononucleosis human individuals (peak neutralization titers of each individual, n=15) and $D_{123}$-ferritin-immunized mice (titers at 2 weeks after the second immunization, combined groups shown in FIG. 6, n=10). Each dot represents individual serum sample and bar indicates mean and s.d. Gp350-based nanoparticles used for immunization are derived from VRC 3422, 3423, 3426, 3427, 3430 and 3431.
Figure 14:
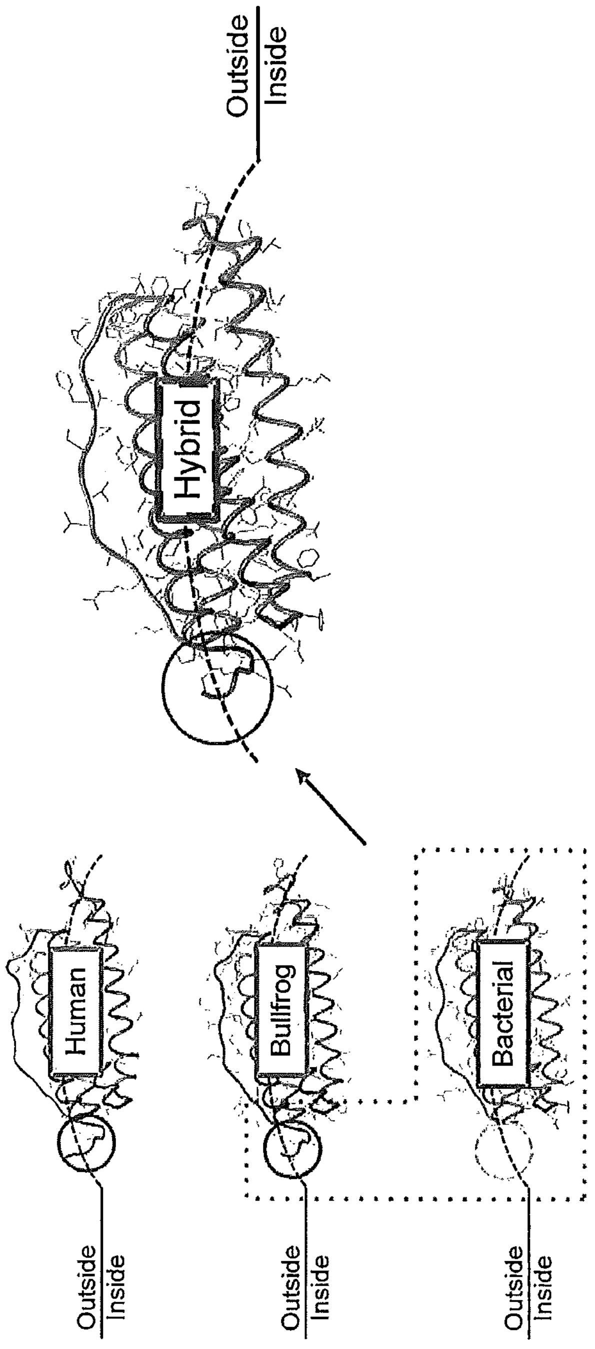
FIG. 14. Generation of bullfrog-*E. coli* and bullfrog-*H. pylori* hybrid ferritins. Crystal structure of ferritin subunit monomers of human (light chain), bullfrog (red cell lower subunit) and bacterial (*E. coli* non-heme ferritin, FtnA) are shown (left). The extended N-terminal parts (circled) in human and bullfrog ferritins are exposed on a surface of assembled ferritin nanoparticles and the corresponding region is missing in *E. coli* (and *H. pylori*) ferritin (circled with dashed line). To make hybrid ferritins the N-terminal extended part of bullfrog ferritin was transplanted to either *E. coli* or *H. pylori* ferritin. The plasmids encoding hybrid *E. coli*-bullfrog and *H. pylori*-bullfrog ferritins are designated as VRC 3384 and 3419, respectively.

Comparison of Serum Neutralization Titers in EBV-Positive Human Individuals and gp350-Based Nanoparticle-Immunized Mice Sera from mice immunized in Examples 3 and 4 were obtained and serum neutralization titers determined. These titers were then compared to neutralization titers observed in humans naturally infected with EBV. FIG. 13. (left) shows a comparison of serum neutralization titer ($IC_{50}$) between a combination of EBV-seropositive individuals and persons with EBV-positive mononucleosis and gp350-based nanoparticle-immunized mice; (right) Comparison of serum neutralization titer ($IC_{50}$) between persons with EBV-positive infectious mononucleosis and $D_{123}$-ferritin-immunized mice.

Example 8

Antigenicity of gH/gL and gH/gL/gp42-Based Nanoparticles

The ability of purified nanoparticles to induce antibody production was tested in mice. Briefly, ten week old BALB/c mice (n=5) were injected intramuscularly with 0.5 ug of either soluble gH/gL, soluble gH/gL/gp42, ferritin-gH/gL or ferritin-gH/gL/gp42. A second round of injections was given three weeks later. At 5 weeks post-first injection, blood was drawn and antibody titers to gH, gL and gp42 were determined using a LIPS (luciferase immunoprecipitation assay) described by Sashihara, et al., Virology 391, 249-256, 2009.

Figure 15:
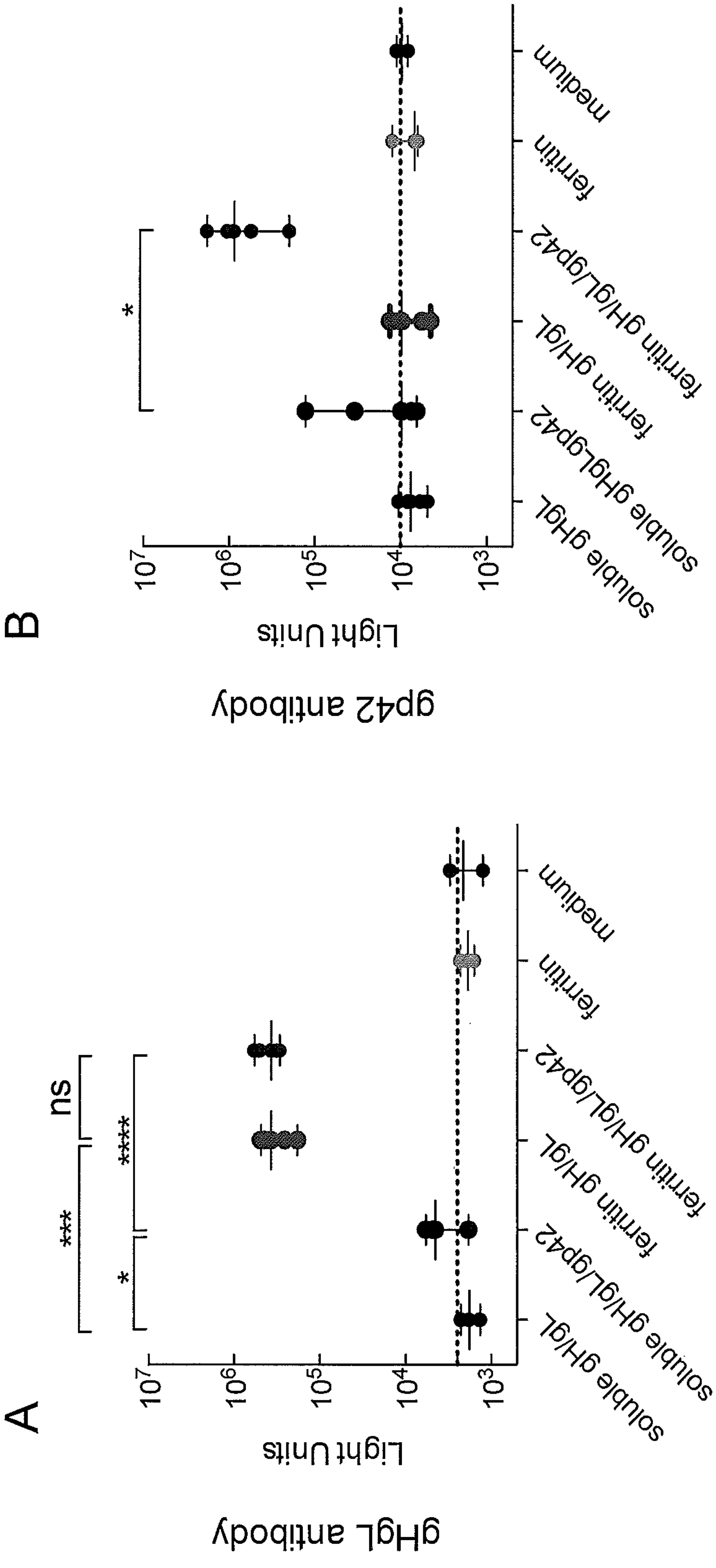
FIG. 15. Comparison of antibody titers of soluble gH/gL, soluble gH/gL/gp42, gH/gL ferritin-based nanoparticle and gH/gL/gp42 ferritin-based nanoparticles in immunized mouse sera. BALB/c mice (n=5) were immunized intramuscularly with 0.5 μg of the indicated proteins with a Ribi adjuvant at week 0 and 3. The antibody titers to gH/gL (A)

The result of this analysis, which is shown in FIG. 15, shows that ferritin-based gH/gL nanoparticles or ferritin-based gH/gL/gp42 nanoparticles induce levels of antibody to the gH/gL complex that are significantly higher than the levels induced by soluble gH or gL protein. Additionally, ferritin-based gH/gL/gp42 nanoparticles induce levels of antibodies to gp42 that are significantly higher than the levels induced by soluble gH/gL/gp42.

Example 9

Comparison of Neutralizing Antibody Induction

The ability of purified nanoparticles to induce neutralizing antibodies in mice was measured using a B-cell and epithelial cell neutralization assay. Briefly, ten week old BALB/c mice (n=5) were immunized as described in Example 8. At 2 weeks post-second injection, blood was drawn and the ability of the sera to inhibit infection of B-cells and epithelial cells by a recombinant reporter virus expressing GFP (Sashihara J., et al., Virology, 391, 249-256, 2009) was tested.

The results of this analysis, which is shown in FIG. 16, shows that ferritin-based gH/gL nanoparticles or ferritin-based gH/gL/gp42 nanoparticles induce levels of neutralizing antibodies to EBV that are significantly higher than the levels induced by soluble gH/gL protein or soluble gH/gL/gp42 protein.

Example 10

Comparison of Kinetics of gH/gL Antibody Titers in Sera from Mice Immunized with 0.5 μg Soluble gH/gL, gH/gL Nanoparticles, Soluble gH/gL/gp42, or gH/gL/gp42 Nanoparticles Ferritin-based nanoparticles and soluble proteins were prepared as described in Example 1. Balb/c mice (n=5) were then injected intramuscularly with 0.5 ug soluble gH/gL, soluble gH/gL/gp42, ferritin-gH/gL or ferritin-gH/gL/gp42 at weeks 0, 3 and 14. Blood was drawn at weeks 2, 5, 13, 16, 20, 24 and 28, and antibody titers to gH/gL were determined using a LIPS assay, as described by Sashihara, et al., Virology 391, 249-256, 2009. The results of this study, which are shown in FIG. 17, demonstrate that gH/gL antibody responses with gH/gL-nanoparticles are higher than soluble gH/gL protein and the antibody titers are sustained >12 weeks after the $3^{rd}$ dose. The results also demonstrate that gH/gL antibody titers in mice immunized with gH/gL/gp42-nanoparticles are higher than soluble gH/gL/gp42 after 2 doses, but comparable to soluble gH/gL/gp42 after 3 doses of vaccine. Finally, the result show that antibody titers are sustained >12 weeks after the $3^{rd}$ dose.

Example 11

Comparison of Kinetics of gp42 Antibody Titers in Sera from Mice Immunized with Soluble gH/gL/42 or gH/gL/gp42 Nanoparticles The production of nanoparticles and soluble proteins, and the immunization and blood draws were performed as described in Example 10. Antibody titers to gp42 were then determined by LIPS assay, as described by Sashihara, et al., Virology 391, 249-256, 2009. The results of this study, which are shown in FIG. 18, demonstrate that gp42 antibody titers in mice immunized with gH/gL/gp42-nanoparticles are higher than soluble gH/gL/gp42 after 2 doses, but comparable to soluble gH/gL/gp42 after 3 doses of vaccines. The results also show that gp42 antibody titers are sustained >12 weeks after the $3^{rd}$ dose.

Example 12

Comparison of Kinetics of B Cell Neutralizing Antibody Titers in Mice Immunized with Soluble gH/gL, gH/gL Nanoparticles, Soluble gH/gL/gp42, or gH/gL/gp42 Nanoparticles The production of nanoparticles and soluble proteins, and the immunization and blood draws were performed as described in Example 10. The ability of the mouse sera to neutralize EBV infection of B cells was then tested, as described in Example 9. The results of this study, which are shown in FIG. 19, demonstrate that B cell neutralizing antibody responses with gH/gL-nanoparticles or gH/gL/gp42-nanoparticles are higher than soluble gH/gL or gH/gL/gp42 proteins, respectively. The results also demonstrate that B cell neutralizing antibody titers are sustained >12 weeks after the 3rd dose.

Example 13

Comparison of Kinetics of Epithelial Cell Neutralizing Antibody Titers in Mice Immunized with Soluble gH/gL, gH/gL Nanoparticles, Soluble gH/gL/gp42, or gH/gL/gp42 Nanoparticles The production of nanoparticles and soluble proteins, and the immunization and blood draws were performed as described in Example 10. Epithelial cell neutralization assay were performed as described in Example 9. The results of this study, which are shown in FIG. 20, demonstrate that epithelial cell neutralizing antibody responses with gH/gL-nanoparticles or gH/gL/gp42-nanoparticles are higher than soluble gH/gL or gH/gL/gp42 proteins, respectively. The results also show that epithelial cell neutralizing antibody titers are sustained >12 weeks after the 3rd dose.

Example 14

B Cell and Epithelial Cell Neutralizing Antibody Titers after the $3^{rd}$ Dose in Sera of Mice Immunized with Soluble Proteins or Nanoparticles Compared to Sera from Naturally Infected Humans The B cell neutralizing antibody titers obtained in Example 12 and the epithelial cell neutralizing antibody titers obtained in Example 13 were compared to neutralization titers observed in human sera from individuals naturally infected with EBV. FIG. 21 shows B cell neutralizing antibody titers (left) or epithelial cell neutralizing titers (right) in human sera compared to sera from mice immunized with soluble proteins or nanoparticles. This comparison shoes that B cell neutralizing antibody titers in mice immunized with nanoparticles are >20-fold higher than that in naturally infected humans, and that epithelial cell neutralizing antibody titers in mice immunized with nanoparticles are >100-fold higher than that in naturally infected humans.

Example 15

Generation of gH/gL-Nanoparticles or gH/gL/gp42-Nanoparticles from Single Polypeptides To facilitate manufacture of dimeric gH/gL-nanoparticle and trimeric gH/gL/gp42-nanoparticles for clinical studies, constructs were made that express a polyprotein capable of forming a nanoparticle containing multiple EBV proteins. Specifically, constructs were made that express either a ferritin-gH/gL polypeptide or a ferritin-gH/gL/gp42 polypeptide. Each of these polypeptides was designed to include furin and picornavirus 2A cleavage sites and so that they produce ferritin-based nanoparticles by self-cleavage. The polypeptides also comprise a leader peptide sequence from human CD5 protein, in order o facilitate secretion of the polyprotein from the cell. FIG. 22A illustrates the structure of two different polyproteins.

Nanoparticles were produced as described in Example 1. Briefly, proteins were purified from supernatant of cells co-transfected with multiple plasmids expressing individual proteins or cells transfected with plasmids expressing the gH/gL or gH/gL/gp42 polypeptide. Purification of nanoparticles by size exclusion chromatography was then performed as described in Example 1A. SDS-PAGE analysis of the purified gH/gL nanoparticles and gH/gL/gp42 nanoparticles (FIG. 22(B) shows that gH/gL-nanoparticles and gH/gL/gp42-nanoparticles can be produced by transient transfection of single plasmids that express a single polyprotein that is processed by self-cleavage.

Example 16

Immunogenicity of gp350 Nanoparticles in Non-Human Primates

To evaluate the ability of purified nanoparticles to induce neutralizing antibodies in a species closer to humans than mice, cynomolgus macaques (*Macaca fascicularis*) were immunized with gp350 nanoparticles. Briefly, twelve monkeys were divided into three groups and given 50 μg of gp350 ectodomain, or 25 μg of either gp350 $D_{123}$-ferritin or gp350 $D_{123}$-encapsulin with adjuvant (Sigma Adjuvant System) on weeks 0, 4 and 12. Blood was drawn prior to immunization and at weeks 6, 8 and 14, and neutralizing antibody titer determined. The results are shown in FIG. 23.

Cross reacting EBV neutralizing antibody was found in all of the monkeys prior to immunization ($IC_{50}$ titers from $10^{1.1}$ to $10^{2.0}$), which is unsurprising since cynomolgus monkeys are naturally infected with a lymphocryptovirus that shares homology with EBV. EBV neutralizing antibody titers were increased after two immunizations (week 6) in all groups and the titers were further boosted by a third dose (week 14). Neutralizing antibody titers in monkeys immunized with gp350 $D_{123}$-ferritin (center four bars) and $D_{123}$-encapsulin (right four bars) were $10^{3.3\pm0.3}$ and $10^{2.8\pm0.3}$, respectively, and were higher than that of soluble gp350-immunized monkeys ($10^{2.4\pm0.6}$) (left four bars). These results demonstrate the immunogenicity of gp350-based nanoparticles in a second species of animal.

Example 17

Protective Immunity Against Experimental Infection of Mice with Recombinant Vaccinia Virus Expressing EBV gp350

The ability of gp350 nanoparticle vaccines to protect mice from challenge with recombinant vaccinia virus expressing EBV gp350 was assessed by immunizing mice as described in Examples 4 and 5. Ten months after the final immunization, the mice were challenged with $10^6$ pfu of recombinant vaccinia virus expressing EBV gp350 by the intranasal route. Body weights and clinical symptoms were monitored daily.

The results of this study, which are shown in FIG. 24, demonstrate that mice immunized with gp350 $D_{123}$-ferritin and gp350 $D_{123}$-encapsulin were partially protected (up to 80% survival) against lethal challenge with vaccinia virus expressing gp350. In contrast, all non-immunized control mice and animals immunized with soluble gp350 ectodomain, with the exception of one, died as a result of the challenge virus infection. These results demonstrate that immunization with gp350-based nanoparticles provides partially protective immunity against challenge with recombinant vaccinia virus expressing gp350.

Example 18

Immunogenicity of gp350 Nanoparticles in Aluminum Phosphate Gel Adjuvant

The ability of purified nanoparticles to induce neutralizing antibodies in aluminum phosphate gel (alum) adjuvant, which is approved for use in humans, was tested in mice. Mice were divided into 6 groups; 3 groups received 5 μg of gp350 $D_{123}$-ferritin and 3 groups received $D_{123}$-encapsulin. The vaccines were given with no adjuvant, aluminum phosphate gel (alum) adjuvant, or Sigma Adjuvant System (SAS) at weeks 0, 4 and 16.

The results of this study, which are shown in FIG. 25, demonstrate that EBV neutralizing antibodies titers were higher in mice immunized with gp350 nanoparticles with adjuvant than in animals immunized with gp350 nanoparticles but without adjuvant. Animals that received gp350 $D_{123}$-ferritin (left) or gp350 $D_{123}$-encapsulin (right) vaccines in SAS adjuvant had about 10-time higher titers of EBV neutralizing antibody than animals that received the same vaccines in alum adjuvant. These results demonstrate that gp350 nanoparticle vaccine in alum adjuvant is capable of inducing EBV neutralizing antibody titers of $10^{2.6\pm0.3}$ to $10^{2.8\pm0.3}$, which are 5-8 times higher than the EBV neutralizing titers in naturally infected humans.

What is claimed:

1. A nanoparticle comprising a first fusion protein, wherein the first fusion protein comprises a monomeric subunit protein joined to at least one immunogenic portion from a first Epstein-Barr Virus (EBV) envelope protein selected from the group consisting of gp350, gH, gL and gp42, wherein the monomeric subunit protein is selected from the group consisting of:

a) a monomeric subunit protein comprising at least 25 contiguous amino acids of an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29; and, b) a monomeric subunit protein comprising an amino acid sequence at least about 80% identical to an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29;

wherein the first fusion protein self-assembles into a nanoparticle; and, wherein the nanoparticle displays the at least one immunogenic portion on its surface.

2. The nanoparticle of claim 1, wherein the monomeric subunit protein comprises an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29.

3. The nanoparticle of claim 1, wherein the at least one immunogenic portion is selected from the group consisting of:

a) an immunogenic portion comprising at least 100 contiguous amino acids from an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:62, SEQ ID NO:65 and SEQ ID NO:68; and, b) an immunogenic portion comprising an amino acid sequence at least 80% identical to an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:62, SEQ ID NO:65 and SEQ ID NO:68 c) an immunogenic portion comprising at least one domain selected from the group consisting of EBV gp350 Domain I, EBV gp350 Domain II and EBV gp350 Domain III; and, d) an immunogenic portion comprising the EBV gp350 CR2-binding site.

4. The nanoparticle of claim 1, wherein the immunogenic portion comprises an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:62, SEQ ID NO:65 and SEQ ID NO:68.

5. The nanoparticle of claim 1, wherein the fusion protein comprises an amino acid sequence at least 80% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:130, SEQ ID NO:134 and SEQ ID NO:146.

6. The nanoparticle of claim 1, wherein the at least one immunogenic portion comprises at least one domain selected from the group consisting of EBV gp350 Domain I, EBV gp350 Domain II, and EBV gp350 Domain III.

7. The nanoparticle of claim 1, wherein the at least one immunogenic portion comprises an EBV gp350 complement receptor 2 (CR-2) binding site.

8. The nanoparticle of claim 1, wherein the monomeric ferritin subunit protein is a hybrid protein comprising at least a portion of a bullfrog ferritin protein joined to at least a portion of a ferritin protein selected from the group consisting of a *Helicobacter pylori* ferritin protein and an *Escherichia coli* ferritin protein.

9. A method to elicit an immune response against Epstein-Barr virus in an individual, comprising administering to the individual the nanoparticle of claim 1.

* * * * *